(12) United States Patent  (10) Patent No.: US 8,299,070 B2
Inoue et al.  (45) Date of Patent: Oct. 30, 2012

(54) INDOLE COMPOUNDS AND PHARMACEUTICAL USE THEREOF

(75) Inventors: Teruhiko Inoue, Takatsuki (JP); Tetsudo Kaya, Takatsuki (JP); Shinichi Kikuchi, Takatsuki (JP); Koji Matsumura, Takatsuki (JP); Ritsuki Masuo, Takatsuki (JP); Motoya Suzuki, Takatsuki (JP); Michihide Maekawa, Takatsuki (JP)

(73) Assignee: Japan Tobacco Inc., Tokyo (JP)

( * ) Notice: Subject to any disclaimer, the term of this patent is extended or adjusted under 35 U.S.C. 154(b) by 0 days.

(21) Appl. No.: 12/954,438

(22) Filed: Nov. 24, 2010

(65) Prior Publication Data
US 2011/0306599 A1  Dec. 15, 2011

Related U.S. Application Data

(60) Provisional application No. 61/283,175, filed on Nov. 30, 2009.

(30) Foreign Application Priority Data

Nov. 25, 2009 (JP) ................. 2009-268040

(51) Int. Cl.
*A61K 31/5355* (2006.01)
*A61K 31/4523* (2006.01)
*A61K 31/416* (2006.01)
*C07D 413/14* (2006.01)
*C07D 211/00* (2006.01)
*C07D 231/56* (2006.01)

(52) U.S. Cl. .................. 514/234.5; 514/338; 514/406; 544/140; 546/199; 548/360.1

(58) Field of Classification Search ............... 514/234.5, 514/338, 406; 544/140; 546/199; 548/360.1
See application file for complete search history.

(56) References Cited

U.S. PATENT DOCUMENTS

| 7,518,000 | B2 | 4/2009 | Jurcak et al. |
| 2010/0144821 | A1 | 6/2010 | Carter et al. |

FOREIGN PATENT DOCUMENTS

| JP | 2003-231687 A | 8/2003 |
| WO | 2005/026175 A1 | 3/2005 |
| WO | 2007/076228 A2 | 7/2007 |
| WO | 2007/088401 A1 | 8/2007 |
| WO | 2008/058402 A1 | 5/2008 |
| WO | 2008/135785 A1 | 11/2008 |

OTHER PUBLICATIONS

"Rheumatoid arthritis. <http://www.ncbi.nlm.nih.gov/pubmedhealth/PMH0001467/> PubMed Health, accessed Apr. 23, 2012".*
Japanese Patent Office, International Search Report in International Patent Application PCT/JP2010/070988 (Dec. 28, 2010) English Translation.

* cited by examiner

*Primary Examiner* — Joseph K. McKane
*Assistant Examiner* — Samantha Shterengarts
(74) *Attorney, Agent, or Firm* — Leydig, Voit & Mayer, Ltd.

(57) ABSTRACT

Provided is an agent for the treatment or prophylaxis of inflammatory diseases, allergic diseases, autoimmune diseases, transplant rejection or the like.
A compound represented by the following formula [I] or a pharmaceutically acceptable salt thereof, or a solvate thereof:

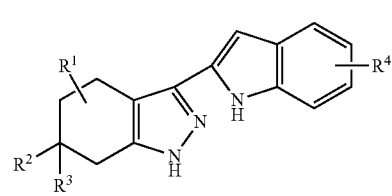

[I]

wherein each symbol is as described in the specification.

49 Claims, No Drawings

INDOLE COMPOUNDS AND PHARMACEUTICAL USE THEREOF

TECHNICAL FIELD OF THE INVENTION

The present invention relates to an indole compound and a pharmaceutical use thereof. More particularly, the present invention relates to a compound for the prophylaxis or treatment of inflammatory diseases, allergic diseases, autoimmune diseases, transplant rejection and the like, by suppression of functional of Th2 cells and/or mast cells by inhibition of inducible T cell kinase (ITK), and use thereof.

BACKGROUND OF THE INVENTION

ITK is a non-receptor type tyrosine kinase belonging to the Tec family and essential for the activation of T cells, and is mainly expressed in T cells, mast cells and natural killer cells. ITK is activated in T cells upon stimulation of T cell receptor (TCR), and is activated in mast cells upon activation of high-affinity immunoglobulin (Ig) E receptor. Subsequent to the receptor stimulation in T cells, Lck, which is one member of the Src tyrosine kinase family, phosphorylates Y511 in the ITK kinase domain activation loop. The activated ITK is, together with Zap-70, necessary for the phosphorylation and activation of PLC-γ. PLC-γ catalyzes formation of inositol 1,4,5-trisphosphoric acid and diacylglycerol, causing calcium mobilization and PKC activation, respectively. These events activate many down stream pathways, and finally cause cytokine production in T cells and degranulation in mast cells.

Studies using ITK knockout mouse have confirmed that ITK is involved in the differentiation of Th2 cells.

Th2 cell is one kind of CD4 positive helper T cells (Th cells), which differentiates from naive T cells by antigen stimulation, and produces cytokine. Cytokines such as interleukin (IL)-4, IL-5, IL-13 and the like produced by Th2 cells are called Th2 cytokine and are known to be involved in the mechanism of allergic disease and the like, since it promotes antibody production by plasma cells differentiated from B cells and activates cells such as eosinophils (one kind of granulocytes) and the like. Like Th2 cell, Th1 cell that differentiates from naive T cells produces so-called Th1 cytokines such as interferon (IFN)-γ and the like, and Th1 cell and Th2 cell maintain an equilibrium relation called Th1/Th2 balance by suppressing functions of each other. An imbalance toward either cytokine is considered to cause diseases specific to each of them. ITK knockout mouse has been reported to selectively inhibit Th2 cell differentiation and Th2 cytokine production.

Moreover, it has been reported that ITK inhibition inhibits activation of mast cells.

Mast cell contains various chemical mediators such as histamine. When an antigen is bound to IgE bound to the cell surface, the established crosslinking triggers cell activation, which consequently causes release of its content (chemical mediators such as histamine and the like) (degranulation). Of the chemical mediators released from the mast cells, histamine and the like have a bronchial smooth muscle constriction action, a blood vessel permeability enhancing effect, a mucous secretory action and the like and cause asthma and allergic diseases.

Therefore, an ITK inhibitor that suppresses growth of Th2 cell and production of Th2 cytokine, and/or suppresses degranulation and production of histamine and the like by suppression of activation of mast cells is expected to show effect as an agent for the treatment or prophylaxis of the diseases involving growth of Th2 cell, production of Th2 cytokine, degranulation, production of histamine and the like, for example, inflammatory diseases, allergic diseases and the like.

Recently, ITK is suggested to be also involved in the activation of Th17 cell, which is one kind of Th cells, and an ITK inhibitor is expected to show effect as an agent for the treatment or prophylaxis of the diseases involving Th17 cell, such as autoimmune diseases (e.g., rheumatism and the like).

In addition, ITK is suggested to be involved in a mixed-lymphocyte reaction. Thus, an ITK inhibitor is expected to show effect as an inhibitor of rejection in transplantation.

Furthermore, ITK is suggested to be involved in HIV infection. Thus, an ITK inhibitor is expected to show effect as a prophylactic or therapeutic agent for HIV infection.

SUMMARY OF THE INVENTION

Problems to be Solved by the Invention

The present invention aims to provide an agent for the treatment or prophylaxis of inflammatory diseases, an agent for the treatment or prophylaxis of allergic diseases, an agent for the treatment or prophylaxis of autoimmune diseases, an inhibitor of rejection in transplantation and the like, which are based on an ITK inhibitory action.

Means of Solving the Problems

The present inventors have conducted intensive studies in an attempt to develop an agent for the treatment or prophylaxis of inflammatory diseases, an agent for the treatment or prophylaxis of allergic diseases, an agent for the treatment or prophylaxis of autoimmune diseases, an inhibitor of rejection in transplantation and the like, which are based on an ITK inhibitory action, and found an indole compound having an ITK inhibitory action, which resulted in the completion of the present invention.

Accordingly, the present invention provides the following.

[1] A compound represented by the following formula [I] or a pharmaceutically acceptable salt thereof:

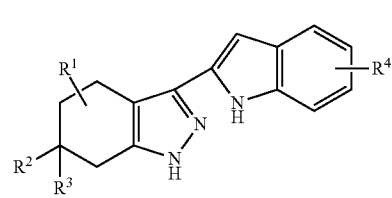

wherein,

R$^1$ is (1) a hydrogen atom, (2) a hydroxy group, or (3) a C$_{1-6}$ alkoxy group optionally substituted by C$_{6-10}$ aryl group(s);

R$^2$ and R$^3$ are the same or different and each is (1) a hydrogen atom, or (2) a C$_{1-6}$ alkyl group optionally substituted by 1 to 3 substituents selected from (a) a hydroxy group, and (b) a C$_{1-6}$ alkoxy group; and $R^4$ is a group represented by

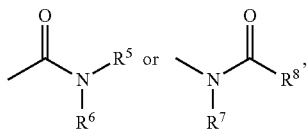

which is bonded to the 5-position or the 6-position of the indole ring,
wherein
$R^5$ is
(1) a hydrogen atom, or
(2) a $C_{1-6}$ alkyl group, and
$R^6$ is
(1) a hydrogen atom,
(2) a $C_{1-6}$ alkyl group optionally substituted by 1 to 3 substituents selected from
  (a) a hydroxy group,
  (b) a $C_{1-6}$ alkoxy group,
  (c) a carboxy group,
  (d) a $C_{1-6}$ alkoxy-carbonyl group,
  (e) a $C_{6-10}$ aryl group,
  (f) a $C_{6-10}$ aryloxy group,
  (g) an amino group optionally mono- or di-substituted by $C_{1-6}$ alkyl group(s),
  (h) a 5- or 6-membered unsaturated heterocyclic group optionally substituted by $C_{1-6}$ alkyl group(s), and
  (i) a 5- or 6-membered saturated heterocyclic group,
(3) a $C_{1-6}$ alkoxy group,
(4) a $C_{6-10}$ aryl group, or
(5) a 5- or 6-membered unsaturated heterocyclic group optionally substituted by 1 to 3 substituents selected from
  (a) a hydroxy group, and
  (b) a $C_{1-6}$ alkoxy group, or
$R^5$ and $R^6$ form, together with the nitrogen atom they are bonded to, a 5- or 6-membered cyclic amine (said cyclic amine is optionally condensed with 5- or 6-membered unsaturated heterocycle) optionally substituted by 1 to 3 substituents selected from
  (a) a hydroxy group,
  (b) a $C_{1-6}$ alkyl group,
  (c) a $C_{1-6}$ alkoxy group, and
  (d) a $C_{1-6}$ alkoxy-carbonyl group;
$R^7$ is
(1) a hydrogen atom, or
(2) a $C_{1-6}$ alkyl group optionally substituted by 1 to 3 substituents selected from
  (a) a hydroxy group,
  (b) a $C_{1-6}$ alkoxy group, and
  (c) an amino group optionally mono- or di-substituted by $C_{1-6}$ alkyl group(s), and
$R^8$ is
(1) a $C_{1-6}$ alkyl group optionally substituted by 1 to 3 substituents selected from
  (a) a hydroxy group,
  (b) a $C_{1-6}$ alkoxy group optionally substituted by $C_{6-10}$ aryl group(s),
  (c) a $C_{3-6}$ cycloalkyl group optionally substituted by $C_{1-6}$ alkoxy group(s),
  (d) a $C_{6-10}$ aryl group,
  (e) a 5- or 6-membered unsaturated heterocyclic group optionally substituted by oxo group(s),
  (f) a 5- to 8-membered saturated heterocyclic group optionally substituted by 1 to 3 substituents selected from
    (i) a hydroxy group,
    (ii) a $C_{1-6}$ alkyl group optionally substituted by 1 to 3 substituents selected from a hydroxy group and a $C_{1-6}$ alkoxy group,
    (iii) a $C_{1-6}$ alkoxy group, and
    (iv) an oxo group,
  (g) a $C_{3-6}$ cycloalkyloxy group,
  (h) a $C_{6-10}$ aryloxy group,
  (i) a 5- or 6-membered unsaturated heterocyclyloxy group,
  (j) a 5- or 6-membered saturated heterocyclyloxy group, and
  (k) an amino group optionally mono- or di-substituted by substituents selected from
    (i) a $C_{1-6}$ alkyl group optionally substituted by 1 to 3 substituents selected from a hydroxy group, a carboxy group and a carboxy-$C_{1-6}$ alkoxy group,
    (ii) a $C_{1-6}$ alkyl-carbonyl group optionally substituted by 1 to 3 substituents selected from a hydroxy group and a $C_{1-6}$ alkoxy group,
    (iii) a $C_{1-6}$ alkoxy-carbonyl group optionally substituted by $C_{6-10}$ aryl group(s), and
    (iv) a $C_{3-6}$ cycloalkyl-carbonyl group optionally substituted by $C_{1-6}$ alkoxy group(s),
(2) a $C_{1-6}$ alkoxy group optionally substituted by $C_{6-10}$ aryl group(s),
(3) a $C_{3-6}$ cycloalkyl group optionally substituted by 1 to 3 substituents selected from
  (a) a hydroxy group, and
  (b) a $C_{1-6}$ alkoxy group,
(4) a $C_{6-10}$ aryl group optionally substituted by $C_{1-6}$ alkyl group(s) optionally substituted by 1 to 3 halogen atoms,
(5) an amino group optionally mono- or di-substituted by $C_{1-6}$ alkyl group(s) optionally substituted by $C_{6-10}$ aryl group(s),
(6) a 5- or 6-membered unsaturated heterocyclic group optionally substituted by $C_{1-6}$ alkyl group(s),
(7) a 5- or 6-membered saturated heterocyclic group optionally substituted by 1 to 3 substituents selected from
  (a) a $C_{1-6}$ alkyl group,
  (b) a $C_{1-6}$ alkyl-carbonyl group, and
  (c) an oxo group,
(8) a $C_{3-6}$ cycloalkyloxy group, or
(9) a $C_{6-10}$ aryl-carbonyl group, or
$R^7$ and $R^8$ form, together with the nitrogen atom and carbon atom they are bonded to, a 5- or 6-membered cyclic amine substituted by an oxo group and optionally further substituted by 1 to 3 substituents selected from
  (a) a hydroxy group,
  (b) a $C_{1-6}$ alkyl group optionally substituted by hydroxy group(s),
  (c) a $C_{1-6}$ alkoxy group, and
  (d) a $C_{3-6}$ cycloalkyl group.

[2] A compound represented by the following formula [I-a] or a pharmaceutically acceptable salt thereof:

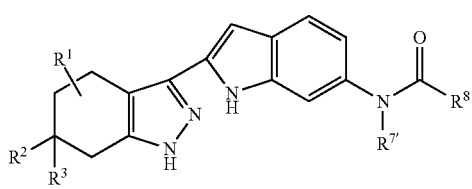

wherein,
R¹ is
(1) a hydrogen atom,
(2) a hydroxy group, or
(3) a $C_{1-6}$ alkoxy group optionally substituted by $C_{6-10}$ aryl group(s);
R² and R³ are the same or different and each is
(1) a hydrogen atom, or
(2) a $C_{1-6}$ alkyl group optionally substituted by 1 to 3 substituents selected from
    (a) a hydroxy group, and
    (b) a $C_{1-6}$ alkoxy group;
R⁷' is a $C_{1-6}$ alkyl group optionally substituted by 1 to 3 substituents selected from
    (a) a hydroxy group,
    (b) a $C_{1-6}$ alkoxy group, and
    (c) an amino group optionally mono- or di-substituted by $C_{1-6}$ alkyl group(s), and
R⁸ is
(1) a $C_{1-6}$ alkyl group optionally substituted by 1 to 3 substituents selected from
    (a) a hydroxy group,
    (b) a $C_{1-6}$ alkoxy group optionally substituted by $C_{6-10}$ aryl group(s),
    (c) a $C_{3-6}$ cycloalkyl group optionally substituted by $C_{1-6}$ alkoxy group(s),
    (d) a $C_{6-10}$ aryl group,
    (e) a 5- or 6-membered unsaturated heterocyclic group optionally substituted by oxo group(s),
    (f) a 5- to 8-membered saturated heterocyclic group optionally substituted by 1 to 3 substituents selected from
        (i) a hydroxy group,
        (ii) a $C_{1-6}$ alkyl group optionally substituted by 1 to 3 substituents selected from a hydroxy group and a $C_{1-6}$ alkoxy group,
        (iii) a $C_{1-6}$ alkoxy group, and
        (iv) an oxo group,
    (g) a $C_{3-6}$ cycloalkyloxy group,
    (h) a $C_{6-10}$ aryloxy group,
    (i) a 5- or 6-membered unsaturated heterocyclyloxy group,
    (j) a 5- or 6-membered saturated heterocyclyloxy group, and
    (k) an amino group optionally mono- or di-substituted by substituents selected from
        (i) a $C_{1-6}$ alkyl group optionally substituted by 1 to 3 substituents selected from a hydroxy group, a carboxy group and a carboxy-$C_{1-6}$ alkoxy group,
        (ii) a $C_{1-6}$ alkyl-carbonyl group optionally substituted by 1 to 3 substituents selected from a hydroxy group and a $C_{1-6}$ alkoxy group,
        (iii) a $C_{1-6}$ alkoxy-carbonyl group optionally substituted by $C_{6-10}$ aryl group(s), and
        (iv) a $C_{3-6}$ cycloalkyl-carbonyl group optionally substituted by $C_{1-6}$ alkoxy group(s), (2) a $C_{1-6}$ alkoxy group optionally substituted by $C_{6-10}$ aryl group(s),
(3) a $C_{3-6}$ cycloalkyl group optionally substituted by 1 to 3 substituents selected from
    (a) a hydroxy group, and
    (b) a $C_{1-6}$ alkoxy group,
(4) a $C_{6-10}$ aryl group optionally substituted by $C_{1-6}$ alkyl group(s) optionally substituted by 1 to 3 halogen atoms,
(5) an amino group optionally mono- or di-substituted by $C_{1-6}$ alkyl group(s) optionally substituted by $C_{6-10}$ aryl group(s),
(6) a 5- or 6-membered unsaturated heterocyclic group optionally substituted by $C_{1-6}$ alkyl group(s),
(7) a 5- or 6-membered saturated heterocyclic group optionally substituted by 1 to 3 substituents selected from
    (a) a $C_{1-6}$ alkyl group,
    (b) a $C_{1-6}$ alkyl-carbonyl group, and
    (c) an oxo group,
(8) a $C_{3-6}$ cycloalkyloxy group, or
(9) a $C_{6-10}$ aryl-carbonyl group, or
R⁷' and R⁸ form, together with the nitrogen atom and carbon atom they are bonded to, a 5- or 6-membered cyclic amine substituted by an oxo group and optionally further substituted by 1 to 3 substituents selected from
    (a) a hydroxy group,
    (b) a $C_{1-6}$ alkyl group optionally substituted by hydroxy group(s),
    (c) a $C_{1-6}$ alkoxy group, and
    (d) a $C_{3-6}$ cycloalkyl group.

[3] The compound according to the above-mentioned [2], wherein
R¹ is a hydrogen atom; and
R² and R³ are the same or different and each is a $C_{1-6}$ alkyl group,
or a pharmaceutically acceptable salt thereof.

[4] The compound according to the above-mentioned [3], wherein
R⁷' is a $C_{1-6}$ alkyl group; and
R⁸ is a $C_{1-6}$ alkyl group substituted by 1 to 3 substituents selected from
    (a) a hydroxy group,
    (b) a $C_{1-6}$ alkoxy group optionally substituted by $C_{6-10}$ aryl group(s),
    (c) a $C_{3-6}$ cycloalkyl group optionally substituted by $C_{1-6}$ alkoxy group(s),
    (d) a $C_{6-10}$ aryl group,
    (e) a 5- or 6-membered unsaturated heterocyclic group optionally substituted by oxo group(s),
    (f) a 5- to 8-membered saturated heterocyclic group optionally substituted by 1 to 3 substituents selected from
        (i) a hydroxy group,
        (ii) a $C_{1-6}$ alkyl group optionally substituted by 1 to 3 substituents selected from a hydroxy group and a $C_{1-6}$ alkoxy group,
        (iii) a $C_{1-6}$ alkoxy group, and
        (iv) an oxo group,
    (g) a $C_{3-6}$ cycloalkyloxy group,
    (h) a $C_{6-10}$ aryloxy group,
    (i) a 5- or 6-membered unsaturated heterocyclyloxy group,
    (j) a 5- or 6-membered saturated heterocyclyloxy group, and
    (k) an amino group optionally mono- or di-substituted by substituents selected from
        (i) a $C_{1-6}$ alkyl group optionally substituted by 1 to 3 substituents selected from a hydroxy group, a carboxy group and a carboxy-$C_{1-6}$ alkoxy group, (ii) a $C_{1-6}$ alkyl-carbonyl group optionally substituted by 1 to 3 substituents selected from a hydroxy group and a $C_{1-6}$ alkoxy group, (iii) a $C_{1-6}$ alkoxy-carbonyl group optionally substituted by $C_{6-10}$ aryl group(s), and (iv) a $C_{3-6}$ cycloalkyl-carbonyl group optionally substituted by $C_{1-6}$ alkoxy group(s), or a pharmaceutically acceptable salt thereof.

[5] A compound selected from the following formulas

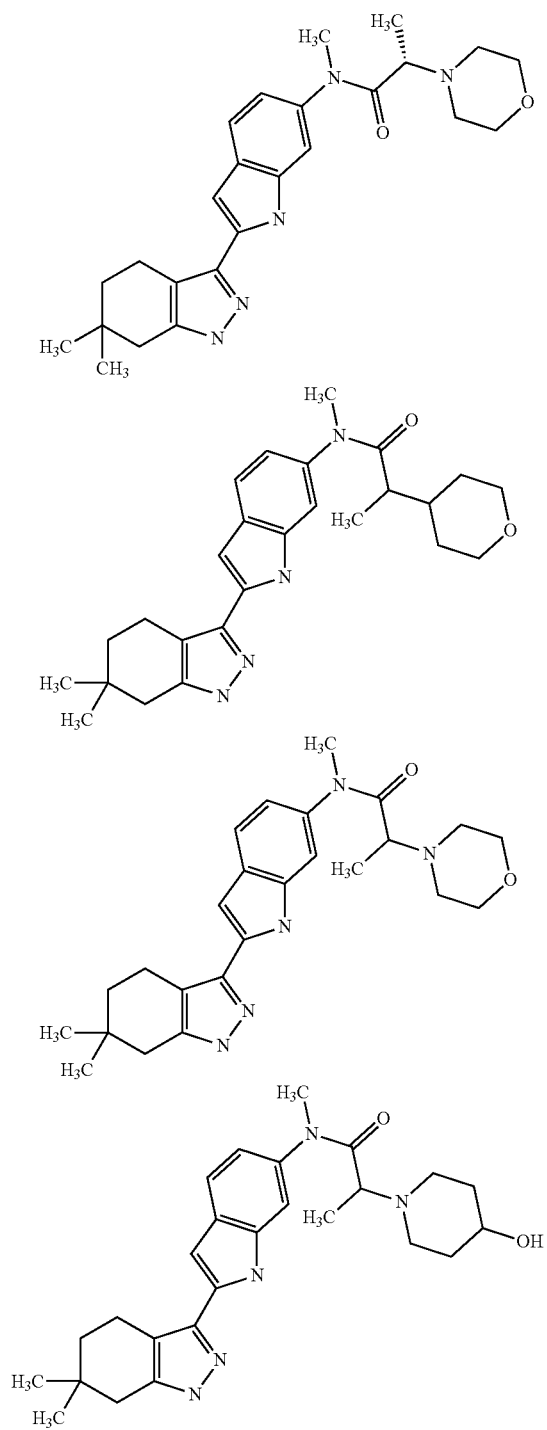

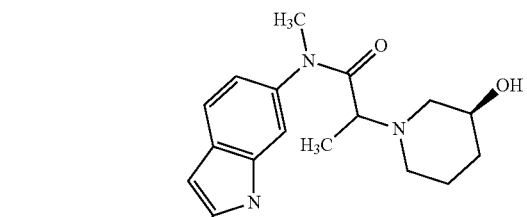

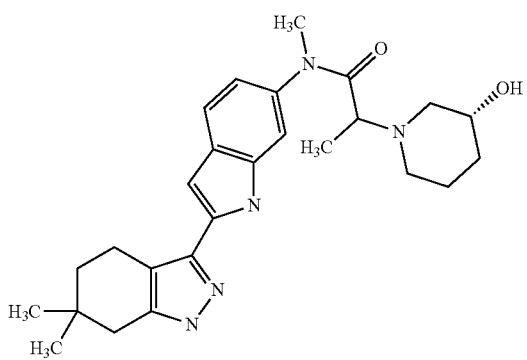

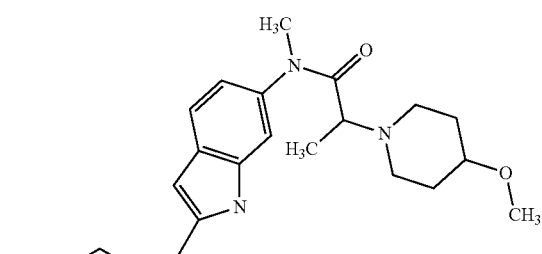

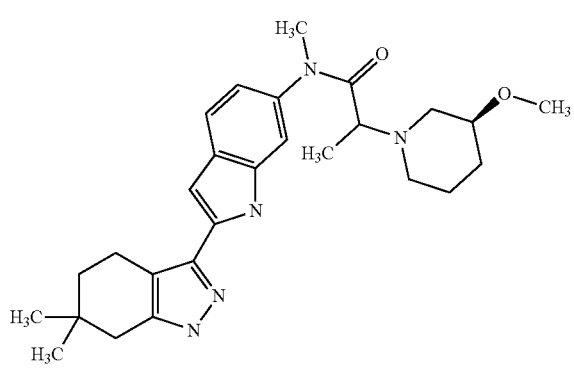

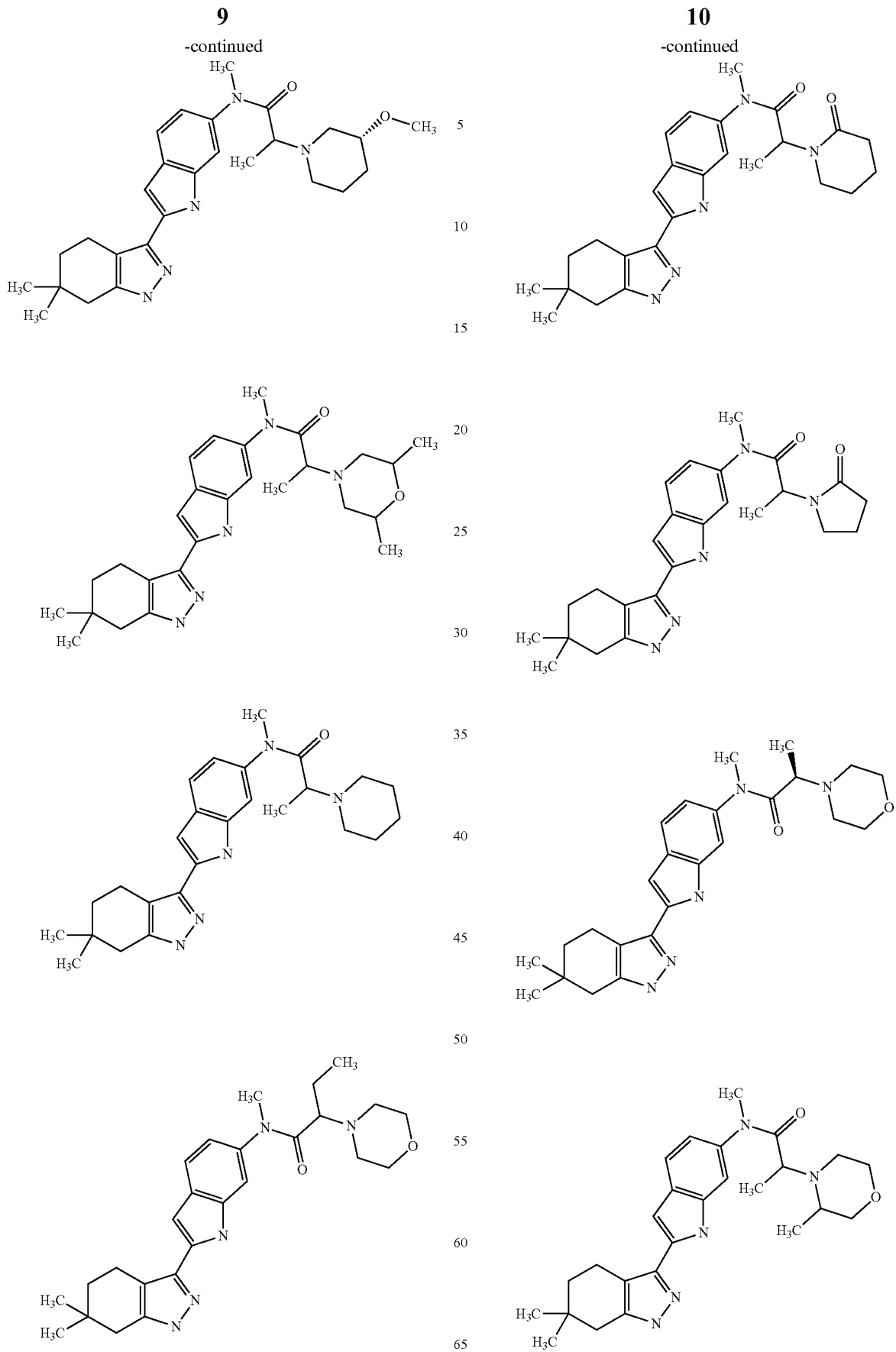

-continued

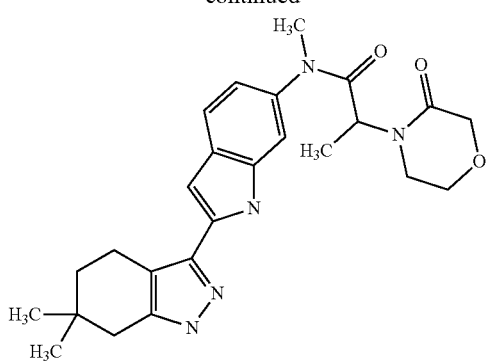

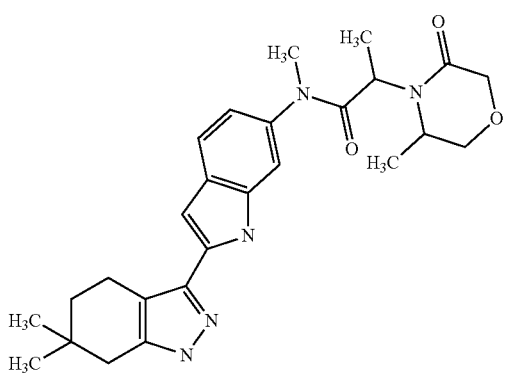

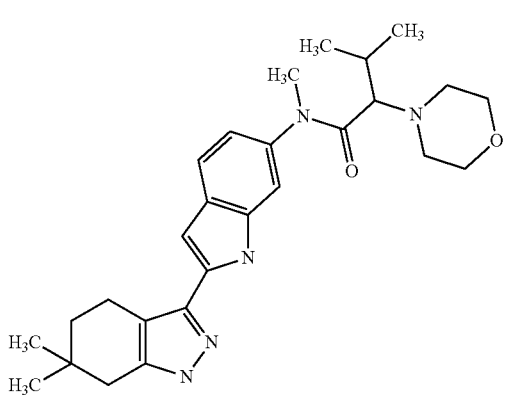

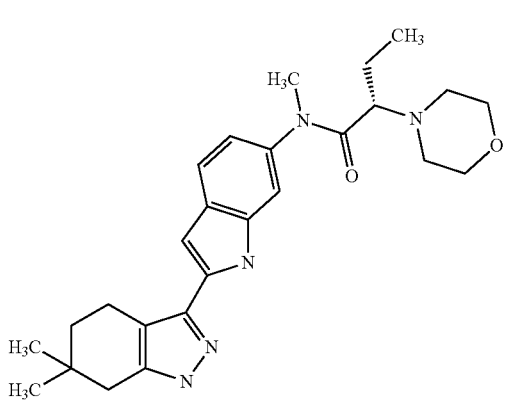

-continued

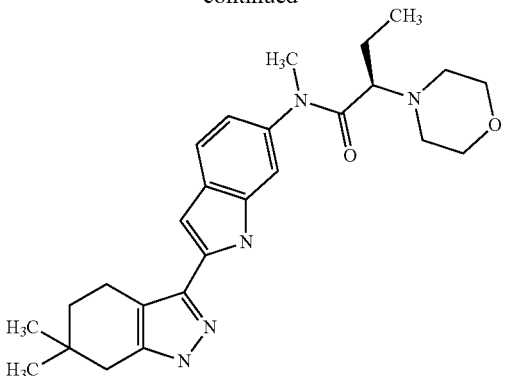

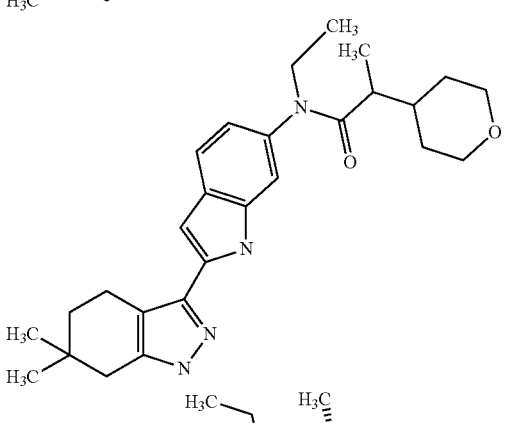

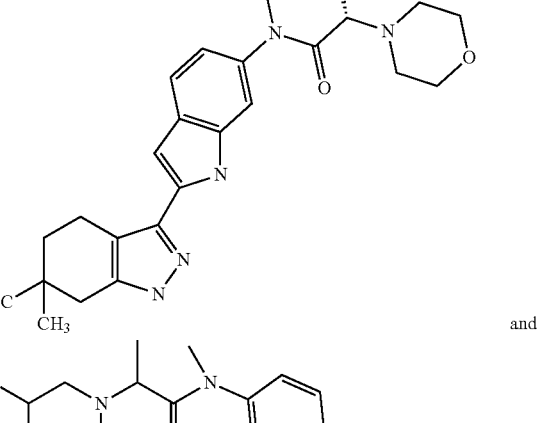

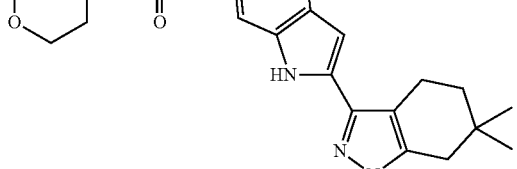

and

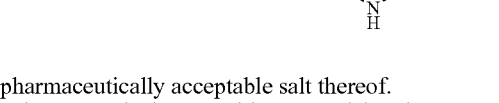

or a pharmaceutically acceptable salt thereof.

[6] A pharmaceutical composition comprising the compound according to any one of the above-mentioned [1] to [5], or a pharmaceutically acceptable salt thereof, and a pharmaceutically acceptable carrier.

[7] An ITK inhibitor comprising the compound according to any one of the above-mentioned [1] to [5], or a pharmaceutically acceptable salt thereof.

[8] An agent for the treatment or prophylaxis of an inflammatory disease, comprising the compound according to any one of the above-mentioned [1] to [5], or a pharmaceutically acceptable salt thereof.

[9] The agent according to the above-mentioned [8], wherein the inflammatory disease is rheumatoid arthritis.

[10] An agent for the treatment or prophylaxis of an allergic disease, comprising the compound according to any one of the above-mentioned [1] to [5], or a pharmaceutically acceptable salt thereof.

[11] An agent for the treatment or prophylaxis of an autoimmune disease, comprising the compound according to any one of the above-mentioned [1] to [5], or a pharmaceutically acceptable salt thereof.

[12] The agent according to the above-mentioned [11], wherein the autoimmune disease is rheumatoid arthritis.

[13] An inhibitor of rejection in transplantation, comprising the compound according to any one of the above-mentioned [1] to [5], or a pharmaceutically acceptable salt thereof.

[14] A method of inhibiting ITK in a mammal, comprising administering a pharmaceutically effective amount of the compound according to any one of the above-mentioned [1] to [5], or a pharmaceutically acceptable salt thereof, to the mammal.

[15] A method for treating or preventing an inflammatory disease in a mammal, comprising administering a pharmaceutically effective amount of the compound according to any one of the above-mentioned [1] to [5], or a pharmaceutically acceptable salt thereof, to the mammal.

[16] The method according to the above-mentioned [15], wherein the inflammatory disease is rheumatoid arthritis.

[17] A method for treating or preventing an allergic disease in a mammal, comprising administering a pharmaceutically effective amount of the compound according to any one of the above-mentioned [1] to [5], or a pharmaceutically acceptable salt thereof, to the mammal.

[18] A method for treating or preventing an autoimmune disease to a mammal, comprising administering a pharmaceutically effective amount of the compound according to any one of the above-mentioned [1] to [5], or a pharmaceutically acceptable salt thereof, to the mammal.

[19] The method according to the above-mentioned [18], wherein the autoimmune diseases is rheumatoid arthritis.

[20] A method of suppressing rejection in transplantation in a mammal, comprising administering a pharmaceutically effective amount of the compound according to any one of the above-mentioned [1] to [5], or a pharmaceutically acceptable salt thereof, to the mammal.

[21] Use of the compound according to any one of the above-mentioned
[1] to [5], or a pharmaceutically acceptable salt thereof, for producing an agent for the treatment or prophylaxis of an inflammatory disease.

[22] The use according to the above-mentioned [21], wherein the inflammatory disease is rheumatoid arthritis.

[23] Use of the compound according to any one of the above-mentioned [1] to [5], or a pharmaceutically acceptable salt thereof, for producing an agent for the treatment or prophylaxis of an allergic disease.

[24] Use of the compound according to any one of the above-mentioned [1] to [5], or a pharmaceutically acceptable salt thereof, for producing an agent for the treatment or prophylaxis of an autoimmune disease.

[25] The use according to the above-mentioned [24], wherein the autoimmune diseases is rheumatoid arthritis.

[26] Use of the compound according to any one of the above-mentioned [1] to [5], or a pharmaceutically acceptable salt thereof, for producing an inhibitor of rejection in transplantation.

[27] A commercial kit comprising (a) a pharmaceutical composition comprising the compound according to any one of the above-mentioned [1] to [5], or a pharmaceutically acceptable salt thereof as an active ingredient and (b) a written description associated therewith, which states that the pharmaceutical composition can or should be used for treating or preventing an inflammatory disease, an allergic disease or an autoimmune disease.

[28] A commercial package comprising (a) a pharmaceutical composition comprising the compound according to any one of the above-mentioned [1] to [5], or a pharmaceutically acceptable salt thereof as an active ingredient and (b) a written description associated therewith, which states that the pharmaceutical composition can or should be used for treating or preventing an inflammatory disease, an allergic disease or an autoimmune disease.

[1'] A compound represented by the following formula [I'] or a pharmaceutically acceptable salt thereof, or a solvate thereof:

[I']

wherein,
$R^{1'}$ is
(1) a hydrogen atom,
(2) a hydroxy group, or
(3) a $C_{1-6}$ alkoxy group optionally substituted by $C_{6-10}$ aryl group(s);
$R^{2'}$ and $R^{3'}$ are the same or different and each is
(1) a hydrogen atom, or
(2) a $C_{1-6}$ alkyl group optionally substituted by 1 to 3 substituents selected from
  (a) a hydroxy group, and
  (b) a $C_{1-6}$ alkoxy group; and
$R^{4'}$ is a group represented by which is bonded to the 5-position or the 6-position of the indole ring,
wherein
$R^{5'}$ is
(1) a hydrogen atom, or
(2) a $C_{1-6}$ alkyl group, and
$R^{6'}$ is
(1) a hydrogen atom,
(2) a $C_{1-6}$ alkyl group optionally substituted by 1 to 3 substituents selected from
  (a) a hydroxy group,
  (b) a $C_{1-6}$ alkoxy group,
  (c) a carboxy group,
  (d) a $C_{1-6}$ alkoxy-carbonyl group,
  (e) a $C_{6-10}$ aryl group,
  (f) a $C_{6-10}$ aryloxy group, (g) an amino group optionally mono- or di-substituted by $C_{1-6}$ alkyl group(s),
(h) a 5- or 6-membered unsaturated heterocyclic group optionally substituted by $C_{1-6}$ alkyl group(s), and
(i) a 5- or 6-membered saturated heterocyclic group,
(3) a $C_{1-6}$ alkoxy group,
(4) a $C_{6-10}$ aryl group, or
(5) a 5- or 6-membered unsaturated heterocyclic group optionally substituted by 1 to 3 substituents selected from
  (a) a hydroxy group, and
  (b) a $C_{1-6}$ alkoxy group, or
$R^{5'}$ and $R^{6'}$ form, together with the nitrogen atom they are bonded to, a 5- or 6-membered cyclic amine (said cyclic amine is optionally condensed with 5- or 6-membered unsaturated heterocycle), which is optionally substituted by 1 to 3 substituents selected from
  (a) a hydroxy group,
  (b) a $C_{1-6}$ alkyl group,
  (c) a $C_{1-6}$ alkoxy group, and
  (d) a $C_{1-6}$ alkoxy-carbonyl group;
$R^{7''}$ is
(1) a hydrogen atom, or
(2) a $C_{1-6}$ alkyl group optionally substituted by 1 to 3 substituents selected from
  (a) a hydroxy group,
  (b) a $C_{1-6}$ alkoxy group, and
  (c) an amino group optionally mono- or di-substituted by $C_{1-6}$ alkyl group(s), and
$R^{8'}$ is
(1) a $C_{1-6}$ alkyl group optionally substituted by 1 to 3 substituents selected from
  (a) a hydroxy group,
  (b) a $C_{1-6}$ alkoxy group optionally substituted by $C_{6-10}$ aryl group(s),
  (c) a $C_{3-6}$ cycloalkyl group optionally substituted by $C_{1-6}$ alkoxy group(s),
  (d) a $C_{6-10}$ aryl group,
  (e) a 5- or 6-membered unsaturated heterocyclic group optionally substituted by oxo group(s),
  (f) a 5- to 8-membered saturated heterocyclic group optionally substituted by 1 to 3 substituents selected from
    (i) a hydroxy group,
    (ii) a $C_{1-6}$ alkyl group optionally substituted by 1 to 3 substituents selected from a hydroxy group and a $C_{1-6}$ alkoxy group,
    (iii) a $C_{1-6}$ alkoxy group, and
    (iv) an oxo group,
  (g) a $C_{3-6}$ cycloalkyloxy group,
  (h) a $C_{6-10}$ aryloxy group,
  (i) a 5- or 6-membered unsaturated heterocyclyloxy group,
  (j) a 5- or 6-membered saturated heterocyclyloxy group, and
  (k) an amino group optionally mono- or di-substituted by substituents selected from
    (i) a $C_{1-6}$ alkyl group,
    (ii) a $C_{1-6}$ alkyl-carbonyl group optionally substituted by 1 to 3 substituents selected from a hydroxy group and a $C_{1-6}$ alkoxy group,
    (iii) a $C_{1-6}$ alkoxy-carbonyl group optionally substituted by $C_{6-10}$ aryl group(s), and
    (iv) a $C_{3-6}$ cycloalkyl-carbonyl group optionally substituted by $C_{1-6}$ alkoxy group(s),
(2) a $C_{1-6}$ alkoxy group optionally substituted by $C_{6-10}$ aryl group(s),
(3) a $C_{3-6}$ cycloalkyl group optionally substituted by 1 to 3 substituents selected from
  (a) a hydroxy group, and
  (b) a $C_{1-6}$ alkoxy group,
(4) a $C_{6-10}$ aryl group optionally substituted by $C_{1-6}$ alkyl group(s) optionally substituted by 1 to 3 halogen atoms,
(5) an amino group optionally mono- or di-substituted by $C_{1-6}$ alkyl group(s) optionally substituted by $C_{6-10}$ aryl group(s),
(6) a 5- or 6-membered unsaturated heterocyclic group optionally substituted by $C_{1-6}$ alkyl group(s),
(7) a 5- or 6-membered saturated heterocyclic group optionally substituted by 1 to 3 substituents selected from
  (a) a $C_{1-6}$ alkyl group,
  (b) a $C_{1-6}$ alkyl-carbonyl group, and
  (c) an oxo group,
(8) a $C_{3-6}$ cycloalkyloxy group, or
(9) a $C_{6-10}$ aryl-carbonyl group, or
$R^{7''}$ and $R^{8'}$ form, together with the nitrogen atom and carbon atom they are bonded to, a 5- or 6-membered cyclic amine substituted by an oxo group and optionally further substituted by 1 to 3 substituents selected from
  (a) a hydroxy group,
  (b) a $C_{1-6}$ alkyl group optionally substituted by hydroxy group(s),
  (c) a $C_{1-6}$ alkoxy group, and
  (d) a $C_{3-6}$ cycloalkyl group.

[2'] A compound represented by the following formula [I'-a] or a pharmaceutically acceptable salt thereof, or a solvate thereof:

[I'-a]

wherein,
$R^{1'}$ is
(1) a hydrogen atom,
(2) a hydroxy group, or
(3) a $C_{1-6}$ alkoxy group optionally substituted by $C_{6-10}$ aryl group(s);
$R^{2'}$ and $R^{3'}$ are the same or different and each is
(1) a hydrogen atom, or
(2) a $C_{1-6}$ alkyl group optionally substituted by 1 to 3 substituents selected from
  (a) a hydroxy group, and
  (b) a $C_{1-6}$ alkoxy group;
$R^{7'''}$ is a $C_{1-6}$ alkyl group optionally substituted by 1 to 3 substituents selected from
  (a) a hydroxy group,
  (b) a $C_{1-6}$ alkoxy group, and
  (c) an amino group optionally mono- or di-substituted by $C_{1-6}$ alkyl group(s), and $R^{8'}$ is (1) a $C_{1-6}$ alkyl group optionally substituted by 1 to 3 substituents selected from
- (a) a hydroxy group,
- (b) a $C_{1-6}$ alkoxy group optionally substituted by $C_{6-10}$ aryl group(s),
- (c) a $C_{3-6}$ cycloalkyl group optionally substituted by $C_{1-6}$ alkoxy group(s),
- (d) a $C_{6-10}$ aryl group,
- (e) a 5- or 6-membered unsaturated heterocyclic group optionally substituted by oxo group(s),
- (f) a 5- to 8-membered saturated heterocyclic group optionally substituted by 1 to 3 substituents selected from
  - (i) a hydroxy group,
  - (ii) a $C_{1-6}$ alkyl group optionally substituted by 1 to 3 substituents selected from a hydroxy group and a $C_{1-6}$ alkoxy group,
  - (iii) a $C_{1-6}$ alkoxy group, and
  - (iv) an oxo group,
- (g) a $C_{3-6}$ cycloalkyloxy group,
- (h) a $C_{6-10}$ aryloxy group,
- (i) a 5- or 6-membered unsaturated heterocyclyloxy group,
- (j) a 5- or 6-membered saturated heterocyclyloxy group, and
- (k) an amino group optionally mono- or di-substituted by substituents selected from
  - (i) a $C_{1-6}$ alkyl group,
  - (ii) a $C_{1-6}$ alkyl-carbonyl group optionally substituted by 1 to 3 substituents selected from a hydroxy group and a $C_{1-6}$ alkoxy group,
  - (iii) a $C_{1-6}$ alkoxy-carbonyl group optionally substituted by $C_{6-10}$ aryl group(s), and
  - (iv) a $C_{3-6}$ cycloalkyl-carbonyl group optionally substituted by $C_{1-6}$ alkoxy group(s), (2) a $C_{1-6}$ alkoxy group optionally substituted by $C_{6-10}$ aryl group(s), (3) a $C_{3-6}$ cycloalkyl group optionally substituted by 1 to 3 substituents selected from
- (a) a hydroxy group, and
- (b) a $C_{1-6}$ alkoxy group, (4) a $C_{6-10}$ aryl group optionally substituted by $C_{1-6}$ alkyl group(s) optionally substituted by 1 to 3 halogen atoms, (5) an amino group optionally mono- or di-substituted by $C_{1-6}$ alkyl group(s) optionally substituted by $C_{6-10}$ aryl group(s), (6) a 5- or 6-membered unsaturated heterocyclic group optionally substituted by $C_{1-6}$ alkyl group(s), (7) a 5- or 6-membered saturated heterocyclic group optionally substituted by 1 to 3 substituents selected from
- (a) a $C_{1-6}$ alkyl group,
- (b) a $C_{1-6}$ alkyl-carbonyl group, and
- (c) an oxo group, (8) a $C_{3-6}$ cycloalkyloxy group, or (9) a $C_{6-10}$ aryl-carbonyl group, or $R^{7'''}$ and $R^{8'}$ form, together with the nitrogen atom and carbon atom they are bonded to, a 5- or 6-membered cyclic amine substituted by an oxo group and optionally further substituted by 1 to 3 substituents selected from
- (a) a hydroxy group,
- (b) a $C_{1-6}$ alkyl group optionally substituted by hydroxy group(s),
- (c) a $C_{1-6}$ alkoxy group, and
- (d) a $C_{3-6}$ cycloalkyl group.

[3'] A pharmaceutical composition comprising the compound according to the above-mentioned [1'] or [2'], or a pharmaceutically acceptable salt thereof, or a solvate thereof, and a pharmaceutically acceptable carrier.

[4'] An agent for the treatment or prophylaxis of an inflammatory disease, comprising the compound according to the above-mentioned [1'] or [2'], or a pharmaceutically acceptable salt thereof, or a solvate thereof.

[5'] An ITK inhibitor comprising the compound according to the above-mentioned [1'] or [2'], or a pharmaceutically acceptable salt thereof, or a solvate thereof.

[6'] An agent for the treatment or prophylaxis of an allergic disease, comprising the compound according to the above-mentioned [1'] or [2'], or a pharmaceutically acceptable salt thereof, or a solvate thereof.

[7'] An agent for the treatment or prophylaxis of an autoimmune disease, comprising the compound according to the above-mentioned [1'] or [2'], or a pharmaceutically acceptable salt thereof, or a solvate thereof.

[8'] An inhibitor of rejection in transplantation, comprising the compound according to the above-mentioned [1'] or [2'], or a pharmaceutically acceptable salt thereof, or a solvate thereof.

[9'] A method for treating or preventing an inflammatory disease in a mammal, comprising administering a pharmaceutically effective amount of the compound according to the above-mentioned [1'] or [2'], or a pharmaceutically acceptable salt thereof, or a solvate thereof to the mammal.

[10'] A method for treating or preventing an allergic disease in a mammal, comprising administering a pharmaceutically effective amount of the compound according to the above-mentioned [1'] or [2'], or a pharmaceutically acceptable salt thereof, or a solvate thereof to the mammal.

[11'] A method for treating or preventing an autoimmune disease in a mammal, comprising administering a pharmaceutically effective amount of the compound according to the above-mentioned [1'] or [2'], or a pharmaceutically acceptable salt thereof, or a solvate thereof to the mammal.

[12'] A method for suppressing rejection in transplantation in a mammal, comprising administering a pharmaceutically effective amount of the compound according to the above-mentioned [1'] or [2'], or a pharmaceutically acceptable salt thereof, or a solvate thereof, to the mammal.

[13'] Use of the compound according to the above-mentioned [1'] or [2'], or a pharmaceutically acceptable salt thereof, or a solvate thereof for producing an agent for the treatment or prophylaxis of an inflammatory disease.

Effect of the Invention

The indole compound of the present invention effectively inhibits ITK activity, suppresses growth and activation of Th2 cell, and/or suppresses activation of mast cells. Therefore, it is effective as an agent for the treatment or prophylaxis of diseases involving growth or activation of Th2 cell or activation of mast cells, for example, allergic diseases, inflammatory diseases and autoimmune diseases, or as an inhibitor of rejection in transplantation.

EMBODIMENT OF INVENTION

The present invention is explained in detail in the following.

The definition of the term used in the present specification is as follows.

The "optionally substituted" includes both substitution and without substitution (no substitution) at substitutable position of an object group. Here, the "no substitution" means that all substitutable positions of an object group are each a hydrogen atom.

Examples of the "halogen atom" include a fluorine atom, a chlorine atom, a bromine atom and an iodine atom.

The "$C_{1-6}$ alkyl group" means a straight chain or branched chain saturated hydrocarbon group having 1 to 6 carbon atoms, and examples thereof include a methyl group, an ethyl group, a propyl group, an isopropyl group, a butyl group, an isobutyl group, a sec-butyl group, a tert-butyl group, a pentyl group, an isopentyl group, a neopentyl group, a 1,2-dimethylpropyl group, a 1-ethylpropyl group, a hexyl group, an isohexyl group, a 1,2,2-trimethylpropyl group, a 1,1-dimethylbutyl group, a 2,2-dimethylbutyl group, a 3,3-dimethylbutyl group, a 2-ethylbutyl group and the like.

The "$C_{1-6}$ alkoxy group" means a hydroxyl group substituted by the above-mentioned "$C_{1-6}$ alkyl group", and examples thereof include a methoxy group, an ethoxy group, a propoxy group, an isopropoxy group, a butoxy group, an isobutoxy group, a sec-butoxy group, a tert-butoxy group, a pentyloxy group, an isopentyloxy group, a neopentyloxy group, a 1,2-dimethylpropyloxy group, a 1-ethylpropyloxy group, a hexyloxy group, an isohexyloxy group, a 1,2,2-trimethylpropyloxy group, a 1,1-dimethylbutyloxy group, a 2,2-dimethylbutyloxy group, a 3,3-dimethylbutyloxy group, a 2-ethylbutyloxy group and the like.

The "$C_{3-6}$ cycloalkyl group" means a monocyclic saturated hydrocarbon group having 3 to 6 carbon atoms, and examples thereof include a cyclopropyl group, a cyclobutyl group, a cyclopentyl group, a cyclohexyl group and the like The "$C_{3-6}$ cycloalkyloxy group" means a hydroxy group substituted by the above-mentioned "$C_{3-6}$ cycloalkyl group", and examples thereof include a cyclopropyloxy group, a cyclobutyloxy group, a cyclopentyloxy group, a cyclohexyloxy group and the like.

The "$C_{6-10}$ aryl group" means an aromatic hydrocarbon group having 6 to 10 carbon atoms, and examples thereof include a phenyl group, a 1-naphthyl group, a 2-naphthyl group and the like. Preferred is a phenyl group.

The "$C_{6-10}$ aryloxy group" means a hydroxy group substituted by the above-mentioned "$C_{6-10}$ aryl group", and examples thereof include a phenoxy group, a 1-naphthyloxy group, a 2-naphthyloxy group and the like. Preferred is a phenoxy group.

The "5- or 6-membered unsaturated heterocyclic group" means a monocyclic unsaturated or partially unsaturated heterocyclic group having 5 or 6 ring-constituting atoms, which contains, besides carbon atoms, 1 to 4 hetero atoms selected from a nitrogen atom, an oxygen atom and a sulfur atom. When the group contains a sulfur atom as a hetero atom, the sulfur atom is optionally mono- or di-oxidized. Examples of such group include a furyl group, a thienyl group, a pyrrolyl group, an oxazolyl group, an oxazolinyl group, an isoxazolyl group, an isoxazolinyl group, a thiazolyl group, a thiazolinyl group, an isothiazolyl group, an isothiazolinyl group, an imidazolyl group, an imidazolinyl group, a pyrazolyl group, a pyrazolinyl group, an oxadiazolyl group (1,2,5-oxadiazolyl group, 1,3,4-oxadiazolyl group, 1,2,4-oxadiazolyl group), a thiadiazolyl group (1,2,5-thiadiazolyl group, 1,3,4-thiadiazolyl group, 1,2,4-thiadiazolyl group), a triazolyl group (1,2,3-triazolyl group, 1,2,4-triazolyl group), a tetrazolyl group, a pyridyl group, a pyrimidinyl group, a pyridazinyl group, a pyrazinyl group, a triazinyl group, a dihydropyridyl group and the like.

The "5- or 6-membered unsaturated heterocyclyloxy group" means a hydroxy group substituted by the above-mentioned "5- or 6-membered unsaturated heterocyclic group", and examples thereof include a furyloxy group, a thienyloxy group, a pyrrolyloxy group, an oxazolyloxy group, an oxazolinyloxy group, an isoxazolyloxy group, an isoxazolinyloxy group, a thiazolyloxy group, a thiazolinyloxy group, an isothiazolyloxy group, an isothiazolinyloxy group, an imidazolyloxy group, an imidazolinyloxy group, a pyrazolyloxy group, a pyrazolinyloxy group, an oxadiazolyloxy group (1,2,5-oxadiazolyloxy group, 1,3,4-oxadiazolyloxy group, 1,2,4-oxadiazolyloxy group), a thiadiazolyloxy group (1,2,5-thiadiazolyloxy group, 1,3,4-thiadiazolyloxy group, 1,2,4-thiadiazolyloxy group), a triazolyloxy group (1,2,3-triazolyloxy group, 1,2,4-triazolyloxy group), a tetrazolyloxy group, a pyridyloxy group, a pyrimidinyloxy group, a pyridazinyloxy group, a pyrazinyloxy group, a triazinyloxy group, a dihydropyridyloxy group and the like.

The "5- to 8-membered saturated heterocyclic group" means a monocyclic saturated heterocyclic group having 5 to 8 ring-constituting atoms, which contains, besides carbon atoms, 1 to 4 hetero atoms selected from a nitrogen atom, an oxygen atom and a sulfur atom. When the group contains a sulfur atom as a hetero atom, the sulfur atom is optionally mono- or di-oxidized. Examples of such group include a pyrrolidinyl group, a tetrahydrofuryl group, a tetrahydropyranyl group, a tetrahydrothienyl group, a tetrahydrothiopyranyl group, an oxazolidinyl group, an isoxazolidinyl group, a thiazolidinyl group, an isothiazolidinyl group, an imidazolidinyl group, a pyrazolidinyl group, a piperidyl group (including piperidino group), a morpholinyl group (including morpholino group), a thiomorpholinyl group (including thiomorpholino group), a piperazinyl group, an azepanyl group, an azocanyl group, a 1,1-dioxideisothiazolidinyl group, a 1,1-dioxidetetrahydrothienyl group, a 1,1-dioxidetetrahydrothiopyranyl group, a 1,1-dioxidethiomorpholinyl group (including 1,1-dioxidethiomorpholino group) and the like.

The "5- or 6-membered saturated heterocyclic group" means, among the above-mentioned "5- to 8-membered saturated heterocyclic groups", a group having 5 or 6 ring-constituting atoms, and examples thereof include a pyrrolidinyl group, a tetrahydrofuryl group, a tetrahydropyranyl group, a tetrahydrothienyl group, a tetrahydrothiopyranyl group, an oxazolidinyl group, an isoxazolidinyl group, a thiazolidinyl group, an isothiazolidinyl group, an imidazolidinyl group, a pyrazolidinyl group, a piperidyl group (including piperidino group), a morpholinyl group (including morpholino group), a thiomorpholinyl group (including thiomorpholino group), a piperazinyl group, a 1,1-dioxideisothiazolidinyl group, a 1,1-dioxidetetrahydrothienyl group, a 1,1-dioxidetetrahydrothiopyranyl group, a 1,1-dioxidethiomorpholinyl group (including 1,1-dioxidethiomorpholino group) and the like.

The "5- or 6-membered saturated heterocyclyloxy group" means a hydroxy group substituted by the above-mentioned "5- or 6-membered saturated heterocyclic group", and examples thereof include a pyrrolidinyloxy group, a tetrahydrofuryloxy group, a tetrahydropyranyloxy group, a tetrahydrothienyloxy group, a tetrahydrothiopyranyloxy group, an oxazolidinyloxy group, an isoxazolidinyloxy group, a thiazolidinyloxy group, an isothiazolidinyloxy group, an imidazolidinyloxy group, a pyrazolidinyloxy group, a piperidyloxy group (including piperidinooxy group), a morpholinyloxy group (including morpholinooxy group), a thiomorpholinyloxy group (including thiomorpholinooxy group), a piperazinyloxy group, a 1,1-dioxideisothiazolidinyloxy group, a 1,1-dioxidetetrahydrothienyloxy group, a 1,1-dioxidetetrahydrothiopyranyloxy group, a 1,1-dioxidethiomorpholinyloxy group (including 1,1-dioxidethiomorpholinooxy group) and the like.

The "$C_{1-6}$ alkyl-carbonyl group" means a carbonyl group to which the above-mentioned "$C_{1-6}$ alkyl group" is bonded, and examples thereof include an acetyl group, a propanoyl group, a butanoyl group, a 2-methylpropanoyl group, a 2,2-dimethylpropanoyl group, a 3-methylbutanoyl group and the like.

The "$C_{1-6}$ alkoxy-carbonyl group" means a carbonyl group to which the above-mentioned "$C_{1-6}$ alkoxy group" is bonded, and examples thereof include a methoxycarbonyl group, an ethoxycarbonyl group, a propoxycarbonyl group, an isopropoxycarbonyl group, a butoxycarbonyl group, an isobutoxycarbonyl group, a sec-butoxycarbonyl group, a tert-butoxycarbonyl group, a pentyloxycarbonyl group, an isopentyloxycarbonyl group, a neopentyloxycarbonyl group, a hexyloxycarbonyl group and the like.

The "$C_{3-6}$ cycloalkyl-carbonyl group" means a carbonyl group to which the above-mentioned "$C_{3-6}$ cycloalkyl group" is bonded, and examples thereof include a cyclopropylcarbonyl group, a cyclobutylcarbonyl group, a cyclopentylcarbonyl group, a cyclohexylcarbonyl group and the like.

The "$C_{6-10}$ aryl-carbonyl group" means a carbonyl group to which the above-mentioned "$C_{6-10}$ aryl group" is bonded, and examples thereof include a benzoyl group and the like.

The "carboxy-$C_{1-6}$ alkoxy group" means the above-mentioned "$C_{1-6}$ alkoxy group" to which a carboxy group is bonded, and examples thereof include a carboxymethoxy group, a 2-carboxyethoxy group, a 3-carboxypropoxy group, a 2-carboxy-1-methylethoxy group, a 4-carboxybutoxy group and the like. Preferred is a carboxymethoxy group.

The "5- or 6-membered cyclic amine" means a saturated heterocycle having 5 or 6 ring-constituting atoms, which contains at least one nitrogen atom besides carbon atoms, further optionally contains 1 to 3 hetero atoms selected from a nitrogen atom, an oxygen atom and a sulfur atom, which is bonded via the nitrogen atom constituting the ring. When the ring contains a sulfur atom as a hetero atom, the sulfur atom is optionally mono- or di-oxidized. Examples of such ring include pyrrolidine, oxazolidine, isoxazolidine, thiazolidine, isothiazolidine, imidazolidine, pyrazolidine, piperidine, morpholine, thiomorpholine, piperazine, 1,1-dioxideisothiazolidine, 1,1-dioxidethiomorpholine and the like.

The "5- or 6-membered unsaturated heterocycle" means a monocyclic unsaturated or partially unsaturated heterocyclic group having 5 or 6 ring-constituting atoms, which contains, besides carbon atoms, 1 to 4 hetero atoms selected from a nitrogen atom, an oxygen atom and a sulfur atom. When the ring contains a sulfur atom as a hetero atom, the sulfur atom is optionally mono- or di-oxidized. Examples of such ring include furan, thiophene, pyrrole, oxazole, isoxazole, thiazole, isothiazole, imidazole, pyrazole, oxadiazole, thiadiazole, triazole, tetrazole, pyridine, pyrimidine, pyridazine, pyrazine, triazine and the like.

Each group of a compound represented by the formula [I] (hereinafter sometimes to be abbreviated as compound [I]) is explained in the following.

$R^1$ is
(1) a hydrogen atom,
(2) a hydroxy group, or
(3) a $C_{1-6}$ alkoxy group (preferably, a methoxy group, an isopropoxy group) optionally substituted by $C_{6-10}$ aryl group(s) (preferably, a phenyl group), and preferably a hydrogen atom.

$R^2$ and $R^3$ are the same or different and each is
(1) a hydrogen atom, or
(2) a $C_{1-6}$ alkyl group (preferably, a methyl group) optionally substituted by 1 to 3 substituents selected from
  (a) a hydroxy group, and
  (b) a $C_{1-6}$ alkoxy group (preferably, a methoxy group), and are preferably the same or different and each is a $C_{1-6}$ alkyl group (preferably, a methyl group).

$R^4$ is a group represented by

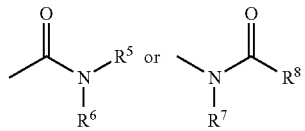

which is bonded to the 5-position or the 6-position of the indole ring.

$R^4$ is preferably

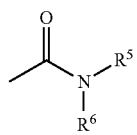

which is bonded to the 5-position or the 6-position of the indole ring, or

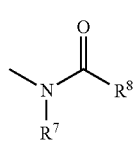

which is bonded to the 6-position of the indole ring, and more preferably

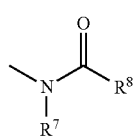

which is bonded to the 6-position of the indole ring.

$R^5$ is
(1) a hydrogen atom, or
(2) a $C_{1-6}$ alkyl group (preferably, a methyl group, an ethyl group).

$R^6$ is
(1) a hydrogen atom,
(2) a $C_{1-6}$ alkyl group (preferably, a methyl group, an ethyl group, an isopropyl group, an isobutyl group, a tert-butyl group, a neopentyl group, a 1,2-dimethylpropyl group, a 1,2,2-trimethylpropyl group) optionally substituted by 1 to 3 substituents selected from
  (a) a hydroxy group,
  (b) a $C_{1-6}$ alkoxy group (preferably, a methoxy group, a propoxy group, an isopropoxy group),
  (c) a carboxy group,
  (d) a $C_{1-6}$ alkoxy-carbonyl group (preferably, a methoxycarbonyl group, a tert-butoxycarbonyl group),
  (e) a $C_{6-10}$ aryl group (preferably, a phenyl group),
  (f) a $C_{6-10}$ aryloxy group (preferably, a phenoxy group),
  (g) an amino group optionally mono- or di-substituted $C_{1-6}$ alkyl groups (preferably, a methyl group),
  (h) a 5- or 6-membered unsaturated heterocyclic group (preferably, a furyl group, a pyrrolyl group, a thiazolyl group, a tetrazolyl group, an imidazolyl group) optionally substituted by $C_{1-6}$ alkyl group(s) (preferably, a methyl group), and (i) a 5- or 6-membered saturated heterocyclic group (preferably, a morpholinyl group),
(3) a $C_{1-6}$ alkoxy group (preferably, a methoxy group),
(4) a $C_{6-10}$ aryl group (preferably, a phenyl group), or
(5) a 5- or 6-membered unsaturated heterocyclic group (preferably, a 1,3,4-thiadiazolyl group) optionally substituted by 1 to 3 substituents selected from
(a) a hydroxy group, and
(b) a $C_{1-6}$ alkoxy group (preferably, a methoxy group).

Alternatively, $R^5$ and $R^6$ may form, together with the nitrogen atom they are bonded to, a 5- or 6-membered cyclic amine (preferably, pyrrolidine, piperidine, piperazine, morpholine) (said cyclic amine is optionally condensed with a 5- or 6-membered unsaturated heterocycle (preferably, imidazole)), which is optionally substituted by 1 to 3 substituents selected from
(a) a hydroxy group,
(b) a $C_{1-6}$ alkyl group (preferably, a methyl group, an ethyl group),
(c) a $C_{1-6}$ alkoxy group (preferably, a methoxy group), and
(d) a $C_{1-6}$ alkoxy-carbonyl group (preferably, a tert-butoxycarbonyl group).

$R^7$ is
(1) a hydrogen atom, or
(2) a $C_{1-6}$ alkyl group (preferably, a methyl group, an ethyl group, a propyl group) optionally substituted by 1 to 3 substituents selected from
(a) a hydroxy group,
(b) a $C_{1-6}$ alkoxy group (preferably, a methoxy group), and
(c) an amino group optionally mono- or di-substituted by $C_{1-6}$ alkyl group(s) (preferably, a methyl group), preferably a $C_{1-6}$ alkyl group (preferably, a methyl group, an ethyl group, a propyl group) optionally substituted by 1 to 3% substituents selected from
(a) a hydroxy group,
(b) a $C_{1-6}$ alkoxy group (preferably, a methoxy group), and
(c) an amino group optionally mono- or di-substituted by $C_{1-6}$ alkyl group(s) (preferably, a methyl group), and more preferably a $C_{1-6}$ alkyl group (preferably, a methyl group, an ethyl group, a propyl group).

$R^8$ is
(1) a $C_{1-6}$ alkyl group (preferably, a methyl group, an ethyl group, a propyl group, an isopropyl group, an isobutyl group, a tert-butyl group, a neopentyl group) optionally substituted by 1 to 3 substituents selected from
(a) a hydroxy group,
(b) a $C_{1-6}$ alkoxy group (preferably, a methoxy group, an ethoxy group, a propoxy group, an isopropoxy group) optionally substituted by $C_{6-10}$ aryl group(s) (preferably, a phenyl group),
(c) a $C_{3-6}$ cycloalkyl group (preferably, a cyclopentyl group, a cyclohexyl group) optionally substituted by $C_{1-6}$ alkoxy group(s) (preferably, a methoxy group),
(d) a $C_{6-10}$ aryl group (preferably, a phenyl group),
(e) a 5- or 6-membered unsaturated heterocyclic group (preferably, an imidazolyl group, a dihydropyridyl group, a pyrazolyl group) optionally substituted by oxo group(s),
(f) a 5- to 8-membered saturated heterocyclic group (preferably, a tetrahydrofuryl group, a tetrahydropyranyl group, a pyrrolidinyl group, a piperidyl group, an azepanyl group, an azocanyl group, a morpholinyl group (including a morpholino group), a 1,1-dioxideisothiazolidinyl group, an oxazolidinyl group, an imidazolidinyl group) optionally substituted by 1 to 3 substituents selected from (i) a hydroxy group,
(ii) a $C_{1-6}$ alkyl group (preferably, a methyl group) optionally substituted by 1 to 3 substituents selected from a hydroxy group and a $C_{1-6}$ alkoxy group (preferably, a methoxy group),
(iii) a $C_{1-6}$ alkoxy group (preferably, a methoxy group), and
(iv) an oxo group,
(g) a $C_{3-6}$ cycloalkyloxy group (preferably, a cyclopentyloxy group),
(h) a $C_{6-10}$ aryloxy group (preferably, a phenoxy group),
(i) a 5- or 6-membered unsaturated heterocyclyloxy group (preferably, a pyridyloxy group),
(j) a 5- or 6-membered saturated heterocyclyloxy group (preferably, a tetrahydrofuryloxy group, a tetrahydropyranyloxy group), and
(k) an amino group optionally mono- or di-substituted by substituents selected from
(i) a $C_{1-6}$ alkyl group (preferably, a methyl group) optionally substituted by 1 to 3 substituents selected from a hydroxy group, a carboxy group and a carboxy-$C_{1-6}$ alkoxy group (preferably, a carboxymethoxy group),
(ii) a $C_{1-6}$ alkyl-carbonyl group (preferably, an acetyl group, a propanoyl group, a 2-methylpropanoyl group, a 2,2-dimethylpropanoyl group, a 3-methylbutanoyl group) optionally substituted by 1 to 3 substituents selected from a hydroxy group and a $C_{1-6}$ alkoxy group (preferably, a methoxy group),
(iii) a $C_{1-6}$ alkoxy-carbonyl group (preferably, a methoxycarbonyl group, a tert-butoxycarbonyl group) optionally substituted by $C_{6-10}$ aryl group(s) (preferably, a phenyl group), and
(iv) a $C_{3-6}$ cycloalkyl-carbonyl group (preferably, a cyclopropylcarbonyl group, a cyclohexylcarbonyl group) optionally substituted by $C_{1-6}$ alkoxy group(s) (preferably, a methoxy group),
(2) a $C_{1-6}$ alkoxy group (preferably, a methoxy group) optionally substituted by $C_{6-10}$ aryl group(s) (preferably, a phenyl group),
(3) a $C_{3-6}$ cycloalkyl group (preferably, a cyclopentyl group, cyclohexyl group) optionally substituted by 1 to 3% substituents selected from
(a) a hydroxy group, and
(b) a $C_{1-6}$ alkoxy group (preferably, a methoxy group),
(4) a $C_{6-10}$ aryl group (preferably, a phenyl group) optionally substituted by $C_{1-6}$ alkyl group(s) (preferably, a methyl group) optionally substituted by 1 to 3 halogen atoms (preferably, a fluorine atom),
(5) an amino group optionally mono- or di-substituted by $C_{1-6}$ alkyl group(s) (preferably, a methyl group) optionally substituted by $C_{6-10}$ aryl group(s) (preferably, a phenyl group),
(6) a 5- or 6-membered unsaturated heterocyclic group (preferably, an isoxazolyl group) optionally substituted by $C_{1-6}$ alkyl group(s) (preferably, a methyl group),
(7) a 5- or 6-membered saturated heterocyclic group (preferably, a tetrahydrofuryl group, a tetrahydropyranyl group, a pyrrolidinyl group, a piperidyl group) optionally substituted by 1 to 3 substituents selected from
(a) a $C_{1-6}$ alkyl group (preferably, a methyl group),
(b) a $C_{1-6}$ alkyl-carbonyl group (preferably, an acetyl group), and
(c) an oxo group,
(8) a $C_{3-6}$ cycloalkyloxy group (preferably, a cyclohexyloxy group), or
(9) a $C_{6-10}$ aryl-carbonyl group (preferably, a benzoyl group).

$R^8$ is preferably a $C_{1-6}$ alkyl group (preferably, a methyl group, an ethyl group, a propyl group, an isopropyl group, an isobutyl group, a tert-butyl group, a neopentyl group) substituted by 1 to 3 substituents selected from (a) a hydroxy group,
(b) a $C_{1-6}$ alkoxy group (preferably, a methoxy group, an ethoxy group, a propoxy group, an isopropoxy group) optionally substituted by $C_{6-10}$ aryl group(s) (preferably, a phenyl group),
(c) a $C_{3-6}$ cycloalkyl group (preferably, a cyclopentyl group, a cyclohexyl group) optionally substituted by $C_{1-6}$ alkoxy group(s) (preferably, a methoxy group),
(d) a $C_{6-10}$ aryl group (preferably, phenyl group),
(e) a 5- or 6-membered unsaturated heterocyclic group (preferably, an imidazolyl group, a dihydropyridyl group, a pyrazolyl group) optionally substituted by oxo group(s),
(f) a 5- to 8-membered saturated heterocyclic group (preferably, a tetrahydrofuryl group, a tetrahydropyranyl group, a pyrrolidinyl group, a piperidyl group, an azepanyl group, an azocanyl group, a morpholinyl group (including a morpholino group), 1,1-dioxideisothiazolidinyl group, an oxazolidinyl group, an imidazolidinyl group) optionally substituted by 1 to 3 substituents selected from
  (i) a hydroxy group,
  (ii) a $C_{1-6}$ alkyl group (preferably, a methyl group) optionally substituted by 1 to 3 substituents selected from a hydroxy group and a $C_{1-6}$ alkoxy group (preferably, a methoxy group),
  (iii) a $C_{1-6}$ alkoxy group (preferably, a methoxy group), and
  (iv) an oxo group,
(g) a $C_{3-6}$ cycloalkyloxy group (preferably, a cyclopentyloxy group),
(h) a $C_{6-10}$ aryloxy group (preferably, a phenoxy group),
(i) a 5- or 6-membered unsaturated heterocyclyloxy group (preferably, a pyridyloxy group),
(j) a 5- or 6-membered saturated heterocyclyloxy group (preferably, a tetrahydrofuryloxy group, a tetrahydropyranyloxy group), and
(k) an amino group optionally mono- or di-substituted by substituents selected from
  (i) a $C_{1-6}$ alkyl group (preferably, a methyl group) optionally substituted by 1 to 3 substituents selected from a hydroxy group, a carboxy group and a carboxy-$C_{1-6}$ alkoxy group (preferably, a carboxymethoxy group),
  (ii) a $C_{1-6}$ alkyl-carbonyl group (preferably, an acetyl group, propanoyl group, a 2-methylpropanoyl group, a 2,2-dimethylpropanoyl group, a 3-methylbutanoyl group) optionally substituted by 1 to 3 substituents selected from a hydroxy group and a $C_{1-6}$ alkoxy group (preferably, a methoxy group),
  (iii) a $C_{1-6}$ alkoxy-carbonyl group (preferably, a methoxycarbonyl group, a tert-butoxycarbonyl group) optionally substituted by $C_{6-10}$ aryl group(s) (preferably, a phenyl group), and
  (iv) a $C_{3-6}$ cycloalkyl-carbonyl group (preferably, a cyclopropylcarbonyl group, a cyclohexylcarbonyl group) optionally substituted by $C_{1-6}$ alkoxy group(s) (preferably, a methoxy group).

$R^8$ is more preferably a $C_{1-6}$ alkyl group (preferably, a methyl group, an ethyl group, propyl group, an isopropyl group) substituted by 1 to 3 substituents selected from
(c) a $C_{3-6}$ cycloalkyl group (preferably, a cyclopentyl group, a cyclohexyl group) optionally substituted by $C_{1-6}$ alkoxy group(s) (preferably, a methoxy group),
(d) a $C_{6-10}$ aryl group (preferably, a phenyl group),
(e) a 5- or 6-membered unsaturated heterocyclic group (preferably, an imidazolyl group, a dihydropyridyl group, pyrazolyl group) optionally substituted by oxo group(s), and
(f) a 5- to 8-membered saturated heterocyclic group (preferably, a morpholinyl group (including a morpholino group)) optionally substituted by 1 to 3 substituents selected from
  (i) a hydroxy group,
  (ii) a $C_{1-6}$ alkyl group (preferably, a methyl group) optionally substituted by 1 to 3 substituents selected from a hydroxy group and a $C_{1-6}$ alkoxy group (preferably, a methoxy group),
  (iii) a $C_{1-6}$ alkoxy group (preferably, a methoxy group), and
  (iv) an oxo group.

$R^8$ is particularly preferably a $C_{1-6}$ alkyl group (preferably, a methyl group, an ethyl group) substituted by 5- to 8-membered saturated heterocyclic group(s) (preferably, a morpholino group) optionally substituted by 1 to 3 substituents selected from
  (i) a hydroxy group,
  (ii) a $C_{1-6}$ alkyl group (preferably, a methyl group) optionally substituted by 1 to 3 substituents selected from a hydroxy group and a $C_{1-6}$ alkoxy group (preferably, a methoxy group),
  (iii) a $C_{1-6}$ alkoxy group (preferably, a methoxy group), and
  (iv) an oxo group.

Alternatively, $R^7$ and $R^8$ may form, together with the nitrogen atom and carbon atom they are bonded to, a 5- or 6-membered cyclic amine substituted by an oxo group (preferably, 2-oxopyrrolidine, 2-oxopiperidine, 2-oxooxazolidine) and optionally further substituted by 1 to 3 substituents selected from
(a) a hydroxy group,
(b) a $C_{1-6}$ alkyl group (preferably, methyl group) optionally substituted by a hydroxy group,
(c) a $C_{1-6}$ alkoxy group (preferably, methoxy group), and
(d) a $C_{3-6}$ cycloalkyl group (preferably, cyclohexyl group).

As Compound [I], a compound wherein
$R^1$ is
(1) a hydrogen atom,
(2) a hydroxy group, or
(3) a $C_{1-6}$ alkoxy group (preferably, a methoxy group, an isopropoxy group) optionally substituted by $C_{6-10}$ aryl group (s) (preferably, a phenyl group);
$R^2$ and $R^3$ are the same or different and each is
(1) a hydrogen atom, or
(2) a $C_{1-6}$ alkyl group (preferably, a methyl group) optionally substituted by 1 to 3 substituents selected from
(a) a hydroxy group, and
(b) a $C_{1-6}$ alkoxy group (preferably, a methoxy group); and
$R^4$ is

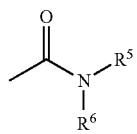

which is bonded to the 5-position or the 6-position of the indole ring, or

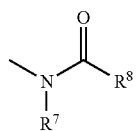

which is bonded to the 6-position of the indole ring (preferably,

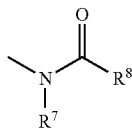

which is bonded to the 6-position of the indole ring),
wherein
R⁵ is
(1) a hydrogen atom, or
(2) a $C_{1-6}$ alkyl group (preferably, a methyl group, an ethyl group), and
R⁶ is
(1) a hydrogen atom,
(2) a $C_{1-6}$ alkyl group (preferably, a methyl group, an ethyl group, an isopropyl group, an isobutyl group, a tert-butyl group, a neopentyl group, a 1,2-dimethylpropyl group, a 1,2,2-trimethylpropyl group) optionally substituted by 1 to 3 substituents selected from
  (a) a hydroxy group,
  (b) a $C_{1-6}$ alkoxy group (preferably, a methoxy group, a propoxy group, an isopropoxy group),
  (c) a carboxy group,
  (d) a $C_{1-6}$ alkoxy-carbonyl group (preferably, a methoxycarbonyl group, a tert-butoxycarbonyl group),
  (e) a $C_{6-10}$ aryl group (preferably, phenyl group),
  (f) a $C_{6-10}$ aryloxy group (preferably, a phenoxy group),
  (g) an amino group optionally mono- or di-substituted by $C_{1-6}$ alkyl group(s) (preferably, a methyl group),
  (h) a 5- or 6-membered unsaturated heterocyclic group (preferably, a furyl group, a pyrrolyl group, a thiazolyl group, a tetrazolyl group, an imidazolyl group) optionally substituted by $C_{1-6}$ alkyl group(s) (preferably, a methyl group), and
  (i) a 5- or 6-membered saturated heterocyclic group (preferably, a morpholinyl group),
(3) a $C_{1-6}$ alkoxy group (preferably, a methoxy group),
(4) a $C_{6-10}$ aryl group (preferably, a phenyl group), or
(5) a 5- or 6-membered unsaturated heterocyclic group (preferably, a 1,3,4-thiadiazolyl group) optionally substituted by 1 to 3 substituents selected from
  (a) a hydroxy group, and
  (b) a $C_{1-6}$ alkoxy group (preferably, a methoxy group), or
R⁵ and R⁶ form, together with the nitrogen atom they are bonded to, a 5- or 6-membered cyclic amine (preferably, pyrrolidine, piperidine, piperazine, morpholine) (said cyclic amine is optionally condensed with 5- or 6-membered unsaturated heterocycle (preferably, imidazole)) optionally substituted by 1 to 3 substituents selected from
  (a) a hydroxy group,
  (b) a $C_{1-6}$ alkyl group (preferably, a methyl group, an ethyl group),
  (c) a $C_{1-6}$ alkoxy group (preferably, a methoxy group), and
  (d) a $C_{1-6}$ alkoxy-carbonyl group (preferably, a tert-butoxycarbonyl group);
R⁷ is
(1) a hydrogen atom, or
(2) a $C_{1-6}$ alkyl group (preferably, a methyl group, an ethyl group, a propyl group) optionally substituted by 1 to 3 substituents selected from
  (a) a hydroxy group,
  (b) a $C_{1-6}$ alkoxy group (preferably, a methoxy group), and
  (c) an amino group optionally mono- or di-substituted by $C_{1-6}$ alkyl group(s) (preferably, a methyl group) [preferably,
a $C_{1-6}$ alkyl group (preferably, a methyl group, an ethyl group, propyl group) optionally substituted by 1 to 3 substituents selected from
  (a) a hydroxy group,
  (b) a $C_{1-6}$ alkoxy group (preferably, a methoxy group), and
  (c) an amino group optionally mono- or di-substituted by $C_{1-6}$ alkyl group(s) (preferably, a methyl group)], and
R⁸ is
(1) a $C_{1-6}$ alkyl group (preferably, a methyl group, an ethyl group, a propyl group, an isopropyl group, an isobutyl group, a tert-butyl group, a neopentyl group) optionally substituted by 1 to 3 substituents selected from
  (a) a hydroxy group,
  (b) a $C_{1-6}$ alkoxy group (preferably, a methoxy group, an ethoxy group, a propoxy group, an isopropoxy group) optionally substituted by $C_{6-10}$ aryl group(s) (preferably, a phenyl group),
  (c) a $C_{3-6}$ cycloalkyl group (preferably, a cyclopentyl group, a cyclohexyl group) optionally substituted by $C_{1-6}$ alkoxy group(s) (preferably, a methoxy group),
  (d) a $C_{6-10}$ aryl group (preferably, a phenyl group),
  (e) a 5- or 6-membered unsaturated heterocyclic group (preferably, an imidazolyl group, a dihydropyridyl group, a pyrazolyl group) optionally substituted by oxo group(s),
  (f) a 5- to 8-membered saturated heterocyclic group (preferably, a tetrahydrofuryl group, a tetrahydropyranyl group, a pyrrolidinyl group, a piperidyl group, an azepanyl group, an azocanyl group, a morpholinyl group (including a morpholino group), a 1,1-dioxide-isothiazolidinyl group, oxazolidinyl group, an imidazolidinyl group) optionally substituted by 1 to 3 substituents selected from
    (i) a hydroxy group,
    (ii) a $C_{1-6}$ alkyl group (preferably, a methyl group) optionally substituted by 1 to 3 substituents selected from a hydroxy group and a $C_{1-6}$ alkoxy group (preferably, a methoxy group),
    (iii) a $C_{1-6}$ alkoxy group (preferably, a methoxy group), and
    (iv) an oxo group,
  (g) a $C_{3-6}$ cycloalkyloxy group (preferably, a cyclopentyloxy group),
  (h) a $C_{6-10}$ aryloxy group (preferably, a phenoxy group),
  (i) a 5- or 6-membered unsaturated heterocyclyloxy group (preferably, a pyridyloxy group),
  (j) a 5- or 6-membered saturated heterocyclyloxy group (preferably, a tetrahydrofuryloxy group, a tetrahydropyranyloxy group), and
  (k) an amino group optionally mono- or di-substituted by substituents selected from
    (i) a $C_{1-6}$ alkyl group (preferably, a methyl group) optionally substituted by 1 to 3 substituents selected from a hydroxy group, a carboxy group and a carboxy-$C_{1-6}$ alkoxy group (preferably, a carboxymethoxy group),
    (ii) a $C_{1-6}$ alkyl-carbonyl group (preferably, an acetyl group, a propanoyl group, a 2-methylpropanoyl group, a 2,2-dimethylpropanoyl group, a 3-methylbutanoyl group) optionally substituted by 1 to 3 substituents selected from a hydroxy group and a $C_{1-6}$ alkoxy group (preferably, a methoxy group),
  (iii) a $C_{1-6}$ alkoxy-carbonyl group (preferably, a methoxycarbonyl group, a tert-butoxycarbonyl group) optionally substituted by $C_{6-10}$ aryl group(s) (preferably, a phenyl group), and
  (iv) a $C_{3-6}$ cycloalkyl-carbonyl group (preferably, a cyclopropylcarbonyl group, a cyclohexylcarbonyl group) optionally substituted by $C_{1-6}$ alkoxy group(s) (preferably, a methoxy group),
(2) a $C_{1-6}$ alkoxy group (preferably, a methoxy group) optionally substituted by $C_{6-10}$ aryl group(s) (preferably, a phenyl group),
(3) a $C_{3-6}$ cycloalkyl group (preferably, a cyclopentyl group, cyclohexyl group) optionally substituted by 1 to 3 substituents selected from
  (a) a hydroxy group, and
  (b) a $C_{1-6}$ alkoxy group (preferably, a methoxy group),
(4) a $C_{6-10}$ aryl group (preferably, a phenyl group) optionally substituted by a $C_{1-6}$ alkyl group (preferably, a methyl group) optionally substituted by 1 to 3 halogen atoms (preferably, a fluorine atom),
(5) an amino group optionally mono- or di-substituted by $C_{1-6}$ alkyl group(s) (preferably, a methyl group) optionally substituted by $C_{6-10}$ aryl group(s) (preferably, a phenyl group),
(6) a 5- or 6-membered unsaturated heterocyclic group (preferably, an isoxazolyl group) optionally substituted by $C_{1-6}$ alkyl group(s) (preferably, a methyl group),
(7) a 5- or 6-membered saturated heterocyclic group (preferably, a tetrahydrofuryl group, a tetrahydropyranyl group, a pyrrolidinyl group, a piperidyl group) optionally substituted by 1 to 3 substituents selected from
  (a) a $C_{1-6}$ alkyl group (preferably, a methyl group),
  (b) a $C_{1-6}$ alkyl-carbonyl group (preferably, an acetyl group), and
  (c) an oxo group,
(8) a $C_{3-6}$ cycloalkyloxy group (preferably, a cyclohexyloxy group), or
(9) a $C_{6-10}$ aryl-carbonyl group (preferably, a benzoyl group), or
$R^7$ and $R^8$ form, together with the nitrogen atom and carbon atom they are bonded to, a 5- or 6-membered cyclic amine substituted by an oxo group (preferably, 2-oxopyrrolidine, 2-oxopiperidine, 2-oxooxazolidine) and optionally further substituted by 1 to 3 substituents selected from
  (a) a hydroxy group,
  (b) a $C_{1-6}$ alkyl group (preferably, a methyl group) optionally substituted by hydroxy group(s),
  (c) a $C_{1-6}$ alkoxy group (preferably, a methoxy group), and
  (d) a $C_{3-6}$ cycloalkyl group (preferably, a cyclohexyl group)
is preferable.

Particularly, a compound wherein
$R^1$ is
(1) a hydrogen atom,
(2) a hydroxy group, or
(3) a $C_{1-6}$ alkoxy group (preferably, a methoxy group, an isopropoxy group) optionally substituted by $C_{6-10}$ aryl group(s) (preferably, a phenyl group);

$R^2$ and $R^3$ are the same or different and each is
(1) a hydrogen atom, or
(2) a $C_{1-6}$ alkyl group (preferably, a methyl group) optionally substituted by 1 to 3 substituents selected from
  (a) a hydroxy group, and
  (b) a $C_{1-6}$ alkoxy group (preferably, a methoxy group);
$R^4$ is

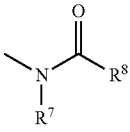

which is bonded to the 6-position of the indole ring,
  wherein
  $R^7$ is a $C_{1-6}$ alkyl group (preferably, a methyl group, an ethyl group, a propyl group) optionally substituted by 1 to 3 substituents selected from
    (a) a hydroxy group,
    (b) a $C_{1-6}$ alkoxy group (preferably, a methoxy group), and
    (c) an amino group optionally mono- or di-substituted by $C_{1-6}$ alkyl group(s) (preferably, a methyl group), and
  $R^8$ is
  (1) a $C_{1-6}$ alkyl group (preferably, a methyl group, an ethyl group, a propyl group, an isopropyl group, an isobutyl group, a tert-butyl group, a neopentyl group) optionally substituted by 1 to 3 substituents selected from
    (a) a hydroxy group,
    (b) a $C_{1-6}$ alkoxy group (preferably, a methoxy group, an ethoxy group, a propoxy group, an isopropoxy group) optionally substituted by $C_{6-10}$ aryl group(s) (preferably, a phenyl group),
    (c) a $C_{3-6}$ cycloalkyl group (preferably, a cyclopentyl group, a cyclohexyl group) optionally substituted by $C_{1-6}$ alkoxy group(s) (preferably, a methoxy group),
    (d) a $C_{6-10}$ aryl group (preferably, a phenyl group),
    (e) a 5- or 6-membered unsaturated heterocyclic group (preferably, an imidazolyl group, a dihydropyridyl group, a pyrazolyl group) optionally substituted by oxo group(s),
    (f) a 5- to 8-membered saturated heterocyclic group (preferably, a tetrahydrofuryl group, a tetrahydropyranyl group, a pyrrolidinyl group, a piperidyl group, an azepanyl group, an azocanyl group, a morpholinyl group (including a morpholino group), a 1,1-dioxide-isothiazolidinyl group, an oxazolidinyl group, imidazolidinyl group) optionally substituted by 1 to 3 substituents selected from
      (i) a hydroxy group,
      (ii) a $C_{1-6}$ alkyl group (preferably, a methyl group) optionally substituted by 1 to 3 substituents selected from a hydroxy group and a $C_{1-6}$ alkoxy group (preferably, a methoxy group),
      (iii) a $C_{1-6}$ alkoxy group (preferably, a methoxy group), and
      (iv) an oxo group,
    (g) a $C_{3-6}$ cycloalkyloxy group (preferably, a cyclopentyloxy group),
    (h) a $C_{6-10}$ aryloxy group (preferably, a phenoxy group),
    (i) a 5- or 6-membered unsaturated heterocyclyloxy group (preferably, a pyridyloxy group),
    (j) a 5- or 6-membered saturated heterocyclyloxy group (preferably, a tetrahydrofuryloxy group, a tetrahydropyranyloxy group), and (k) an amino group optionally mono- or di-substituted by substituents selected from
  (i) a $C_{1-6}$ alkyl group (preferably, a methyl group) optionally substituted by 1 to 3 substituents selected from a hydroxy group, a carboxy group and a carboxy-$C_{1-6}$ alkoxy group (preferably, a carboxymethoxy group),
  (ii) a $C_{1-6}$ alkyl-carbonyl group (preferably, an acetyl group, a propanoyl group, a 2-methylpropanoyl group, a 2,2-dimethylpropanoyl group, a 3-methylbutanoyl group) optionally substituted by 1 to 3 substituents selected from a hydroxy group and a $C_{1-6}$ alkoxy group (preferably, a methoxy group),
  (iii) a $C_{1-6}$ alkoxy-carbonyl group (preferably, a methoxycarbonyl group, a tert-butoxycarbonyl group) optionally substituted by $C_{6-10}$ aryl group(s) (preferably, a phenyl group), and
  (iv) a $C_{3-6}$ cycloalkyl-carbonyl group (preferably, a cyclopropylcarbonyl group, a cyclohexylcarbonyl group) optionally substituted by $C_{1-6}$ alkoxy group(s) (preferably, a methoxy group),
(2) a $C_{1-6}$ alkoxy group (preferably, a methoxy group) optionally substituted by $C_{6-10}$ aryl group(s) (preferably, a phenyl group),
(3) a $C_{3-6}$ cycloalkyl group (preferably, a cyclopentyl group, a cyclohexyl group) optionally substituted by 1 to 3 substituents selected from
  (a) a hydroxy group, and
  (b) a $C_{1-6}$ alkoxy group (preferably, a methoxy group),
(4) a $C_{6-10}$ aryl group (preferably, a phenyl group) optionally substituted by a $C_{1-6}$ alkyl group (preferably, a methyl group) optionally substituted by 1 to 3 halogen atoms (preferably, a fluorine atom),
(5) an amino group optionally mono- or di-substituted by $C_{1-6}$ alkyl group(s) (preferably, a methyl group) optionally substituted by $C_{6-10}$ aryl group(s) (preferably, to a phenyl group),
(6) a 5- or 6-membered unsaturated heterocyclic group (preferably, an isoxazolyl group) optionally substituted by $C_{1-6}$ alkyl group(s) (preferably, a methyl group),
(7) a 5- or 6-membered saturated heterocyclic group (preferably, a tetrahydrofuryl group, a tetrahydropyranyl group, a pyrrolidinyl group, a piperidyl group) optionally substituted by 1 to 3 substituents selected from
  (a) a $C_{1-6}$ alkyl group (preferably, a methyl group),
  (b) a $C_{1-6}$ alkyl-carbonyl group (preferably, an acetyl group), and
  (c) an oxo group,
(8) a $C_{3-6}$ cycloalkyloxy group (preferably, a cyclohexyloxy group), or
(9) a $C_{6-10}$ aryl-carbonyl group (preferably, a benzoyl group), or
$R^7$ and $R^8$ form, together with the nitrogen atom and carbon atom they are bonded to, a 5- or 6-membered cyclic amine substituted by an oxo group (preferably, 2-oxopyrrolidine, 2-oxopiperidine, 2-oxooxazolidine) and optionally further substituted by 1 to 3 substituents selected from
  (a) a hydroxy group,
  (b) a $C_{1-6}$ alkyl group (preferably, a methyl group) optionally substituted by hydroxy group(s),
  (c) a $C_{1-6}$ alkoxy group (preferably, a methoxy group), and
  (d) a $C_{3-6}$ cycloalkyl group (preferably, a cyclohexyl group),
that is, a compound represented by the above-mentioned formula [I-a] is particularly preferable.

As a compound represented by the formula [I-a], a compound wherein
$R^1$ is a hydrogen atom;
$R^2$ and $R^3$ are the same or different and each is a $C_{1-6}$ alkyl group (preferably, a methyl group);
$R^{7'}$ is a $C_{1-6}$ alkyl group (preferably, a methyl group, an ethyl group, a propyl group), and
$R^8$ is a $C_{1-6}$ alkyl group (preferably, a methyl group, an ethyl group, a propyl group, an isopropyl group, an isobutyl group, a tert-butyl group, a neopentyl group) substituted by 1 to 3 substituents selected from
  (a) a hydroxy group,
  (b) a $C_{1-6}$ alkoxy group (preferably, a methoxy group, an ethoxy group, a propoxy group, an isopropoxy group) optionally substituted by $C_{6-10}$ aryl group(s) (preferably, a phenyl group),
  (c) a $C_{3-6}$ cycloalkyl group (preferably, a cyclopentyl group, a cyclohexyl group) optionally substituted by $C_{1-6}$ alkoxy group(s) (preferably, a methoxy group),
  (d) a $C_{6-10}$ aryl group (preferably, a phenyl group),
  (e) a 5- or 6-membered unsaturated heterocyclic group (preferably, an imidazolyl group, a dihydropyridyl group, a pyrazolyl group) optionally substituted by oxo group(s),
  (f) a 5- to 8-membered saturated heterocyclic group (preferably, a tetrahydrofuryl group, a tetrahydropyranyl group, a pyrrolidinyl group, a piperidyl group, an azepanyl group, an azocanyl group, a morpholinyl group (including a morpholino group), a 1,1-dioxideisothiazolidinyl group, a oxazolidinyl group, an imidazolidinyl group) optionally substituted by 1 to 3 substituents selected from
    (i) a hydroxy group,
    (ii) a $C_{1-6}$ alkyl group (preferably, a methyl group) optionally substituted by 1 to 3 substituents selected from a hydroxy group and a $C_{1-6}$ alkoxy group (preferably, a methoxy group),
    (iii) a $C_{1-6}$ alkoxy group (preferably, a methoxy group), and
    (iv) an oxo group,
  (g) a $C_{3-6}$ cycloalkyloxy group (preferably, a cyclopentyloxy group),
  (h) a $C_{6-10}$ aryloxy group (preferably, a phenoxy group),
  (i) a 5- or 6-membered unsaturated heterocyclyloxy group (preferably, a pyridyloxy group),
  (j) a 5- or 6-membered saturated heterocyclyloxy group (preferably, a tetrahydrofuryloxy group, a tetrahydropyranyloxy group), and
  (k) an amino group optionally mono- or di-substituted by substituents selected from
    (i) a $C_{1-6}$ alkyl group (preferably, a methyl group) optionally substituted by 1 to 3 substituents selected from a hydroxy group, a carboxy group and a carboxy-$C_{1-6}$ alkoxy group (preferably, a carboxymethoxy group),
    (ii) a $C_{1-6}$ alkyl-carbonyl group (preferably, an acetyl group, a propanoyl group, a 2-methylpropanoyl group, a 2,2-dimethylpropanoyl group, a 3-methylbutanoyl group) optionally substituted by 1 to 3 substituents selected from a hydroxy group and a $C_{1-6}$ alkoxy group (preferably, a methoxy group),
    (iii) a $C_{1-6}$ alkoxy-carbonyl group (preferably, a methoxycarbonyl group, a tert-butoxycarbonyl group) optionally substituted by $C_{6-10}$ aryl group(s) (preferably, a phenyl group), and
    (iv) a $C_{3-6}$ cycloalkyl-carbonyl group (preferably, a cyclopropylcarbonyl group, a cyclohexylcarbonyl group) optionally substituted by $C_{1-6}$ alkoxy group(s) (preferably, a methoxy group)
is preferable.

In another embodiment, as compound [I], a compound represented by the above-mentioned formula [I'] (hereinafter sometimes to be abbreviated as compound [I']) is preferable. Each group of compound [I'] is explained in the following.

$R^{1'}$ is
(1) a hydrogen atom,
(2) a hydroxy group, or
(3) a $C_{1-6}$ alkoxy group (preferably, a methoxy group, an isopropoxy group) optionally substituted by $C_{6-10}$ aryl group(s) (preferably, a phenyl group).

$R^{2'}$ and $R^{3'}$ are the same or different and each is
(1) a hydrogen atom, or
(2) a $C_{1-6}$ alkyl group (preferably, a methyl group) optionally substituted by 1 to 3 substituents selected from
  (a) a hydroxy group, and
  (b) a $C_{1-6}$ alkoxy group (preferably, a methoxy group).

$R^{4'}$ is a group represented by

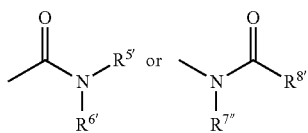

which is bonded to the 5-position or the 6-position of the indole ring.

$R^{4'}$ is preferably

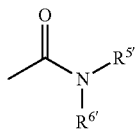

which is bonded to the 5-position or the 6-position of the indole ring, or

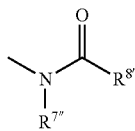

which is bonded to the 6-position of the indole ring, more preferably,

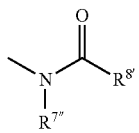

which is bonded to the 6-position of the indole ring.

$R^{5'}$ is
(1) a hydrogen atom, or
(2) a $C_{1-6}$ alkyl group (preferably, a methyl group, an ethyl group).

$R^{6'}$ is
(1) a hydrogen atom,
(2) a $C_{1-6}$ alkyl group (preferably, a methyl group, an ethyl group, an isopropyl group, an isobutyl group, a tert-butyl group, a neopentyl group, a 1,2-dimethylpropyl group, a 1,2,2-trimethylpropyl group) optionally substituted by 1 to 3 substituents selected from
  (a) a hydroxy group,
  (b) a $C_{1-6}$ alkoxy group (preferably, a methoxy group, a propoxy group, an isopropoxy group),
  (c) a carboxy group,
  (d) a $C_{1-6}$ alkoxy-carbonyl group (preferably, a methoxycarbonyl group, a tert-butoxycarbonyl group),
  (e) a $C_{6-10}$ aryl group (preferably, a phenyl group),
  (f) a $C_{6-10}$ aryloxy group (preferably, a phenoxy group),
  (g) an amino group optionally mono- or di-substituted by $C_{1-6}$ alkyl group(s) (preferably, a methyl group),
  (h) a 5- or 6-membered unsaturated heterocyclic group (preferably, a furyl group, a pyrrolyl group, a thiazolyl group, a tetrazolyl group, an imidazolyl group) optionally substituted by $C_{1-6}$ alkyl group(s) (preferably, a methyl group), and
  (i) a 5- or 6-membered saturated heterocyclic group (preferably, a morpholinyl group),
(3) a $C_{1-6}$ alkoxy group (preferably, a methoxy group),
(4) a $C_{6-10}$ aryl group (preferably, a phenyl group), or
(5) a 5- or 6-membered unsaturated heterocyclic group (preferably, a 1,3,4-thiadiazolyl group) optionally substituted by 1 to 3 substituents selected from
  (a) a hydroxy group, and
  (b) a $C_{1-6}$ alkoxy group (preferably, a methoxy group).

Alternatively, $R^{5'}$ and $R^{6'}$ may form, together with the nitrogen atom they are bonded to, a 5- or 6-membered cyclic amine (preferably, pyrrolidine, piperidine, piperazine, morpholine) (said cyclic amine is optionally condensed with 5- or 6-membered unsaturated heterocycle (preferably, imidazole)), which is optionally substituted by 1 to 3 substituents selected from
  (a) a hydroxy group,
  (b) a $C_{1-6}$ alkyl group (preferably, a methyl group, an ethyl group),
  (c) a $C_{1-6}$ alkoxy group (preferably, a methoxy group), and
  (d) a $C_{1-6}$ alkoxy-carbonyl group (preferably, a tert-butoxycarbonyl group).

$R^{7''}$ is
(1) a hydrogen atom, or
(2) a $C_{1-6}$ alkyl group (preferably, a methyl group, an ethyl group, a propyl group) optionally substituted by 1 to 3 substituents selected from
  (a) a hydroxy group,
  (b) a $C_{1-6}$ alkoxy group (preferably, a methoxy group), and
  (c) an amino group optionally mono- or di-substituted by $C_{1-6}$ alkyl group(s) (preferably, a methyl group),
preferably a $C_{1-6}$ alkyl group (preferably, a methyl group, an ethyl group, a propyl group) optionally substituted by 1 to 3 substituents selected from
  (a) a hydroxy group,
  (b) a $C_{1-6}$ alkoxy group (preferably, a methoxy group), and
  (c) an amino group optionally mono- or di-substituted by $C_{1-6}$ alkyl group(s) (preferably, a methyl group).

$R^{8'}$ is
(1) a $C_{1-6}$ alkyl group (preferably, a methyl group, an ethyl group, a propyl group, an isopropyl group, an isobutyl group, a tert-butyl group, a neopentyl group) optionally substituted by 1 to 3 substituents selected from
  (a) a hydroxy group,
  (b) a $C_{1-6}$ alkoxy group (preferably, a methoxy group, an ethoxy group, a propoxy group, an isopropoxy group) optionally substituted by $C_{6-10}$ aryl group(s) (preferably, a phenyl group), (c) a $C_{3-6}$ cycloalkyl group (preferably, a cyclopentyl group, a cyclohexyl group) optionally substituted by $C_{1-6}$ alkoxy group(s) (preferably, a methoxy group),
(d) a $C_{6-10}$ aryl group (preferably, a phenyl group),
(e) a 5- or 6-membered unsaturated heterocyclic group (preferably, an imidazolyl group, a dihydropyridyl group, a pyrazolyl group) optionally substituted by oxo group(s),
(f) a 5- to 8-membered saturated heterocyclic group (preferably, a tetrahydrofuryl group, a tetrahydropyranyl group, a pyrrolidinyl group, a piperidyl group, an azepanyl group, an azocanyl group, a morpholinyl group, a 1,1-dioxideisothiazolidinyl group, an oxazolidinyl group, an imidazolidinyl group) optionally substituted by 1 to 3 substituents selected from
  (i) a hydroxy group,
  (ii) a $C_{1-6}$ alkyl group (preferably, a methyl group) optionally substituted by 1 to 3 substituents selected from a hydroxy group and a $C_{1-6}$ alkoxy group (preferably, a methoxy group),
  (iii) a $C_{1-6}$ alkoxy group (preferably, a methoxy group), and
  (iv) an oxo group,
(g) a $C_{3-6}$ cycloalkyloxy group (preferably, a cyclopentyloxy group),
(h) a $C_{6-10}$ aryloxy group (preferably, a phenoxy group),
(i) a 5- or 6-membered unsaturated heterocyclyloxy group (preferably, a pyridyloxy group),
(j) a 5- or 6-membered saturated heterocyclyloxy group (preferably, a tetrahydrofuryloxy group, a tetrahydropyranyloxy group), and
(k) an amino group optionally mono- or di-substituted by substituents selected from
  (i) a $C_{1-6}$ alkyl group (preferably, a methyl group),
  (ii) a $C_{1-6}$ alkyl-carbonyl group (preferably, an acetyl group, a propanoyl group, a 2-methylpropanoyl group, a 2,2-dimethylpropanoyl group, a 3-methylbutanoyl group) optionally substituted by 1 to 3 substituents selected from a hydroxy group and a $C_{1-6}$ alkoxy group (preferably, a methoxy group),
  (iii) a $C_{1-6}$ alkoxy-carbonyl group (preferably, a methoxycarbonyl group, a tert-butoxycarbonyl group) optionally substituted by $C_{6-10}$ aryl group(s) (preferably, a phenyl group), and
  (iv) a $C_{3-6}$ cycloalkyl-carbonyl group (preferably, a cyclopropylcarbonyl group, a cyclohexylcarbonyl group) optionally substituted by $C_{1-6}$ alkoxy group(s) (preferably, a methoxy group),
(2) a $C_{1-6}$ alkoxy group (preferably, a methoxy group) optionally substituted by $C_{6-10}$ aryl group(s) (preferably, a phenyl group),
(3) a $C_{3-6}$ cycloalkyl group (preferably, a cyclopentyl group, cyclohexyl group) optionally substituted by 1 to 3 substituents selected from
  (a) a hydroxy group, and
  (b) a $C_{1-6}$ alkoxy group (preferably, a methoxy group),
(4) a $C_{6-10}$ aryl group (preferably, a phenyl group) optionally substituted by $C_{1-6}$ alkyl group(s) (preferably, a methyl group) optionally substituted by 1 to 3 halogen atoms (preferably, a fluorine atom),
(5) an amino group optionally mono- or di-substituted by $C_{1-6}$ alkyl group(s) (preferably, a methyl group) optionally substituted by $C_{6-10}$ aryl group(s) (preferably, a phenyl group),
(6) a 5- or 6-membered unsaturated heterocyclic group (preferably, an isoxazolyl group) optionally substituted by $C_{1-6}$ alkyl group(s) (preferably, a methyl group),
(7) a 5- or 6-membered saturated heterocyclic group (preferably, a tetrahydrofuryl group, a tetrahydropyranyl group, a pyrrolidinyl group, a piperidyl group) optionally substituted by 1 to 3 substituents selected from
  (a) a $C_{1-6}$ alkyl group (preferably, a methyl group),
  (b) a $C_{1-6}$ alkyl-carbonyl group (preferably, an acetyl group), and
  (c) an oxo group,
(8) a $C_{3-6}$ cycloalkyloxy group (preferably, a cyclohexyloxy group), or
(9) a $C_{6-10}$ aryl-carbonyl group (preferably, a benzoyl group).

Alternatively, $R^{7''}$ and $R^{8'}$ may form, together with the nitrogen atom and carbon atom they are bonded to, a 5- or 6-membered cyclic amine substituted by an oxo group (preferably, 2-oxopyrrolidine, 2-oxopiperidine, 2-oxooxazolidine) and optionally further substituted by 1 to 3 substituents selected from
(a) a hydroxy group,
(b) a $C_{1-6}$ alkyl group (preferably, a methyl group) optionally substituted by hydroxy group(s),
(c) a $C_{1-6}$ alkoxy group (preferably, a methoxy group), and
(d) a $C_{3-6}$ cycloalkyl group (preferably, a cyclohexyl group).

As compound [I'], a compound wherein
$R^{1'}$ is
(1) a hydrogen atom,
(2) a hydroxy group, or
(3) a $C_{1-6}$ alkoxy group (preferably, a methoxy group, an isopropoxy group) optionally substituted by $C_{6-10}$ aryl group(s) (preferably, a phenyl group);
$R^{2'}$ and $R^{3'}$ are the same or different and each is
(1) a hydrogen atom, or
(2) a $C_{1-6}$ alkyl group (preferably, a methyl group) optionally substituted by 1 to 3 substituents selected from
(a) a hydroxy group, and
(b) a $C_{1-6}$ alkoxy group (preferably, a methoxy group);
$R^{4'}$ is

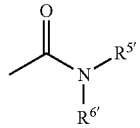

which is bonded to the 5-position or the 6-position of the indole ring, or

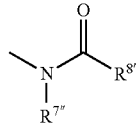

which is bonded to the 6-position of the indole ring (preferably,

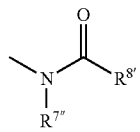

which is bonded to the 6-position of the indole ring), wherein
R⁵' is
(1) a hydrogen atom, or
(2) a $C_{1-6}$ alkyl group (preferably, a methyl group, an ethyl group), and R⁵' is
(1) a hydrogen atom,
(2) a $C_{1-6}$ alkyl group (preferably, a methyl group, an ethyl group, an isopropyl group, an isobutyl group, a tert-butyl group, a neopentyl group, a 1,2-dimethylpropyl group, a 1,2,2-trimethylpropyl group) optionally substituted by 1 to 3 substituents selected from
  (a) a hydroxy group,
  (b) a $C_{1-6}$ alkoxy group (preferably, a methoxy group, a propoxy group, an isopropoxy group),
  (c) a carboxy group,
  (d) a $C_{1-6}$ alkoxy-carbonyl group (preferably, a methoxycarbonyl group, a tert-butoxycarbonyl group),
  (e) a $C_{6-10}$ aryl group (preferably, a phenyl group),
  (f) a $C_{6-40}$ aryloxy group (preferably, a phenoxy group),
  (g) an amino group optionally mono- or di-substituted by $C_{1-6}$ alkyl group(s) (preferably, a methyl group),
  (h) a 5- or 6-membered unsaturated heterocyclic group (preferably, a furyl group, a pyrrolyl group, a thiazolyl group, a tetrazolyl group, an imidazolyl group) optionally substituted by $C_{1-6}$ alkyl group(s) (preferably, a methyl group), and
  (i) a 5- or 6-membered saturated heterocyclic group (preferably, a morpholinyl group),
(3) a $C_{1-6}$ alkoxy group (preferably, a methoxy group),
(4) a $C_{6-10}$ aryl group (preferably, a phenyl group), or
(5) a 5- or 6-membered unsaturated heterocyclic group (preferably, a 1,3,4-thiadiazolyl group) optionally substituted by 1 to 3 substituents selected from
  (a) a hydroxy group, and
  (b) a $C_{1-6}$ alkoxy group (preferably, a methoxy group), or R⁵' and R⁶' form, together with the nitrogen atom they are bonded to, a 5- or 6-membered cyclic amine (preferably, pyrrolidine, piperidine, piperazine, morpholine) (said cyclic amine is optionally condensed with 5- or 6-membered unsaturated heterocycle (preferably, imidazole)), which is optionally substituted by 1 to 3 substituents selected from
  (a) a hydroxy group,
  (b) a $C_{1-6}$ alkyl group (preferably, a methyl group, an ethyl group),
  (c) a $C_{1-6}$ alkoxy group (preferably, a methoxy group), and
  (d) a $C_{1-6}$ alkoxy-carbonyl group (preferably, a tert-butoxycarbonyl group);

R⁷'' is
(1) a hydrogen atom, or
(2) a $C_{1-6}$ alkyl group (preferably, a methyl group, an ethyl group, a propyl group) optionally substituted by 1 to 3 substituents selected from
  (a) a hydroxy group,
  (b) a $C_{1-6}$ alkoxy group (preferably, a methoxy group), and
  (c) an amino group optionally mono- or di-substituted by $C_{1-6}$ alkyl group(s) (preferably, a methyl group) [preferably,
a $C_{1-6}$ alkyl group (preferably, a methyl group, an ethyl group, a propyl group) optionally substituted by 1 to 3 substituents selected from
  (a) a hydroxy group,
  (b) a $C_{1-6}$ alkoxy group (preferably, a methoxy group), and
  (c) an amino group optionally mono- or di-substituted by $C_{1-6}$ alkyl group(s) (preferably, a methyl group)], and R⁸' is
(1) a $C_{1-6}$ alkyl group (preferably, a methyl group, an ethyl group, a propyl group, an isopropyl group, an isobutyl group, a tert-butyl group, a neopentyl group) optionally substituted by 1 to 3 substituents selected from
  (a) a hydroxy group,
  (b) a $C_{1-6}$ alkoxy group (preferably, a methoxy group, ethoxy group, a propoxy group, an isopropoxy group) optionally substituted by $C_{6-10}$ aryl group(s) (preferably, a phenyl group),
  (c) a $C_{3-6}$ cycloalkyl group (preferably, a cyclopentyl group, a cyclohexyl group) optionally substituted by $C_{1-6}$ alkoxy group(s) (preferably, a methoxy group),
  (d) a $C_{6-10}$ aryl group (preferably, a phenyl group),
  (e) a 5- or 6-membered unsaturated heterocyclic group (preferably, an imidazolyl group, a dihydropyridyl group, pyrazolyl group) optionally substituted by oxo group(s),
  (f) a 5- to 8-membered saturated heterocyclic group (preferably, a tetrahydrofuryl group, a tetrahydropyranyl group, a pyrrolidinyl group, a piperidyl group, an azepanyl group, an azocanyl group, a morpholinyl group, a 1,1-dioxideisothiazolidinyl group, an oxazolidinyl group, an imidazolidinyl group) optionally substituted by 1 to 3 substituents selected from
    (i) a hydroxy group,
    (ii) a $C_{1-6}$ alkyl group (preferably, a methyl group) optionally substituted by 1 to 3 substituents selected from a hydroxy group and a $C_{1-6}$ alkoxy group (preferably, a methoxy group),
    (iii) a $C_{1-6}$ alkoxy group (preferably, a methoxy group), and
    (iv) an oxo group,
  (g) a $C_{3-6}$ cycloalkyloxy group (preferably, a cyclopentyloxy group),
  (h) a $C_{6-10}$ aryloxy group (preferably, a phenoxy group),
  (i) a 5- or 6-membered unsaturated heterocyclyloxy group (preferably, a pyridyloxy group),
  (j) a 5- or 6-membered saturated heterocyclyloxy group (preferably, a tetrahydrofuryloxy group, a tetrahydropyranyloxy group), and
  (k) an amino group optionally mono- or di-substituted by substituents selected from
    (i) a $C_{1-6}$ alkyl group (preferably, a methyl group),
    (ii) a $C_{1-6}$ alkyl-carbonyl group (preferably, an acetyl group, a propanoyl group, a 2-methylpropanoyl group, a 2,2-dimethylpropanoyl group, a 3-methylbutanoyl group) optionally substituted by 1 to 3 substituents selected from a hydroxy group and a $C_{1-6}$ alkoxy group (preferably, a methoxy group),
    (iii) a $C_{1-6}$ alkoxy-carbonyl group (preferably, a methoxycarbonyl group, a tert-butoxycarbonyl group) optionally substituted by $C_{6-10}$ aryl group(s) (preferably, a phenyl group), and
    (iv) a $C_{3-6}$ cycloalkyl-carbonyl group (preferably, a cyclopropylcarbonyl group, a cyclohexylcarbonyl group) optionally substituted by $C_{1-6}$ alkoxy group(s) (preferably, a methoxy group),
(2) a $C_{1-6}$ alkoxy group (preferably, a methoxy group) optionally substituted by $C_{6-10}$ aryl group(s) (preferably, a phenyl group),
(3) a $C_{3-6}$ cycloalkyl group (preferably, a cyclopentyl group, a cyclohexyl group) optionally substituted by 1 to 3 substituents selected from (a) a hydroxy group, and
(b) a $C_{1-6}$ alkoxy group (preferably, a methoxy group),
(4) a $C_{6-10}$ aryl group (preferably, a phenyl group) optionally substituted by $C_{1-6}$ alkyl group(s) (preferably, a methyl group) optionally substituted by 1 to 3 halogen atoms (preferably, a fluorine atom),
(5) an amino group optionally mono- or di-substituted by $C_{1-6}$ alkyl group(s) (preferably, a methyl group) optionally substituted by $C_{6-10}$ aryl group(s) (preferably, a phenyl group),
(6) a 5- or 6-membered unsaturated heterocyclic group (preferably, an isoxazolyl group) optionally substituted by $C_{1-6}$ alkyl group(s) (preferably, a methyl group),
(7) a 5- or 6-membered saturated heterocyclic group (preferably, a tetrahydrofuryl group, a tetrahydropyranyl group, a pyrrolidinyl group, a piperidyl group) optionally substituted by 1 to 3 substituents selected from
(a) a $C_{1-6}$ alkyl group (preferably, a methyl group),
(b) a $C_{1-6}$ alkyl-carbonyl group (preferably, an acetyl group), and
(c) an oxo group,
(8) a $C_{3-6}$ cycloalkyloxy group (preferably, a cyclohexyloxy group), or
(9) a $C_{6-10}$ aryl-carbonyl group (preferably, a benzoyl group), or
$R^{7'}$ and $R^{8'}$ form, together with the nitrogen atom and carbon atom they are bonded to, a 5- or 6-membered cyclic amine substituted by an oxo group (preferably, 2-oxopyrrolidine, 2-oxopiperidine, 2-oxooxazolidine) and optionally further substituted by 1 to 3 substituents selected from
(a) a hydroxy group,
(b) a $C_{1-6}$ alkyl group (preferably, a methyl group) optionally substituted by hydroxy group(s),
(c) a $C_{1-6}$ alkoxy group (preferably, a methoxy group), and
(d) a $C_{3-6}$ cycloalkyl group (preferably, a cyclohexyl group)
is preferable.

Among the above, a compound wherein
$R^{1'}$ is
(1) a hydrogen atom,
(2) a hydroxy group, or
(3) a $C_{1-6}$ alkoxy group (preferably, a methoxy group, an isopropoxy group) optionally substituted by $C_{6-10}$ aryl group(s) (preferably, a phenyl group);
$R^{2'}$ and $R^{3'}$ are the same or different and each is
(1) a hydrogen atom, or
(2) a $C_{1-6}$ alkyl group (preferably, a methyl group) optionally substituted by 1 to 3 substituents selected from
(a) a hydroxy group, and
(b) a $C_{1-6}$ alkoxy group (preferably, a methoxy group);
$R^{4'}$ is

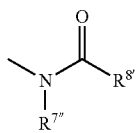

which is bonded to the 6-position of the indole ring, wherein
$R^{7''}$ is a $C_{1-6}$ alkyl group (preferably, a methyl group, an ethyl group, a propyl group) optionally substituted by 1 to 3 substituents selected from
(a) a hydroxy group,
(b) a $C_{1-6}$ alkoxy group (preferably, a methoxy group), and
(c) an amino group optionally mono- or di-substituted by $C_{1-6}$ alkyl group(s) (preferably, a methyl group), and
$R^{8'}$ is
(1) a $C_{1-6}$ alkyl group (preferably, a methyl group, an ethyl group, a propyl group, an isopropyl group, an isobutyl group, a tert-butyl group, a neopentyl group) optionally substituted by 1 to 3 substituents selected from
(a) a hydroxy group,
(b) a $C_{1-6}$ alkoxy group (preferably, a methoxy group, an ethoxy group, a propoxy group, an isopropoxy group) optionally substituted by $C_{6-10}$ aryl group(s) (preferably, a phenyl group),
(c) a $C_{3-6}$ cycloalkyl group (preferably, a cyclopentyl group, a cyclohexyl group) optionally substituted by $C_{1-6}$ alkoxy group(s) (preferably, a methoxy group),
(d) a $C_{6-10}$ aryl group (preferably, a phenyl group),
(e) a 5- or 6-membered unsaturated heterocyclic group (preferably, imidazolyl group, dihydropyridyl group, a pyrazolyl group) optionally substituted by oxo group(s),
(f) a 5- to 8-membered saturated heterocyclic group (preferably, a tetrahydrofuryl group, a tetrahydropyranyl group, a pyrrolidinyl group, a piperidyl group, an azepanyl group, an azocanyl group, a morpholinyl group, a 1,1-dioxideisothiazolidinyl group, an oxazolidinyl group, an imidazolidinyl group) optionally substituted by 1 to 3 substituents selected from
(i) a hydroxy group,
(ii) a $C_{1-6}$ alkyl group (preferably, a methyl group) optionally substituted by 1 to 3 substituents selected from a hydroxy group and a $C_{1-6}$ alkoxy group (preferably, a methoxy group),
(iii) a $C_{1-6}$ alkoxy group (preferably, a methoxy group), and
(iv) an oxo group,
(g) a $C_{3-6}$ cycloalkyloxy group (preferably, a cyclopentyloxy group),
(h) a $C_{6-10}$ aryloxy group (preferably, a phenoxy group),
(i) a 5- or 6-membered unsaturated heterocyclyloxy group (preferably, a pyridyloxy group),
(j) a 5- or 6-membered saturated heterocyclyloxy group (preferably, a tetrahydrofuryloxy group, a tetrahydropyranyloxy group), and
(k) an amino group optionally mono- or di-substituted by substituents selected from
(i) a $C_{1-6}$ alkyl group (preferably, a methyl group),
(ii) a $C_{1-6}$ alkyl-carbonyl group (preferably, an acetyl group, a propanoyl group, a 2-methylpropanoyl group, a 2,2-dimethylpropanoyl group, a 3-methylbutanoyl group) optionally substituted by 1 to 3 substituents selected from a hydroxy group and a $C_{1-6}$ alkoxy group (preferably, a methoxy group),
(iii) a $C_{1-6}$ alkoxy-carbonyl group (preferably, a methoxycarbonyl group, a tert-butoxycarbonyl group) optionally substituted by $C_{6-10}$ aryl group(s) (preferably, a phenyl group), and
(iv) a $C_{3-6}$ cycloalkyl-carbonyl group (preferably, a cyclopropylcarbonyl group, a cyclohexylcarbonyl group) optionally substituted by $C_{1-6}$ alkoxy group(s) (preferably, a methoxy group), (2) a $C_{1-6}$ alkoxy group (preferably, a methoxy group) optionally substituted by $C_{6-10}$ aryl group(s) (preferably, a phenyl group), (3) a $C_{3-6}$ cycloalkyl group (preferably, a cyclopentyl group, a cyclohexyl group) optionally substituted by 1 to 3 substituents selected from
   (a) a hydroxy group, and
   (b) a $C_{1-6}$ alkoxy group (preferably, a methoxy group), (4) a $C_{6-10}$ aryl group (preferably, a phenyl group) optionally substituted by $C_{1-6}$ alkyl group(s) (preferably, a methyl group) optionally substituted by 1 to 3 halogen atoms (preferably, a fluorine atom), (5) an amino group optionally mono- or di-substituted by $C_{1-6}$ alkyl group(s) (preferably, a methyl group) optionally substituted by $C_{6-10}$ aryl group(s) (preferably, a phenyl group), (6) a 5- or 6-membered unsaturated heterocyclic group (preferably, an isoxazolyl group) optionally substituted by $C_{1-6}$ alkyl group(s) (preferably, a methyl group), (7) a 5- or 6-membered saturated heterocyclic group (preferably, a tetrahydrofuryl group, a tetrahydropyranyl group, a pyrrolidinyl group, a piperidyl group) optionally substituted by 1 to 3 substituents selected from
   (a) a $C_{1-6}$ alkyl group (preferably, a methyl group),
   (b) a $C_{1-6}$ alkyl-carbonyl group (preferably, an acetyl group), and
   (c) an oxo group, (8) a $C_{3-6}$ cycloalkyloxy group (preferably, a cyclohexyloxy group), or (9) a $C_{6-10}$ aryl-carbonyl group (preferably, a benzoyl group), or $R^{7''}$ and $R^{8'}$ form, together with the nitrogen atom and carbon atom they are bonded to, a 5- or 6-membered cyclic amine substituted by an oxo group (preferably, 2-oxopyrrolidine, 2-oxopiperidine, 2-oxooxazolidine) and optionally further substituted by 1 to 3 substituents selected from
   (a) a hydroxy group,
   (b) a $C_{1-6}$ alkyl group (preferably, a methyl group) optionally substituted by hydroxy group(s),
   (c) a $C_{1-6}$ alkoxy group (preferably, a methoxy group), and
   (d) a $C_{3-6}$ cycloalkyl group (preferably, a cyclohexyl group), that is, a compound represented by the above-mentioned formula [I'-a] is particularly preferable.

A pharmaceutically acceptable salt of compound [I] may be any salt as long as it forms a nontoxic salt with the compound of the present invention, and examples thereof include salts with inorganic acid, salts with organic acid, salts with inorganic base, salts with organic base, salts with amino acid and the like.

Examples of the salts with inorganic acid include salts with hydrochloric acid, nitric acid, sulfuric acid, phosphoric acid, hydrobromic acid and the like.

Examples of the salts with organic acid include salts with oxalic acid, maleic acid, citric acid, fumaric acid, lactic acid, malic acid, succinic acid, tartaric acid, acetic acid, trifluoroacetic acid, gluconic acid, ascorbic acid, methanesulfonic acid, benzenesulfonic acid, p-toluenesulfonic acid and the like.

Examples of the salts with inorganic base include sodium salt, potassium salt, calcium salt, magnesium salt, ammonium salt and the like.

Examples of the salts with organic base include salts with methylamine, diethylamine, trimethylamine, triethylamine, ethanolamine, diethanolamine, triethanolamine, ethylenediamine, tris(hydroxymethyl)methylamine, dicyclohexylamine, N,N'-dibenzylethylenediamine, guanidine, pyridine, picoline, choline, cinchonine, meglumine and the like.

Examples of the salts with amino acid include salts with lysine, arginine, aspartic acid, glutamic acid and the like.

When a salt of compound [I] is desired, each salt can be obtained by reacting compound [I] with inorganic base, organic base, inorganic acid, organic acid or amino acid according to a known method.

The "solvate" is compound [I] or a pharmaceutically acceptable salt thereof, which is coordinated with a solvent molecule, and also encompasses hydrates. The solvate is preferably a pharmaceutically acceptable solvate, examples thereof include a hydrate, ethanolate, dimethyl sulfoxidate and the like of compound [I] or a pharmaceutically acceptable salt thereof. Specific examples include semihydrate, 1 hydrate, 2 hydrate or 1 ethanolate of compound [I], 1 hydrate of sodium salt or 2/3 ethanolate of 2 hydrochloride of compound [I], and the like.

The solvates can be obtained by a known method.

In addition, various "isomers" are present in a compound represented by the formula [I]. For example, cis form and trans form are present as geometric isomers, and when an asymmetric carbon atom is present, enantiomers and diastereomers are present as stereoisomers due to the asymmetric carbon atom. Furthermore, when axis asymmetry is present, stereoisomers are present due to the axis asymmetry. Tautomers can also be present in some cases.

Alternatively, stereoisomers derived from the direction of an unshared electron pair on nitrogen atom may also be present. Therefore, all of these isomers and mixtures thereof are encompassed in the scope of the present invention.

In addition, compound [I] may be labeled with isotope (e.g., $^3H$, $^{14}C$, $^{35}S$ etc.).

A deuterium converter obtained by converting $^1H$ of compound [I] to $^2H$ (D) is also encompassed in a compound represented by the formula [I].

As compound [I] or a pharmaceutically acceptable salt thereof or a solvate thereof, substantially purified compound [I] or a pharmaceutically acceptable salt thereof or a solvate thereof is preferable. More preferred is compound [I] or a pharmaceutically acceptable salt thereof or a solvate thereof, which is purified to have a purity of more than 80%.

In the present invention, a prodrug of compound [I] or a pharmaceutically acceptable salt thereof, or a solvate thereof (hereinafter to be sometimes abbreviated as the compound of the present invention) can also be a useful medicament. The "prodrug" is a derivative of the compound of the present invention having a chemically or metabolically degradable group which, after administration to the body, restores to the original compound by, for example, hydrolysis, solvolysis or decomposition under physiological conditions, and shows inherent efficacy. It includes a noncovalent complex, and a salt. Prodrug is utilized for, for example, improvement of absorption on oral administration, or targeting to a target moiety.

Examples of the modified moiety include, in the compound of the present invention, a highly reactive functional group such as a hydroxyl group, a carboxyl group, an amino group and the like.

Specific examples of the hydroxyl-modifying group include an acetyl group, a propanonyl group, a 2-methylpropanoyl group, a 2,2-dimethylpropanoyl group, a palmitoyl group, a benzoyl group, a 4-methylbenzoyl group, a dimethylcarbamoyl group, dimethylaminomethylcarbonyl group, a sulfo group, an alanyl group, a fumaryl group, a 3-carboxybenzoyl group, a 2-carboxyethylcarbonyl group, a 3-sodium carboxylatobenzoyl group and the like.

Specific examples of the carboxyl-modifying group include a methyl group, an ethyl group, a propanoyl group, a 2-methylpropanoyl group, a butyl group, an isobutyl group, a tert-butyl group, a 2,2-dimethylpropanoyloxymethyl group, a carboxymethyl group, a dimethylaminomethyl group, a 1-(acetyloxy)ethyl group, a 1-(ethoxycarbonyloxy)ethyl group, a 1-(isopropyloxycarbonyloxy)ethyl group, a 1-(cyclohexyloxycarbonyloxy)ethyl group, a (5-methyl-2-oxo-1, 3-dioxol-4-yl)methyl group, a benzyl group, a phenyl group, an o-tolyl group, a morpholinoethyl group, an N,N-diethylcarbamoylmethyl group, a phthalidyl group and the like.

Specific examples of the amino-modifying group include a tert-butyl group, a docosanoyl group, a 2,2-dimethylpropanoylmethyloxy group, an alanyl group, a hexylcarbamoyl group, a pentylcarbamoyl group, a 3-methylthio-1-(acetylamino)propylcarbonyl group, a 1-sulfo-1-(3-ethoxy-4-hydroxyphenyl)methyl group, a (5-methyl-2-oxo-1,3-dioxol-4-yl)methyl group, a (5-methyl-2-oxo-1,3-dioxol-4-yl) methoxycarbonyl group, a tetrahydrofuranyl group, a pyrrolidylmethyl group and the like.

When the indole compound of the present invention is used as a medicament, particularly a pharmaceutical composition, a chemically stable compound is preferable.

Examples of the "pharmaceutical composition" include oral preparations such as tablet, capsule, granule, powder, troche, syrup, emulsion, suspension and the like, and parenteral agents such as external preparation, suppository, injection, eye drop, nasal preparations, pulmonary preparation and the like.

The pharmaceutical composition of the present invention is produced according to a method known in the art of pharmaceutical preparations, by mixing etc. the compound of the present invention with a suitable amount of at least one kind of pharmaceutically acceptable carrier and the like as appropriate. While the content of the compound of the present invention in the pharmaceutical composition varies depending on the dosage form, dose and the like, it is, for example, 0.1 to 100 wt % of the whole composition.

Examples of the "pharmaceutically acceptable carrier" include various organic or inorganic carrier substances conventionally used as preparation materials, for example, excipient, disintegrant, binder, glidant, lubricant and the like for solid preparations, and solvent, solubilizing agent, suspending agent, isotonicity agent, buffering agent, soothing agent and the like for liquid preparations. Where necessary, moreover, additives such as preservative, antioxidant, colorant, sweetening agent and the like are used.

Examples of the "excipient" include lactose, sucrose, D-mannitol, D-sorbitol, cornstarch, dextrin, microcrystalline cellulose, crystalline cellulose, carmellose, carmellose calcium, sodium carboxymethyl starch, low-substituted hydroxypropylcellulose, gum arabic and the like.

Examples of the "disintegrant" include carmellose, carmellose calcium, carmellose sodium, sodium carboxymethyl starch, croscarmellose sodium, crospovidone, low-substituted hydroxypropylcellulose, hydroxypropylmethylcellulose, crystalline cellulose and the like.

Examples of the "binder" include hydroxypropylcellulose, hydroxypropylmethylcellulose, povidone, crystalline cellulose, sucrose, dextrin, starch, gelatin, carmellose sodium, gum arabic and the like.

Examples of the "glidant" include light anhydrous silicic acid, magnesium stearate and the like.

Examples of the "lubricant" include magnesium stearate, calcium stearate, talc and the like.

Examples of the "solvent" include purified water, ethanol, propylene glycol, macrogol, sesame oil, corn oil, olive oil and the like.

Examples of the "solubilizing agents" include propylene glycol, D-mannitol, benzyl benzoate, ethanol, triethanolamine, sodium carbonate, sodium citrate and the like.

Examples of the "suspending agent" include benzalkonium chloride, carmellose, hydroxypropylcellulose, propylene glycol, povidone, methylcellulose, glycerol monostearate and the like.

Examples of the "isotonicity agent" include glucose, D-sorbitol, sodium chloride, D-mannitol and the like.

Examples of the "buffering agent" include sodium hydrogenphosphate, sodium acetate, sodium carbonate, sodium citrate and the like.

Examples of the "soothing agent" include benzyl alcohol and the like.

Examples of the "preservative" include ethyl parahydroxybenzoate, chlorobutanol, benzyl alcohol, sodium dehydroacetate, sorbic acid and the like.

Examples of the "antioxidant" include sodium sulfite, ascorbic acid and the like.

Examples of the "colorant" include food colors (e.g., Food Color Red No. 2 or 3, Food Color Yellow No. 4 or 5 etc.), β-carotene and the like.

Examples of the "sweetening agent" include saccharin sodium, dipotassium glycyrrhizinate, aspartame and the like.

The pharmaceutical composition of the present invention can be administered orally or parenterally (e.g., topical, rectal, intravenous administration etc.) to human as well as mammals other than human (e.g., mouse, rat, hamster, guinea pig, rabbit, cat, dog, swine, bovine, horse, sheep, monkey etc.). The dose varies depending on the subject of administration, disease, symptom, dosage form, administration route and the like. For example, the daily dose for oral administration to an adult patient (body weight: about 60 kg) is generally within the range of about 1 mg to 1 g, based on compound [I] as the active ingredient. This amount can be administered in one to several portions.

The compound of the present invention has an inducible T cell kinase (ITK)-inhibitory activity. Therefore, the compound of the present invention can be used as an active ingredient of an agent for the treatment or prophylaxis of inflammatory diseases, an agent for the treatment or prophylaxis of allergic diseases, an agent for the treatment or prophylaxis of autoimmune diseases, an inhibitor of rejection in transplantation and the like.

To "inhibit ITK" or "has ITK inhibitory activity" means to inhibit the function of ITK to eliminate or attenuate the activity or have such activity. For example, it means to measure the ITK inhibitory activity based on the conditions in the below-mentioned Experimental Example 1, and administer a compound having an inhibitory activity to a mammal inclusive of human to inhibit the function of ITK. To "inhibit ITK" preferably means to "inhibit human ITK". The "ITK inhibitor" is preferably a "human ITK inhibitor".

While the inflammatory disease is not particularly limited, examples thereof include rheumatoid arthritis, inflammatory bowel disease and the like.

While the allergic disease is not particularly limited, examples thereof include atopic dermatitis, asthma, allergic rhinitis and the like.

While the autoimmune disease is not particularly limited, examples thereof include rheumatoid arthritis, systemic lupus erythematosus, psoriasis, inflammatory bowel disease and the like.

The compound of the present invention can be used in combination with one or a plurality of other medicaments (hereinafter to be also referred to as a concomitant drug) according to a method generally employed in the medical field (hereinafter to be referred to as combined use).

The administration period of the compound of the present invention and a concomitant drug is not limited, and they may be administered to an administration subject as combination preparation, or the both preparations may be administered simultaneously or at given intervals as individual preparations. In addition, the pharmaceutical composition of the present invention and a concomitant drug may be used in the form of a kit. The dose of the concomitant drug is similar to the clinically-employed dose and can be appropriately selected according to the subject of administration, disease, symptom, dosage form, administration route, administration time, combination and the like. The administration form of the concomitant drug is not particularly limited, and it only needs to be combined with the compound of the present invention.

Next, one example of the production methods of the compound to practice the present invention is explained below. However, the production method of the compound of the present invention is not limited thereto.

Even if no directly corresponding disclosure is found in the following Production Methods, the steps may be modified for efficient production of the compound, such as introduction of a protecting group into a functional group with deprotection in a subsequent step, subjecting a functional group as a precursor to each step, followed by conversion to a desired functional group at a suitable stage, changing the order of Production Methods and steps, and the like.

The treatment after reaction in each step may be conventional ones, where isolation and purification can be performed as necessary according to a method appropriately selected from conventional methods such as crystallization, recrystallization, distillation, partitioning, silica gel chromatography, preparative HPLC and the like, or a combinatin of those methods.

Production Method 1

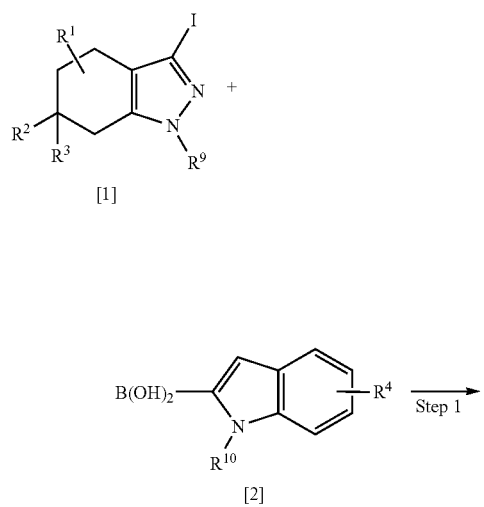

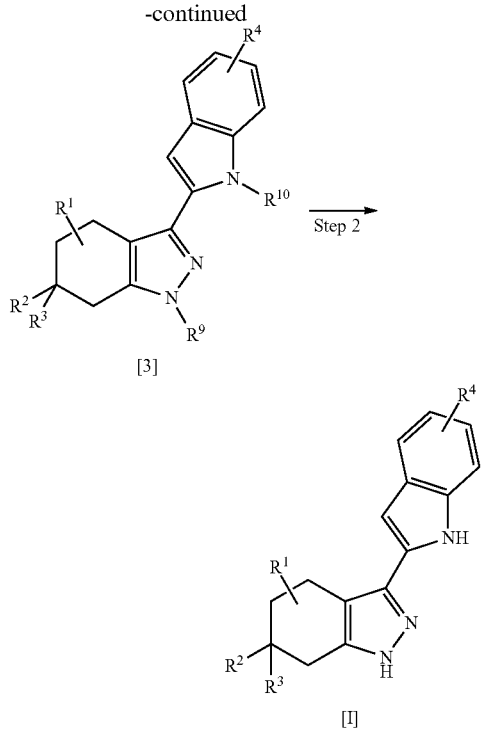

wherein $R^9$ and $R^{10}$ are the same or different and each is an amino-protecting group; and other symbols are as defined above.

Examples of the "amino-protecting group" for $R^9$ or $R^{10}$ include a tert-butoxycarbonyl group, an ethoxycarbonyl group, a trityl group, a tetrahydropyranyl group, a methoxymethyl group, a 2-(trimethylsilyl)ethoxymethyl group, a p-toluenesulfonyl group and the like, with preference given to a tert-butoxycarbonyl group.

(Step 1)

Compound [3] can be obtained by subjecting compound [1] and compound [2] to the Suzuki coupling reaction. For example, compound [3] can be obtained by reacting compound [1] with compound [2] in a solvent under heating in the presence of a base and a palladium catalyst. The reaction is preferably performed by gradually adding compound [2] in the presence of all other reagents under heating.

Examples of the palladium catalyst to be used for the reaction include tetrakistriphenylphosphinepalladium, (bis (diphenylphosphino)ferrocene)palladium dichloride-methylene chloride complex and the like.

Examples of the base to be used for the reaction include potassium phosphate, sodium carbonate, sodium hydrogen carbonate, potassium carbonate, triethylamine and the like.

Preferable examples of the solvent to be used for the reaction include ether solvents such as 1,4-dioxane, tetrahydrofuran, diethyl ether, 1,2-dimethoxyethane and the like; alcohol solvents such as methanol, ethanol, n-propanol, isopropanol and the like; hydrocarbon solvents such as toluene, hexane, xylene and the like; polar solvents such as N,N-dimethylformamide, dimethyl sulfoxide, acetonitrile and the like; and a mixed solvent thereof with water.

Compound [1] and compound [2] may be commercially available products, or can be obtained according to the following production methods 2 and 3, or a conventional method.

(Step 2)

Compound [I] can be obtained by removing $R^9$ and $R^{10}$ of compound [3] by a general deprotection reaction. The deprotection reaction may be performed under conditions suitable for the kinds or a combination of $R^9$ and $R^{10}$. For example, when both $R^9$ and $R^{10}$ are tert-butoxycarbonyl groups, compound [I] can be obtained by treating compound [3] in a solvent in the presence of a base at room temperature.

Examples of the base to be used for the reaction include sodium hydroxide, lithium hydroxide, sodium carbonate and the like.

Preferable examples of the solvent to be used for the reaction include ether solvents such as 1,4-dioxane, tetrahydrofuran and the like; alcohol solvents such as methanol, ethanol, n-propanol, isopropanol and the like; polar solvents such as N,N-dimethylformamide, dimethyl sulfoxide, acetonitrile and the like; and a mixed solvent thereof with water.

Production Method 2

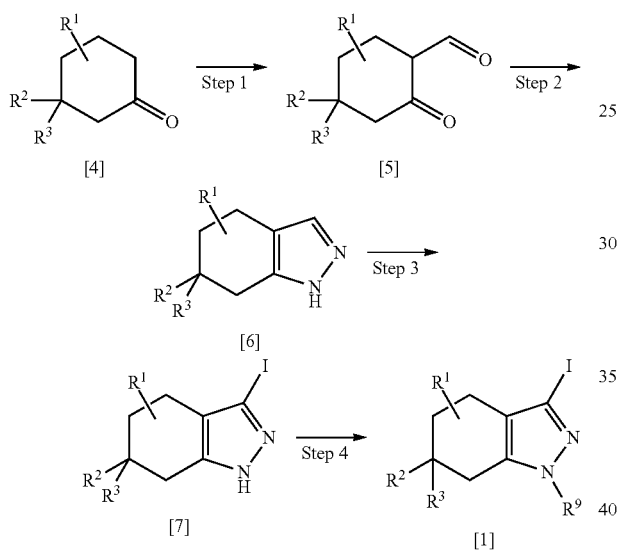

wherein each symbol is as defined above.

(Step 1)

Compound [5] can be obtained by reacting compound [4] with ethyl formate in a solvent in the presence of a base.

Examples of the base to be used for the reaction include sodium hydride, potassium tert-butoxide, sodium hydroxide, potassium hydroxide, sodium methoxide, sodium ethoxide, lithium diisopropylamide, lithium hexamethyl disilazide and the like.

Preferable examples of the solvent to be used for the reaction include ether solvents such as 1,4-dioxane, tetrahydrofuran, diethyl ether, 1,2-dimethoxyethane and the like; alcohol solvents such as methanol, ethanol, n-propanol, isopropanol and the like; and polar solvents such as N,N-dimethylformamide, dimethyl sulfoxide, acetonitrile and the like.

Compound [4] may be a commercially available product, or can be obtained by a conventional method.

(Step 2)

Compound [6] can be obtained by reacting compound [5] with hydrazine in a solvent at a temperature of from room temperature to under heating. This step is sometimes preferably performed from room temperature to under heating. In addition, an acid may be used as necessary for the reaction.

Preferable examples of the solvent to be used for the reaction include alcohol solvents such as methanol, ethanol, n-propanol, isopropanol and the like; and polar solvents such as N,N-dimethylformamide, dimethyl sulfoxide, acetonitrile and the like.

Examples of the acid to be used for the reaction include hydrochloric acid, sulfuric acid, p-toluenesulfonic acid, pyridium p-toluenesulfonate and the like.

(Step 3)

Compound [7] can be obtained by reacting compound [6] with iodine in a solvent in the presence of a base at a temperature from room temperature to under heating.

Examples of the base to be used for the reaction include potassium hydroxide, sodium hydroxide, potassium carbonate, sodium carbonate and the like.

Preferable examples of the solvent to be used for the reaction include ether solvents such as 1,4-dioxane, tetrahydrofuran and the like; alcohol solvents such as methanol, ethanol, n-propanol, isopropanol and the like; polar solvents such as N,N-dimethylformamide, dimethyl sulfoxide, acetonitrile and the like; and a mixed solvent thereof with water.

(Step 4)

Compound [1] can be obtained by introducing an amino-protecting group ($R^9$) into compound [7]. For example, when $R^9$ is a tert-butoxycarbonyl group, compound [1] can be obtained by reacting compound [7] with di-tert-butyl dicarbonate in a solvent from room temperature to under heating in the presence of a base.

Examples of the base to be used for the reaction include tertiary amines such as triethylamine, 4-dimethylaminopyridine and the like.

Preferable examples of the solvent to be used for the reaction include ether solvents such as 1,4-dioxane, tetrahydrofuran and the like; ester solvents such as ethyl acetate and the like; hydrocarbon solvents such as toluene, hexane, xylene and the like; and polar solvents such as N,N-dimethylformamide, dimethyl sulfoxide, acetonitrile and the like.

Production Method 3

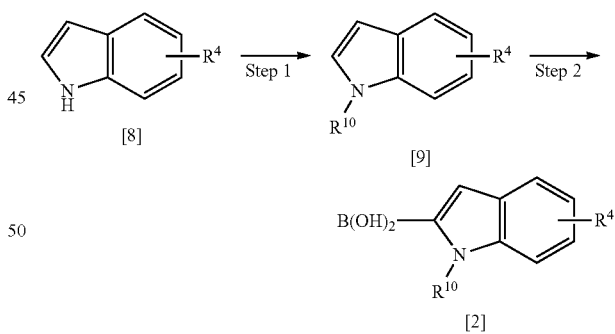

wherein each symbol is as defined above.

(Step 1)

Compound [9] can be obtained by introducing an amino-protecting group ($R^{10}$) into compound [8]. For example, when $R^{10}$ is a tert-butoxycarbonyl group, compound [9] can be obtained by reacting compound [8] with di-tert-butyl dicarbonate in a solvent from room temperature to under heating in the presence of a base.

Examples of the base to be used for the reaction include tertiary amines such as 4-dimethylaminopyridine, triethylamine and the like, with preference given to 4-dimethylaminopyridine.

Preferable examples of the solvent to be used for the reaction include ether solvents such as 1,4-dioxane, tetrahydrofuran and the like; ester solvents such as ethyl acetate and the like; hydrocarbon solvents such as toluene, hexane, xylene and the like; and polar solvents such as N,N-dimethylformamide, dimethyl sulfoxide, acetonitrile and the like.

Compound [8] may be a commercially available product, or can be obtained by a conventional method.

(Step 2)

Compound [2] can be obtained by reacting compound [9] with borate in a solvent under cooling in the presence of a base. The reaction is preferably performed by gradually adding dropwise a base under cooling in the presence of borate.

Examples of the borate to be used for the reaction include triisopropyl borate, trimethyl borate and the like.

Examples of the base to be used for the reaction include butyllithium, lithium diisopropylamide, lithium hexamethyl disilazide and the like.

Preferable examples of the solvent to be used for the reaction include ether solvents such as 1,4-dioxane, tetrahydrofuran, diethyl ether, 1,2-dimethoxyethane and the like.

Compound [I-b], which is compound [I] wherein $R^4$ is a group represented by

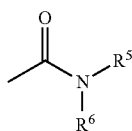

which is bonded to the 5-position or the 6-position of the indole ring, can also be produced according to the following production method 4 or 7.

Production Method 4

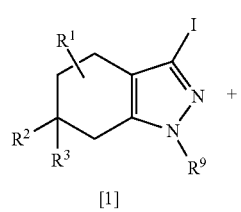

[1]

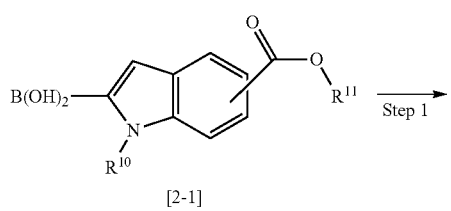

[2-1]

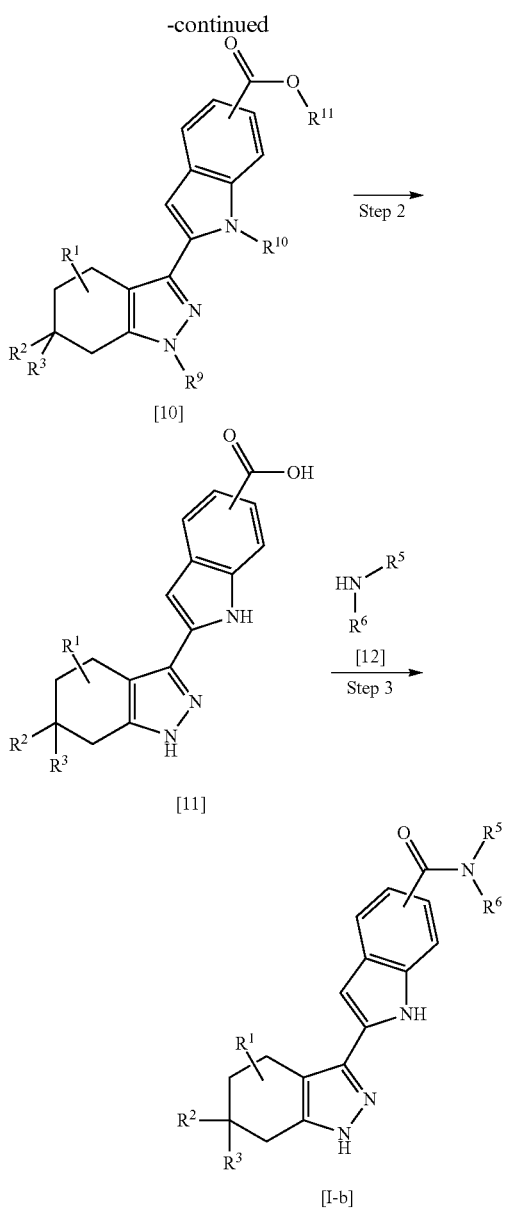

wherein $R^{11}$ is a carboxy-protecting group; and other symbols are as defined above.

Examples of the "carboxy-protecting group" for $R^{11}$ include an alkyl group such as a methyl group, an ethyl group, a tert-butyl group and the like, a tert-butyldimethylsilyl group, a benzyl group, a methoxyethoxymethyl group and the like.

(Step 1)

Compound [10] can be obtained in the same manner as in production method 1, from compound [1] and compound [2-1] obtained in the same manner as in production method 3.

(Step 2)

Compound [11] can be obtained by removing $R^{11}$ of compound [10] by a deprotection reaction. The deprotection reaction may be performed under conditions suitable for the kind of $R^{11}$. For example, when $R^{11}$ is an alkyl group, compound [11] can be obtained by hydrolyzing compound [10] in a solvent in the presence of a base at a temperature from room temperature to under heating, and acidifying the obtained solution.

Examples of the base to be used for the reaction include potassium carbonate, sodium carbonate, lithium hydroxide, sodium hydroxide, potassium hydroxide, lithium hydride, sodium hydride, potassium hydride and the like.

Preferable examples of the solvent to be used for the reaction include a mixed solvent of water with alcohol solvents such as methanol, ethanol, n-propanol, isopropanol and the like; and a mixed solvent thereof with ether solvents such as 1,4-dioxane, tetrahydrofuran and the like.

(Step 3)

Compound [I-b] can be obtained by reacting compound [11] with amine [12] in a solvent in the presence of a condensing agent at a temperature from cooling to heating. An activator may be used to smoothly perform the reaction.

Examples of the condensing agent to be used for the reaction include N,N'-carbonyldiimidazole, N,N'-dicyclohexylcarbodiimide, N,N'-diisopropylcarbodiimide, 1-ethyl-3-(3-dimethylaminopropyl)carbodiimide hydrochloride (EDC) and the like.

Examples of the activator to be used for the reaction include hydroxysuccinimide, 1-hydroxybenzotriazole and the like.

Preferable examples of the solvent to be used for the reaction include hydrocarbon solvents such as benzene, toluene, hexane, xylene and the like; halogenated solvents such as dichloromethane, chloroform, carbon tetrachloride, 1,2-dichloroethane and the like; ether solvents such as 1,4-dioxane, diethyl ether, 1,2-dimethoxyethane, tetrahydrofuran and the like; polar solvents such as N,N-dimethylformamide, dimethyl sulfoxide, acetonitrile and the like; pyridine; and a mixed solvent thereof.

Amine [12] may be a commercially available product, or can be obtained by a conventional method.

Compound [I-c], which is compound [I] wherein $R^4$ is a group represented by

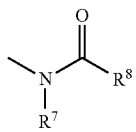

which is bonded to the 5-position or the 6-position of the indole ring, can also be produced by the following production method 5 or 6.

Production Method 5

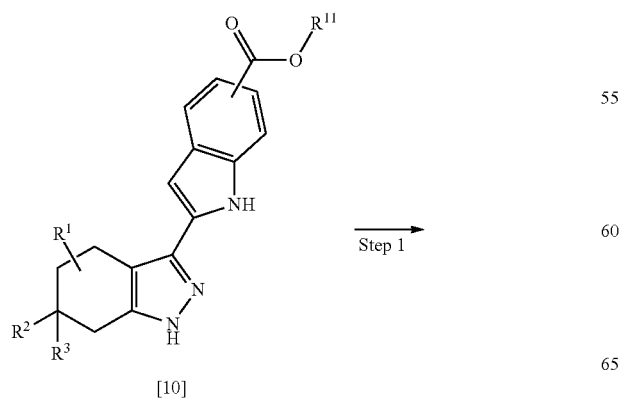

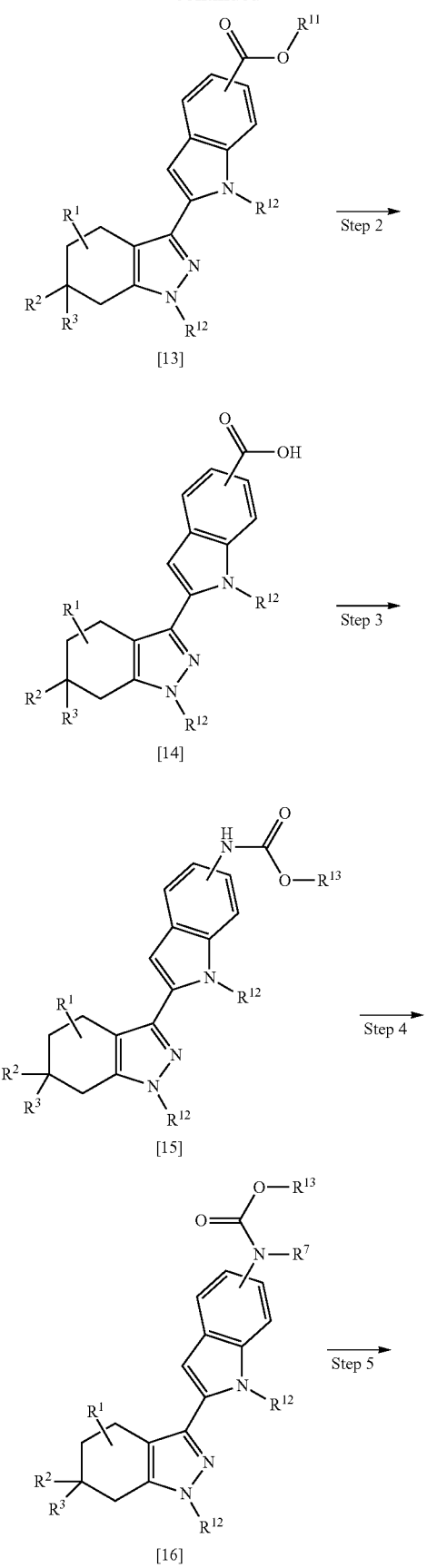

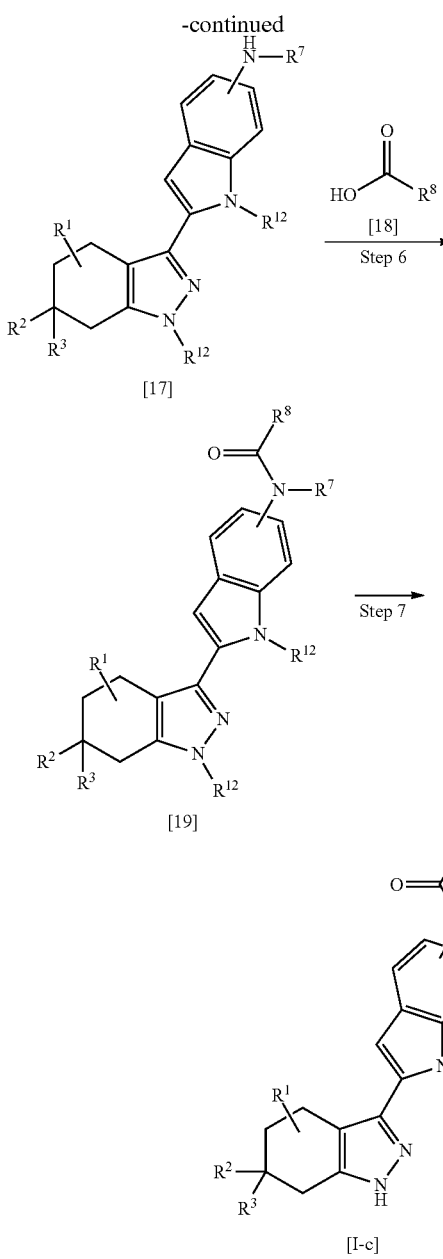

wherein $R^{12}$ is an amino-protecting group; $R^{13}$ is an alkyl group such as a methyl group, an ethyl group, a tert-butyl group and the like, a benzyl group and the like; and other symbols are as defined above.

Examples of the "amino-protecting group" for $R^{12}$ include a 2-(trimethylsilyl)ethoxymethyl group, a trityl group, a tetrahydropyranyl group, a methoxymethyl group, a p-toluenesulfonyl group and the like, with preference given to a 2-(trimethylsilyl)ethoxymethyl group.

(Step 1)

Compound [13] can be obtained by introducing an amino-protecting group ($R^{12}$) into compound [10]. For example, when $R^{12}$ is a 2-(trimethylsilyl)ethoxymethyl group, compound [13] can be obtained by reacting compound [10] with 2-(trimethylsilyl)ethoxymethyl chloride in a solvent under cooling in the presence of a base.

Examples of the base to be used for the reaction include sodium hydride and the like.

Examples of the solvent to be used for the reaction include ether solvents such as 1,4-dioxane, diethyl ether, 1,2-dimethoxyethane, tetrahydrofuran and the like; and polar solvents such as N,N-dimethylformamide, dimethyl sulfoxide, acetonitrile and the like.

(Step 2)

Compound [14] can be obtained by removing $R^{11}$ of compound [13]. The reaction can be performed in the same manner as in step 2 of production method 4.

(Step 3)

Compound [15] can be obtained by subjecting compound [14] to the Curtius rearrangement with diphenylphosphoryl azide to give the corresponding isocyanate, and reacting the obtained isocyanate with the corresponding alcohol ($R^{13}OH$). The Curtius rearrangement can also be performed by reacting the acid chloride of compound [14] with sodium azide to produce the corresponding acid azide, followed by heating. When the alcohol ($R^{13}OH$) is present in the Curtius rearrangement, isocyanate is immediately reacted with the alcohol to give compound [15]. For example, when $R^{13}$ is a benzyl group, compound [15] can be obtained by reacting compound [14] by dropwise addition of diphenylphosphoryl azide in a solvent under heating in the presence of benzyl alcohol and a tertiary amine.

Examples of the tertiary amine to be used for the reaction include triethylamine and the like.

Preferable examples of the solvent to be used for the reaction include hydrocarbon solvents such as benzene, toluene, hexane, xylene and the like; and ether solvents such as 1,4-dioxane, diethyl ether, 1,2-dimethoxyethane, tetrahydrofuran and the like.

(Step 4)

When $R^7$ is not a hydrogen atom, compound [16] can be obtained by introducing $R^7$ by reacting compound [15] with a corresponding alkylating agent in a solvent under ice-cooling to room temperature in the presence of a base.

The alkylating agent to be used for the reaction may be any as long as it can introduce $R^7$, and examples thereof include methyl iodide, ethyl iodide, benzyloxymethane chloride and the like.

Examples of the base to be used for the reaction include sodium hydride, butyllithium, lithium diisopropylamide, lithium hexamethyl disilazide and the like.

Preferable examples of the solvent to be used for the reaction include hydrocarbon solvents such as benzene, toluene, hexane, xylene and the like; ether solvents such as 1,4-dioxane, diethyl ether, 1,2-dimethoxyethane, tetrahydrofuran and the like; and polar solvents such as N,N-dimethylformamide, dimethyl sulfoxide, acetonitrile and the like.

When $R^7$ is a hydrogen atom, compound [15] can be directly subjected to step 5 without performing step 4.

(Step 5)

Compound [17] can be obtained by reducing compound [16] by a conventional method. For example, when $R^{13}$ is a benzyl group, compound [17] can be obtained by a conventional method such as catalytic reduction and the like. The catalytic reduction can be performed, for example, in a solvent in the presence of a metal catalyst from room temperature to heating at normal pressure to under pressurization and using a hydrogen gas. As a hydrogen source, ammonium formate, cyclohexene, dicyclohexene and the like may be used.

Examples of the metal catalyst to be used for the reaction include palladium carbon, palladium hydroxide, palladium black, Raney-nickel and the like.

Preferable examples of the solvent to be used for the reaction include alcohol solvents such as methanol, ethanol, n-propanol, isopropanol and the like; ether solvents such as 1,4-dioxane, tetrahydrofuran and the like; ester solvents such as ethyl acetate and the like; and a mixed solvent thereof.

(Step 6)

Compound [19] can be obtained by condensing compound [17] with compound [18] according to an amide condensation method generally used. For example, compound [18] is treated with a halogenating agent in a solvent at room temperature to give the corresponding acid halide. Then, the obtained acid halide is condensed with compound [17] in the presence of a tertiary amine or pyridine from cooling to room temperature to give compound [19].

Examples of the halogenating agent to be used for the reaction include oxalyl chloride, thionyl chloride, phosphorus oxychloride, phosphorus pentachloride and the like.

Examples of the tertiary amine to be used for the reaction include triethylamine and the like.

Preferable examples of the solvent to be used for the reaction include halogenated solvents such as dichloromethane, chloroform, carbon tetrachloride, 1,2-dichloroethane and the like; ether solvents such as 1,4-dioxane, diethyl ether, 1,2-dimethoxyethane, tetrahydrofuran and the like; and a mixed solvent thereof with water.

Compound [18] may be a commercially available product, or can be obtained according to a conventional method. When the corresponding acid halide is commercially available, it may also be used.

In addition, compound [19] can also be obtained by condensing compound [17] and compound [18] in the same manner as in step 3 of production method 4.

(Step 7)

Compound [I-c] can be obtained by removing $R^{12}$ of compound [19] by a deprotection reaction. The deprotection reaction may be performed using conditions suitable for the kind of $R^{12}$. For example, when $R^{12}$ is a 2-(trimethylsilyl) ethoxymethyl group, compound [I-c] can be obtained by reacting compound [19] in a solvent under heating in the presence of tetrabutylammonium fluoride and ethylenediamine.

Preferable examples of the solvent to be used for the reaction include ether solvents such as 1,4-dioxane, tetrahydrofuran and the like; and polar solvents such as N,N-dimethylformamide, dimethyl sulfoxide, acetonitrile and the like.

Production Method 6

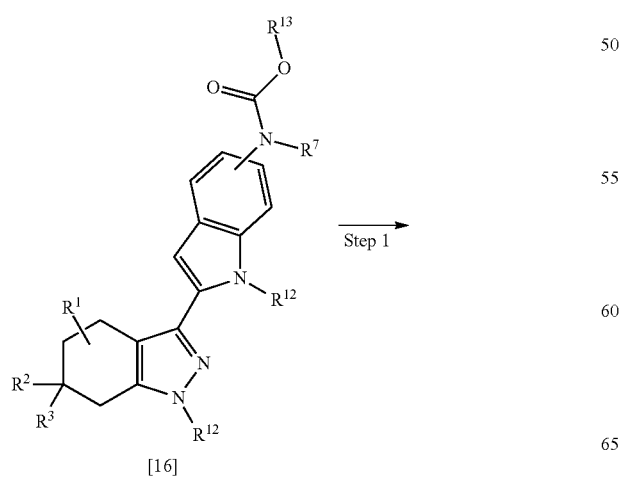

[16]

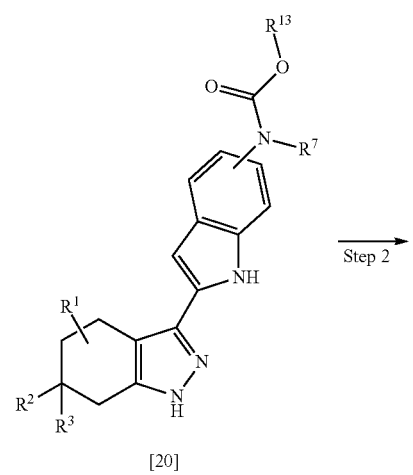

[20]

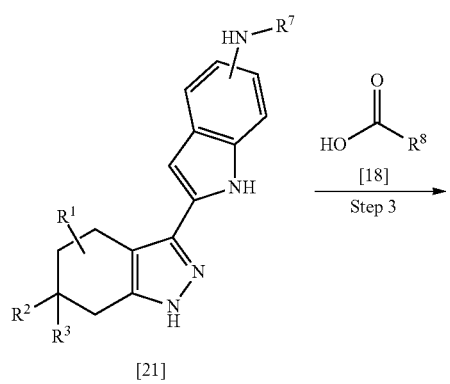

[21]

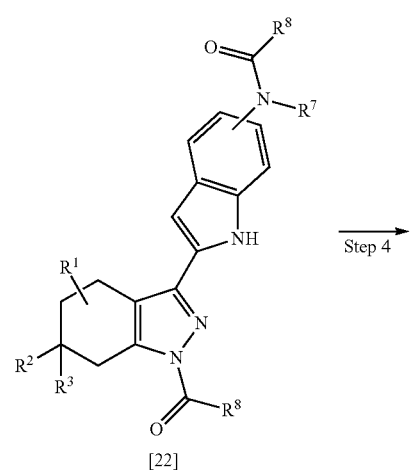

[22]

-continued

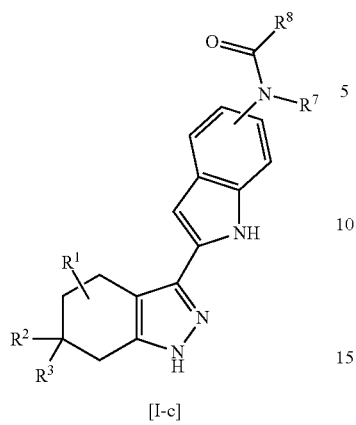

[I-c]

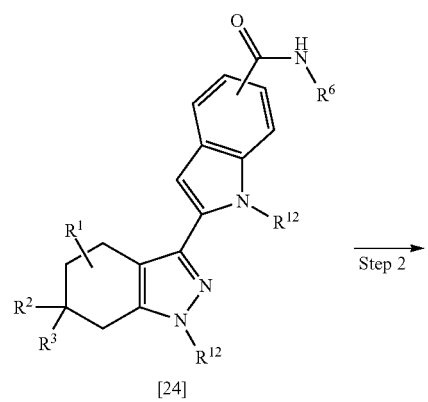

[24]

wherein each symbol is as defined above.

(Step 1)
Compound [20] can be obtained by removing $R^{12}$ of compound [16] obtained in step 4 of production method 5. The reaction can be performed in the same manner as in step 7 of production method 5.

(Step 2)
Compound [21] can be obtained by subjecting compound [20] to a reduction reaction. The reaction can be performed in the same manner as in step 5 of production method 5.

(Step 3)
Compound [22] can be obtained by condensing compound [21] % and compound [18]. The reaction can be performed in the same manner as in step 6 of production method 5.

Alternatively, compound [I-c] is sometimes directly obtained by the above-mentioned reaction without performing step 4.

(Step 4)
Compound [I-c] can be obtained from compound [22] by removing an acyl group on the pyrazole ring. For example, compound [I-c] can be obtained by hydrolyzing compound [22] in a solvent from room temperature to heating in the presence of a base.

Examples of the base to be used for the reaction include potassium carbonate, sodium carbonate, lithium hydroxide, sodium hydroxide, potassium hydroxide, lithium hydride, sodium hydride, potassium hydride and the like.

Examples of the solvent to be used for the reaction include aqueous alcohol solvents such as methanol, ethanol, n-propanol, isopropanol and the like; and a mixed solvent thereof with ether solvents such as 1,4-dioxane, tetrahydrofuran and the like.

ProductionMethod 7

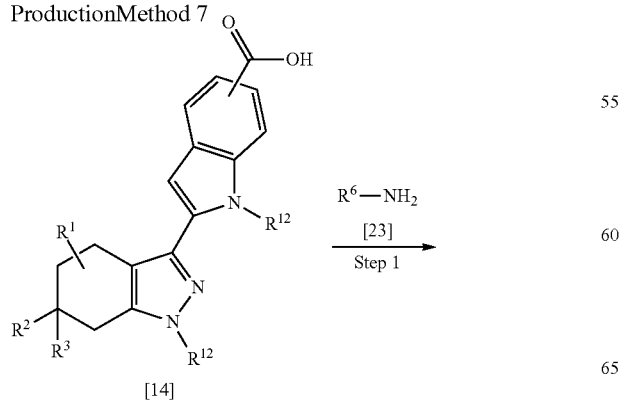

[14]

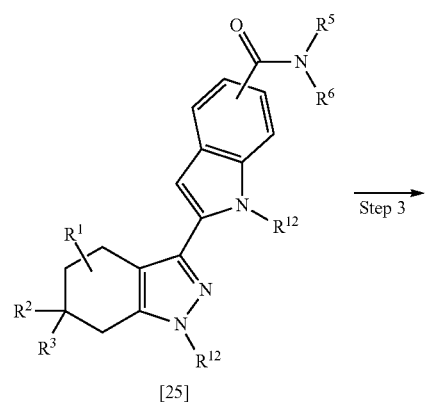

[25]

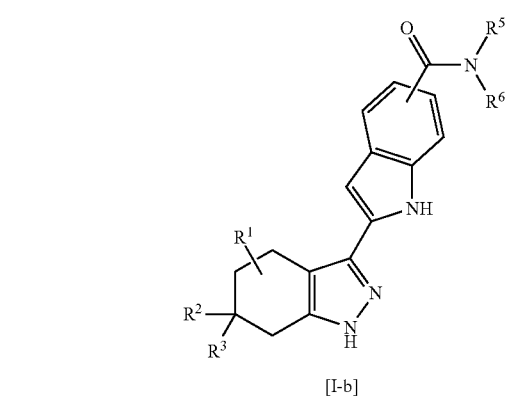

[I-b]

(Step 1)
Compound [24] can be obtained by condensing compound [14] obtained in step 2 of production method 5 with amine [23]. The reaction can be performed in the same manner as in step 3 of production method 4.

(Step 2)

Compound [25] can be obtained by reacting compound [23] with the corresponding alkylating agent to introduce $R^5$. The reaction can be performed in the same manner as in step 4 of production method 5.

(Step 3)

Compound [I-b] can be obtained by removing $R^{12}$ of compound [25] by a deprotection reaction. The reaction can be performed in the same manner as in step 7 of production method 5.

EXAMPLES

The present invention is explained in detail in the following by referring to Reference Examples, Examples and Experimental Example, which are not to be construed as limitative.

The room temperature in Reference Examples and Examples means 1-40° C.

Reference Example 1

Production of tert-butyl 3-iodo-6,6-dimethyl-4,5,6,7-tetrahydroindazole-1-carboxylate (Step 1)

Production of 3-iodo-6,6-dimethyl-4,5,6,7-tetrahydro-1H-indazle

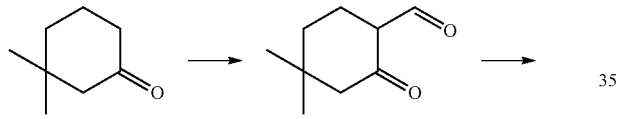

Under a nitrogen atmosphere, to a suspension of sodium hydride (28 g, 697 mmol) in tetrahydrofuran (500 ml) was added dropwise a solution of 3,3-dimethylcyclohexanone (80 g, 634 mmol) in tetrahydrofuran (250 ml) under ice-cooling over about 1 hr, and the mixture was stirred for 1 hr. Then, a solution of ethyl formate (99 g, 1.3 mol) in tetrahydrofuran (250 ml) was added dropwise over about 1 hr, and the mixture was stirred under ice-cooling for 1 hr, and at room temperature for 1 hr. To the reaction mixture were added water and ethyl acetate, and the organic layer was separated and extracted with 2 N aqueous sodium hydroxide solution. The aqueous layer was acidified with concentrated hydrochloric acid, and extracted with ethyl acetate. Then, the organic layer was washed with saturated brine, and dried over sodium sulfate. Sodium sulfate was removed by filtration, and the filtrate was concentrated under reduced pressure to give 4,4-dimethyl-2-oxocyclohexanecarbaldehyde. To a solution of the obtained 4,4-dimethyl-2-oxocyclohexanecarbaldehyde in methanol (376 ml) was added dropwise a solution of hydrazine monohydrate (31 ml, 640 mmol) in methanol (31 ml) with heating under reflux over about 1 hr, and the mixture was stirred for 15 min. The reaction mixture was concentrated under reduced pressure, ethyl acetate and water were added, and the organic layer was separated. Then, the organic layer was washed with saturated brine, and dried over sodium sulfate. Sodium sulfate was removed by filtration, and the filtrate was concentrated under reduced pressure to give 6,6-dimethyl-4,5,6,7-tetrahydro-1H-indazole. To a solution of the obtained 6,6-dimethyl-4,5,6,7-tetrahydro-1H-indazole in N,N-dimethylformamide (1.4 L) were added iodine (232 g, 915 mmol) and potassium hydroxide (121 g, 1.8 mol) at room temperature, and the mixture was stirred for about 4 hr. Then, under ice-cooling, an aqueous solution (800 ml) of sodium hydrogensulfite (80 g) was added dropwise. Water (2 L) was added, and the mixture was extracted with ethyl acetate. The organic layer was washed successively with water and saturated brine, and dried over sodium sulfate. Sodium sulfate was removed by filtration, and the filtrate was concentrated under reduced pressure. Then, hexane (350 ml) was added to the residue, and the mixture was stirred at room temperature. The precipitated crystals were collected by filtration, washed with hexane, and dried under reduced pressure to give 3-iodo-6,6-dimethyl-4,5,6,7-tetrahydro-1H-indazole (41 g, yield 23%).

$^1$H-NMR (400 MHz, DMSO-$d_6$) δ: 0.94 (s, 6H), 1.47 (t, 2H, J=6.38 Hz), 2.21 (t, 2H, J=6.38 Hz), 2.33 (s, 2H), 12.69 (s, 1H).

(Step 2)

Production of tert-butyl 3-iodo-6,6-dimethyl-4,5,6,7-tetrahydroindazole-1-carboxylate

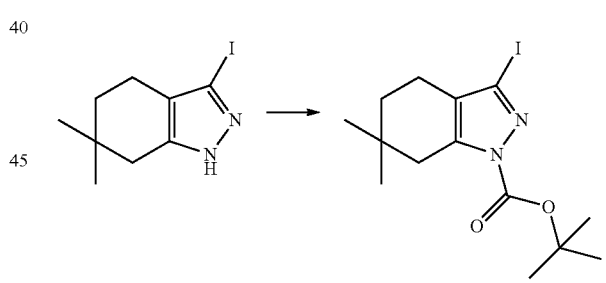

To a solution of 3-iodo-6,6-dimethyl-4,5,6,7-tetrahydro-1H-indazole (41 g, 147 mmol), triethylamine (22 ml, 155 mmol) and 4-dimethylaminopyridine (824 mg, 7 mmol) in tetrahydrofuran (163 ml) was added dropwise a solution of di-tert-butyl dicarbonate (34 g, 155 mmol) in tetrahydrofuran (41 ml) at room temperature over 40 min, and the mixture was stirred for 30 min. Then, the reaction mixture is concentrated under reduced pressure. The residue was slurry-washed in hexane (130 ml) at 60° C. and ice-cooled. The crystals were collected by filtration, washed with hexane, and dried under reduced pressure to give the title compound (53 g, yield 95%).

$^1$H-NMR (400 MHz, DMSO-$d_6$) δ: 0.95 (s, 6H), 1.46 (t, 2H, J=6.38 Hz), 1.56 (s, 9H), 2.23 (t, 2H, J=6.26 Hz), 2.63 (s, 2H).

Reference Example 2

Production of 1-tert-butyl 6-methyl 2-boronylindole-1,6-dicarboxylate (Step 1)

Production of methyl 1H-indole-6-carboxylate

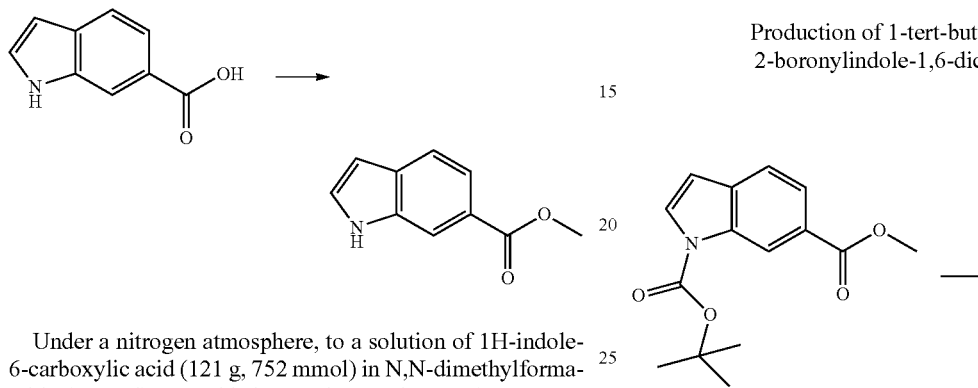

Under a nitrogen atmosphere, to a solution of 1H-indole-6-carboxylic acid (121 g, 752 mmol) in N,N-dimethylformamide (360 ml) was added potassium carbonate (124 g, 900 mmol), and the mixture was stirred at room temperature for 1 hr. Then, iodomethane (56 ml, 900 mmol) was added dropwise at room temperature over 15 min, and the mixture was stirred for 2 hr. Then, to the reaction solution were added water (1.2 L) and hexane (100 ml), and the mixture was stirred at room temperature for 1 hr. The precipitated crystals were collected by filtration, washed successively with water and hexane, and dried under reduced pressure to give the title compound (115 g, yield 87%).

$^1$H-NMR (400 MHz, DMSO-$d_6$) δ: 3.85 (3H, s), 6.53 (1H, d, J=1.61 Hz), 7.60-7.63 (3H, m), 8.07 (1H, s), 11.48 (1H, s).

(Step 2)

Production of 1-tert-butyl 6-methyl indole-1,6-dicarboxylate

To a solution of methyl 1H-indole-6-carboxylate (124 g, 708 mmol) in tetrahydrofuran (500 ml) was added 4-dimethylaminopyridine (865 mg, 7 mmol). Then, a solution of di-tert-butyl dicarbonate (156 g, 715 mmol) in tetrahydrofuran (150 ml) was added dropwise at room temperature over about 1 hr, and the mixture was stirred for 1 hr. The reaction mixture was concentrated, and the residue was purified by silica gel chromatography to give the title compound (193 g, yield 99%).

$^1$H-NMR (400 MHz, DMSO-$d_6$) δ: 1.65 (9H, s), 3.89 (3H, s), 6.82H, dd, J=3.63, 0.86 Hz), 7.74 (1H, d, J=8.06 Hz), 7.85 (1H, dd, J=8.06, 0.86 Hz), 7.87 (1H, d, J=3.63 Hz), 8.76 (1H, d, J=0.81 Hz).

(Step 3)

Production of 1-tert-butyl 6-methyl 2-boronylindole-1,6-dicarboxylate

To a solution of 1-tert-butyl 6-methyl indole-1,6-dicarboxylate (107 g, 389 mmol) in tetrahydrofuran (135 ml) was added triisopropyl borate (135 ml, 584 mmol), and the inside temperature was cooled to −5° C. Then, a solution (253 ml, 506 mmol) of lithium diisopropylamide in hexane was added dropwise over 1.5 hr while maintaining the inside temperature at −5° C. or below, and the mixture was further stirred for 1 hr. Then, to the reaction solution was added dropwise 10% aqueous citric acid solution (1.2 L) under ice-cooling. The aqueous layer was extracted three times with ethyl acetate. The combined organic layers were washed with saturated brine, and dried over magnesium sulfate. Magnesium sulfate was removed by filtration, and the filtrate was concentrated under reduced pressure. The residue was slurry-washed with a mixed solvent of ethyl acetate (333 ml) and hexane (666 ml), and the precipitate was collected by filtration, washed with hexane, and dried under reduced pressure to give the title compound (73 g, yield 59%).

$^1$H-NMR (400 MHz, DMSO-$d_6$) δ: 1.62 (s, 9H), 3.88 (s, 3H), 6.72 (d, 1H, J=0.88 Hz), 7.68 (t, 1H, J=4.08 Hz), 7.82 (dd, 1H, J=8.16, 1.54 Hz), 8.33 (s, 2H), 8.78 (t, 1H, J=0.77 Hz).

Reference Example 3

Production of (S)-2-(morpholin-4-yl)propionic acid (Step 1)

Production of benzyl (S)-2-(morpholin-4-yl)propionate

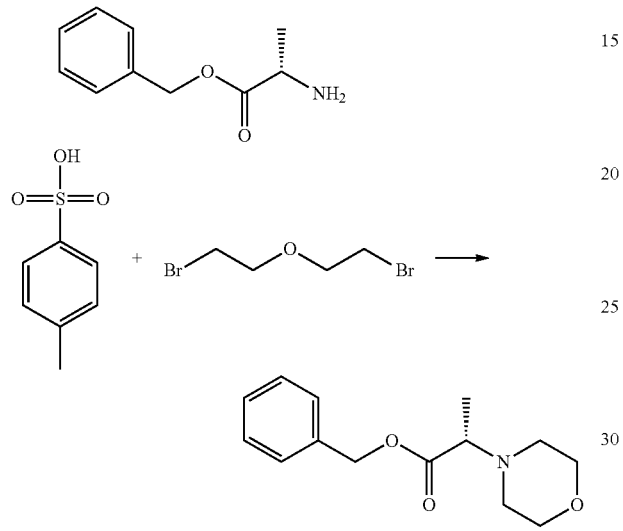

Under an argon atmosphere, to a solution of L-alanine benzyl ester tosylate (3.4 g, 9.7 mmol) and triethylamine (6.8 ml) in dimethyl sulfoxide (17 ml) was added a solution of 1-bromo-2-(2-bromoethoxy)ethane (1.5 ml, 12 mmol) in dimethyl sulfoxide (3 ml) under ice-cooling, and the mixture was stirred at room temperature for 24 hr. To the reaction solution were added water and ethyl acetate, and the organic layer was separated. Then, the organic layer was washed with saturated brine, and dried over sodium sulfate. Sodium sulfate was removed by filtration, and the filtrate was concentrated under reduced pressure. The residue was purified by silica gel chromatography to give the title compound (1.6 g, yield 64%).

$^1$H-NMR (400 MHz, DMSO-$d_6$) δ: 1.20 (d, 3H, J=7.25 Hz), 2.44-2.59 (m, 4H), 3.35 (q, 1H, J=7.25 Hz), 3.47-3.59 (m, 4H), 5.16-5.09 (m, 2H), 7.29-7.40 (m, 5H).

(Step 2)

Production of (S)-2-(morpholin-4-yl)propionic acid

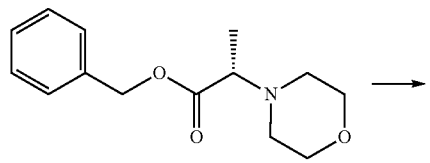

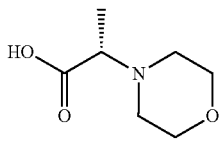

Under an argon atmosphere, to a solution of benzyl (S)-2-(morpholin-4-yl)propionate (43 g, 172 mmol) in methanol (430 ml) was added 20% palladium hydroxide-carbon (4.3 g) at room temperature, and the mixture was stirred for 3 hr under a hydrogen atmosphere at normal pressure. The reaction mixture was filtered through celite, and the filtrate was concentrated under reduced pressure to give the title compound (25.4 g, 93%).

$^1$H-NMR (400 MHz, DMSO-$d_6$) δ: 1.17 (d, 3H, J=6.98 Hz), 2.47-2.63 (m, 4H), 3.17 (q, 1H, J=6.98 Hz), 3.50-3.63 (m, 4H).

Reference Example 4

Production of (3-oxomorpholin-4-yl)acetic acid (Step 1)

Production of 2-chloro-N-(2-hydroxyethyl)acetamide

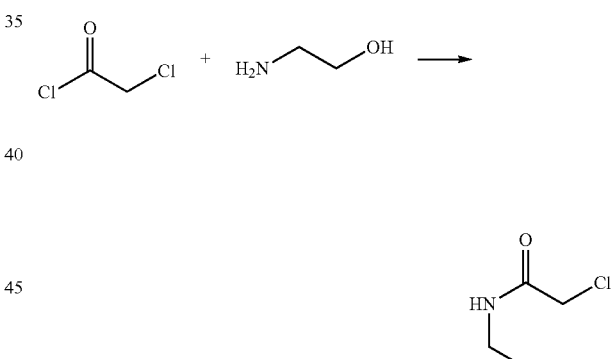

Under an argon atmosphere, to a solution of 2-aminoethanol (5 g, 82 mmol) and triethylamine (11.4 ml, 82 mmol) in tetrahydrofuran (60 ml) was added dropwise chloroacetyl chloride (6.2 ml, 78 mmol) under ice-cooling over 30 min, and the mixture was stirred for 1 hr. The reaction mixture was further stirred at room temperature for 3 hr, and dried over magnesium sulfate. Magnesium sulfate was removed by filtration, and the filtrate was concentrated under reduced pressure. The residue was purified by silica gel chromatography to give the title compound (3.2 g, yield 30%).

$^1$H-NMR (400 MHz, DMSO-$d_6$) δ: 3.16 (q, 2H, J=5.87 Hz), 3.42 (q, 2H, J=5.87 Hz), 4.06 (s, 2H), 4.71 (t, 1H, J=5.45 Hz), 8.18 (s, 1H).

(Step 2)

Production of morpholin-3-one

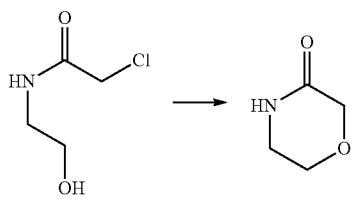

Under an argon atmosphere, to a solution of 2-chloro-N-(2-hydroxyethyl)acetamide (3.2 g, 23 mmol) in tetrahydrofuran (64 ml) was added sodium hydride (1.2 g, 30 mmol) under ice-cooling, and the mixture was stirred for 1 hr. Then, the mixture was stirred at room temperature for 1 hr, and further at 60° C. for 4 hr. After cooling, water (540 μl) was added, and the reaction mixture was dried over magnesium sulfate. Magnesium sulfate was removed by filtration, and the filtrate was concentrated under reduced pressure. The residue was purified by silica gel chromatography to give the title compound (232 mg, yield 10%).

$^1$H-NMR (400 MHz, DMSO-$d_6$) δ: 3.20-3.23 (m, 2H), 3.70-3.73 (m, 2H), 3.96 (s, 2H), 7.88-8.07 (brs, 1H).

(Step 3)

Production of benzyl (3-oxomorpholin-4-yl)acetate

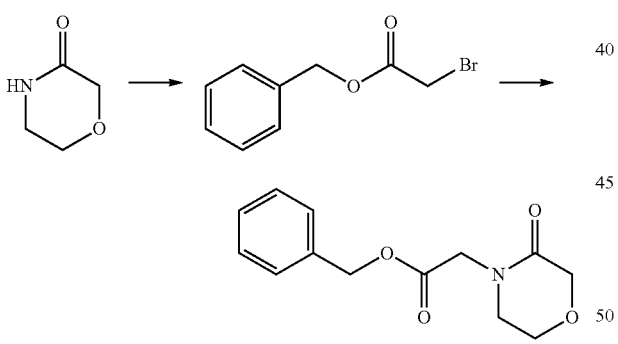

Under an argon atmosphere, to a solution of morpholin-3-one (220 mg, 2.2 mmol) in N,N-dimethylformamide (2.2 ml) was added sodium hydride (105 mg, 2.6 mmol) under ice-cooling, and the mixture was stirred for 1 hr. Then, benzyl bromoacetate (379 μl, 2.4 mmol) was added, and the mixture was stirred for 2 hr. To the reaction solution were added water and ethyl acetate, and the organic layer was separated. The aqueous layer was extracted twice with ethyl acetate, and the combined organic layers were washed successively with water and saturated brine, and dried over sodium sulfate. Sodium sulfate was removed by filtration, and the filtrate was concentrated under reduced pressure. The residue was purified by silica gel chromatography to give the title compound (321 mg, yield 59%).

$^1$H-NMR (400 MHz, DMSO-$d_6$) δ: 3.40-3.43 (m, 2H), 3.83-3.85 (m, 2H), 4.08 (s, 2H), 4.21 (s, 2H), 5.16 (s, 2H), 7.32-7.41 (m, 5H).

(Step 4)

Production of (3-oxomorpholin-4-yl)acetic acid

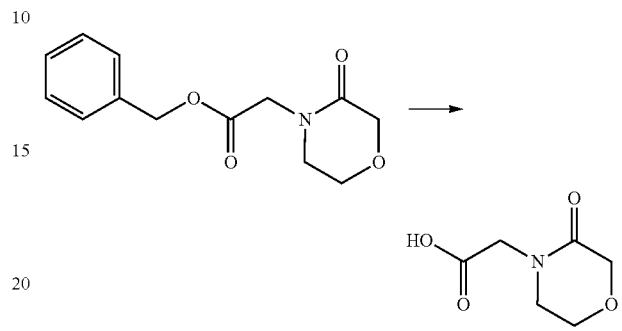

Under an argon atmosphere, to a solution of benzyl (3-oxomorpholin-4-yl)acetate (319 mg, 1.3 mmol) in methanol (5 ml) was added 20% palladium hydroxide-carbon (64 mg) at room temperature. Then, the mixture was stirred for 2 hr under a hydrogen atmosphere at normal pressure. The reaction mixture was filtered through celite, and the filtrate was concentrated under reduced pressure to give the title compound (206 mg, yield over weight).

$^1$H-NMR (400 MHz, DMSO-$d_6$) δ: 3.37-3.40 (m, 2H), 3.82-3.84 (m, 2H), 4.03 (s, 2H), 4.06 (s, 2H), 12.22-13.57 (brs, 1H).

Reference Example 5

Production of tert-butyl 6-benzyloxymethyl-3-iodo-6-methyl-4,5,6,7-tetrahydroindazole-1-carboxylate (Step 1)

Production of 7-methyl-1,4-dioxaspiro[4.5]decan-8-one

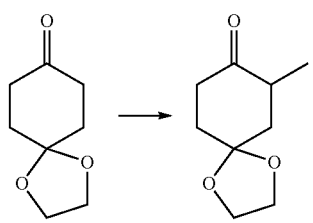

Under a nitrogen atmosphere, to a solution of lithium bis(trimethylsilyl)amide (1M, 100 ml, 100 mmol) in tetrahydrofuran (200 ml) was added dropwise a solution of 1,4-dioxaspiro[4.5]decan-8-one (15.6 g, 100 mmol) in tetrahydrofuran (50 ml) at −78° C. over about 30 min, and the mixture was stirred for 30 min. Then, methyl iodide (2.5 ml, 120 mmol) was added dropwise over 5 min, and the mixture was stirred at −78° C. for 30 min, and at room temperature for 2 hr. To the reaction mixture was added saturated aqueous ammonium chloride solution, and the mixture was extracted three times with diethyl ether. The combined organic layers were dried over magnesium sulfate. Magnesium sulfate was removed by filtration, and the filtrate was concentrated under reduced pressure. The residue was purified by silica gel chromatography to give the title compound (10.6 g, yield 62%).

$^1$H-NMR (400 MHz, DMSO-d$_6$) δ: 0.90 (3H, d, J=6.62 Hz), 1.65 (1H, t, J=13.01 Hz), 1.84-2.04 (3H, m), 2.19 (1H, ddd, J=14.50, 5.13, 3.03 Hz), 2.49-2.69 (2H, m), 3.85-4.06 (4H, m).

(Step 2)

Production of 7-hydroxymethyl-7-methyl-1,4-dioxaspiro[4.5]decan-8-one

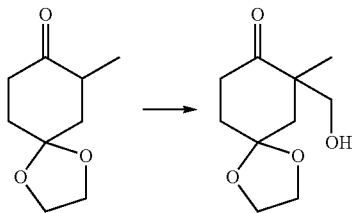

7-Methyl-1,4-dioxaspiro[4.5]decan-8-one (10.5 g, 62 mmol) was dissolved in methanolic potassium hydroxide solution (10 w/w %, 60 g). To the solution was added dropwise a solution of aqueous formaldehyde solution (37%, 4.6 ml) in methanol (5 ml) under ice-cooling over 20 min, and the mixture was stirred for 30 min. Then, to the reaction mixture were added 1 N hydrochloric acid and saturated aqueous ammonium chloride solution, and the mixture was extracted three times with chloroform. The combined organic layers were dried over magnesium sulfate. Magnesium sulfate was removed by filtration, and the filtrate was concentrated under reduced pressure. The residue was purified by silica gel chromatography to give the title compound (6.9 g, yield 56%).

$^1$H-NMR (400 MHz, DMSO-d$_6$) δ: 0.98 (3H, s), 1.67 (1H, dd, J=14.00, 1.41 Hz), 1.86-1.97 (2H, m), 2.08 (1H, dd, J=14.00, 1.61 Hz), 2.33-2.48 (2H, m), 3.42-3.50 (2H, m), 3.90-3.95 (4H, m), 4.63 (1H, t, J=5.24 Hz).

(Step 3)

Production of (7-methyl-1,4-dioxaspiro[4.5]deca-7-yl)methanol

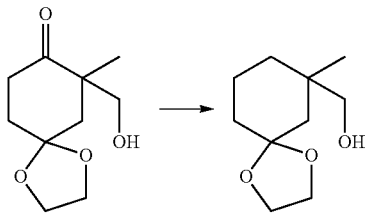

To a solution of 7-hydroxymethyl-7-methyl-1,4-dioxaspiro[4.5]decan-8-one (6.9 g, 65 mmol) in methanol (40 ml) was added p-toluenesulfonylhydrazide (7.4 g, 40 mmol), and the mixture was heated under reflux for 3 hr. Then, to the reaction solution were added methanol (120 ml), sodium cyanoborohydride (2.9 g, 46 mmol) and a solution (100 ml) of zinc chloride (3.1 g, 23 mmol) in methanol, and the mixture was heated under reflux for 2 hr. After cooling, 1 N aqueous sodium hydroxide solution (700 ml) was added, the mixture was filtered through celite, and the filtrate was extracted three times with ethyl acetate. The combined organic layers were washed successively with water and saturated brine, and dried over sodium sulfate. Sodium sulfate was removed by filtration, and the filtrate was concentrated under reduced pressure. The residue was purified by silica gel chromatography to give the title compound (4.0 g, yield 61%).

$^1$H-NMR (400 MHz, DMSO-d$_6$) δ: 0.96 (3H, s), 1.18-1.87 (8H, m), 3.18 (1H, d, J=8.06 Hz), 3.35 (1H, dd, J=10.88, 6.45 Hz), 3.51 (1H, dd, J=10.88, 9.07 Hz), 3.93-3.94 (4H, m).

(Step 4)

Production of 7-benzyloxymethyl-7-methyl-1,4-dioxaspiro[4.5]decane

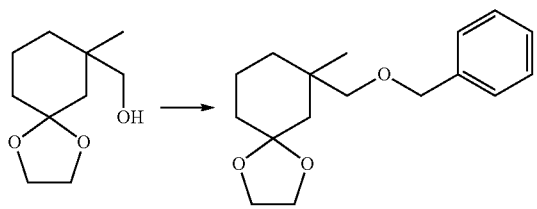

Under a nitrogen atmosphere, to a solution of (7-methyl-1,4-dioxaspiro[4.5]deca-7-yl)methanol (4.0 g, 21 mmol) in N,N-dimethylformamide (40 ml) was added sodium hydride (1.1 g, 27 mmol) under ice-cooling, and the mixture was stirred for 30 min. Then, to the reaction mixture was added benzyl bromide (3.1 ml, 25 mmol) at room temperature, and the mixture was further stirred for 1 hr. To the reaction mixture were added diethyl ether and water, and the organic layer was separated. Then, the organic layer was washed successively with water and saturated brine, and dried over sodium sulfate. Sodium sulfate was removed by filtration, and the filtrate was concentrated under reduced pressure. The residue was purified by silica gel chromatography to give the title compound (5.7 g, yield 93%).

$^1$H-NMR (400 MHz, DMSO-d$_6$) δ: 0.95 (3H, s), 1.14-1.19 (1H, m), 1.32-1.59 (7H, m), 3.20 (2H, dd, J=28.41, 8.66 Hz), 3.77-3.85 (4H, m), 4.45 (2H, s), 7.29-7.33 (5H, m).

(Step 5)

Production of 3-benzyloxymethyl-3-methylcyclohexanone

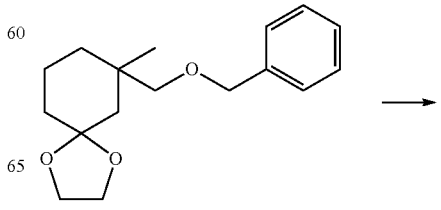

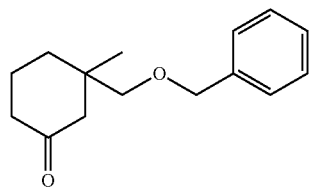

To a solution of 7-benzyloxymethyl-7-methyl-1,4-dioxaspiro[4.5]decane (5.3 g, 19 mmol) in a mixed solvent of acetone (42 ml) and water (11 ml) was added pyridinium p-toluenesulfonate (4.8 g, 19 mmol), and the mixture was stirred with heating at 80° C. for 2 hr. After cooling, to the reaction mixture were added ethyl acetate and water, and the organic layer was separated. The aqueous layer was extracted with ethyl acetate, and the combined organic layers were washed successively with water and saturated brine, and dried over sodium sulfate. Sodium sulfate was removed by filtration, and the filtrate was concentrated under reduced pressure. The residue was purified by silica gel chromatography to give the title compound (3.9 g, yield 88%).

$^1$H-NMR (400 MHz, DMSO-$d_6$) δ: 0.88 (3H, s), 1.43-1.49 (1H, m), 1.72-1.84 (3H, m), 2.01 (1H, dt, J=13.67, 1.43 Hz), 2.17-2.26 (2H, m), 2.32 (1H, d, J=13.45 Hz), 3.17 (2H, dd, J=10.81, 8.82 Hz), 4.47 (2H, s), 7.26-7.38 (5H, m).

(Step 6)

Production of tert-butyl 6-benzyloxymethyl-3-iodo-6-methyl-4,5,6,7-tetrahydroindazole-1-carboxylate

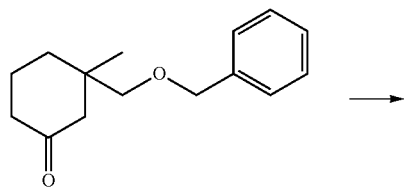

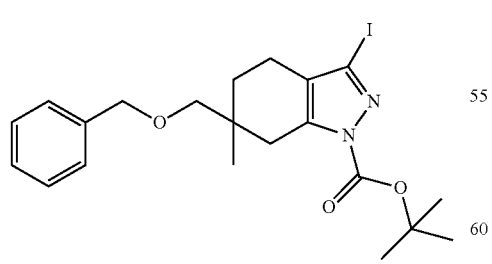

In the same manner as in Reference Example 1, the title compound (3.8 g) was obtained from 3-benzyloxymethyl-3-methylcyclohexanone (3.9 g).

Reference Example 6

Production of (2-oxopiperidin-1-yl)acetic acid (Step 1)

Production of benzyl (2-oxopiperidin-1-yl)acetate

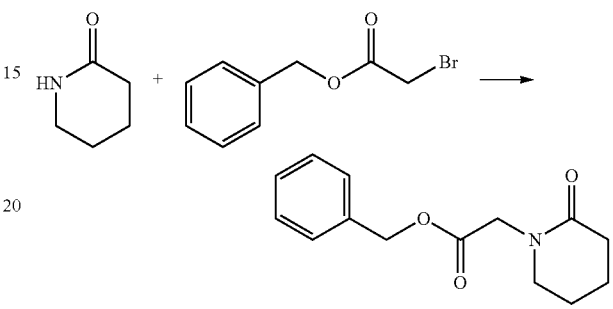

Under a nitrogen atmosphere, to a solution of piperidin-2-one (9.8 g, 99 mmol) in N,N-dimethylformamide (100 ml) was added sodium hydride (4.4 g, 110 mmol) under ice-cooling, and the mixture was stirred for 1 hr. Then, benzyl bromoacetate (19 ml, 120 mmol) was added, and the mixture was further stirred for 2 hr. To the reaction mixture were added ethyl acetate and water, and the organic layer was separated, washed successively with water and saturated brine, and dried over sodium sulfate. Sodium sulfate was removed by filtration, and the filtrate was concentrated under reduced pressure. The residue was purified by silica gel chromatography to give the title compound (6.0 g, yield 24%).

$^1$H-NMR (400 MHz, DMSO-$d_6$) δ: 1.62-1.66 (4H, m), 2.11 (2H, t, J=6.45 Hz), 3.10-3.12 (2H, m), 4.21 (2H, s), 5.18 (2H, s), 7.21-7.40 (5H, m).

(Step 2)

Production of (2-oxopiperidin-1-yl)acetic acid

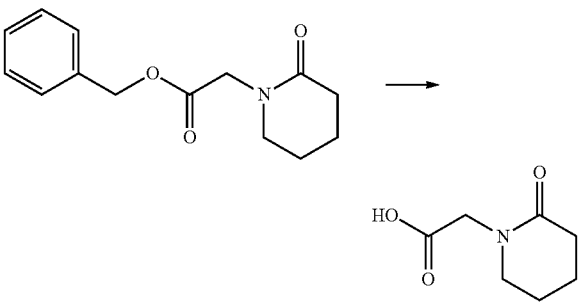

Under a nitrogen atmosphere, to a solution of benzyl (2-oxopiperidin-1-yl)acetate (6.0 g, 24 mmol) in methanol (60 ml) was added 20% palladium hydroxide-carbon (400 mg) at room temperature, and the mixture was stirred for 4 hr under a hydrogen atmosphere at normal pressure. The reaction mixture was filtered through celite, and the filtrate was concentrated under reduced pressure to give the title compound (4.0 g, yield over weight).

¹H-NMR (400 MHz, DMSO-d₆) δ: 1.71-1.74 (4H, m), 2.23 (2H, t, J=6.04 Hz), 3.17-3.31 (2H, m), 3.94 (2H, s), 12.58 (1H, s).

Example 1

Production of N-[2-(6,6-dimethyl-4,5,6,7-tetrahydro-1H-indazol-3-yl)-1H-indol-6-yl]-N-methylacetamide (Step 1)

Production of 1-tert-butyl 6-methyl 2-(1-tert-butoxycarbonyl-6,6-dimethyl-4,5,6,7-tetrahydro-1H-indazol-3-yl)indole-1,6-dicarboxylate

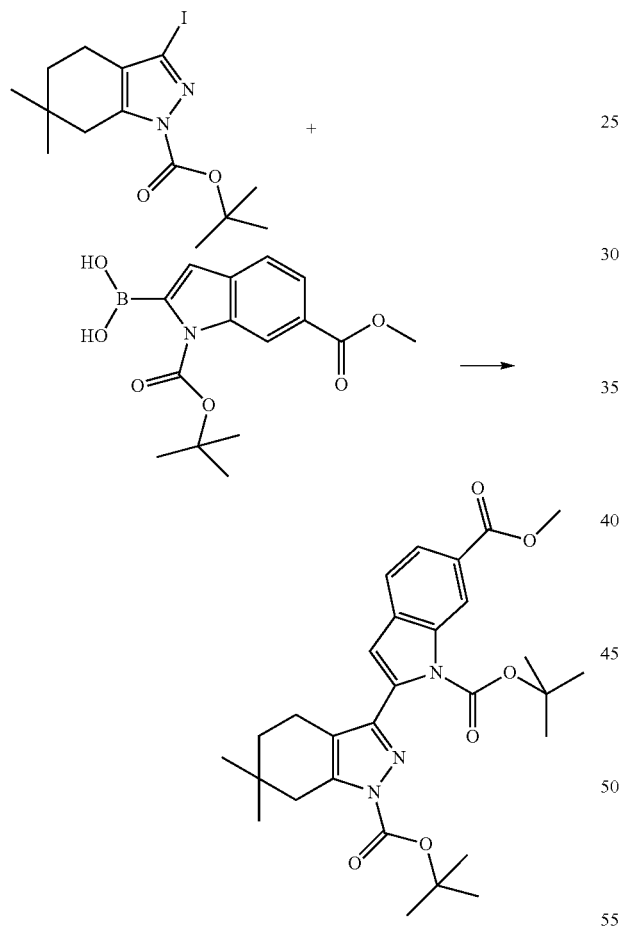

Under an argon atmosphere, to a solution of tert-butyl 3-iodo-6,6-dimethyl-4,5,6,7-tetrahydroindazole-1-carboxylate obtained in Reference Example 1 (49 g, 130 mmol), potassium phosphate (110 g, 520 mmol) and (bis(diphenylphosphino)ferrocene)palladium dichloride-methylene chloride complex (11 g, 13 mmol) in a mixed solvent of 1,4-dioxane (780 ml) and water (330 ml) was added 1-tert-butyl 6-methyl 2-boronylindole-1,6-dicarboxylate (42 g, 130 mmol) obtained in Reference Example 2 in portions of 2 g with heating at 110° C. over 15 min, and the mixture was stirred for 5 min. After cooling, to the reaction mixture were added water and ethyl acetate, and the organic layer was separated. Then, the organic layer was washed successively with water and saturated brine, and dried over sodium sulfate. Sodium sulfate was removed by filtration, and the filtrate was concentrated under reduced pressure. The residue was purified by silica gel chromatography to give the title compound (40 g, yield 58%).

¹H-NMR (400 MHz, DMSO-d₆) δ: 1.01 (s, 6H), 1.40 (s, 9H), 1.48 (t, 2H, J=6.15 Hz), 1.57 (s, 9H), 2.41 (t, 2H, J=5.80 Hz), 2.72 (s, 2H), 3.90 (s, 3H), 7.06 (s, 1H), 7.77 (d, 1H, J=8.35 Hz), 7.89 (dd, 1H, J=8.35, 1.16 Hz), 8.73 (t, 1H, J=0.70 Hz).

(Step 2)

Production of methyl 2-(6,6-dimethyl-4,5,6,7-tetrahydro-1H-indazol-3-yl)indole-6-carboxylate

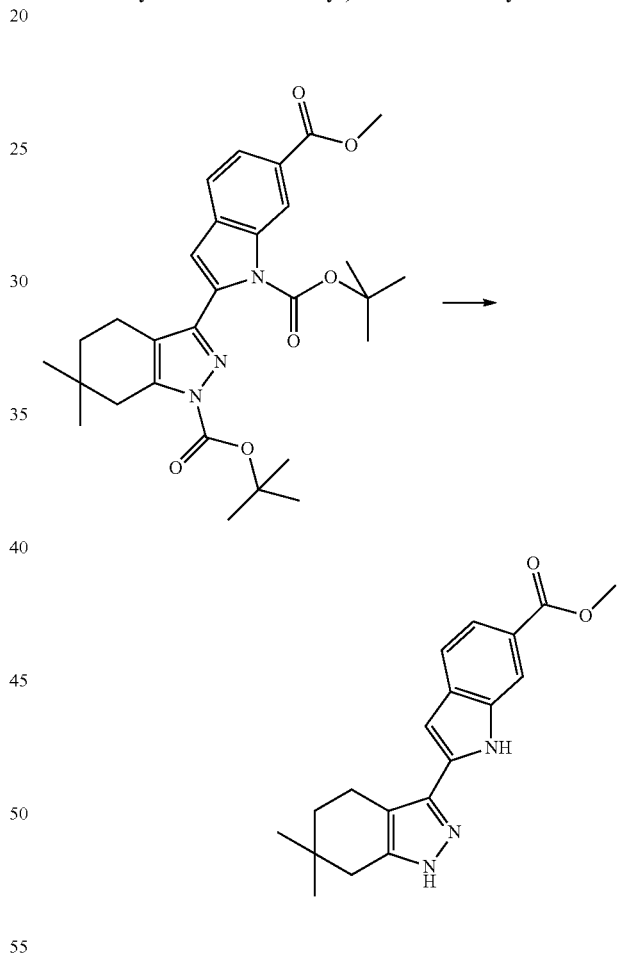

To a solution of 1-tert-butyl 6-methyl 2-(1-tert-butoxycarbonyl-6,6-dimethyl-4,5,6,7-tetrahydro-1H-indazol-3-yl)indole-1,6-dicarboxylate (39 g, 75 mmol) in a mixed solvent of methanol (180 ml) and tetrahydrofuran (120 ml) was added dropwise 2 N aqueous sodium hydroxide solution (149 ml, 298 mmol) under ice-cooling over 15 min, and the mixture was stirred for 15 min. Then, 1 N hydrochloric acid was added dropwise to adjust the pH to 5. The precipitated crystals were collected by filtration, washed with water, and dried under reduced pressure to give the title compound (23 g, yield 97%).

¹H-NMR (400 MHz, DMSO-d₆) δ: 1.01 (s, 6H), 1.58 (t, 2H, J=6.38 Hz), 2.42 (s, 2H), 2.68 (t, 2H, J=6.15 Hz), 3.85 (s, 3H), 6.67 (s, 1H), 7.59 (s, 2H), 8.07 (s, 1H), 11.71 (s, 1H), 12.66 (s, 1H).

(Step 3)

Production of methyl 2-{6,6-dimethyl-1-[2-(trimethylsilyl)ethoxymethyl]-4,5,6,7-tetrahydro-1H-indazol-3-yl}-1-[2-(trimethylsilyl)ethoxymethyl]-1H-indole-6-carboxylate

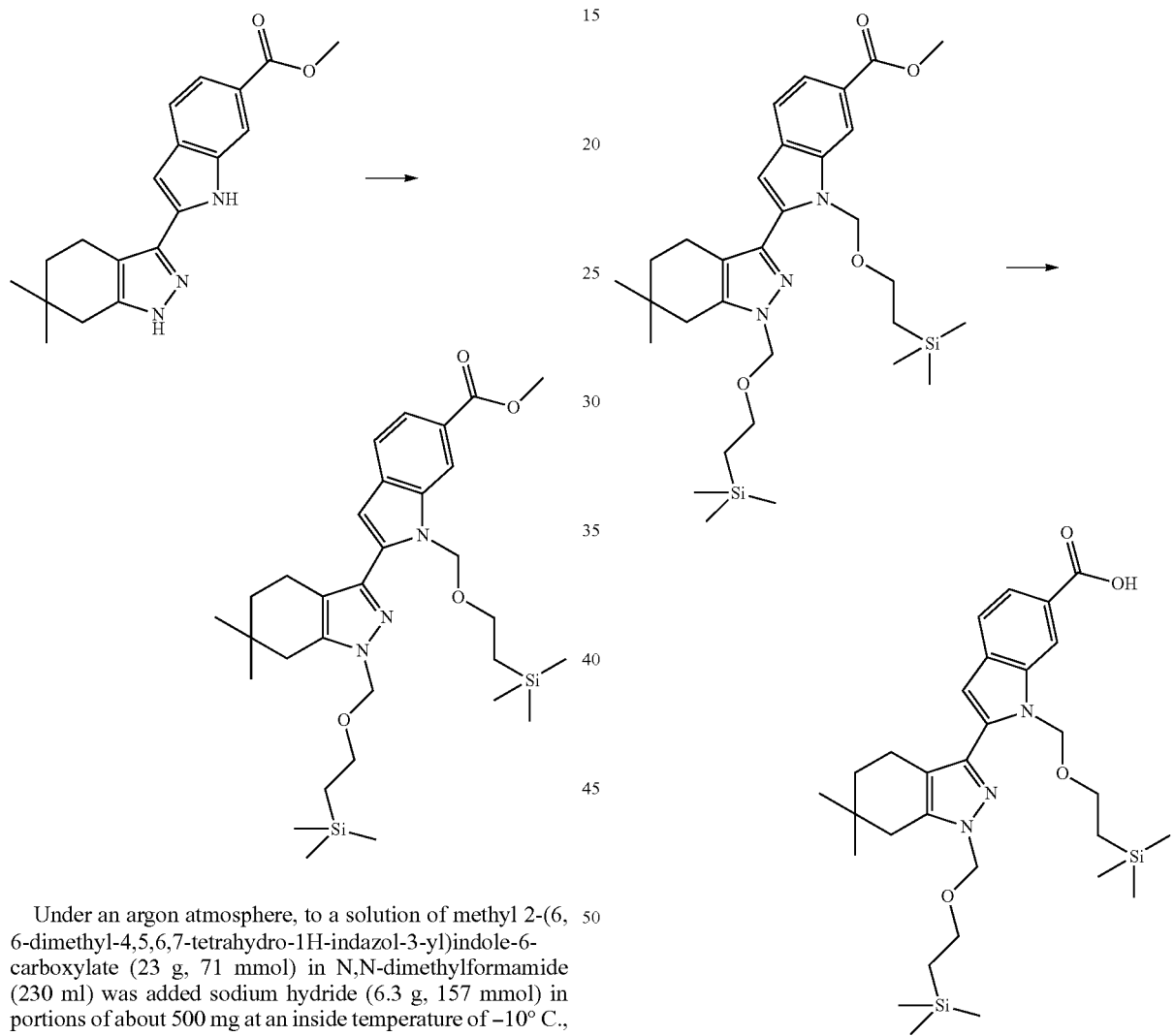

Under an argon atmosphere, to a solution of methyl 2-(6,6-dimethyl-4,5,6,7-tetrahydro-1H-indazol-3-yl)indole-6-carboxylate (23 g, 71 mmol) in N,N-dimethylformamide (230 ml) was added sodium hydride (6.3 g, 157 mmol) in portions of about 500 mg at an inside temperature of –10° C., and the mixture was stirred for 30 min. Then, 2-(trimethylsilyl)ethoxymethyl chloride (26 g, 157 mmol) was added dropwise over 15 min, and the mixture was further stirred for 2 hr. To the reaction mixture were added ethyl acetate and water, and the organic layer was separated. Then, the organic layer was washed successively with water and saturated brine, and dried over sodium sulfate. Sodium sulfate was removed by filtration, and the filtrate was concentrated under reduced pressure. The residue was purified by silica gel chromatography to give the title compound (33 g, yield 80%).

¹H-NMR (400 MHz, DMSO-d₆) δ: –0.21 (s, 9H), –0.03 (s, 9H), 0.68 (t, 2H, J=8.00 Hz), 0.87 (t, 2H, J=8.12 Hz), 1.03 (s, 6H), 1.54 (t, 2H, J=6.26 Hz), 2.50 (s, 2H), 2.63 (t, 2H, J=6.26 Hz), 3.30-3.31 (m, 2H), 3.59 (t, 2H, J=8.00 Hz), 3.87 (s, 3H), 5.42 (s, 2H), 6.14 (s, 2H), 6.83 (d, 1H, J=0.70 Hz), 7.67-7.72 (m, 2H), 8.22 (s, 1H).

(Step 4)

Production of 2-{6,6-dimethyl-1-[2-(trimethylsilyl)ethoxymethyl]-4,5,6,7-tetrahydro-1H-indazol-3-yl}-1-[2-(trimethylsilyl)ethoxymethyl]-1H-indole-6-carboxylic acid To a solution of methyl 2-{6,6-dimethyl-1-[2-(trimethylsilyl)ethoxymethyl]-4,5,6,7-tetrahydro-1H-indazol-3-yl}-1-[2-(trimethylsilyl)ethoxymethyl]-1H-indole-6-carboxylate (33 g, 57 mmol) in a mixed solvent of tetrahydrofuran (165 ml) and methanol (165 ml) was added 4 N aqueous sodium hydroxide solution (71 ml, 284 mmol), and the mixture was heated at 60° C. for 2 hr. After cooling, the reaction mixture was concentrated, 10% aqueous citric acid solution was added to the residue to adjust the pH to 5, and the mixture was extracted with ethyl acetate. Then, the organic layer was washed with saturated brine, and dried over sodium sulfate.

Sodium sulfate was removed by filtration, and the filtrate was concentrated under reduced pressure to give the title compound (31 g, yield 97%).

$^1$H-NMR (400 MHz, DMSO-d$_6$) δ: −0.21--−0.20 (m, 9H), −0.05--−0.03 (m, 9H), 0.68-0.71 (m, 2H), 0.85-0.91 (m, 2H), 1.03 (s, 6H), 1.54 (t, 2H, J=6.06 Hz), 2.63 (t, 2H, J=5.95 Hz), 3.57-3.61 (m, 2H), 5.42 (s, 2H), 6.13 (d, 2H, J=3.53 Hz), 6.82 (t, 1H, J=3.42 Hz), 7.65-7.70 (m, 2H), 8.20 (s, 1H).

(Step 5)

Production of benzyl (2-{6,6-dimethyl-1-[2-(trimethylsilyl)ethoxymethyl]-4,5,6,7-tetrahydro-1H-indazol-3-yl}-1-[2-(trimethylsilyl)ethoxymethyl]-H-indol-6-yl)carbamate

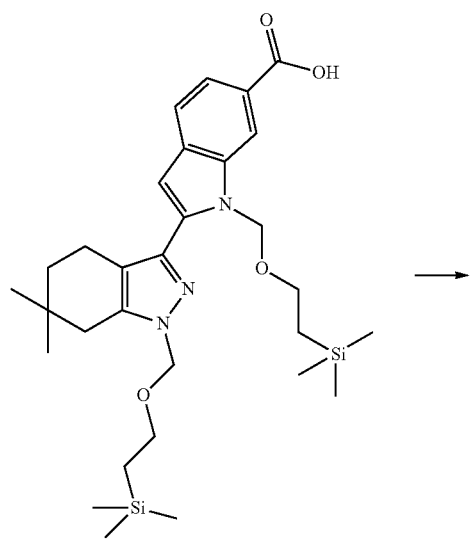

Under an argon atmosphere, to a solution of 2-{6,6-dimethyl-1-[2-(trimethylsilyl)ethoxymethyl]-4,5,6,7-tetrahydro-1H-indazol-3-yl}-1-[2-(trimethylsilyl)ethoxymethyl]-1H-indole-6-carboxylic acid (26 g, 45 mmol), triethylamine (8.2 ml, 59 mmol) and benzyl alcohol (18 ml, 180 mmol) in toluene (260 ml) was added dropwise diphenylphosphoryl azide (12 ml, 54 mmol) at 115° C. over 2 hr. After cooling, water was added to the reaction mixture, and the organic layer was separated. Then, the organic layer was washed successively with water and saturated brine, and dried over magnesium sulfate. Magnesium sulfate was removed by filtration, and the filtrate was concentrated under reduced pressure. The residue was purified by silica gel chromatography, and slurry-washed in hexane (210 ml) with heating at 60° C. The resulting crystals were collected by filtration, washed with hexane, and dried under reduced pressure to give the title compound (28 g, yield 91%).

$^1$H-NMR (400 MHz, DMSO-d$_6$) δ: −0.19 (s, 9H), −0.03 (s, 9H), 0.69 (t, 2H, J=8.16 Hz), 0.86 (t, 2H, J=8.05 Hz), 1.02 (s, 6H), 1.52 (t, 2H, J=6.18 Hz), 2.59 (t, 2H, J=6.06 Hz), 3.58 (t, 2H, J=8.05 Hz), 5.17 (s, 2H), 5.38 (s, 2H), 5.96 (s, 2H), 6.61 (s, 1H), 7.10 (dd, 1H, J=8.49, 1.65 Hz), 7.34-7.46 (m, 6H), 7.86 (s, 1H), 9.71 (s, 1H).

(Step 6)

Production of benzyl N-(2-{6,6-dimethyl-1-[2-(trimethylsilyl)ethoxymethyl]-4,5,6,7-tetrahydro-1H-indazol-3-yl}-1-[2-(trimethylsilyl)ethoxymethyl]-1H-indol-6-yl)-N-methylcarbamate

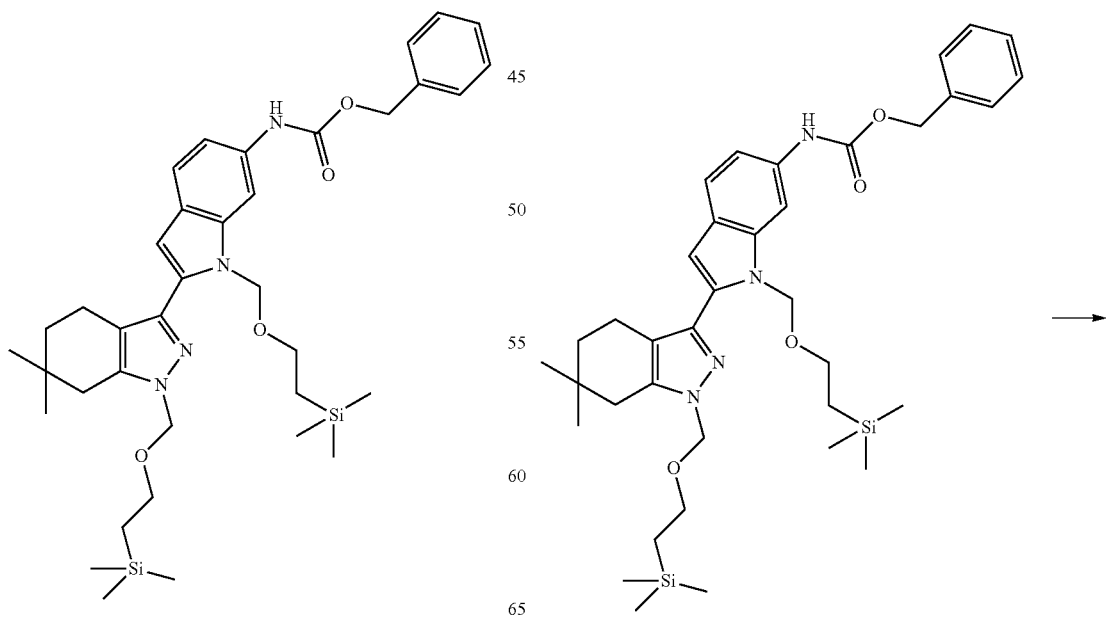

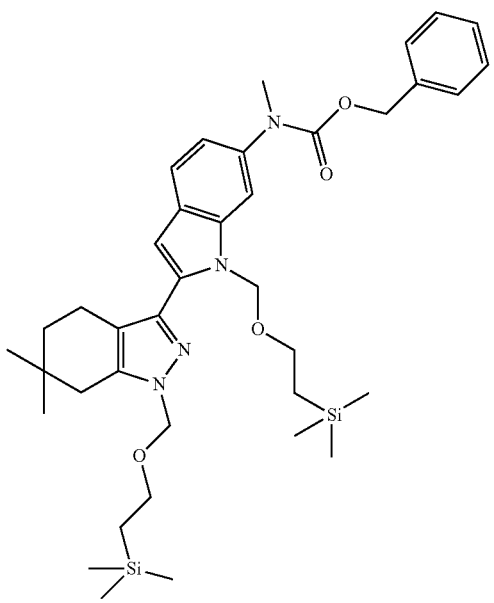

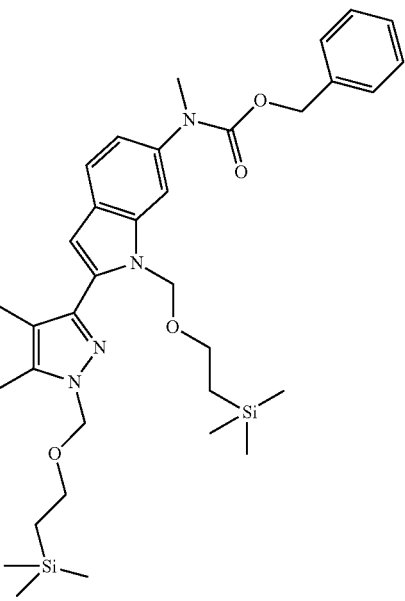

(Step 7)

Production of N-(2-{6,6-dimethyl-1-[2-(trimethylsilyl)ethoxymethyl]-4,5,6,7-tetrahydro-1H-indazol-3-yl}-1-[2-(trimethylsilyl)ethoxymethyl]-1H-indol-6-yl)-N-methylamine Under an argon atmosphere, to a solution of benzyl (2-{6,6-dimethyl-1-[2-(trimethylsilyl)ethoxymethyl]-4,5,6,7-tetrahydro-1H-indazol-3-yl}-1-[2-(trimethylsilyl)ethoxymethyl]-1H-indol-6-yl)carbamate (3 g, 4.6 mmol) in N,N-dimethylformamide (30 ml) was added sodium hydride (219 mg, 5.5 mmol) under ice-cooling, and the mixture was stirred for 10 min. Then, to the reaction mixture was added methyl iodide (0.6 ml, 6.9 mmol), and the mixture was further stirred for 3 hr. To the reaction mixture were added ethyl acetate and water, and the organic layer was separated. Then, the organic layer was washed successively with water and saturated brine, and dried over sodium sulfate. Sodium sulfate was removed by filtration, and the filtrate was concentrated under reduced pressure. The residue was purified by silica gel chromatography to give the title compound (2.2 g, yield 69%).

$^1$H-NMR (400 MHz, DMSO-$d_6$) δ: −0.21 (s, 9H), −0.03 (s, 9H), 0.66 (t, 2H, J=8.01 Hz), 0.86 (t, 2H, J=8.01 Hz), 1.02 (s, 6H), 1.53 (t, 2H, J=6.01 Hz), 2.49 (s, 2H), 2.60 (t, 2H, J=6.01 Hz), 3.29 (s, 3H), 3.29 (t, 2H, J=8.01), 3.59 (t, 2H, J=8.01 Hz), 5.09 (s, 2H), 5.39 (s, 2H), 6.00 (s, 2H), 6.70 (s, 1H), 7.03 (dd, 1H, J=8.41, 2.00 Hz), 7.26-7.37 (m, 5H), 7.44-7.59 (m, 2H).

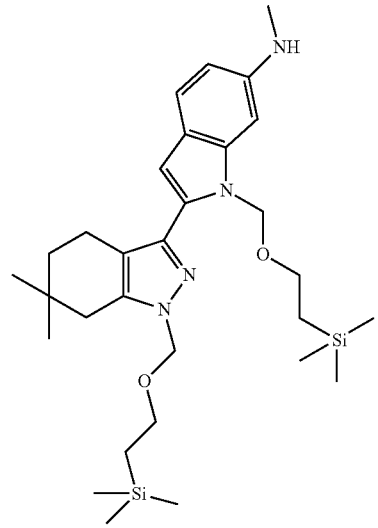

A solution of benzyl N-(2-{6,6-dimethyl-1-[2-(trimethylsilyl)ethoxymethyl]-4,5,6,7-tetrahydro-1H-indazol-3-yl}-1-[2-(trimethylsilyl)ethoxymethyl]-1H-indol-6-yl)-N-methylcarbamate (2.2 g, 3.1 mmol), 10% palladium-carbon (216 mg) and ammonium formate (989 mg, 16 mmol) in ethanol (30 ml) was heated under reflux for 2.5 hr. After cooling, the reaction mixture was filtered through celite, and the filtrate was concentrated. The residue was purified by silica gel chromatography to give the title compound (1.4 g, yield 79%).

$^1$H-NMR (400 MHz, DMSO-$d_6$) δ: −0.18 (s, 9H), −0.03 (s, 9H), 0.69 (t, 2H, J=8.41 Hz), 0.86 (t, 2H, J=8.41 Hz), 1.01 (s, 6H), 1.52 (t, 2H, J=6.41 Hz), 2.47 (s, 2H), 2.57 (t, 2H, J=6.41 Hz), 2.73 (d, 3H, J=5.21 Hz), 3.31 (t, 2H, J=8.41), 3.58 (t, 2H,

J=8.41 Hz), 5.36 (s, 2H), 5.50 (q, 1H, J=5.21 Hz), 5.94 (s, 2H), 6.42-6.55 (m, 3H), 7.25 (d, 1H, J=8.41 Hz).

(Step 8)

Production of N-[2-(6,6-dimethyl-4,5,6,7-tetrahydro-1H-indazol-3-yl)-1H-indol-6-yl]-N-methylacetamide

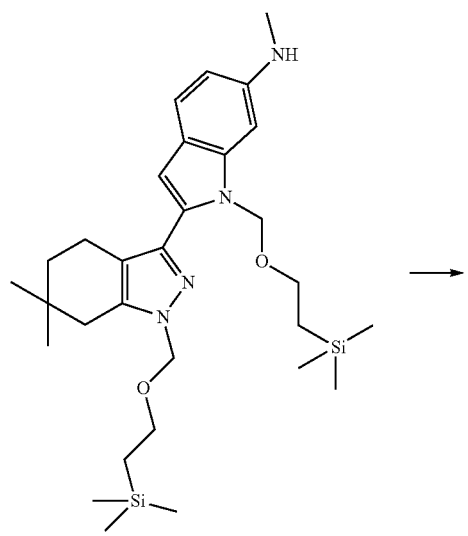

→

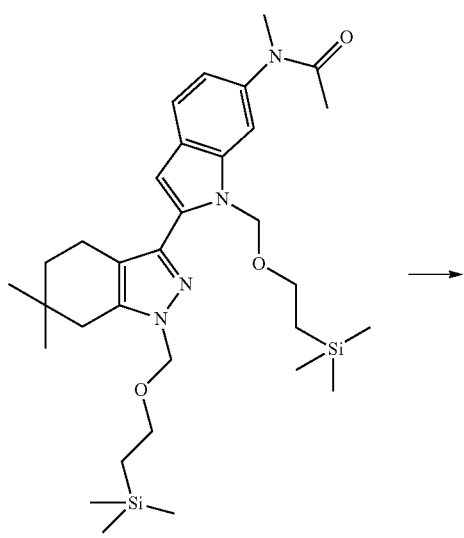

→

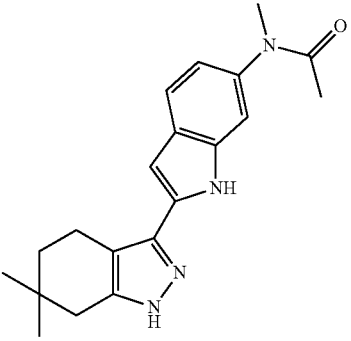

Under an argon atmosphere, to a solution of N-(2-{6,6-dimethyl-1-[2-(trimethylsilyl)ethoxymethyl]-4,5,6,7-tetrahydro-1H-indazol-3-yl}-1-[2-(trimethylsilyl)ethoxymethyl]-1H-indol-6-yl)-N-methylamine (100 mg, 0.18 mmol) and triethylamine (75 μl, 0.54 mmol) in chloroform (1.5 ml) was added acetyl chloride (19 μl, 0.27 mmol) at room temperature, and the mixture was stirred for 2 hr. Water was added to the reaction mixture, and the mixture was extracted three times with ethyl acetate. The combined organic layers were washed successively with water and saturated brine, and dried over sodium sulfate. Sodium sulfate was removed by filtration, and the filtrate was concentrated under reduced pressure to give N-(2-{6,6-dimethyl-1-[2-(trimethylsilyl)ethoxymethyl]-4,5,6,7-tetrahydro-1H-indazol-3-yl}-1-[2-(trimethylsilyl)ethoxymethyl]-1H-indol-6-yl)-N-methylacetamide. A solution of the obtained N-(2-{6,6-dimethyl-1-[2-(trimethylsilyl)ethoxymethyl]-4,5,6,7-tetrahydro-1H-indazol-3-yl}-1-[2-(trimethylsilyl)ethoxymethyl]-1H-indol-6-yl)-N-methylacetamide in N,N-dimethylformamide (1.4 ml) was added to tetrabutylammonium fluoride (1.8 ml, 1.8 mmol) concentrated in advance under reduced pressure. Ethylenediamine (0.7 ml) was added, and the mixture was stirred with heating at 90° C. for 24 hr. After cooling, water and ethyl acetate were added, and the organic layer was separated. Then, the aqueous layer was extracted twice with ethyl acetate. The combined organic layers were washed successively with water and saturated brine, and dried over sodium sulfate. Sodium sulfate was removed by filtration, and the filtrate was concentrated under reduced pressure. The residue was purified by thin layer silica gel chromatography to give the title compound (26 mg, yield 42%).

Example 2

Production of N-[2-(6,6-dimethyl-4,5,6,7-tetrahydro-1H-indazol-3-yl)-1H-indol-6-yl]-N-ethylacetamide (Step 1)

Production of N-(2-{6,6-dimethyl-1-[2-(trimethylsilyl)ethoxymethyl]-4,5,6,7-tetrahydro-1H-indazol-3-yl}-1-[2-(trimethylsilyl)ethoxymethyl]-1H-indol-6-yl)-N-ethylamine

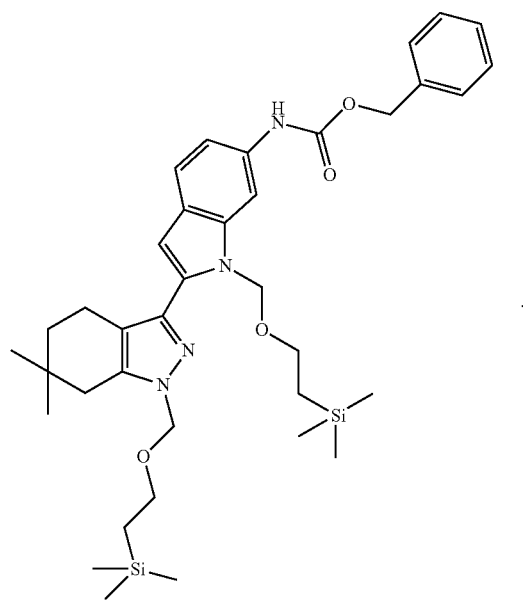

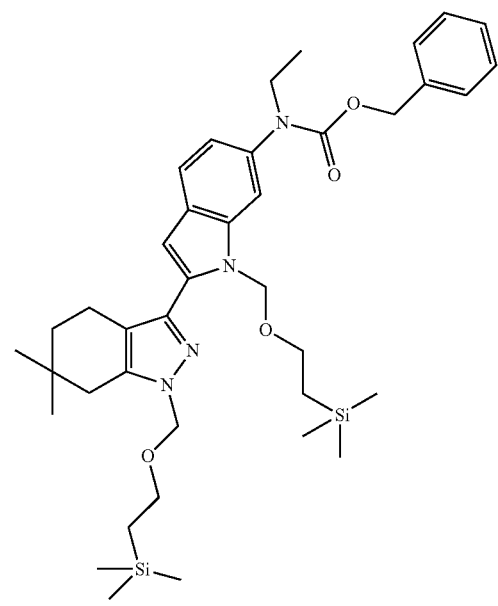

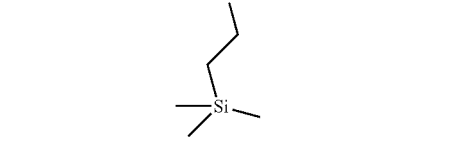

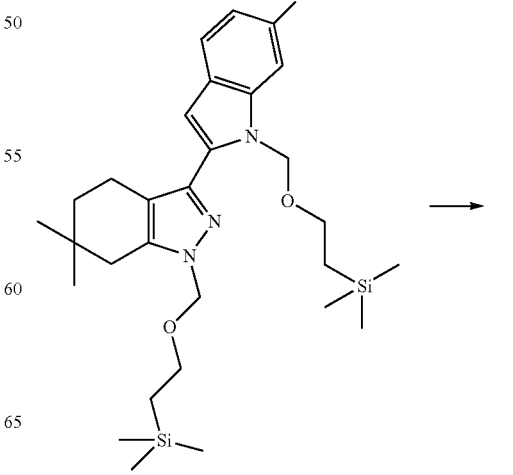

Under a nitrogen atmosphere, benzyl N-(2-{6,6-dimethyl-1-[2-(trimethylsilyl)ethoxymethyl]-4,5,6,7-tetrahydro-1H-indazol-3-yl}-1-[2-(trimethylsilyl)ethoxymethyl]-1H-indol-6-yl)-N-ethylcarbamate was obtained in the same manner as in Example 1, Step 6, from benzyl (2-{6,6-dimethyl-1-[2-(trimethylsilyl)ethoxymethyl]-4,5,6,7-tetrahydro-1H-indazol-3-yl}-1-[2-(trimethylsilyl)ethoxymethyl]-1H-indol-6-yl)carbamate obtained in Example 1, Step 5. To a solution of the obtained benzyl N-(2-{6,6-dimethyl-1-[2-(trimethylsilyl)ethoxymethyl]-4,5,6,7-tetrahydro-1H-indazol-3-yl}-1-[2-(trimethylsilyl)ethoxymethyl]-1H-indol-6-yl)-N-ethylcarbamate (979 mg, 1.4 mmol) in methanol (8 ml) was added 20% palladium hydroxide-carbon (400 mg). Then, the mixture was stirred under a hydrogen atmosphere at normal pressure for 1.5 hr. After the reaction, the reaction mixture was filtered through celite, and the filtrate was concentrated under reduced pressure. The residue was purified by silica gel chromatography to give the title compound (802 mg, yield 100%).

$^1$H-NMR (400 MHz, DMSO-$d_6$) δ: −0.18 (s, 9H), −0.03 (s, 9H), 0.72 (t, 2H, J=8.0 Hz), 0.89 (t, 2H, J=8 Hz), 1.05 (s, 6H), 1.21-1.24 (m, 3H), 1.52-1.57 (m, 2H), 2.50 (s, 2H), 2.56-2.64 (m, 2H), 3.10-3.13 (m, 2H), 3.32-3.36 (m, 2H), 3.61 (t, 2H, J=8.0 Hz), 5.39 (s, 2H), 5.96 (s, 2H), 6.50 (s, 2H), 6.51-6.54 (m, 1H), 6.61 (brs, 1H), 7.27 (d, 1H, J=8.0 Hz).

(Step 2)

Production of N-[2-(6,6-dimethyl-4,5,6,7-tetrahydro-1H-indazol-3-yl)-1H-indol-6-yl]-N-ethylacetamide

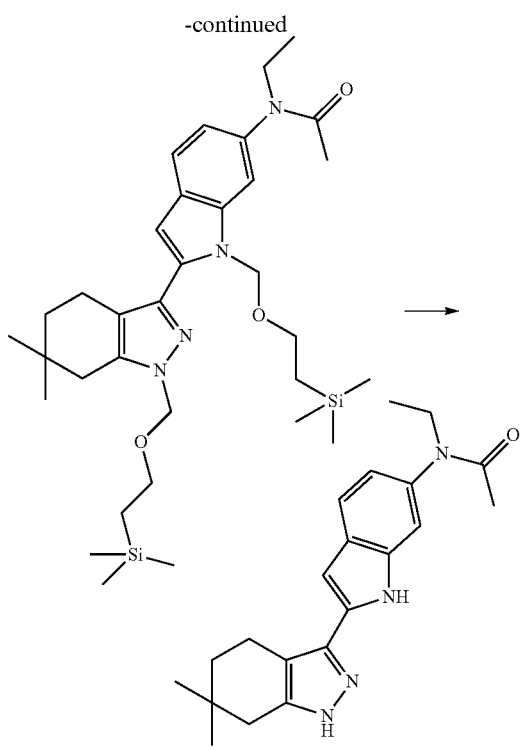

In the same manner as in Example 1, Step 8, the title compound (24 mg, yield 35%) was obtained from N-(2-{6,6-dimethyl-1-[2-(trimethylsilyl)ethoxymethyl]-4,5,6,7-tetrahydro-1H-indazol-3-yl}-1-[2-(trimethylsilyl)ethoxymethyl]-1H-indol-6-yl)-N-ethylamine (110 mg, 0.19 mmol).

Example 3

Production of benzyl N-{2-(6,6-dimethyl-4,5,6,7-tetrahydro-1H-indazol-3-yl)-1H-indol-6-yl}-N-methylcarbamate

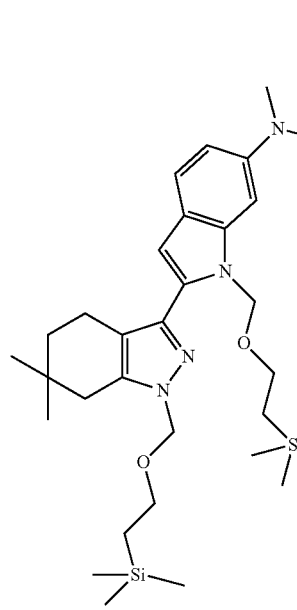

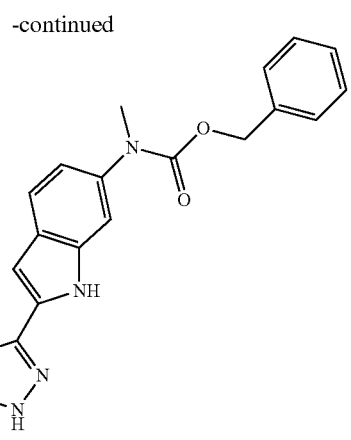

A solution of benzyl N-(2-{6,6-dimethyl-1-[2-(trimethylsilyl)ethoxymethyl]-4,5,6,7-tetrahydro-1H-indazol-3-yl}-1-[2-(trimethylsilyl)ethoxymethyl]-1H-indol-6-yl)-N-methylcarbamate (13 g, 19 mmol) obtained in Example 1, Step 6, in N,N-dimethylformamide (102 ml) was added to tetrabutylammonium fluoride (93 ml, 93 mmol) concentrated in advance under reduced pressure, and then ethylenediamine (19 ml) was added. The mixture was stirred with heating at 90° C. for 7 hr. After cooling, water and ethyl acetate were added, and the organic layer was separated. Then, the aqueous layer was extracted with ethyl acetate. The combined organic layers were washed successively with water, 10% aqueous citric acid solution and saturated brine, and dried over sodium sulfate. Sodium sulfate was removed by filtration, and the filtrate was concentrated under reduced pressure. The residue was purified by silica gel chromatography to give the title compound (7.2 g, yield 91%).

Example 4

Production of (S)—N-[2-(6,6-dimethyl-4,5,6,7-tetrahydro-1H-indazol-3-yl)-1H-indol-6-yl]-N-methyl-2-(morpholin-4-yl)propionamide (Step 1)

Production of N-[2-(6,6-dimethyl-4,5,6,7-tetrahydro-1H-indazol-3-yl)-1H-indol-6-yl]-N-methylamine

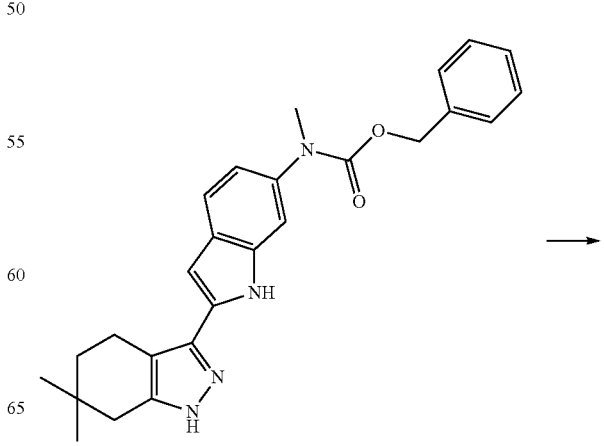

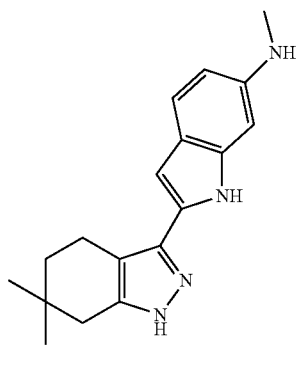

Under a nitrogen atmosphere, to a solution of benzyl N-{2-(6,6-dimethyl-4,5,6,7-tetrahydro-1H-indazol-3-yl)-1H-indol-6-yl}-N-methylcarbamate obtained in Example 3 (7.2 g, 17 mmol) in ethanol (72 ml) were added 10% palladium-carbon (723 mg) and ammonium formate (2.5 g, 39 mmol), and the mixture was stirred with heating at 65° C. for 40 min. After cooling, the reaction mixture was filtered through celite, and the filtrate was concentrated under reduced pressure. The residue was slurry-washed in water (300 ml). The precipitate was collected by filtration, washed with water, and dried under reduced pressure to give the title compound (4.5 g, yield 90%).

$^1$H-NMR (400 MHz, DMSO-$d_6$) δ: 1.00 (s, 6H), 1.56 (t, 2H, J=6.41 Hz), 2.38 (s, 2H), 2.61 (t, 2H, J=6.41 Hz), 2.69 (d, 3H, J=4.81 Hz), 5.24-5.34 (m, 1H), 6.33-6.46 (m, 3H), 7.18 (d, 1H, J=8.41 Hz), 10.65 (s, 1H), 12.28 (s, 1H).

(Step 2)

Production of (S)—N-[2-(6,6-dimethyl-4,5,6,7-tetrahydro-1H-indazol-3-yl)-1H-indol-6-yl]-N-methyl-2-(morpholin-4-yl)propionamide

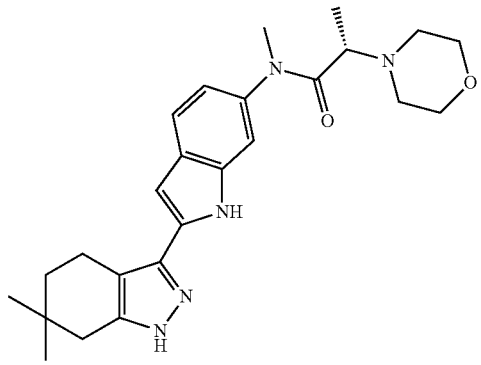

To a solution of N-{2-(6,6-dimethyl-4,5,6,7-tetrahydro-1H-indazol-3-yl)-1H-indol-6-yl}-N-methylamine (45 mg, 0.15 mmol) in pyridine (1 ml) were added (S)-2-(morpholin-4-yl)propionic acid obtained in Reference Example 3 (110 mg, 0.69 mmol) and 1-ethyl-3-(3-dimethylaminopropyl)carbodiimide hydrochloride (106 mg, 0.55 mmol) at room temperature, and the mixture was stirred for 14 hr. To the reaction mixture were added chloroform and water, and the organic layer was separated. The organic layer was dried over sodium sulfate. Sodium sulfate was removed by filtration, and the filtrate was concentrated under reduced pressure. Then, the residue was dissolved in a mixed solvent of tetrahydrofuran (1 ml) and methanol (1 ml). To the solution was added 2 N aqueous sodium hydroxide solution (0.35 ml) at room temperature, and the mixture was stirred for 20 min. To the reaction mixture were added chloroform and water, and the organic layer was separated. The organic layer was dried over sodium sulfate. Sodium sulfate was removed by filtration, and the filtrate was concentrated under reduced pressure. The residue was purified by thin layer silica gel chromatography to give the title compound (52 mg, yield 78%).

Example 5

Production of (S)—N-[2-(6,6-dimethyl-4,5,6,7-tetrahydro-1H-indazol-3-yl)-1H-indol-6-yl]-N-methyl-2-(morpholin-4-yl)propionamide hydrochloride

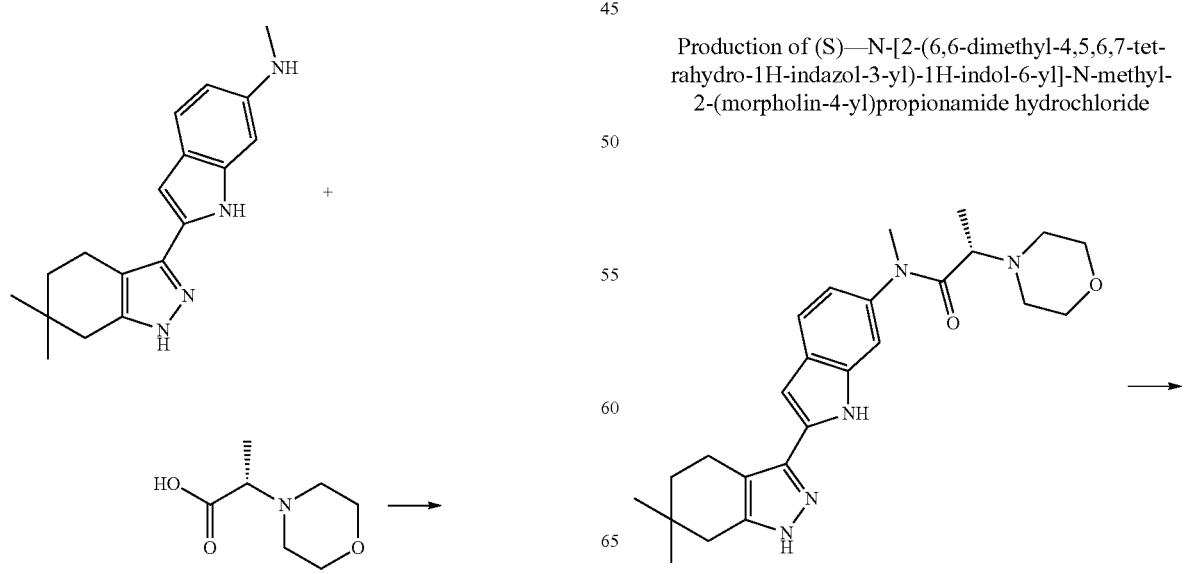

-continued

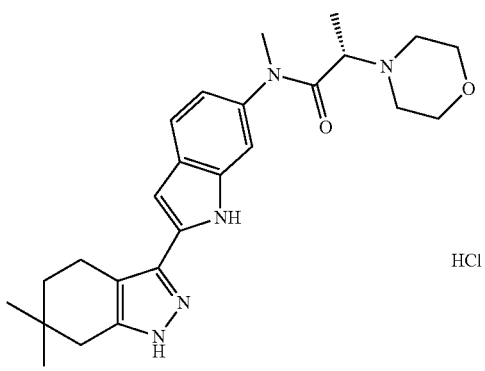

HCl

To a solution of (S)—N-[2-(6,6-dimethyl-4,5,6,7-tetrahydro-1H-indazol-3-yl)-1H-indol-6-yl]-N-methyl-2-(morpholin-4-yl)propionamide obtained in Example 4 (100 mg, 0.23 mmol) in ethyl acetate (1 ml) was added 4 N hydrochloric acid/ethyl acetate (0.06 ml, 0.24 mmol) at room temperature, and the mixture was stirred for 30 min. The precipitated crystals were collected by filtration, washed with ethyl acetate, and dried under reduced pressure to give the title compound (75 mg, 69%).

Example 6

Production of N-[2-(6,6-dimethyl-4,5,6,7-tetrahydro-1H-indazol-3-yl)-1H-indol-6-yl]-N-methyl-2-(3-oxomorpholin-4-yl)acetamide

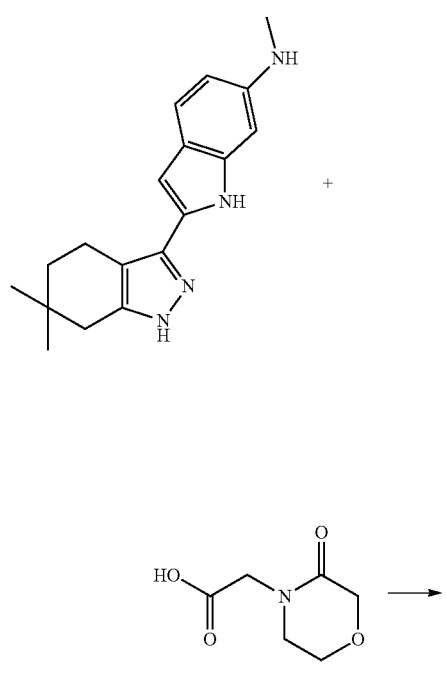

-continued

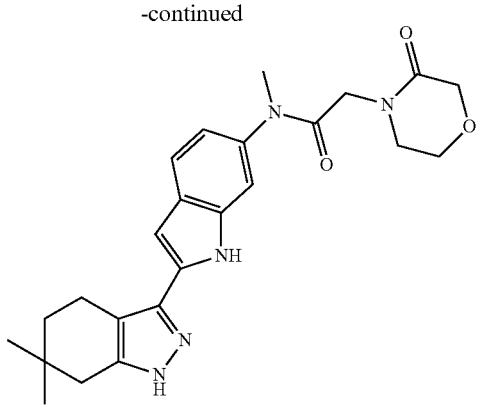

Under an argon atmosphere, to a solution of N-[2-(6,6-dimethyl-4,5,6,7-tetrahydro-1H-indazol-3-yl)-1H-indol-6-yl]-N-methylamine obtained in Example 4, Step 1 (40 mg, 0.14 mmol) and (3-oxomorpholin-4-yl)acetic acid obtained in Reference Example 4 (76 mg, 0.48 mmol) in pyridine (1.3 ml) was added 1-ethyl-3-(3-dimethylaminopropyl)carbodiimide hydrochloride (91 mg, 0.48 mmol) at room temperature, and the mixture was stirred at room temperature for 12 hr. Then, the reaction mixture was concentrated under reduced pressure. The residue was dissolved in methanol (1.2 ml), 2 N aqueous sodium hydroxide solution (1.0 ml) was added, and the mixture was stirred at room temperature for 45 min. Then, to the reaction mixture were added water and ethyl acetate, and the organic layer was separated. The aqueous layer was extracted twice with ethyl acetate, and the combined organic layers were washed successively with water and saturated brine, and dried over sodium sulfate. Sodium sulfate was removed by filtration, and the filtrate was concentrated under reduced pressure. The residue was purified by silica gel chromatography to give the title compound (40 mg, yield 67%).

Example 7

Production of 2-(6,6-dimethyl-4,5,6,7-tetrahydro-1H-indazol-3-yl)-1H-indole-6-carboxylic acid (2-hydroxy-1-methylethyl)methylamide (Step 1)

Production of 2-{6,6-dimethyl-1-[2-(trimethylsilyl)ethoxymethyl]-4,5,6,7-tetrahydro-1H-indazol-3-yl}-1-[2-(trimethylsilyl)ethoxymethyl]-1H-indole-6-carboxylic acid (2-hydroxy-1-mthylethyl)amide

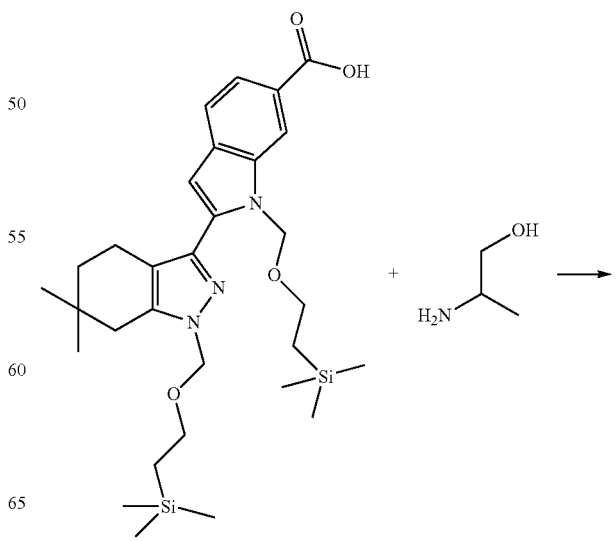

89
-continued

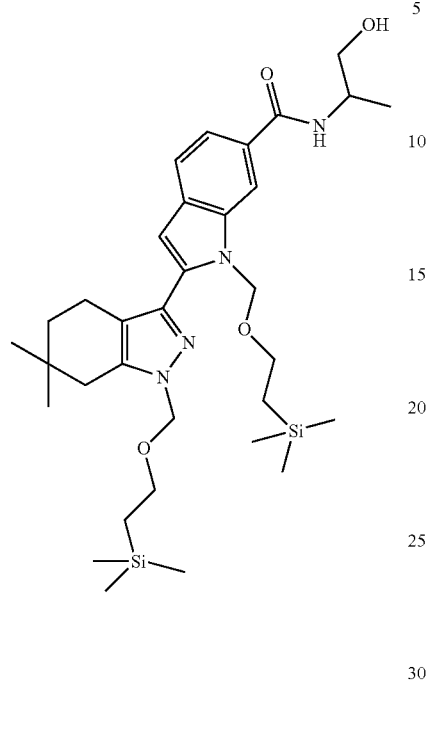

To a solution of 2-{6,6-dimethyl-1-[2-(trimethylsilyl)ethoxymethyl]-4,5,6,7-tetrahydro-1H-indazol-3-yl}-1-[2-(trimethylsilyl)ethoxymethyl]-1H-indole-6-carboxylic acid obtained in Example 1, Step 4 (500 mg, 0.88 mmol) in N,N-dimethylformamide (5 ml) were added 1-hydroxybenzotriazole monohydrate (161 mg, 1.1 mmol), 1-ethyl-3-(3-dimethylaminopropyl)carbodiimide hydrochloride (202 mg, 1.1 mmol) and 2-amino-1-propanol (84 mg, 1.1 mmol) at room temperature, and the mixture was stirred at room temperature for 7 hr. To the reaction mixture were added water and ethyl acetate, and the organic layer was separated. Then, the organic layer was washed successively with water and saturated brine, and dried over sodium sulfate. Sodium sulfate was removed by filtration, and the filtrate was concentrated under reduced pressure. The residue was purified by silica gel chromatography to give the title compound (511 mg, yield 93%).

$^1$H-NMR (400 MHz, DMSO-d$_6$) δ: −0.22 (s, 9H), −0.03 (s, 9H), 0.68 (t, 2H, J=8.12 Hz), 0.87 (t, 2H, J=8.12 Hz), 1.03 (s, 6H), 1.17 (d, 3H, J=6.72 Hz), 1.54 (t, 2H, J=6.26 Hz), 2.50 (s, 2H), 2.62 (t, 2H, J=6.26 Hz), 3.29 (t, 2H, J=8.12 Hz), 3.35-3.39 (m, 1H), 3.48-3.53 (m, 1H), 3.60 (t, 2H, J=8.12 Hz), 4.01-4.11 (m, 1H), 4.74 (t, 1H, J=5.68 Hz), 5.41 (s, 2H), 6.11 (s, 2H), 6.76 (s, 1H), 7.57-7.67 (m, 2H), 8.01 (d, 1H, J=7.88 Hz), 8.15 (s, 1H).

90
(Step 2)

Production of 2-{6,6-dimethyl-1-[2-(trimethylsilyl)ethoxymethyl]-4,5,6,7-tetrahydro-1H-indazol-3-yl}-1-[2-(trimethylsilyl)ethoxymethyl]-1H-indole-6-carboxylic acid [2-(tert-butyldiphenylsilyloxy)-1-methylethyl]amide

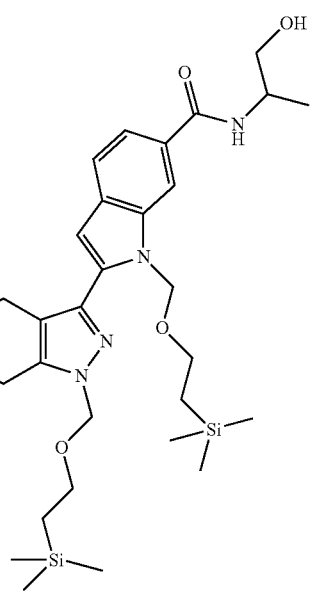

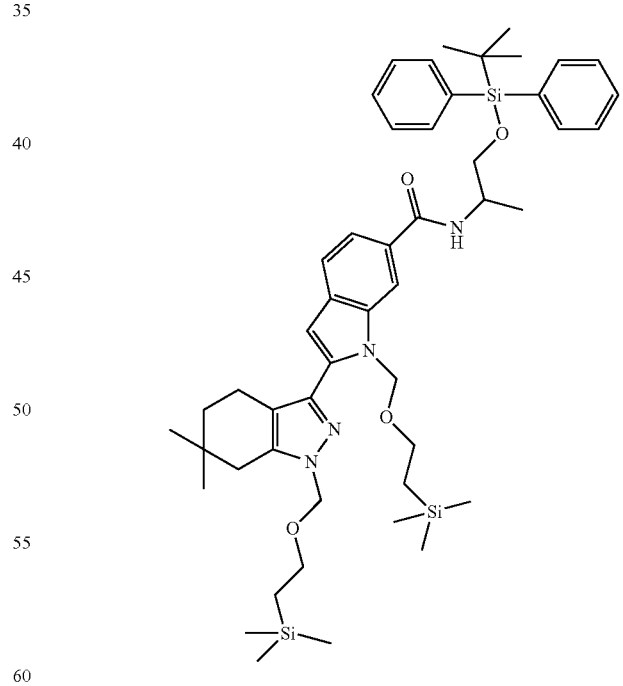

To a solution of 2-{6,6-dimethyl-1-[2-(trimethylsilyl)ethoxymethyl]-4,5,6,7-tetrahydro-1H-indazol-3-yl}-1-[2-(trimethylsilyl)ethoxymethyl]-1H-indole-6-carboxylic acid (2-hydroxy-1-methylethyl)amide (265 mg, 0.42 mmol) in N,N-dimethylformamide (2.7 ml) were added imidazole (35 mg, 0.51 mmol) and tert-butyldiphenylsilyl chloride (132 μl, 0.51 mmol) under ice-cooling, and the mixture was stirred at room temperature for 8 hr. Then, to the reaction mixture were added water and ethyl acetate, and the organic layer was separated. Then, the organic layer was washed successively with water and saturated brine, and dried over sodium sulfate. Sodium sulfate was removed by filtration, and the filtrate was concentrated under reduced pressure. The residue was purified by silica gel chromatography to give the title compound (341 mg, yield 93%).

$^1$H-NMR (400 MHz, DMSO-$d_6$) δ: −0.24 (s, 9H), −0.03 (s, 9H), 0.64 (t, 2H, J=8.12 Hz), 0.87 (t, 2H, J=8.12 Hz), 1.00 (s, 9H), 1.02 (s, 6H), 1.26 (d, 3H, J=6.96 Hz), 1.53 (t, 2H, J=6.38 Hz), 2.50 (s, 2H), 2.60-2.65 (m, 2H), 3.24-3.28 (m, 5H), 3.55-3.65 (m, 3H), 3.70-3.77 (m, 1H), 4.23-4.34 (m, 1H), 5.41 (s, 2H), 6.09 (s, 2H), 6.76 (s, 1H), 7.36-7.47 (m, 6H), 7.58-7.67 (m, 6H), 8.10-8.16 (m, 2H).

(Step 3)

Production of 2-{6,6-dimethyl-1-[2-(trimethylsilyl) ethoxymethyl]-4,5,6,7-tetrahydro-1H-indazol-3-yl}-1-[2-(trimethylsilyl)ethoxymethyl]-1H-indole-6-carboxylic acid [(2-(tert-butyldiphenylsilyloxy)-1-methylethyl]methylamide

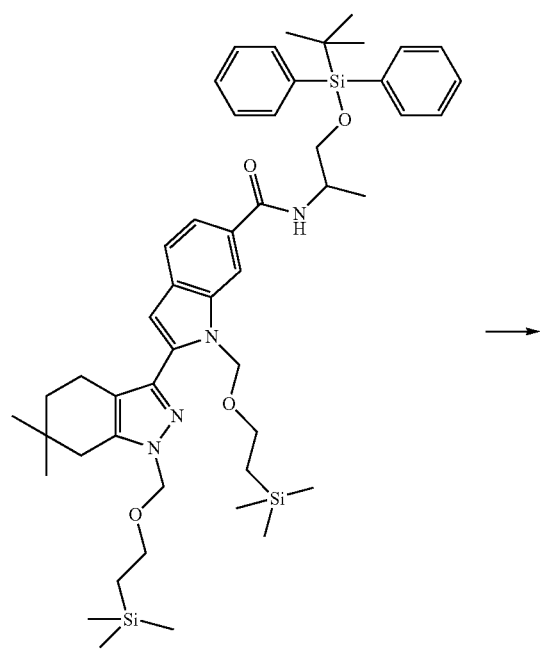

→

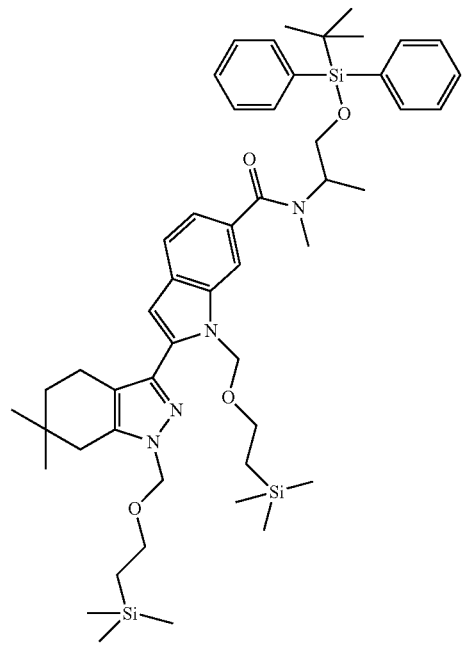

Under an argon atmosphere, to a solution of 2-{6,6-dimethyl-1-[2-(trimethylsilyl)ethoxymethyl]-4,5,6,7-tetrahydro-1H-indazol-3-yl}-1-[2-(trimethylsilyl)ethoxymethyl]-1H-indole-6-carboxylic acid [2-(tert-butyldiphenylsilyloxy)-1-methylethyl]amide (337 mg, 0.39 mmol) in N,N-dimethylformamide (3.4 ml) were added sodium hydride (19 mg, 0.47 mmol) and methyl iodide (36 μl, 0.58 mmol) under ice-cooling, and the mixture was stirred at room temperature for 3 hr. To the reaction mixture were added water and ethyl acetate, and the organic layer was separated. Then, the organic layer was washed successively with water and saturated brine, and dried over sodium sulfate. Sodium sulfate was removed by filtration, and the filtrate was concentrated under reduced pressure. The residue was purified by silica gel chromatography to give the title compound (149 mg, yield 44%).

$^1$H-NMR (400 MHz, DMSO-$d_6$) δ: −0.23 (s, 9H), −0.05 (s, 9H), 0.59-0.62 (br m, 2H), 0.86 (dd, 2H, J=10.44, 5.80 Hz), 0.98 (s, 9H), 1.02 (s, 6H), 1.08 (br s, 3H), 1.54 (t, 2H, J=6.26 Hz), 2.50 (s, 2H), 2.61-2.64 (br m, 2H), 2.83 (s, 3H), 3.21-3.29 (m, 2H), 3.38-3.46 (m, 0.6H), 3.54-3.83 (m, 1.4H), 3.58 (t, 2H, J=8.00 Hz), 4.04-4.17 (m, 0.6H), 4.72-4.90 (br m, 0.4H), 5.39-5.41 (br m, 2H), 5.69-5.83 (m, 0.6H), 5.96-6.09 (m, 1.4H), 6.77 (s, 1H), 7.11 (d, 1H, J=9.04 Hz), 7.17-7.75 (m, 12H).

93
(Step 4)

Production of 2-(6,6-dimethyl-4,5,6,7-tetrahydro-1H-indazol-3-yl)-1H-indole-6-carboxylic acid (2-hydroxy-1-methylethyl)methylamide

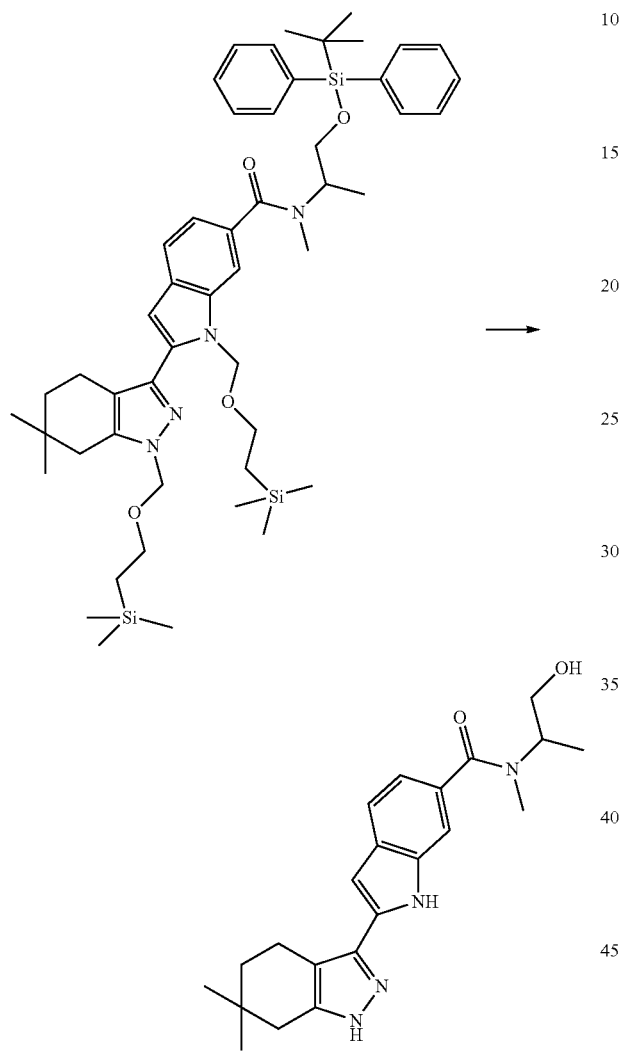

A solution of 2-{6,6-dimethyl-1-[2-(trimethylsilyl)ethoxymethyl]-4,5,6,7-tetrahydro-1H-indazol-3-yl}-1-[2-(trimethylsilyl)ethoxymethyl]-1H-indole-6-carboxylic acid [2-(tert-butyldiphenylsilyloxy)-1-methylethyl]methylamide (145 mg, 0.17 mmol) in N,N-dimethylformamide (1.2 ml) was added to tetrabutylammonium fluoride (1.7 ml, 1.7 mmol) concentrated in advance under reduced pressure. Ethylenediamine (0.29 ml) was added, and the mixture was stirred with heating at 90° C. for 14 hr. After cooling, to the mixture were added water and ethyl acetate, and the organic layer was separated, washed successively with water, 10% aqueous citric acid solution and saturated brine, and dried over sodium sulfate. Sodium sulfate was removed by filtration, and the filtrate was concentrated under reduced pressure. The residue was purified by silica gel chromatography to give the title compound (57 mg, yield 90%).

94
Example 8

Production of N-[2-(6-hydroxymethyl-6-methyl-4,5,6,7-tetrahydro-1H-indazol-3-yl)-1H-indol-6-yl]-N-methyl-2-(2-oxopiperidin-1-yl)acetamide (Step 1)

Production of N-(2-{6-benzyloxymethyl-6-methyl-1-[2-(trimethylsilyl)ethoxymethyl]-4,5,6,7-tetrahydro-1H-indazol-3-yl}-1-[2-(trimethylsilyl)ethoxymethyl]-1H-indol-6yl)-N-methylamine In the same manner as in Example 1, step 7, the title compound was obtained from tert-butyl 6-benzyloxymethyl-3-iodo-6-methyl-4,5,6,7-tetrahydroindazole-1-carboxylate obtained in Reference Example 5 and 1-tert-butyl 6-methyl 2-boronylindole-1,6-dicarboxylate obtained in Reference Example 2.

(Step 2)

Production of N-(2-{6-hydroxymethyl-6-methyl-1-[2-(trimethylsilyl)ethoxymethyl]-4,5,6,7-tetrahydro-1H-indazol-3-yl}-1-[2-(trimethylsilyl)ethoxymethyl]-1H-indol-6-yl)-N-methyl-2-(2-oxopiperidin-1-yl)acetamide

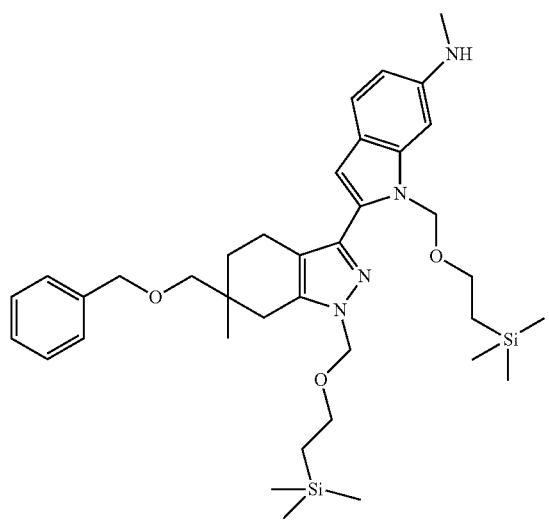

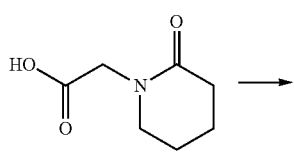

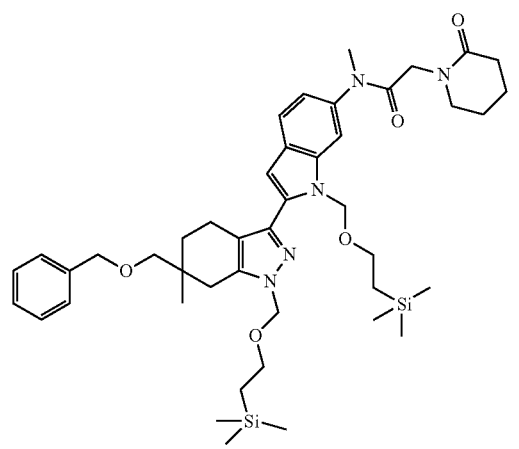

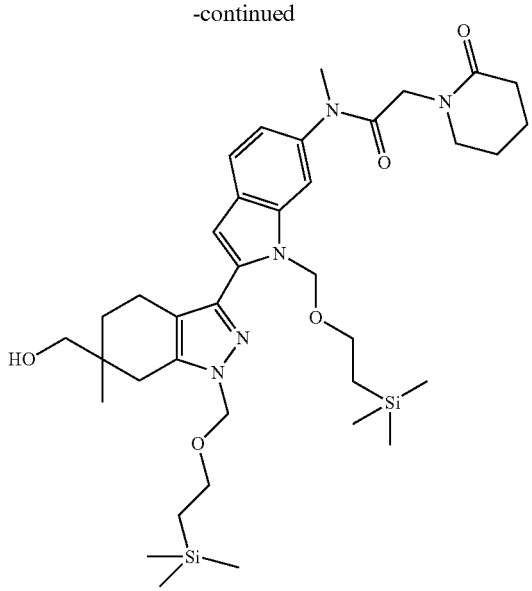

To a solution of N-(2-{6-benzyloxymethyl-6-methyl-1-[2-(trimethylsilyl)ethoxymethyl]-4,5,6,7-tetrahydro-1H-indazol-3-yl}-1-[2-(trimethylsilyl)ethoxymethyl]-1H-indol-6-yl)-N-methylamine (150 mg, 0.23 mmol) in N,N-dimethylformamide (3 ml) were added (2-oxopiperidin-1-yl)acetic acid obtained in Reference Example 6 (43 mg, 0.27 mmol), 1-ethyl-3-(3-dimethylaminopropyl)carbodiimide hydrochloride (52 mg, 0.27% mmol) and 1-hydroxybenzotriazole monohydrate (37 mg, 0.27 mmol), and the mixture was stirred at room temperature overnight. To the reaction mixture were added ethyl acetate and water, and the organic layer was separated, washed successively with water and saturated brine, and dried over sodium sulfate. Sodium sulfate was removed by filtration, and the filtrate was concentrated under reduced pressure. The residue was purified by silica gel chromatography to give N-(2-{6-benzyloxymethyl-6-methyl-1-[2-(trimethylsilyl)ethoxymethyl]-4,5,6,7-tetrahydro-1H-indazol-3-yl}-1-[2-(trimethylsilyl)ethoxymethyl]-1H-indol-6-yl)-N-methyl-2-(2-oxopiperidin-1-yl)acetamide (158 mg). Under a nitrogen atmosphere, to a solution of the obtained N-(2-{6-benzyloxymethyl-6-methyl-1-[2-(trimethylsilyl)ethoxymethyl]-4,5,6,7-tetrahydro-1H-indazol-3-yl}-1-[2-(trimethylsilyl)ethoxymethyl]-1H-indol-6-yl)-N-methyl-2-(2-oxopiperidin-1-yl)acetamide (158 mg) in a mixed solvent of methanol (0.8 ml) and tetrahydrofuran (0.8 ml) was added 20% palladium hydroxide-carbon (150 mg) at room temperature, and the mixture was stirred under a hydrogen atmosphere at normal pressure for 4 hr. The reaction mixture was filtered through celite, and the filtrate was concentrated under reduced pressure to give the title compound (120 mg, yield 75%).

$^1$H-NMR (400 MHz, DMSO-$d_6$) δ: −0.21 (9H, s), −0.04 (9H, s), 0.67 (2H, t, J=7.86 Hz), 0.86 (2H, t, J=8.06 Hz), 0.93 (3H, s), 1.44-1.73 (6H, m), 2.12-2.21 (2H, m), 2.39 (1H, d, J=16.52 Hz), 2.59-2.65 (2H, m), 2.59 (1H, d, J=16.52 Hz), 3.22 (3H, s), 3.27 (2H, s), 3.31 (2H, t, J=8.06 Hz), 3.59 (2H, t, J=7.86 Hz), 3.81 (2H, s), 4.71 (1H, t, J=5.44 Hz), 5.38 (1H, d, J=11.28 Hz), 5.41 (1H, d, J=11.69 Hz), 6.02 (1H, d, J=10.48 Hz), 6.07 (1H, d, J=10.88 Hz), 6.74 (1H, s), 7.06 (1H, d, J=7.66 Hz), 7.60 (1H, s), 7.64 (1H, d, J=8.06 Hz).

97

(Step 3)

Production of N-[2-(6-hydroxymethyl-6-methyl-4,5,6,7-tetrahydro-1H-indazol-3-yl)-1H-indol-6-yl]-N-methyl-2-(2-oxopiperidin-1-yl)acetamide

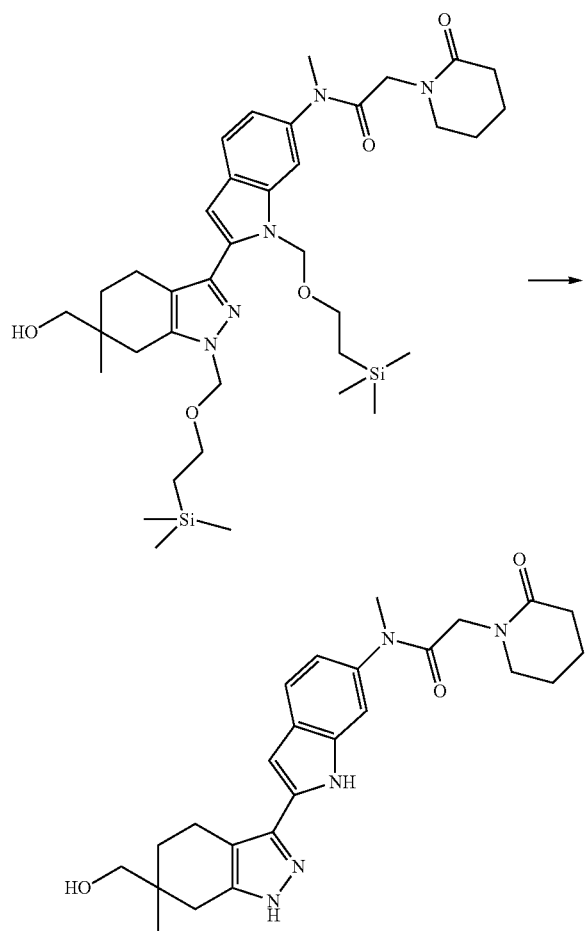

98

A solution of N-(2-{6-hydroxymethyl-6-methyl-1-[2-(trimethylsilyl)ethoxymethyl]-4,5,6,7-tetrahydro-1H-indazol-3-yl}-1-[2-(trimethylsilyl)ethoxymethyl]-1H-indol-6-yl)-N-methyl-2-(2-oxopiperidin-1-yl)acetamide (63 mg, 0.09 mmol) in N,N-dimethylformamide (1.5 ml) was added to tetrabutylammonium fluoride (0.6 ml, 0.6 mmol) concentrated in advance under reduced pressure. Ethylenediamine (0.2 ml) was added, and the mixture was stirred with heating at 80° C. overnight. After cooling, water and ethyl acetate were added, and the organic layer was separated. Then, the organic layer was washed successively with water and saturated brine, and dried over sodium sulfate. Sodium sulfate was removed by filtration, and the filtrate was concentrated under reduced pressure. The residue was purified by thin layer silica gel chromatography to give the title compound (5.5 mg, yield 16%).

The compounds of Examples 9-381 were obtained in the same manner as in the above-mentioned Examples. The structural formulas and $^1$H-NMR spectrum data thereof are shown in Tables 1-1 to 1-78.

In the Tables, the compounds in an optically active form are indicated with (an optically active form) under Example No.

$^1$H-NMR spectra were measured in CDCl$_3$ or DMSO-D$_6$, with tetramethylsilane as an internal standard, and all δ values are shown in ppm. Unless specifically indicated in the Table, the resolution capability was measured at 400 MHz.

The symbols in the Tables mean the following.

| | |
|---|---|
| s: | singlet |
| d: | doublet |
| t: | triplet |
| q: | quartet |
| dd: | double doublet |
| ddd: | double double doublet |
| brs: | broad singlet |
| m: | multiplet |
| J: | coupling constant |

TABLE 1-1

| Ex. No. | structural formula | NMR | MS (M + H) | MS (M − H) |
|---|---|---|---|---|
| 1 | (structure shown) | $^1$H-NMR (DMSO-D$_6$) δ: 1.01 (6H, s), 1.55-1.61 (2H, m), 1.75 (3H, s), 2.41 (2H, s), 2.63-2.69 (2H, m), 3.17 (3H, s), 6.57-6.61 (1H, m), 6.85-6.90 (1H, m), 7.21-7.25 (1H, m), 7.52-7.57 (1H, m), 11.41 (1H, br s), 12.54 (1H, br s). | 337 | 335 |

TABLE 1-1-continued

| Ex. No. | structural formula | NMR | MS (M + H) | MS (M − H) |
|---|---|---|---|---|
| 2 | | ¹H-NMR (DMSO-D₆) δ: 1.01 (s, 6H), 1.03 (t, 3H, J = 7.00 Hz), 1.58 (t, 2H, J = 6.29 Hz), 2.41 (s, 2H), 2.62-2.73 (m, 2H), 3.66 (q, 2H, J = 7.00 Hz), 6.60 (s, 1H), 6.84 (d, 1H, J = 8.05 Hz), 7.21 (s, 1H), 7.55 (d, 1H, J = 8.05 Hz), 11.38 (s, 1H), 12.53 (s, 1H). | 351 | 349 |
| 3 | | ¹H-NMR (DMSO-D₆) δ: 1.01 (6H, s, 6H), 1.57 (2H, t, 2H, J = 6.01 Hz), 2.41 (2H, s, 2H), 2.65 (2H, t, 2H, J = 6.01 Hz), 3.27 (3H, s, 3H), 5.09 (2H, s, 2H), 6.56 (1H, s, 1H), 6.89 (1H, d, 1H, J = 8.01 Hz), 7.28-7.34 (6H, m, 6H), 7.47 (1H, d, 1H, J = 8.01 Hz), 11.28 (1H, s, 1H), 12.49 (1H, s, 1H). | 429 | 427 |
| 4 | | ¹H-NMR (DMSO-D₆) δ: 0.95-1.07 (3H, m), 1.01 (6H, s), 1.54-1.61 (2H, m), 2.21-2.30 (2H, m), 2.37-2.48 (2H, m), 2.41 (2H, s), 2.62-2.73 (2H, m), 3.16-3.24 (1H, m), 3.19 (3H, s), 3.44-3.53 (4H, m), 6.57-6.62 (1H, m), 6.86-6.93 (1H, m), 7.26-7.32 (1H, m), 7.51-7.57 (1H, m), 11.39 (1H, br s), 12.53 (1H, br s). | 436 | 434 |
| 5 | HCl | ¹H-NMR (DMSO-D₆) δ: 1.01 (6H, s), 1.36 (3H, d, J = 5.8 Hz), 1.54-1.62 (2H, m), 2.42 (2H, s), 2.63-2.72 (2H, m), 2.96-3.17 (2H, m), 3.20-3.50 (6H, m), 3.65-3.99 (4H, m), 6.63-6.69 (1H, m), 6.96-7.03 (1H, m), 7.34-7.40 (1H, m), 7.61-7.66 (1H, m), 10.29 (1H, br s), 11.48 (1H, br s), 12.60 (1H, br s). | 436 | 434 |

TABLE 1-2
| Ex. No. | structural formula | NMR | MS (M + H) | MS (M − H) |
|---|---|---|---|---|
| 6 | 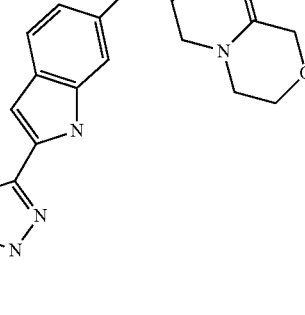 | ¹H-NMR (DMSO-D₆) δ: 1.01 (6H, s), 1.54-1.61 (2H, m), 2.42 (2H, s), 2.63-2.71 (2H, m), 3.21 (3H, s), 3.31-3.37 (2H, m), 3.76-3.81 (2H, m), 3.83-3.87 (2H, m), 4.00 (2H, s), 6.57-6.64 (1H, m), 6.90-6.97 (1H, m), 7.29-7.33 (1H, m), 7.55-7.61 (1H, m), 11.48 (1H, br s), 12.55 (1H, br s). | 436 | 434 |
| 7 | 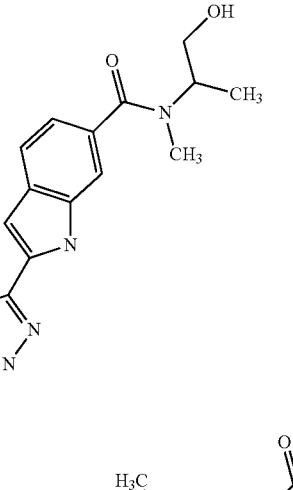 | ¹H-NMR (DMSO-D₆) δ: 1.01 (6H, s), 1.04-1.10 (3H, m), 1.54-1.60 (2H, m), 2.42 (2H, s), 2.65-2.70 (2H, m), 2.82 (3H, s), 3.20-3.54 (2H, m), 3.84-4.04 (1H, m), 4.46-4.89 (1H, m), 6.60 (1H, d, J = 1.2 Hz), 7.00 (1H, dd, J = 8.1, 1.4 Hz), 7.41-7.43 (1H, m), 7.51 (1H, d, J = 8.1 Hz), 11.38 (1H, br s), 12.52 (1H, br s). | 381 | 379 |
| 8 | 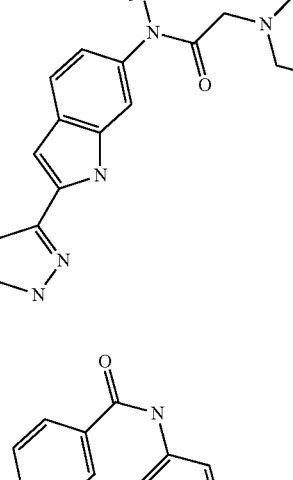 | ¹H-NMR (DMSO-D₆) δ: 0.92 (3H, s), 1.53-1.68 (6H, m), 2.17 (2H, s), 2.29 (1H, d, J = 16.12 Hz), 2.54 (1H, d, J = 16.12 Hz), 2.59-2.77 (2H, m), 3.19 (3H, s), 3.20-3.25 (2H, m), 3.26 (2H, s), 3.77 (2H, s), 4.62 (1H, s), 6.60 (1H, s), 6.92 (1H, d, J = 7.66 Hz), 7.31 (1H, s), 7.56 (1H, d, J = 7.66 Hz), 11.38 (1H, s), 12.50 (1H, s). | 450 | 448 |
| 9 | 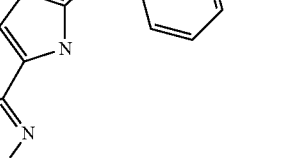 | ¹H-NMR (DMSO-D₆) δ: 1.02 (s, 6H), 1.59 (t, 2H, J = 6.29 Hz), 2.43 (s, 2H), 2.66-2.75 (m, 2H), 6.66 (s, 1H), 7.08 (t, 1H, J = 7.39 Hz), 7.34 (t, 2H, J = 7.94 Hz), 7.61 (s, 2H), 7.81 (d, 2H, J = 7.50 Hz), 8.02 (s, 1H), 10.15 (s, 1H), 11.64 (s, 1H), 12.61 (s, 1H). | 385 | 383 |

TABLE 1-2-continued
| Ex. No. | structural formula | NMR | MS (M + H) | MS (M − H) |
|---|---|---|---|---|
| 10 | 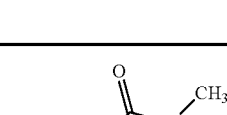 | $^1$H-NMR (DMSO-D$_6$) δ: 0.99 (s, 6H), 1.55 (t, 2H, J = 6.29 Hz), 2.40 (s, 2H), 2.58-2.67 (m, 2H), 3.39 (s, 3H), 6.49 (s, 1H), 6.82 (d, 1H, J = 7.94 Hz), 7.07-7.18 (m, 3H), 7.20-7.29 (m, 3H), 7.43 (s, 1H), 11.37 (s, 1H), 12.54 (s, 1H). | 397 399 | |
TABLE 1-3
| Ex. No. | structural formula | NMR | MS (M + H) | MS (M − H) |
|---|---|---|---|---|
| 11 | | $^1$H-NMR (DMSO-D$_6$) δ: 0.92 (9H, s), 1.01 (6H, s), 1.56-1.61 (2H, m), 2.42 (2H, s), 2.65-2.71 (2H, m), 3.12 (2H, d, J = 6.3 Hz), 6.61 (1H, s), 7.47-7.54 (2H, m), 7.92 (1H, s), 8.17 (1H, t, J = 6.3 Hz), 11.51 (1H, br s), 12.57 (1H, br s). | 379 | 377 |
| 12 | | $^1$H-NMR (DMSO-D$_6$, 300 MHz) δ: 0.89 (3H, s), 0.91 (3H, s), 1.01 (6H, s), 1.55-1.61 (2H, m), 1.81-1.92 (1H, m), 2.42 (2H, s), 2.64-2.71 (2H, m), 3.06-3.12 (2H, m), 6.61 (1H, s), 7.45-7.54 (2H, m), 7.90-7.93 (1H, m), 8.26-8.32 (1H, m), 11.51 (1H, br s), 12.56 (1H, br s). | 365 | 363 |
| 13 | | $^1$H-NMR (DMSO-D$_6$) δ: 0.92 (9H, s), 1.01 (6H, s), 1.09 (3H, d, J = 6.8 Hz), 1.53-1.62 (2H, m), 2.42 (2H, s), 2.63-2.77 (2H, m), 3.96-4.06 (1H, m), 6.61 (1H, s), 7.43-7.57 (2H, m), 7.72-7.80 (1H, m), 7.89 (1H, br s), 11.47 (1H, br s), 12.56 (1H, br s). | 393 | 391 |

TABLE 1-3-continued

| Ex. No. | structural formula | NMR | MS (M + H) | MS (M − H) |
|---|---|---|---|---|
| 14 | | ¹H-NMR (DMSO-D₆) δ: 1.01 (6H, s), 1.54-1.61 (2H, m), 2.21 (3H, s), 2.29-2.38 (4H, m), 2.42 (2H, s), 2.64-2.71 (2H, m), 3.44-3.61 (4H, m), 6.59-6.62 (1H, m), 6.97-7.01 (1H, m), 7.42-7.46 (1H, m), 7.51-7.55 (1H, m), 11.45 (1H, br s), 12.57 (1H, br s). | 392 | 390 |
| 15 | | ¹H-NMR (DMSO-D₆) δ: 0.67-1.17 (9H, m), 1.01 (6H, s), 1.54-1.62 (2H, m), 2.42 (2H, s), 2.64-2.73 (2H, m), 3.03 (3H, s), 3.36 (2H, s), 6.60 (1H, s), 6.96-7.08 (1H, m), 7.41-7.48 (1H, m), 7.49-7.56 (1H, m), 11.38 (1H, br s), 12.55 (1H, br s). | 393 | 391 |

TABLE 1-4

| Ex. No. | structural formula | NMR | MS (M + H) | MS (M − H) |
|---|---|---|---|---|
| 16 | | ¹H-NMR (DMSO-D₆) δ: 1.01 (6H, s), 1.30-1.43 (2H, m), 1.53-1.61 (2H, m), 1.69-1.82 (2H, m), 2.42 (2H, s), 2.62-2.73 (2H, m), 3.13-3.22 (2H, m), 3.64-4.01 (3H, m), 4.78 (1H, d, J = 4.2 Hz), 6.59-6.63 (1H, m), 6.96-7.01 (1H, m), 7.42-7.45 (1H, m), 7.50-7.55 (1H, m), 11.44 (1H, br s), 12.56 (1H, br s). | 393 | 391 |
| 17 | | ¹H-NMR (DMSO-D₆, 300 MHz) δ: 0.72-0.95 (6H, m), 1.01 (6H, s), 1.54-1.62 (2H, m), 1.93-2.06 (1H, m), 2.42 (2H, s), 2.64-2.72 (2H, m), 2.94 (3H, s), 3.17-3.30 (2H, m), 6.60 (1H, s), 6.94-6.99 (1H, m), 7.37-7.43 (1H, m), 7.50-7.54 (1H, m), 11.41 (1H, br s), 12.55 (1H, br s). | 379 | 377 |

TABLE 1-4-continued

| Ex. No. | structural formula | NMR | MS (M + H) | MS (M − H) |
|---|---|---|---|---|
| 18 | | ¹H-NMR (DMSO-D₆, 300 MHz) δ: 0.75-0.81 (6H, m), 0.95-1.04 (4H, m), 1.01 (6H, s), 1.13-1.27 (2H, m), 1.55-1.61 (2H, m), 2.39-2.43 (2H, m), 2.65-2.73 (2H, m), 2.79-2.90 (4H, m), 6.59-6.62 (1H, m), 6.88-7.00 (1H, m), 7.37-7.40 (1H, m), 7.50-7.54 (1H, m), 11.36 (1H, br s), 12.54 (1H, br s). | 407 | 405 |
| 19 | | ¹H-NMR (DMSO-D₆) δ: 1.01 (6H, s), 1.55-1.61 (2H, m), 2.42 (2H, s), 2.64-2.72 (2H, m), 3.46-3.57 (4H, m), 3.58-3.67 (4H, m), 6.60-6.63 (1H, m), 6.99-7.04 (1H, m), 7.45-7.48 (1H, m), 7.51-7.56 (1H, m), 11.47 (1H, br s), 12.57 (1H, br s). | 379 | 377 |
| 20 | | ¹H-NMR (DMSO-D₆) δ: 1.01 (6H, s), 1.15 (3H, d, J = 6.7 Hz), 1.55-1.62 (2H, m), 2.42 (2H, s), 2.64-2.73 (2H, m), 3.33-3.39 (1H, m), 3.45-3.53 (1H, m), 3.98-4.09 (1H, m), 4.71 (1H, br s), 6.61 (1H, br s), 7.46-7.54 (2H, m), 7.88-7.95 (2H, m), 11.53 (1H, br s), 12.58 (1H, br s). | 367 | 365 |

TABLE 1-5

| Ex. No. | structural formula | NMR | MS (M + H) | MS (M − H) |
|---|---|---|---|---|
| 21 | | ¹H-NMR (DMSO-D₆) δ: 1.01 (6H, s), 1.15 (3H, d, J = 6.7 Hz), 1.55-1.62 (2H, m), 2.42 (2H, s), 2.64-2.72 (2H, m), 3.26-3.31 (1H, m), 3.28 (3H, s), 3.40-3.46 (1H, m), 4.18-4.26 (1H, m), 6.59-6.65 (1H, m), 7.45-7.55 (2H, m), 7.90-7.94 (1H, m), 8.05 (1H, d, J = 8.1 Hz), 11.53 (1H, br s), 12.58 (1H, br s). | 381 | 379 |
| 22 | | ¹H-NMR (DMSO-D₆) δ: 1.01 (6H, s), 1.06-1.14 (3H, m), 1.54-1.61 (2H, m), 2.42 (2H, s), 2.64-2.72 (2H, m), 2.81 (3H, s), 3.08-3.56 (5H, m), 3.95-4.26 (1H, m), 6.57-6.64 (1H, m), 6.94-6.99 (1H, m), 7.40-7.43 (1H, m), 7.49-7.54 (1H, m), 11.41 (1H, br s), 12.56 (1H, br s). | 395 | 393 |
| 23 | | ¹H-NMR (DMSO-D₆) δ: 0.91 (3H, d, J = 7.0 Hz), 0.93 (3H, d, J = 7.0 Hz), 1.01 (6H, s), 1.55-1.61 (2H, m), 1.90-2.00 (1H, m), 2.42 (2H, s), 2.65-2.72 (2H, m), 3.53 (2H, t, J = 5.6 Hz), 3.80-3.88 (1H, m), 4.56 (1H, t, J = 5.7 Hz), 6.60-6.63 (1H, m), 7.48-7.54 (2H, m), 7.74-7.79 (1H, m), 7.90-7.94 (1H, m), 11.52 (1H, br s), 12.58 (1H, br s). | 395 | 393 |
| 24 | | ¹H-NMR (DMSO-D₆) δ: 0.91 (3H, d, J = 5.8 Hz), 0.93 (3H, d, J = 5.8 Hz), 1.01 (6H, s), 1.54-1.62 (2H, m), 1.85-1.95 (1H, m), 2.42 (2H, s), 2.64-2.73 (2H, m), 3.26 (3H, s), 3.42-3.51 (2H, m), 3.97-4.04 (1H, m), 6.59-6.65 (1H, m), 7.48-7.55 (2H, m), 7.88-7.98 (2H, m), 11.51 (1H, br s), 12.57 (1H, br s). | 409 | 407 |

TABLE 1-5-continued
| Ex. No. | structural formula | NMR | MS (M + H) | MS (M − H) |
|---|---|---|---|---|
| 25 | 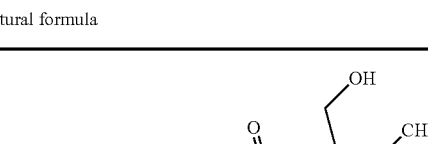 | ¹H-NMR (DMSO-D$_6$) δ: 0.68-1.05 (6H, m), 1.01 (6H, s), 1.55-1.62 (2H, m), 1.72-1.97 (1H, m), 2.42 (2H, s), 2.64-2.71 (2H, m), 2.79-2.87 (3H, m), 3.45-3.71 (3H, m), 4.66-4.85 (1H, m), 6.56-6.61 (1H, m), 6.95-7.07 (1H, m), 7.39-7.55 (2H, m), 11.36-11.42 (1H, m), 12.52-12.57 (1H, m). | 409 | 407 |
TABLE 1-6
| Ex. No. | structural formula | NMR | MS (M + H) | MS (M − H) |
|---|---|---|---|---|
| 26 | 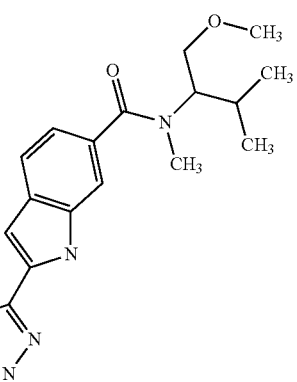 | ¹H-NMR (DMSO-D$_6$) δ: 0.69-1.05 (6H, m), 1.00 (6H, s), 1.53-1.61 (2H, m), 1.76-1.98 (1H, m), 2.41 (2H, s), 2.63-2.71 (2H, m), 2.75-2.84 (3H, m), 3.25-3.31 (3H, m), 3.42-3.65 (3H, m), 6.55-6.62 (1H, m), 6.91-6.98 (1H, m), 7.37-7.42 (1H, m), 7.46-7.54 (1H, m), 11.37-11.44 (1H, m), 12.54 (1H, br s). | 423 | 421 |
| 27 | 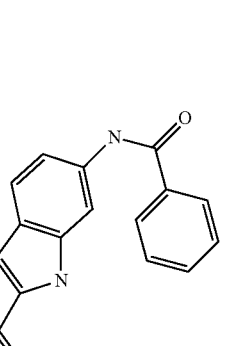 | ¹H-NMR (DMSO-D$_6$) δ: 1.01 (6H, s), 1.58 (2H, t, J = 6.40 Hz), 2.41 (2H, s), 2.63-2.69 (2H, m), 6.52 (1H, s), 7.28 (1H, d, J = 8.60 Hz), 7.44 (1H, d, J = 8.60 Hz), 7.49-7.63 (3H, m), 7.95-8.05 (3H, m), 10.14 (1H, s), 11.24 (1H, s), 12.46 (1H, s). | 385 | 383 |

TABLE 1-6-continued

| Ex. No. | structural formula | NMR | MS (M + H) | MS (M − H) |
|---|---|---|---|---|
| 28 | | $^1$H-NMR (DMSO-D$_6$) δ: 1.00 (6H, s), 1.07-1.13 (3H, m), 1.53-1.60 (2H, m), 2.28-2.35 (2H, m), 2.40 (2H, s), 2.62-2.69 (2H, m), 6.46-6.50 (1H, m), 7.03-7.08 (1H, m), 7.35-7.39 (1H, m), 7.87-7.91 (1H, m), 9.72 (1H, br s), 11.11 (1H, br s), 12.41 (1H, br s). | 337 | 335 |
| 29 | | $^1$H-NMR (DMSO-D$_6$) δ: 1.00 (6H, s), 1.52-1.59 (2H, m), 2.40 (2H, s), 2.60-2.69 (2H, m), 5.69 (2H, br s), 6.41-6.45 (1H, m), 6.80-6.86 (1H, m), 7.29-7.34 (1H, m), 7.65-7.68 (1H, m), 8.36 (1H, br s), 11.00 (1H, br s), 12.40 (1H, br s). | 324 | 322 |
| 30 | | $^1$H-NMR (DMSO-D$_6$) δ: 0.99 (6H, s), 1.55 (2H, t, J = 6.06 Hz), 2.39 (2H, s), 2.58-2.66 (2H, m), 3.40 (3H, s), 6.49 (1H, s), 6.81 (1H, d, J = 8.60 Hz), 7.07 (1H, s), 7.11-7.22 (3H, m), 7.23-7.30 (2H, m), 7.38 (1H, d, J = 8.38 Hz), 11.22 (1H, s), 12.48 (1H, s). | 399 | 397 |
| 31 | | $^1$H-NMR (DMSO-D$_6$) δ: 0.99 (6H, s), 1.53-1.58 (2H, m), 2.39 (2H, s), 2.59-2.65 (2H, m), 3.43 (3H, s), 6.50 (1H, s), 6.84-6.88 (1H, m), 7.09-7.12 (1H, m), 7.36-7.42 (2H, m), 7.50-7.59 (2H, m), 7.60-7.65 (1H, m), 11.25 (1H, br s), 12.49 (1H, br s). | 467 | 465 |

TABLE 1-7

| Ex. No. | structural formula | NMR | MS (M + H) | MS (M − H) |
|---|---|---|---|---|
| 32 | | ¹H-NMR (DMSO-D₆, 300 MHz) δ: 0.91 (3H, t, J = 7.5 Hz), 1.01 (6H, s), 1.54-1.61 (2H, m), 1.95-2.05 (2H, m), 2.41 (2H, s), 2.62-2.71 (2H, m), 3.18 (3H, s), 6.57-6.61 (1H, m), 6.84-6.89 (1H, m), 7.21-7.24 (1H, m), 7.51-7.57 (1H, m), 11.39 (1H, br s), 12.53 (1H, br s). | 351 | 349 |
| 33 | | ¹H-NMR (DMSO-D₆, 300 MHz) δ: 1.01 (6H, s), 1.25-1.36 (2H, m), 1.41-1.71 (8H, m), 2.41 (2H, s), 2.52-2.60 (1H, m), 2.64-2.70 (2H, m), 3.18 (3H, s), 6.57-6.62 (1H, m), 6.83-6.89 (1H, m), 7.22-7.26 (1H, m), 7.51-7.57 (1H, m), 11.38 (1H, br s), 12.54 (1H, br s). | 391 | 389 |
| 34 | | ¹H-NMR (DMSO-D₆) δ: 1.01 (6H, s), 1.03 (3H, d, J = 6.8 Hz), 1.55-1.61 (2H, m), 2.41 (2H, s), 2.64-2.70 (2H, m), 3.20 (3H, s), 4.00-4.15 (2H, m), 6.58-6.64 (1H, m), 6.86-6.91 (1H, m), 7.22-7.30 (1H, m), 7.52-7.59 (1H, m), 11.41 (1H, br s), 12.53 (1H, br s). | 367 | 365 |
| 35 | | ¹H-NMR (DMSO-D₆) δ: 1.01 (6H, s), 1.55-1.61 (2H, m), 2.42 (2H, s), 2.63-2.71 (2H, m), 3.21 (3H, s), 3.66-3.76 (2H, m), 4.48 (1H, t, J = 5.7 Hz), 6.57-6.63 (1H, m), 6.84-6.90 (1H, m), 7.21-7.27 (1H, m), 7.50-7.58 (1H, m), 11.42 (1H, br s), 12.54 (1H, br s). | 353 | 351 |

TABLE 1-7-continued

| Ex. No. | structural formula | NMR | MS (M + H) | MS (M − H) |
|---|---|---|---|---|
| 36 | | ¹H-NMR (DMSO-D₆) δ: 1.01 (6H, s), 1.55-1.61 (2H, m), 2.41 (2H, s), 2.63-2.72 (2H, m), 3.14-3.24 (6H, m), 3.73 (2H, s), 6.57-6.63 (1H, m), 6.85-6.92 (1H, m), 7.23-7.27 (1H, m), 7.52-7.58 (1H, m), 11.42 (1H, br s), 12.54 (1H, br s). | 367 | 365 |

TABLE 1-8

| Ex. No. | structural formula | NMR | MS (M + H) | MS (M − H) |
|---|---|---|---|---|
| 37 | | ¹H-NMR (DMSO-D₆) δ: 1.01 (6H, s), 1.20 (6H, br s), 1.54-1.61 (2H, m), 2.41 (2H, s), 2.63-2.71 (2H, m), 3.30 (3H, s), 4.88 (1H, br s), 6.54-6.62 (1H, m), 6.82-6.90 (1H, m), 7.21-7.28 (1H, m), 7.46-7.51 (1H, m), 11.32 (1H, br s), 12.51 (1H, br s). | 381 | 379 |
| 38 | | ¹H-NMR (DMSO-D₆) δ: 0.74 (3H, t, J = 7.4 Hz), 1.01 (6H, s), 1.40-1.50 2H, m), 1.55-1.61 (2H, m), 1.95-2.02 (2H, m), 2.42 (2H, s), 2.64-2.69 (2H, m), 3.18 (3H, s), 6.57-6.61 (1H, m), 6.82-6.88 (1H, m), 7.20-7.23 (1H, m), 7.52-7.57 (1H, m), 11.40 (1H, br s), 12.54 (1H, br s). | 365 | 363 |
| 39 | | ¹H-NMR (DMSO-D₆) δ: 0.90 (3H, s), 0.92 (3H, s), 1.01 (6H, s), 1.55-1.61 (2H, m), 2.42 (2H, s), 2.45-2.53 (1H, m), 2.64-2.70 (2H, m), 3.16 (3H, s), 6.58-6.62 (1H, m), 6.85-6.90 (1H, m), 7.21-7.26 (1H, m), 7.53-7.58 (1H, m), 11.39 (1H, br s), 12.54 (1H, br s). | 365 | 363 |

TABLE 1-8-continued

| Ex. No. | structural formula | NMR | MS (M + H) | MS (M − H) |
|---|---|---|---|---|
| 40 |  | ¹H-NMR (DMSO-D₆) δ: 0.75 (3H, s), 0.77 (3H, s), 1.01 (6H, s), 1.55-1.61 (2H, m), 1.89-1.93 (2H, m), 1.94-2.02 (1H, m), 2.42 (2H, s), 2.64-2.70 (2H, m), 3.18 (3H, s), 6.57-6.61 (1H, m), 6.81-6.86 (1H, m), 7.18-7.22 (1H, m), 7.52-7.58 (1H, m), 11.40 (1H, br s), 12.54 (1H, br s). | 379 | 377 |
| 41 |  | ¹H-NMR (DMSO-D₆) δ: 1.01 (6H, s), 1.08 (3H, d, J = 6.4 Hz), 1.54-1.61 (2H, m), 2.42 (2H, s), 2.64-2.70 (2H, m), 3.04 (3H, s), 3.21 (3H, s), 3.79 (1H, q, J = 6.3 Hz), 6.58-6.62 (1H, m), 6.86-6.91 (1H, m), 7.24-7.28 (1H, m), 7.54-7.60 (1H, m), 11.40 (1H, br s), 12.53-12.55 (1H, br m). | 381 | 379 |

TABLE 1-9

| Ex. No. | structural formula | NMR | MS (M + H) | MS (M − H) |
|---|---|---|---|---|
| 42 |  | ¹H-NMR (DMSO-D₆) δ: 1.01 (6H, s), 1.12-1.49 (6H, m), 1.53-1.63 (2H, m), 2.41 (2H, s), 2.63-2.69 (2H, m), 2.93-3.58 (6H, m), 6.54-6.58 (1H, m), 6.80-6.86 (1H, m), 7.18-7.25 (1H, m), 7.44-7.49 (1H, m), 11.29 (1H, br s), 12.51 (1H, br s). | 395 | 393 |

TABLE 1-9-continued

| Ex. No. | structural formula | NMR | MS (M + H) | MS (M − H) |
|---|---|---|---|---|
| 43 | | ¹H-NMR (DMSO-D₆) δ: 1.01 (6H, s), 1.54-1.61 (2H, m), 2.41 (2H, s), 2.64-2.72 (2H, m), 3.18-3.27 (1H, m), 3.20 (3H, s), 3.40-3.48 (1H, m), 3.97-4.04 (1H, m), 4.50-4.56 (1H, m), 4.77 (1H, d, J = 6.6 Hz), 6.56-6.64 (1H, m), 6.87-6.93 (1H, m), 7.26-7.31 (1H, m), 7.51-7.57 (1H, m), 11.42 (1H, br s), 12.53 (1H, br s). | 383 | 381 |
| 44 | | ¹H-NMR (DMSO-D₆) δ: 0.97-1.05 (3H, m), 1.01 (6H, s), 1.55-1.60 (2H, m), 2.42 (2H, s), 2.64-2.70 (2H, m), 3.18 (3H, s), 3.29-3.37 (2H, m), 3.75 (2H, s), 6.58-6.61 (1H, m), 6.85-6.91 (1H, m), 7.22-7.27 (1H, m), 7.52-7.55 (1H, m), 11.43 (1H, br s), 12.54 (1H, br s). | 381 | 379 |
| 45 | | ¹H-NMR (DMSO-D₆) δ: 1.01 (6H, s), 1.55-1.61 (2H, m), 2.42 (2H, s), 2.64-2.69 (2H, m), 3.23 (3H, s), 4.41 (2H, s), 6.60-6.63 (1H, m), 6.71-6.78 (2H, m), 6.87-6.93 (1H, m), 6.99-7.04 (1H, m), 7.20-7.27 (2H, m), 7.36-7.40 (1H, m), 7.56-7.61 (1H, m), 11.47 (1H, br s), 12.55 (1H, br s). | 429 | 427 |
| 46 | | ¹H-NMR (DMSO-D₆) δ: 1.01 (6H, s), 1.03 (3H, d, J = 6.9 Hz), 1.56-1.61 (2H, m), 2.41 (2H, s), 2.64-2.71 (2H, m), 3.20 (3H, s), 4.01-4.10 (1H, m), 4.73 (1H, d, J = 7.3 Hz), 6.57-6.62 (1H, m), 6.85-6.91 (1H, m), 7.23-7.28 (1H, m), 7.53-7.58 (1H, m), 11.43 (1H, br s), 12.54 (1H, br s). | 367 | 365 |

TABLE 1-10

| Ex. No. | structural formula | NMR | MS (M + H) | MS (M − H) |
| --- | --- | --- | --- | --- |
| 47 | | $^1$H-NMR (DMSO-D$_6$) δ: 1.01 (6H, s), 1.54-1.62 (2H, m), 2.39-2.44 (2H, m), 2.64-2.70 (2H, m), 3.08 (6H, s), 3.22 (3H, s), 3.30-3.38 (1H, m), 3.43-3.52 (1H, m), 3.86-3.94 (1H, m), 6.58-6.66 (1H, m), 6.87-6.98 (1H, m), 7.25-7.34 (1H, m), 7.53-7.63 (1H, m), 11.46 (1H, br s), 12.55 (1H, br s). | 411 | 40 |
| 48 | | $^1$H-NMR (DMSO-D$_6$) δ: 1.01 (6H, s), 1.55-1.61 (2H, m), 2.41 (2H, s), 2.63-2.71 (2H, m), 3.10 (3H, s), 3.21 (3H, s), 3.35-3.43 (1H, m), 3.45-3.54 (1H, m), 3.75-3.81 (1H, m), 4.68-4.74 (1H, m), 6.58-6.64 (1H, m), 6.87-6.93 (1H, m), 7.25-7.32 (1H, m), 7.54-7.63 (1H, m), 11.43 (1H, br s), 12.55 (1H, br s). | 397 | 395 |
| 49 | | $^1$H-NMR (DMSO-D$_6$) δ: 0.66 (3H, t, J = 7.4 Hz), 1.01 (6H, s), 1.26-1.38 (1H, m), 1.41-1.54 (1H, m), 1.55-1.61 (2H, m), 2.42 (2H, s), 2.63-2.70 (2H, m), 3.21 (3H, s), 3.82-3.90 (1H, m), 4.67 (1H, d, J = 7.7 Hz), 6.58-6.62 (1H, m), 6.84-6.90 (1H, m), 7.21-7.30 (1H, m), 7.51-7.61 (1H, m), 11.43 (1H, br s), 12.55 (1H, br s). | 381 | 379 |
| 50 | | $^1$H-NMR (DMSO-D$_6$) δ: 0.61-0.77 (3H, m), 1.01 (6H, s), 1.39-1.65 (4H, m), 2.42 (2H, s), 2.63-2.70 (2H, m), 3.09 (3H, s), 3.22 (3H, s), 3.58-3.67 (1H, m), 6.57-6.67 (1H, m), 6.82-6.94 (1H, m), 7.21-7.31 (1H, m), 7.53-7.63 (1H, m), 11.42 (1H, br s), 12.55 (1H, br s). | 395 | 393 |

TABLE 1-10-continued

| Ex. No. | structural formula | NMR | MS (M + H) | MS (M − H) |
|---|---|---|---|---|
| 51 | | ¹H-NMR (DMSO-D₆) δ: 1.00 (6H, s), 1.53-1.61 (2H, m), 2.41 (2H, s), 2.63-2.69 (2H, m), 3.17 (3H, s), 4.17 (2H, d, J = 6.0 Hz), 6.13 (1H, t, J = 6.1 Hz), 6.55-6.59 (1H, m), 6.85-6.90 (1H, m), 7.16-7.23 (3H, m), 7.25-7.31 (3H, m), 7.50-7.55 (1H, m), 11.35 (1H, br s), 12.51 (1H, br s). | 428 | 426 |

TABLE 1-11

| Ex. No. | structural formula | NMR | MS (M + H) | MS (M − H) |
|---|---|---|---|---|
| 52 | | ¹H-NMR (DMSO-D₆) δ: 1.01 (6H, s), 1.52-1.69 (3H, m), 1.70-1.80 (1H, m), 1.84-1.96 (2H, m), 2.41 (2H, s), 2.62-2.71 (2H, m), 3.19 (3H, s), 3.59-3.66 (1H, m), 3.77-3.85 (1H, m), 4.15-4.23 (1H, m), 6.56-6.63 (1H, m), 6.84-6.93 (1H, m), 7.22-7.29 (1H, m), 7.51-7.59 (1H, m), 11.42 (1H, br s), 12.54 (1H, br s). | 393 | 391 |
| 53 | | ¹H-NMR (DMSO-D₆) δ: 1.01 (6H, s), 1.53-1.61 (2H, m), 2.41 (2H, s), 2.62-2.73 (2H, m), 3.07 (3H, s), 3.13-3.26 (1H, m), 3.21 (3H, s), 3.38-3.45 (1H, m), 4.08-4.16 (1H, m), 4.98 (1H, d, J = 7.3 Hz), 6.57-6.63 (1H, m), 6.85-6.92 (1H, m), 7.25-7.31 (1H, m), 7.52-7.59 (1H, m), 11.44 (1H, br s), 12.53 (1H, br s). | 397 | 395 |
| 54 | | ¹H-NMR (DMSO-D₆) δ: 1.01 (6H, s), 1.54-1.61 (2H, m), 2.41 (2H, s), 2.62-2.69 (2H, m), 3.14 (3H, s), 5.47 (2H, br s), 6.54-6.58 (1H, m), 6.83-6.88 (1H, m), 7.21-7.25 (1H, m), 7.48-7.54 (1H, m), 11.32 (1H, br s), 12.51 (1H, br s). | 338 | 336 |

TABLE 1-11-continued
| Ex. No. | structural formula | NMR | MS (M + H) | MS (M − H) |
|---|---|---|---|---|
| 55 | 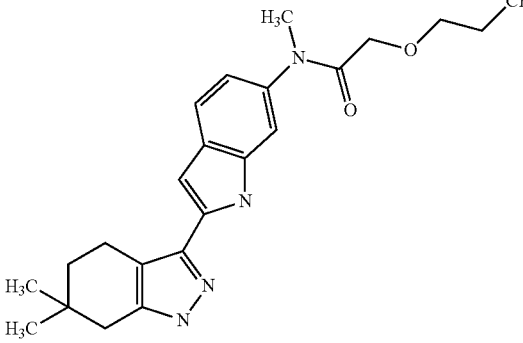 | ¹H-NMR (DMSO-D₆) δ: 0.79 (3H, t, J = 7.5 Hz), 1.01 (6H, s), 1.37-1.46 (2H, m), 1.55-1.61 (2H, m), 2.41 (2H, s), 2.64-2.69 (2H, m), 3.19 (3H, s), 3.22-3.27 (2H, m), 3.76 (2H, s), 6.58-6.61 (1H, m), 6.85-6.90 (1H, m), 7.23-7.26 (1H, m), 7.51-7.56 (1H, m), 11.41 (1H, br s), 12.54 (1H, br s). | 395 | 393 |
| 56 | 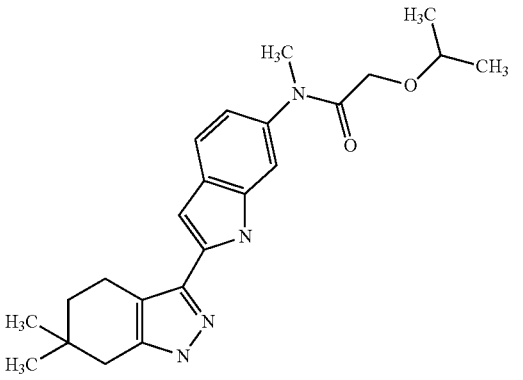 | ¹H-NMR (DMSO-D₆) δ: 0.94 (3H, s), 0.96 (3H, s), 1.01 (6H, s), 1.55-1.61 (2H, m), 2.41 (2H, s), 2.64-2.71 (2H, m), 3.18 (3H, s), 3.38-3.47 (1H, m), 3.75 (2H, s), 6.57-6.63 (1H, m), 6.85-6.91 (1H, m), 7.23-7.27 (1H, m), 7.51-7.57 (1H, m), 11.41 (1H, br s), 12.53 (1H, br s). | 395 | 393 |
TABLE 1-12
| Ex. No. | structural formula | NMR | MS (M + H) | MS (M − H) |
|---|---|---|---|---|
| 57 | 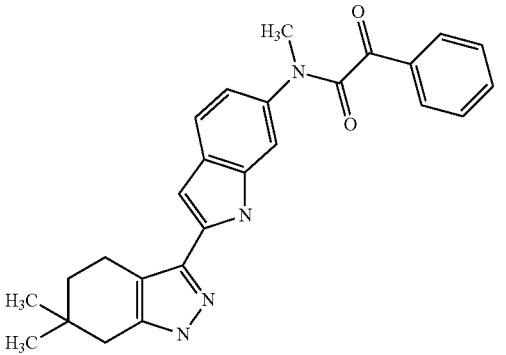 | ¹H-NMR (DMSO-D₆) δ: 0.98 (6H, s), 1.51-1.57 (2H, m), 2.39 (2H, s), 2.58-2.63 (2H, m), 3.43 (3H, s), 6.46-6.51 (1H, m), 6.82-6.88 (1H, m), 7.20-7.23 (1H, m), 7.33-7.39 (1H, m), 7.48-7.54 (2H, m), 7.63-7.68 (1H, m), 7.77-7.82 (2H, m), 11.38 (1H, br s), 12.51 (1H, br s). | 427 | 425 |

TABLE 1-12-continued

| Ex. No. | structural formula | NMR | MS (M + H) | MS (M − H) |
|---|---|---|---|---|
| 58 | | ¹H-NMR (DMSO-D₆) δ: 0.86 (3H, d, J = 6.9 Hz), 1.01 (6H, s), 1.55-1.61 (2H, m), 2.41 (2H, s), 2.62-2.73 (3H, m), 3.04-3.09 (1H, m), 3.11 (3H, s), 3.18 (3H, br s), 3.45-3.50 (1H, m), 6.58-6.62 (1H, m), 6.83-6.89 (1H, m), 7.23-7.27 (1H, m), 7.52-7.58 (1H, m), 11.40 (1H, br s), 12.53 (1H, br s). | 395 | 393 |
| 59 | | ¹H-NMR (DMSO-D₆) δ: 1.00 (6H, s), 1.54-1.59 (2H, m), 2.22 (3H, s), 2.40 (2H, s), 2.62-2.68 (2H, m), 3.38 (3H, s), 6.02 (1H, s), 6.52-6.56 (1H, m), 6.81-6.86 (1H, m), 7.15-7.18 (1H, m), 7.41-7.45 (1H, m), 11.35 (1H, br s), 12.52 (1H, br s). | 404 | 402 |
| 60 | | ¹H-NMR (DMSO-D₆) δ: 1.01 (6H, s), 1.22-1.38 (1H, m), 1.39-1.48 (2H, m), 1.55-1.71 (4H, m), 2.42 (2H, s), 2.64-2.70 (2H, m), 2.92-3.00 (2H, m), 3.17 (3H, s), 3.69-3.77 (2H, m), 6.59-6.62 (1H, m), 6.86-6.91 (1H, m), 7.23-7.26 (1H, m), 7.54-7.59 (1H, m), 11.38 (1H, br s), 12.54 (1H, br s). | 407 | 405 |
| 61 | | ¹H-NMR (DMSO-D₆) δ: 0.87 (3H, d, J = 6.9 Hz), 1.01 (6H, s), 1.55-1.60 (2H, m), 2.41 (2H, s), 2.52-2.58 (1H, m), 2.64-2.70 (2H, m), 3.12-3.19 (1H, m), 3.18 (3H, s), 3.49-3.56 (1H, m), 4.51 (1H, t, J = 5.4 Hz), 6.58-6.62 (1H, m), 6.86-6.90 (1H, m), 7.25-7.28 (1H, m), 7.53-7.56 (1H, m), 11.37 (1H, br s), 12.52 (1H, br s). | 381 | 379 |

TABLE 1-13
| Ex. No. | structural formula | NMR | MS (M + H) | MS (M − H) |
|---|---|---|---|---|
| 62 | 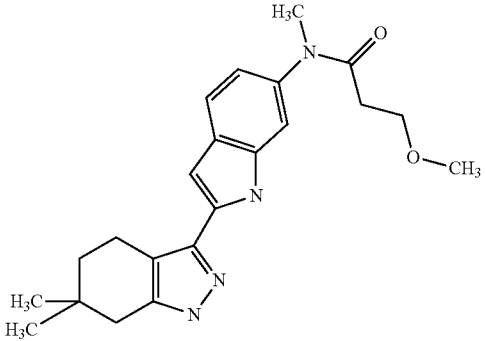 | ¹H-NMR (DMSO-D₆) δ: 1.01 (6H, s), 1.54-1.61 (2H, m), 2.21-2.27 (2H, m), 2.41 (2H, s), 2.63-2.70 (2H, m), 3.12 (3H, s), 3.18 (3H, s), 3.44-3.50 (2H, m), 6.57-6.63 (1H, m), 6.83-6.90 (1H, m), 7.20-7.26 (1H, m), 7.51-7.57 (1H, m), 11.42 (1H, br s), 12.54 (1H, br s). | 381 | 379 |
| 63 | 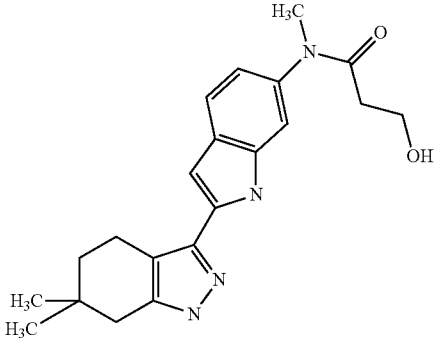 | ¹H-NMR (DMSO-D₆) δ: 1.01 (6H, s), 1.55-1.61 (2H, m), 2.15-2.23 (2H, m), 2.41 (2H, s), 2.62-2.72 (2H, m), 3.18 (3H, s), 3.50-3.59 (2H, m), 4.39 (1H, t, J = 5.1 Hz), 6.57-6.63 (1H, m), 6.84-6.91 (1H, m), 7.21-7.27 (1H, m), 7.51-7.59 (1H, m), 11.42 (1H, br s), 12.54 (1H, br s). | 367 | 365 |
| 64 | 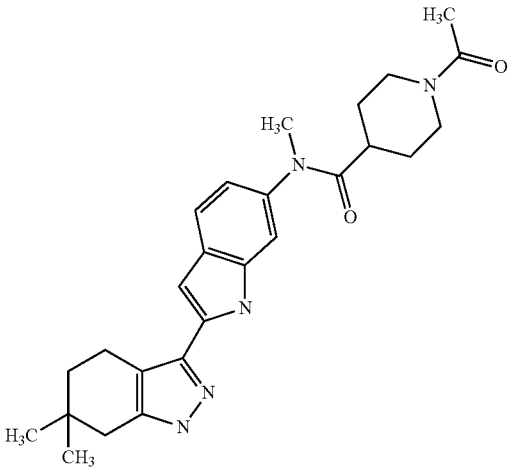 | ¹H-NMR (DMSO-D₆) δ: 1.01 (6H, s), 1.34-1.46 (1H, m), 1.51-1.62 (5H, m), 1.92 (3H, s), 2.15-2.23 (1H, m), 2.42 (2H, s), 2.44-2.53 (1H, m), 2.63-2.76 (3H, m), 3.17 (3H, s), 3.65-3.73 (1H, m), 4.21-4.29 (1H, m), 6.57-6.64 (1H, m), 6.86-6.94 (1H, m), 7.23-7.28 (1H, m), 7.54-7.59 (1H, m), 11.40 (1H, br s), 12.54 (1H, br s). | 448 | 446 |

TABLE 1-13-continued

| Ex. No. | structural formula | NMR | MS (M + H) | MS (M − H) |
|---|---|---|---|---|
| 65 | | ¹H-NMR (DMSO-D₆) δ: 1.01 (6H, s), 1.40-1.54 (4H, m), 1.56-1.68 (4H, m), 2.00 (3H, s), 2.09-2.19 (1H, m), 2.42 (2H, s), 2.61-2.72 (4H, m), 3.16 (3H, s), 6.57-6.64 (1H, m), 6.84-6.91 (1H, m), 7.20-7.27 (1H, m), 7.52-7.58 (1H, m), 11.38 (1H, br s), 12.54 (1H, br s). | 420 | 418 |
| 66 | | ¹H-NMR (DMSO-D₆) δ: 1.01 (6H, s), 1.54-1.61 (2H, m), 1.69-1.79 (1H, m), 1.96-2.06 (1H, m), 2.42 (2H, s), 2.63-2.74 (2H, m), 2.85-2.94 (1H, m), 3.20 (3H, s), 3.47-3.54 (1H, m), 3.55-3.65 (2H, m), 3.66-3.73 (1H, m), 6.57-6.63 (1H, m), 6.85-6.92 (1H, m), 7.21-7.27 (1H, m), 7.54-7.59 (1H, m), 11.42 (1H, br s), 12.54 (1H, br s). | 393 | 391 |

TABLE 1-14

| Ex. No. | structural formula | NMR | MS (M + H) | MS (M − H) |
|---|---|---|---|---|
| 67 | | ¹H-NMR (DMSO-D₆) δ: 0.64 (3H, d, J = 6.9 Hz), 0.72 (3H, d, J = 6.9 Hz), 1.01 (6H, s), 1.55-1.61 (2H, m), 1.70-1.80 (1H, m), 2.42 (2H, s), 2.63-2.71 (2H, m), 3.22 (3H, s), 3.63-3.70 (1H, m), 4.59 (1H, d, J = 8.1 Hz), 6.57-6.62 (1H, m), 6.83-6.89 (1H, m), 7.22-7.27 (1H, m), 7.52-7.57 (1H, m), 11.37 (1H, br s), 12.51 (1H, br s). | 395 | 393 |

TABLE 1-14-continued

| Ex. No. | structural formula | NMR | MS (M + H) | MS (M − H) |
|---|---|---|---|---|
| 68 | | $^1$H-NMR (DMSO-D$_6$) δ: 1.01 (6H, s), 1.56-1.61 (2H, m), 2.42 (2H, s), 2.64-2.71 (2H, m), 3.20 (3H, s), 5.05 (1H, d, J = 7.3 Hz), 5.49 (1H, d, J = 7.3 Hz), 6.58-6.63 (1H, m), 6.67-6.75 (1H, m), 6.98-7.03 (2H, m), 7.11-7.17 (1H, m), 7.18-7.23 (3H, m), 7.47-7.54 (1H, m), 11.43 (1H, br s), 12.54 (1H, br s). | 429 | 427 |
| 69 | | $^1$H-NMR (DMSO-D$_6$) δ: 1.01 (6H, s), 1.08 (6H, s), 1.56-1.60 (2H, m), 2.18 (2H, s), 2.41 (2H, s), 2.65-2.69 (2H, m), 3.20 (3H, s), 4.94 (1H, s), 6.59-6.61 (1H, m), 6.83-6.87 (1H, m), 7.21-7.23 (1H, m), 7.53-7.57 (1H, m), 11.42 (1H, br s), 12.54 (1H, br s). | 395 | 393 |
| 70 | | $^1$H-NMR (DMSO-D$_6$) δ: 0.91 (3H, t, J = 7.5 Hz), 1.01 (6H, s), 1.56-1.61 (2H, m), 1.97-2.05 (2H, m), 2.43 (2H, s), 2.66-2.71 (2H, m), 3.18 (3H, s), 6.63-6.66 (1H, m), 6.85-6.90 (1H, m), 7.24-7.27 (1H, m), 7.52-7.58 (1H, m), 11.41 (1H, br s). | 351 | 349, 385 |
| 71 | | $^1$H-NMR (DMSO-D$_6$) δ: 1.01 (6H, s), 1.26-1.36 (1H, m), 1.54-1.60 (2H, m), 1.62-1.76 (2H, m), 1.87-1.97 (1H, m), 2.05-2.13 (1H, m), 2.28-2.36 (1H, m), 2.41 (2H, s), 2.63-2.71 (2H, m), 3.18 (3H, s), 3.47-3.53 (1H, m), 3.55-3.61 (1H, m), 4.05-4.13 (1H, m), 6.57-6.62 (1H, m), 6.83-6.88 (1H, m), 7.20-7.26 (1H, m), 7.52-7.56 (1H, m), 11.41 (1H, br s), 12.53 (1H, br s). | 407 | 405 |

TABLE 1-15

| Ex. No. | structural formula | NMR | MS (M + H) | MS (M − H) |
|---|---|---|---|---|
| 72 | | ¹H-NMR (DMSO-D₆) δ: 0.63-0.76 (2H, m), 0.92-1.06 (1H, m), 1.01 (6H, s), 1.09-1.21 (2H, m), 1.49-1.62 (7H, m), 1.64-1.75 (1H, m), 1.87-1.93 (2H, m), 2.41 (2H, s), 2.63-2.70 (2H, m), 3.18 (3H, s), 6.56-6.62 (1H, m), 6.78-6.85 (1H, m), 7.17-7.21 (1H, m), 7.51-7.57 (1H, m), 11.39 (1H, br s), 12.53 (1H, br s). | 419 | 417 |
| 73 | | ¹H-NMR (DMSO-D₆) δ: 1.01 (6H, s), 1.54-1.62 (2H, m), 2.42 (2H, s), 2.63-2.73 (2H, m), 3.23 (3H, s), 4.48 (2H, s), 5.97-6.03 (2H, m), 6.60-6.67 (1H, m), 7.01-7.07 (1H, m), 7.38-7.42 (1H, m), 7.44-7.50 (2H, m), 7.58-7.63 (1H, m), 11.56 (1H, br s), 12.57 (1H, br s). | 430 | 42 |
| 74 | | ¹H-NMR (DMSO-D₆) δ: 0.62-1.06 (2H, m), 1.01 (6H, s), 1.28-1.49 (2H, m), 1.55-1.93 (6H, m), 2.10-2.29 (1H, m), 2.41 (2H, s), 2.64-2.71 (2H, m), 3.12-3.18 (6H, m), 3.19-3.24 (1H, m), 6.58-6.63 (1H, m), 6.85-6.89 (1H, m), 7.21-7.27 (1H, m), 7.52-7.58 (1H, m), 11.36 (1H, br s), 12.53 (1H, br s). | 435 | 433 |
| 75 | | ¹H-NMR (DMSO-D₆) δ: 0.95 (6H, s), 1.01 (6H, s), 1.55-1.61 (2H, m), 2.42 (2H, s), 2.64-2.70 (2H, m), 3.11 (2H, s), 3.13 (3H, s), 4.36 (2H, s), 6.59-6.63 (1H, m), 6.84-6.88 (1H, m), 7.25-7.31 (4H, m), 7.32-7.37 (2H, m), 7.49-7.53 (1H, m), 11.41 (1H, br s), 12.53 (1H, br s). | 485 | 483 |

TABLE 1-15-continued
| Ex. No. | structural formula | NMR | MS (M + H) | MS (M − H) |
|---|---|---|---|---|
| 76 | 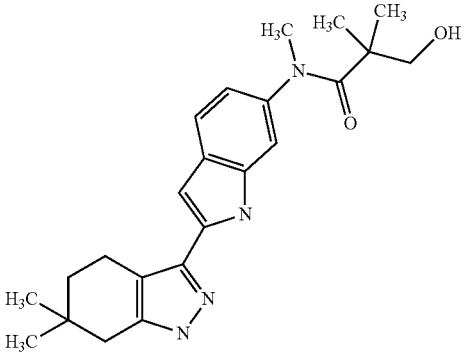 | $^1$H-NMR (DMSO-D$_6$) δ: 0.85 (6H, s), 1.01 (6H, s), 1.54-1.62 (2H, m), 2.41 (2H, s), 2.61-2.75 (2H, m), 3.13 (3H, s), 3.23 (2H, d, J = 5.6 Hz), 4.48-4.56 (1H, m), 6.55-6.64 (1H, m), 6.85-6.95 (1H, m), 7.24-7.32 (1H, m), 7.48-7.56 (1H, m), 11.37 (1H, br s), 12.53 (1H, br s). | 395 | 393 |
TABLE 1-16
| Ex. No. | structural formula | NMR | MS (M + H) | MS (M − H) |
|---|---|---|---|---|
| 77 | 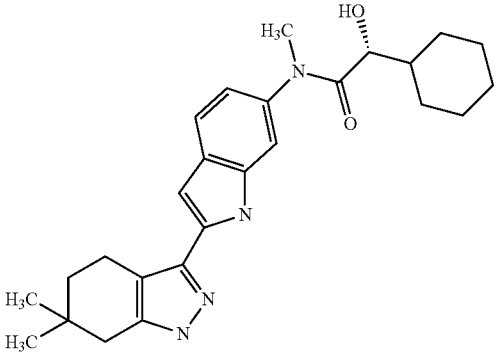 | $^1$H-NMR (DMSO-D$_6$) δ: 0.62-0.86 (2H, m), 0.94-1.13 (3H, m), 1.01 (6H, s), 1.26-1.33 (1H, m), 1.44-1.64 (6H, m), 1.66-1.74 (1H, m), 2.41 (2H, s), 2.64-2.70 (2H, m), 3.21 (3H, s), 3.62-3.67 (1H, m), 4.65 (1H, d, J = 7.7 Hz), 6.58-6.63 (1H, m), 6.83-6.88 (1H, m), 7.22-7.27 (1H, m), 7.52-7.57 (1H, m), 11.41 (1H, br s), 12.53 (1H, br s). | 435 | 43 |
| 78 | 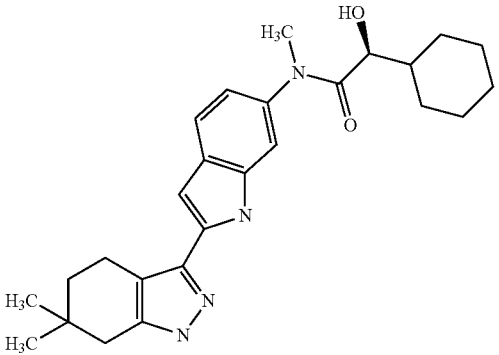 | $^1$H-NMR (DMSO-D$_6$) δ: 0.61-0.86 (2H, m), 0.92-1.15 (3H, m), 1.01 (6H, s), 1.26-1.33 (1H, m), 1.44-1.63 (6H, m), 1.67-1.74 (1H, m), 2.42 (2H, s), 2.64-2.70 (2H, m), 3.21 (3H, s), 3.62-3.67 (1H, m), 4.65 (1H, d, J = 7.7 Hz), 6.57-6.62 (1H, m), 6.83-6.88 (1H, m), 7.21-7.26 (1H, m), 7.53-7.57 (1H, m), 11.42 (1H, br s), 12.54 (1H, br s). | 435 | 433 |

TABLE 1-16-continued

| Ex. No. | structural formula | NMR | MS (M + H) | MS (M − H) |
|---|---|---|---|---|
| 79 | | ¹H-NMR (DMSO-D₆) δ: 1.01 (6H, s), 1.24-1.33 (2H, m), 1.36-1.47 (4H, m), 1.55-1.61 (2H, m), 2.17-2.35 (4H, m), 2.41 (2H, s), 2.63-2.71 (2H, m), 2.78-2.87 (2H, m), 3.17 (3H, s), 6.57-6.61 (1H, m), 6.83-6.89 (1H, m), 7.21-7.27 (1H, m), 7.50-7.56 (1H, m), 11.40 (1H, br s), 12.53 (1H, br s). | 420 | 418 |
| 80 | | ¹H-NMR (DMSO-D₆) δ: 1.01 (6H, s), 1.54-1.61 (2H, m), 2.27-2.37 (4H, m), 2.41 (2H, s), 2.63-2.71 (2H, m), 2.86 (2H, s), 3.18 (3H, s), 3.46-3.53 (4H, m), 6.57-6.64 (1H, m), 6.85-6.92 (1H, m), 7.24-7.31 (1H, m), 7.51-7.57 (1H, m), 11.41 (1H, br s), 12.53 (1H, br s). | 422 | 420 |
| 81 | | ¹H-NMR (DMSO-D₆) δ: 1.01 (6H, s), 1.27-1.39 (2H, m), 1.55-1.61 (2H, m), 1.68-1.77 (2H, m), 2.00-2.10 (2H, m), 2.41 (2H, s), 2.52-2.59 (2H, m), 2.64-2.71 (2H, m), 2.84 (2H, s), 3.01-3.09 (1H, m), 3.17 (6H, s), 6.56-6.62 (1H, m), 6.82-6.90 (1H, m), 7.22-7.28 (1H, m), 7.49-7.57 (1H, m), 11.41 (1H, br s), 12.53 (1H, br s). | 450 | 448 |

TABLE 1-17

| Ex. No. | structural formula | NMR | MS (M + H) | MS (M − H) |
|---|---|---|---|---|
| 82 | | ¹H-NMR (DMSO-D₆) δ: 0.62-0.74 (2H, m), 1.01 (6H, s), 1.37-1.50 (2H, m), 1.56-1.61 (2H, m), 1.63-1.70 (2H, m), 1.86-1.94 (2H, m), 2.10-2.20 (1H, m), 2.41 (2H, s), 2.64-2.70 (2H, m), 2.95-3.05 (1H, m), 3.12-3.19 (6H, m), 6.58-6.64 (1H, m), 6.85-6.91 (1H, m), 7.21-7.27 (1H, m), 7.53-7.58 (1H, m), 11.36 (1H, br s), 12.53 (1H, br s). | 435 | 433 |

TABLE 1-17-continued

| Ex. No. | structural formula | NMR | MS (M + H) | MS (M − H) |
|---|---|---|---|---|
| 83 | | ¹H-NMR (DMSO-D₆) δ: 1.01 (6H, s), 1.55-1.61 (2H, m), 1.85-1.93 (2H, m), 2.14-2.21 (2H, m), 2.41 (2H, s), 2.64-2.70 (2H, m), 3.19 (3H, s), 3.29-3.37 (1H, m), 3.71 (2H, s), 6.59-6.64 (1H, m), 6.90-6.96 (1H, m), 7.28-7.33 (1H, m), 7.55-7.60 (1H, m), 11.46 (1H, br s), 12.54 (1H, br s). | 420 | 418 |
| 84 | | ¹H-NMR (DMSO-D₆) δ: 0.97-1.09 (2H, m), 1.01 (6H, s), 1.23-1.34 (2H, m), 1.49-1.62 (4H, m), 1.74-1.86 (2H, m), 2.16-2.26 (1H, m), 2.41 (2H, s), 2.63-2.71 (2H, m), 3.15 (3H, s), 3.59-3.67 (1H, m), 4.19-4.26 (1H, m), 6.56-6.63 (1H, m), 6.82-6.89 (1H, m), 7.19-7.26 (1H, m), 7.51-7.57 (1H, m), 11.36 (1H, br s), 12.53 (1H, br s). | 421 | 419 |
| 85 | | ¹H-NMR (DMSO-D₆) δ: 0.94-1.06 (8H, m), 1.28-1.37 (2H, m), 1.55-1.60 (2H, m), 1.61-1.79 (4H, m), 2.20-2.29 (1H, m), 2.41 (2H, s), 2.62-2.71 (2H, m), 3.15 (6H, s), 3.19-3.24 (1H, m), 6.57-6.64 (1H, m), 6.83-6.89 (1H, m), 7.20-7.27 (1H, m), 7.52-7.58 (1H, m), 11.36 (1H, br s), 12.53 (1H, br s). | 435 | 433 |
| 86 | | ¹H-NMR (DMSO-D₆) δ: 1.01 (6H, s), 1.54-1.61 (2H, m), 2.41 (2H, s), 2.63-2.71 (2H, m), 3.23 (3H, s), 4.53 (2H, s), 6.59-6.66 (1H, m), 7.01-7.08 (1H, m), 7.17-7.22 (1H, m), 7.25-7.31 (1H, m), 7.37-7.44 (1H, m), 7.57-7.63 (1H, m), 8.12-8.17 (2H, m), 11.49 (1H, br s), 12.55 (1H, br s). | 430 | 428 |

TABLE 1-18

| Ex. No. | structural formula | NMR | MS (M + H) | MS (M − H) |
|---|---|---|---|---|
| 87 | | ¹H-NMR (DMSO-D₆) δ: 1.01 (6H, s), 1.53-1.61 (2H, m), 1.65-1.83 (2H, m), 2.41 (2H, s), 2.61-2.72 (2H, m), 3.19 (3H, s), 3.48-3.66 (4H, m), 3.73-3.84 (2H, m), 3.99-4.07 (1H, m), 6.54-6.66 (1H, m), 6.84-6.94 (1H, m), 7.21-7.33 (1H, m), 7.50-7.58 (1H, m), 11.43 (1H, br s), 12.55 (1H, br s). | 423 | 421 |
| 88 | | ¹H-NMR (DMSO-D₆) δ: 1.01 (6H, s), 1.22-1.33 (2H, m), 1.54-1.61 (2H, m), 1.65-1.74 (2H, m), 2.41 (2H, s), 2.62-2.71 (2H, m), 3.19 (3H, s), 3.21-3.27 (2H, m), 3.35-3.44 (1H, m), 3.66-3.74 (2H, m), 3.82 (2H, s), 6.57-6.64 (1H, m), 6.86-6.93 (1H, m), 7.24-7.30 (1H, m), 7.51-7.57 (1H, m), 11.43 (1H, br s), 12.54 (1H, br s). | 437 | 435 |
| 89 | | ¹H-NMR (DMSO-D₆) δ: 1.01 (6H, s), 1.54-1.63 (2H, m), 2.42 (2H, s), 2.64-2.73 (2H, m), 3.23 (3H, s), 4.59 (2H, s), 6.60-6.67 (1H, m), 6.82 (1H, s), 7.01-7.07 (1H, m), 7.04 (1H, s), 7.36-7.42 (1H, m), 7.48 (1H, s), 7.57-7.65 (1H, m), 11.53 (1H, br s), 12.56 (1H, br s). | 403 | 401 |
| 90 | | ¹H-NMR (DMSO-D₆) δ: 0.90-1.04 (1H, m), 1.01 (6H, s), 1.22-1.47 (3H, m), 1.48-1.61 (3H, m), 1.63-1.71 (1H, m), 2.00-2.07 (1H, m), 2.18-2.26 (1H, m), 2.42 (2H, s), 2.63-2.71 (2H, m), 3.18 (3H, s), 3.22-3.30 (1H, m), 3.59-3.67 (1H, m), 3.72-3.78 (1H, m), 6.56-6.63 (1H, m), 6.79-6.87 (1H, m), 7.18-7.25 (1H, m), 7.51-7.57 (1H, m), 11.40 (1H, br s), 12.54 (1H, br s). | 421 | 419 |

TABLE 1-18-continued
| Ex. No. | structural formula | NMR | MS (M + H) | MS (M − H) |
|---|---|---|---|---|
| 91 | 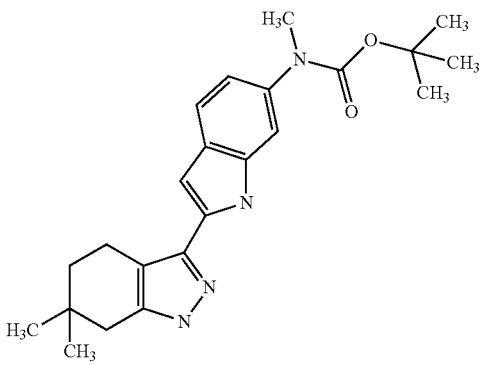 | ¹H-NMR (DMSO-D₆) δ: 0.89 (9H, s), 1.01 (6H, s), 1.55-1.61 (2H, m), 1.98 (2H, s), 2.41 (2H, s), 2.64-2.71 (2H, m), 3.17 (3H, s), 6.55-6.63 (1H, m), 6.77-6.85 (1H, m), 7.16-7.23 (1H, m), 7.51-7.57 (1H, m), 11.38 (1H, br s), 12.53 (1H, br s). | 393 | 391 |
TABLE 1-19
| Ex. No. | structural formula | NMR | MS (M + H) | MS (M − H) |
|---|---|---|---|---|
| 92 | 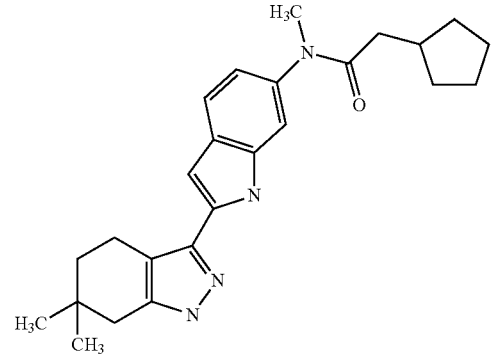 | ¹H-NMR (DMSO-D₆) δ: 0.87-0.98 (2H, m), 1.01 (6H, s), 1.35-1.46 (4H, m), 1.55-1.61 (2H, m), 1.61-1.70 (2H, m), 2.00-2.06 (2H, m), 2.08-2.17 (1H, m), 2.41 (2H, s), 2.64-2.71 (2H, m), 3.18 (3H, s), 6.56-6.62 (1H, m), 6.80-6.87 (1H, m), 7.18-7.24 (1H, m), 7.51-7.57 (1H, m), 11.37 (1H, br s), 12.53 (1H, br s). | 405 | 403 |
| 93 | 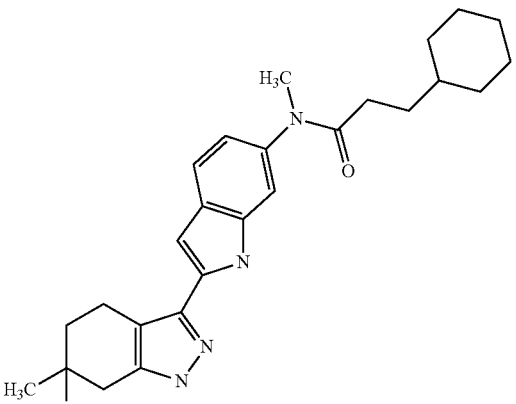 | ¹H-NMR (DMSO-D₆) δ: 0.63-0.75 (2H, m), 1.01 (6H, s), 1.03-1.14 (4H, m), 1.30-1.38 (2H, m), 1.41-1.49 (2H, m), 1.50-1.60 (5H, m), 1.98-2.05 (2H, m), 2.41 (2H, s), 2.64-2.71 (2H, m), 3.17 (3H, s), 6.57-6.64 (1H, m), 6.82-6.88 (1H, m), 7.20-7.25 (1H, m), 7.52-7.57 (1H, m), 11.39 (1H, br s), 12.54 (1H, br s). | 433 | 431 |

TABLE 1-19-continued

| Ex. No. | structural formula | NMR | MS (M + H) | MS (M − H) |
|---|---|---|---|---|
| 94 | | ¹H-NMR (DMSO-D₆) δ: 0.92-0.99 (2H, m), 1.01 (6H, s), 1.46-1.53 (2H, m), 1.56-1.61 (2H, m), 1.89-1.98 (3H, m), 2.41 (2H, s), 2.64-2.70 (2H, m), 3.16-3.26 (2H, m), 3.18 (3H, s), 3.69-3.75 (2H, m), 6.56-6.63 (1H, m), 6.81-6.87 (1H, m), 7.18-7.24 (1H, m), 7.52-7.58 (1H, m), 11.40 (1H, br s), 12.54 (1H, br s). | 421 | 419 |
| 95 stereoisomer of Ex. No. 96 | | ¹H-NMR (DMSO-D₆) δ: 1.01 (6H, s), 1.06-1.18 (1H, m), 1.31-1.49 (2H, m), 1.56-1.61 (2H, m), 1.65-1.77 (2H, m), 2.42 (2H, s), 2.64-2.72 (2H, m), 2.90-2.96 (1H, m), 3.05-3.13 (1H, m), 3.21 (3H, s), 3.36-3.42 (1H, m), 3.62-3.69 (1H, m), 3.75-3.81 (1H, m), 4.75 (1H, d, J = 7.7 Hz), 6.57-6.64 (1H, m), 6.85-6.91 (1H, m), 7.22-7.27 (1H, m), 7.53-7.58 (1H, m), 11.43 (1H, br s), 12.53 (1H, br s). | 437 | 435 |
| 96 stereoisomer of Ex. No. 95 | | ¹H-NMR (DMSO-D₆) δ: 0.93-1.11 (2H, m), 1.01 (6H, s), 1.28-1.85 (5H, m), 2.42 (2H, s), 2.64-2.70 (2H, m), 2.97-3.16 (2H, m), 3.21 (3H, s), 3.57-3.78 (2H, m), 4.45-4.49 (1H, m), 4.96 (1H, d, J = 8.1 Hz), 6.58-6.61 (1H, m), 6.84-6.89 (1H, m), 7.23-7.27 (1H, m), 7.52-7.57 (1H, m), 11.42 (1H, br s), 12.53 (1H, br s). | 437 | 435 |

TABLE 1-20

| Ex. No. | structural formula | NMR | MS (M + H) | MS (M − H) |
|---|---|---|---|---|
| 97 | | ¹H-NMR (DMSO-D₆) δ: 0.48-0.60 (1H, m), 0.72-0.84 (1H, m), 0.91 (3H, d, J = 6.7 Hz), 1.01 (6H, s), 1.06-1.18 (2H, m), 1.35-1.45 (1H, m), 1.51-1.70 (8H, m), 2.05-2.14 (1H, m), 2.42 (2H, s), 2.64-2.71 (2H, m), 3.18 (3H, s), 6.58-6.63 (1H, m), 6.80-6.86 (1H, m), 7.19-7.24 (1H, m), 7.53-7.58 (1H, m), 11.37 (1H, br s), 12.53 (1H, br s). | 433 | 431 |
| 98 | | ¹H-NMR (DMSO-D₆) δ: 0.77-0.89 (1H, m), 0.92 (3H, d, J = 6.7 Hz), 1.01 (6H, s), 1.05-1.14 (1H, m), 1.45-1.54 (2H, m), 1.56-1.69 (3H, m), 2.09-2.17 (1H, m), 2.42 (3H, s), 2.65-2.70 (2H, m), 3.14-3.25 (2H, m), 3.19 (3H, s), 3.72-3.81 (2H, m), 6.57-6.62 (1H, m), 6.81-6.86 (1H, m), 7.20-7.24 (1H, m), 7.54-7.59 (1H, m), 11.38 (1H, br s), 12.54 (1H, br s). | 435 | 433 |
| 99 | stereoisomer of Ex. No. 100 | ¹H-NMR (DMSO-D₆) δ: 1.01 (6H, s), 1.08-1.65 (10H, m), 1.76-1.84 (1H, m), 2.42 (2H, s), 2.65-2.71 (2H, m), 2.84 (3H, s), 3.15 (3H, s), 3.36-3.40 (1H, m), 6.58-6.64 (1H, m), 6.84-6.89 (1H, m), 7.21-7.27 (1H, m), 7.53-7.59 (1H, m), 11.38 (1H, br s), 12.53 (1H, br s). | 435 | 433 |
| 100 | stereoisomer of Ex. No. 99 | ¹H-NMR (DMSO-D₆) δ: 0.80-1.08 (2H, m), 1.01 (6H, s), 1.16-1.34 (2H, m), 1.51-1.66 (4H, m), 1.81-1.96 (2H, m), 2.20-2.30 (1H, m), 2.42 (2H, s), 2.65-2.77 (3H, m), 3.12 (3H, s), 3.16 (3H, s), 6.59-6.65 (1H, m), 6.85-6.92 (1H, m), 7.23-7.29 (1H, m), 7.54-7.59 (1H, m), 11.38 (1H, br s), 12.54 (1H, br s). | 435 | 433 |
| 101 | | ¹H-NMR (DMSO-D₆) δ: 0.66-0.78 (2H, m), 1.01 (6H, s), 1.36-1.48 (2H, m), 1.55-1.65 (4H, m), 1.68-1.76 (2H, m), 2.06-2.15 (1H, m), 2.42 (2H, s), 2.64-2.72 (2H, m), 3.15 (3H, s), 3.20-3.29 (1H, m), 4.36 (1H, d, J = 4.6 Hz), 6.59-6.65 (1H, m), 6.83-6.90 (1H, m), 7.21-7.28 (1H, m), 7.53-7.61 (1H, m), 11.35 (1H, br s), 12.52 (1H, br s). | 421 | 419 |

TABLE 1-21

| Ex. No. | structural formula | NMR | MS (M + H) | MS (M − H) |
|---|---|---|---|---|
| 102 | | ¹H-NMR (DMSO-D₆) δ: 1.01 (6H, s), 1.15-1.45 (6H, m), 1.49-1.62 (4H, m), 1.67-1.78 (2H, m), 2.41 (2H, s), 2.62-2.71 (2H, m), 3.23 (3H, s), 4.57-4.64 (1H, m), 6.52-6.57 (1H, m), 6.83-6.89 (1H, m), 7.22-7.27 (1H, m), 7.42-7.48 (1H, m), 11.26 (1H, br s), 12.49 (1H, br s). | 421 | 419 |
| 103 | | ¹H-NMR (DMSO-D₆) δ: 0.94-1.06 (1H, m), 1.01 (6H, s), 1.37-1.44 (2H, m), 1.55-1.61 (2H, m), 1.64-1.71 (1H, m), 1.86-1.96 (3H, m), 2.41 (2H, s), 2.63-2.71 (2H, m), 2.80-2.87 (1H, m), 3.13-3.21 (1H, m), 3.18 (3H, s), 3.61-3.68 (2H, m), 6.58-6.62 (1H, m), 6.82-6.87 (1H, m), 7.18-7.23 (1H, m), 7.52-7.57 (1H, m), 11.39 (1H, br s), 12.53 (1H, br s). | 421 | 419 |
| 104 | | ¹H-NMR (DMSO-D₆) δ: 1.01 (6H, s), 1.02 (3H, d, J = 7.0 Hz), 1.54-1.62 (2H, m), 2.21-2.29 (2H, m), 2.38-2.49 (2H, m), 2.42 (2H, s), 2.64-2.70 (2H, m), 3.15-3.24 (1H, m), 3.19 (3H, s), 3.45-3.51 (4H, m), 6.56-6.62 (1H, m), 6.85-6.93 (1H, m), 7.26-7.33 (1H, m), 7.51-7.57 (1H, m), 11.39 (1H, br s), 12.54 (1H, br s). | 436 | 434 |
| 105 | | ¹H-NMR (DMSO-D₆) δ: 1.01 (6H, s), 1.55-1.61 (2H, m), 1.64-1.73 (4H, m), 2.14-2.20 (2H, m), 2.42 (2H, s), 2.64-2.73 (2H, m), 3.17-3.26 (2H, m), 3.19 (3H, s), 3.77 (2H, s), 6.58-6.64 (1H, m), 6.89-6.96 (1H, m), 7.27-7.33 (1H, m), 7.54-7.61 (1H, m), 11.45 (1H, br s), 12.54 (1H, br s). | 434 | 432 |

TABLE 1-21-continued

| Ex. No. | structural formula | NMR | MS (M + H) | MS (M − H) |
|---|---|---|---|---|
| 106 | | ¹H-NMR (DMSO-D₆) δ: 1.01 (6H, s), 1.02 (3H, s), 1.40 (3H, s), 1.55-1.61 (2H, m), 2.41 (2H, s), 2.59-2.71 (3H, m), 2.78-2.86 (1H, m), 3.14-3.19 (1H, m), 3.24 (3H, s), 6.59-6.64 (1H, m), 6.88-6.93 (1H, m), 7.25-7.29 (1H, m), 7.56-7.61 (1H, m), 11.39 (1H, br s), 12.52 (1H, br s). | 435 | 433 |

TABLE 1-22

| Ex. No. | structural formula | NMR | MS (M + H) | MS (M − H) |
|---|---|---|---|---|
| 107 | | ¹H-NMR (DMSO-D₆) δ: 1.01 (6H, s), 1.22-1.39 (2H, m), 1.54-1.66 (4H, m), 1.95-2.06 (2H, m), 2.42 (2H, s), 2.53-2.61 (2H, m), 2.64-2.70 (2H, m), 2.82 (2H, s), 3.17 (3H, s), 3.29-3.37 (1H, m), 4.46 (1H, d, J = 3.9 Hz), 6.57-6.61 (1H, m), 6.83-6.88 (1H, m), 7.22-7.26 (1H, m), 7.50-7.56 (1H, m), 11.40 (1H, br s), 12.53 (1H, br s). | 436 | 434 |
| 108 | | ¹H-NMR (DMSO-D₆) δ: 1.00 (3H, d, J = 7.7 Hz), 1.01 (6H, s), 1.20-1.32 (2H, m), 1.52-1.67 (4H, m), 2.19-2.29 (1H, m), 2.35-2.47 (1H, m), 2.42 (2H, s), 2.57-2.64 (1H, m), 2.65-2.70 (2H, m), 3.17 (3H, s), 3.18-3.25 (1H, m), 3.27-3.37 (1H, m), 4.45 (1H, d, J = 3.9 Hz), 6.56-6.61 (1H, m), 6.83-6.90 (1H, m), 7.23-7.29 (1H, m), 7.50-7.57 (1H, m), 11.39 (1H, br s), 12.53 (1H, br s). | 450 | 448 |
| 109 | | ¹H-NMR (DMSO-D₆) δ: 0.85-0.97 (1H, m), 1.01 (6H, s), 1.23-1.39 (2H, m), 1.45-1.53 (1H, m), 1.55-1.63 (2H, m), 1.67-1.76 (2H, m), 1.79-1.89 (1H, m), 2.42 (2H, s), 2.64-2.70 (2H, m), 2.71-2.78 (1H, m), 2.80-2.91 (2H, m), 3.17 (3H, s), 3.28-3.43 (1H, m), 4.48 (1H, d, J = 4.9 Hz), 6.57-6.62 (1H, m), 6.83-6.90 (1H, m), 7.21-7.27 (1H, m), 7.50-7.58 (1H, m), 11.40 (1H, br s), 12.53 (1H, br s). | 436 | 434 |

TABLE 1-22-continued
| Ex. No. | structural formula | NMR | MS (M + H) | MS (M − H) |
|---|---|---|---|---|
| 110 | 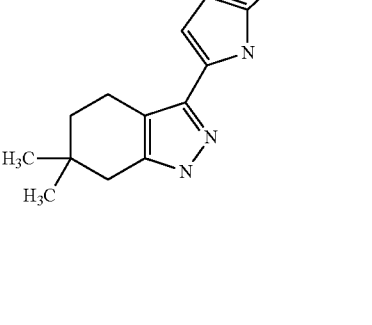 | ¹H-NMR (DMSO-D₆) δ: 0.89-0.99 (1H, m), 1.01 (6H, s), 1.26-1.39 (1H, m), 1.44-1.53 (1H, m), 1.55-1.62 (2H, m), 1.67-1.78 (2H, m), 1.80-1.90 (1H, m), 2.42 (2H, s), 2.63-2.70 (2H, m), 2.71-2.78 (1H, m), 2.80-2.93 (2H, m), 3.17 (3H, s), 3.33-3.44 (1H, m), 4.48 (1H, d, J = 4.6 Hz), 6.57-6.62 (1H, m), 6.82-6.90 (1H, m), 7.21-7.27 (1H, m), 7.49-7.58 (1H, m), 11.40 (1H, br s), 12.53 (1H, br s). | 436 | 434 |
| 111 | 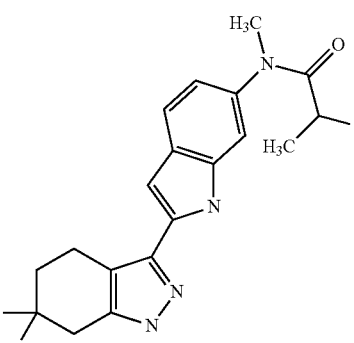 | ¹H-NMR (DMSO-D₆) δ: 0.90-1.09 (2H, m), 1.01 (6H, s), 1.20-1.36 (2H, m), 1.40-1.62 (4H, m), 1.69-2.26 (4H, m), 2.41 (2H, s), 2.57-2.79 (4H, m), 3.18 (3H, s), 3.21-3.41 (1H, m), 4.41-4.50 (1H, m), 6.55-6.63 (1H, m), 6.83-6.91 (1H, m), 7.22-7.31 (1H, m), 7.51-7.57 (1H, m), 11.38 (1H, br s), 12.53 (1H, br s). | 450 | 448 |
TABLE 1-23
| Ex. No. | structural formula | NMR | MS (M + H) | MS (M − H) |
|---|---|---|---|---|
| 112 | 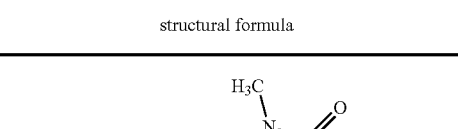 | ¹H-NMR (DMSO-D₆) δ: 0.90-1.09 (3H, m), 1.01 (6H, s), 1.19-2.27 (10H, m), 2.42 (2H, s), 2.57-2.80 (3H, m), 3.18 (3H, s), 3.22-3.41 (1H, m), 4.40-4.51 (1H, m), 6.54-6.63 (1H, m), 6.83-6.91 (1H, m), 7.23-7.32 (1H, m), 7.51-7.57 (1H, m), 11.38 (1H, br s), 12.53 (1H, br s). | 450 | 448 |

TABLE 1-23-continued
| Ex. No. | structural formula | NMR | MS (M + H) | MS (M − H) |
|---|---|---|---|---|
| 113 | 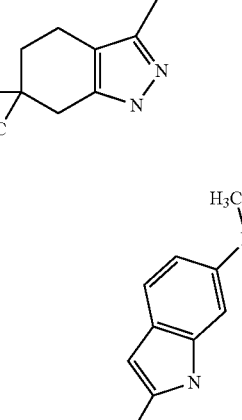 | ¹H-NMR (DMSO-D₆) δ: 0.96-1.04 (9H, m), 1.23-1.36 (2H, m), 1.54-1.62 (2H, m), 1.67-1.78 (2H, m), 2.04-2.12 (1H, m), 2.22-2.30 (1H, m), 2.37-2.45 (1H, m), 2.42 (2H, s), 2.58-2.75 (3H, m), 3.00-3.08 (1H, m), 3.17 (3H, s), 3.18 (3H, s), 3.19-3.25 (1H, m), 6.57-6.61 (1H, m), 6.84-6.90 (1H, m), 7.25-7.30 (1H, m), 7.50-7.56 (1H, m), 11.40 (1H, br s), 12.53 (1H, br s). | 464 | 462 |
| 114 | 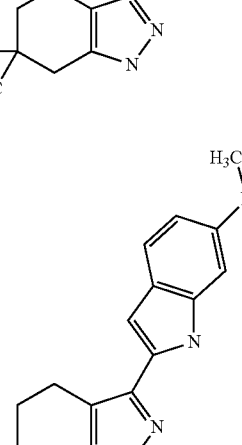 | ¹H-NMR (DMSO-D₆) δ: 0.89-1.06 (1H, m), 1.01 (6H, s), 1.23-1.39 (1H, m), 1.49-1.62 (3H, m), 1.79-1.88 (2H, m), 1.90-2.00 (1H, m), 2.42 (2H, s), 2.47-2.55 (1H, m), 2.63-2.69 (2H, m), 2.75-2.82 (1H, m), 2.85-2.94 (2H, m), 3.05-3.14 (1H, m), 3.15-3.21 (6H, m), 6.56-6.62 (1H, m), 6.83-6.90 (1H, m), 7.21-7.27 (1H, m), 7.50-7.58 (1H, m), 11.41 (1H, br s), 12.53 (1H, br s). | 450 | 448 |
| 115 | 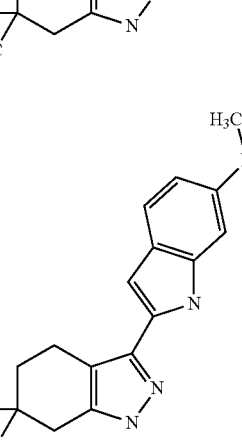 | ¹H-NMR (DMSO-D₆) δ: 0.90-0.99 (1H, m), 1.01 (6H, s), 1.23-1.40 (1H, m), 1.48-1.62 (3H, m), 1.78-1.88 (2H, m), 1.90-2.00 (1H, m), 2.42 (2H, s), 2.48-2.55 (1H, m), 2.63-2.70 (2H, m), 2.75-2.82 (1H, m), 2.84-2.94 (2H, m), 3.04-3.14 (1H, m), 3.15-3.21 (6H, m), 6.56-6.62 (1H, m), 6.83-6.90 (1H, m), 7.21-7.28 (1H, m), 7.49-7.58 (1H, m), 11.41 (1H, br s), 12.53 (1H, br s). | 450 | 448 |
| 116 |  | ¹H-NMR (DMSO-D₆) δ: 0.90-1.11 (10H, m), 1.20-1.65 (4H, m), 1.80-2.34 (4H, m), 2.42 (2H, s), 2.47-2.59 (1H, m), 2.63-2.75 (2H, m), 2.83-3.05 (1H, m), 3.06-3.30 (7H, m), 6.56-6.63 (1H, m), 6.84-6.91 (1H, m), 7.24-7.31 (1H, m), 7.51-7.58 (1H, m), 11.40 (1H, br s), 12.53 (1H, br s). | 464 | 462 |

TABLE 1-24

| Ex. No. | structural formula | NMR | MS (M + H) | MS (M − H) |
|---|---|---|---|---|
| 117 | | ¹H-NMR (DMSO-D₆) δ: 0.90-1.08 (10H, m), 1.19-1.64 (4H, m), 1.80-2.05 (3H, m), 2.11-2.35 (1H, m), 2.42 (2H, s), 2.48-2.57 (1H, m), 2.63-2.75 (2H, m), 2.83-3.30 (8H, m), 6.57-6.62 (1H, m), 6.85-6.94 (1H, m), 7.24-7.31 (1H, m), 7.51-7.58 (1H, m), 11.40 (1H, br s), 12.53 (1H, br s). | 464 | 462 |
| 118 | | ¹H-NMR (DMSO-D₆) δ: 0.92-1.09 (12H, m), 1.55-1.60 (2H, m), 1.61-2.37 (2H, m), 2.41 (2H, s), 2.56-2.88 (6H, m), 3.18 (3H, s), 3.44-3.84 (2H, m), 6.55-6.63 (1H, m), 6.83-6.91 (1H, m), 7.22-7.30 (1H, m), 7.50-7.56 (1H, m), 11.41 (1H, br s), 12.54 (1H, br s). | 450 | 448 |
| 119 | | ¹H-NMR (DMSO-D₆) δ: 0.96 (6H, d, J = 6.3 Hz), 1.01 (6H, s), 1.56-1.60 (2H, m), 1.62-1.69 (2H, m), 2.42 (2H, s), 2.57-2.63 (2H, m), 2.65-2.71 (2H, m), 2.84 (2H, s), 3.18 (3H, s), 3.44-3.55 (2H, m), 6.57-6.63 (1H, m), 6.84-6.90 (1H, m), 7.23-7.28 (1H, m), 7.50-7.57 (1H, m), 11.42 (1H, br s), 12.54 (1H, br s). | 450 | 448 |
| 120 | | ¹H-NMR (DMSO-D₆) δ: 0.90-1.12 (15H, m), 1.54-1.62 (2H, m), 1.76-2.03 (2H, m), 2.28-2.56 (4H, m), 2.64-2.70 (2H, m), 3.15-3.24 (4H, m), 3.40-3.84 (2H, m), 6.57-6.63 (1H, m), 6.84-6.91 (1H, m), 7.25-7.30 (1H, m), 7.51-7.58 (1H, m), 11.42 (1H, br s), 12.54 (1H, br s). | 464 | 462 |

TABLE 1-24-continued
| Ex. No. | structural formula | NMR | MS (M + H) | MS (M − H) |
|---|---|---|---|---|
| 121 | 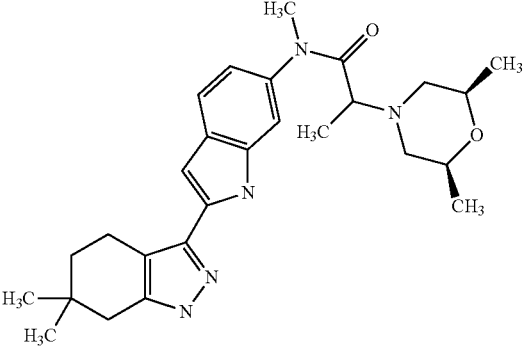 | ¹H-NMR (DMSO-D₆) δ: 0.92-1.13 (15H, m), 1.55-1.61 (2H, m), 1.76-2.02 (2H, m), 2.29-2.56 (4H, m), 2.63-2.70 (2H, m), 3.16-3.24 (4H, m), 3.38-3.51 (2H, m), 6.57-6.62 (1H, m), 6.84-6.90 (1H, m), 7.25-7.30 (1H, m), 7.52-7.56 (1H, m), 11.42 (1H, br s), 12.54 (1H, br s). | 464 | 462 |
TABLE 1-25
| Ex. No. | structural formula | NMR | MS (M + H) | MS (M − H) |
|---|---|---|---|---|
| 122 | 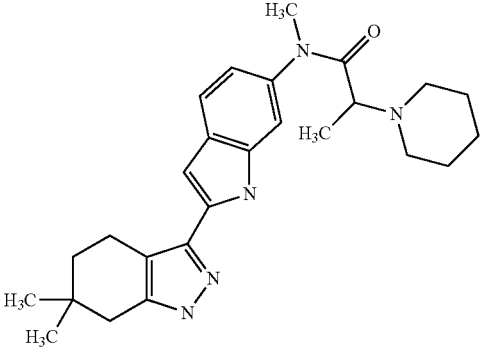 | ¹H-NMR (DMSO-D₆) δ: 0.97-1.04 (9H, m), 1.26-1.34 (2H, m), 1.35-1.43 (4H, m), 1.53-1.62 (2H, m), 2.18-2.27 (2H, m), 2.37-2.45 (2H, m), 2.42 (2H, s), 2.64-2.70 (2H, m), 3.18 (3H, s), 3.19-3.23 (1H, m), 6.57-6.62 (1H, m), 6.84-6.91 (1H, m), 7.24-7.30 (1H, m), 7.50-7.56 (1H, m), 11.37 (1H, br s), 12.53 (1H, br s). | 434 | 432 |
| 123 | 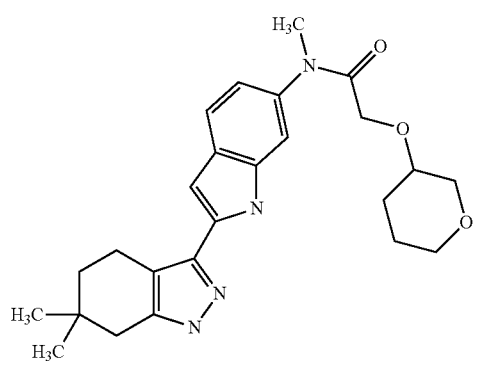 | ¹H-NMR (DMSO-D₆) δ: 1.01 (6H, s), 1.26-1.38 (2H, m), 1.53-1.65 (3H, m), 1.76-1.86 (1H, m), 2.42 (2H, s), 2.63-2.72 (2H, m), 3.03-3.14 (1H, m), 3.19 (3H, s), 3.21-3.30 (2H, m), 3.50-3.57 (1H, m), 3.60-3.67 (1H, m), 3.77-3.88 (2H, m), 6.57-6.65 (1H, m), 6.85-6.93 (1H, m), 7.23-7.30 (1H, m), 7.51-7.57 (1H, m), 11.42 (1H, br s), 12.54 (1H, br s). | 437 | 435 |

TABLE 1-25-continued

| Ex. No. | structural formula | NMR | MS (M + H) | MS (M − H) |
|---|---|---|---|---|
| 124 | | ¹H-NMR (DMSO-D₆) δ: 0.78-0.91 (1H, m), 1.01 (6H, s), 1.05-1.51 (6H, m), 1.52-1.69 (4H, m), 1.76-1.83 (1H, m), 2.14-2.26 (1H, m), 2.42 (2H, s), 2.64-2.71 (2H, m), 3.15 (3H, s), 6.59-6.63 (1H, m), 6.83-6.89 (1H, m), 7.22-7.26 (1H, m), 7.53-7.58 (1H, m), 11.34 (1H, br s), 12.19 (1H, br s). | 405 | 403 |
| 125 | | ¹H-NMR (DMSO-D₆) δ: 0.89-0.97 (3H, m), 1.01 (6H, s), 1.56-1.61 (2H, m), 2.06-2.31 (2H, m), 2.41 (2H, s), 2.65-2.70 (2H, m), 2.72-2.94 (3H, m), 3.16-3.25 (3H, m), 3.78-3.84 (2H, m), 6.59-6.64 (1H, m), 6.89-6.98 (1H, m), 7.28-7.34 (1H, m), 7.54-7.61 (1H, m), 11.42 (1H, br s), 12.51 (1H, br s). | 422 | 420 |
| 126 | | ¹H-NMR (DMSO-D₆) δ: 1.01 (6H, s), 1.55-1.61 (2H, m), 1.80 (1H, br s), 2.13-2.18 (3H, m), 2.41 (2H, s), 2.64-2.70 (2H, m), 2.92-2.97 (2H, m), 3.21 (3H, s), 6.58-6.63 (1H, m), 6.84-6.89 (1H, m), 7.22-7.26 (1H, m), 7.53-7.58 (1H, m), 11.37 (1H, br s), 12.51 (1H, br s). | 366 | 364 |

TABLE 1-26

| Ex. No. | structural formula | NMR | MS (M + H) | MS (M − H) |
|---|---|---|---|---|
| 127 | | ¹H-NMR (DMSO-D₆) δ: 1.01 (6H, s), 1.46-1.69 (8H, m), 2.34-2.45 (2H, m), 2.42 (2H, s), 2.64-2.72 (2H, m), 3.18 (3H, s), 3.29-3.36 (2H, m), 3.82 (2H, s), 6.58-6.65 (1H, m), 6.90-6.96 (1H, m), 7.27-7.35 (1H, m), 7.54-7.60 (1H, m), 11.44 (1H, br s), 12.54 (1H, br s). | 448 | 446 |

TABLE 1-26-continued
| Ex. No. | structural formula | NMR | MS (M + H) | MS (M − H) |
|---|---|---|---|---|
| 128 | 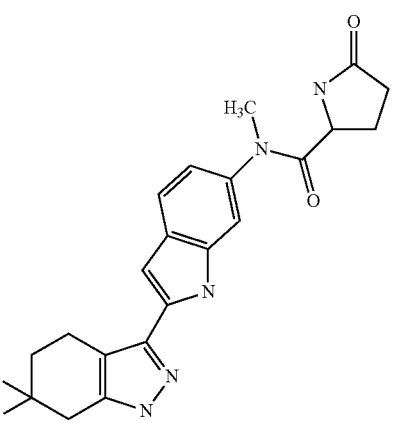 | $^1$H-NMR (DMSO-D$_6$) δ: 1.01 (6H, s), 1.55-1.61 (2H, m), 1.81-2.02 (3H, m), 2.08-2.18 (1H, m), 2.41 (2H, s), 2.64-2.70 (2H, m), 3.21 (3H, s), 4.00-4.04 (1H, m), 6.59-6.63 (1H, m), 6.88-6.93 (1H, m), 7.27-7.30 (1H, m), 7.55-7.59 (1H, m), 7.63 (1H, br s), 11.45 (1H, br s), 12.55 (1H, br s). | 406 | 404 |
| 129 | 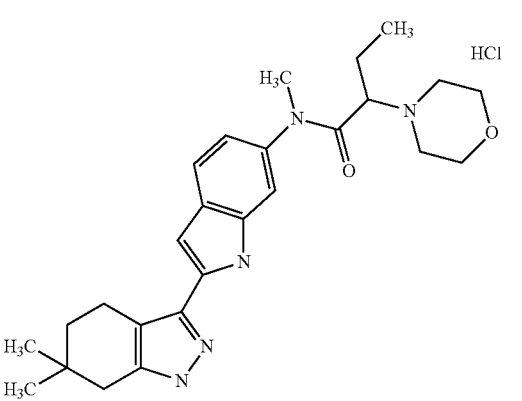 | $^1$H-NMR (DMSO-D$_6$) δ: 0.84-0.92 (3H, m), 1.01 (6H, s), 1.54-1.61 (2H, m), 1.72-1.85 (2H, m), 2.42 (2H, s), 2.64-2.71 (2H, m), 3.01-3.52 (5H, m), 3.32 (3H, s), 3.72-3.98 (5H, m), 6.63-6.67 (1H, m), 6.95-7.01 (1H, m), 7.33-7.37 (1H, m), 7.61-7.65 (1H, m), 10.25 (1H, br s), 11.49 (1H, br s). | 450 | 448 |
| 130 | 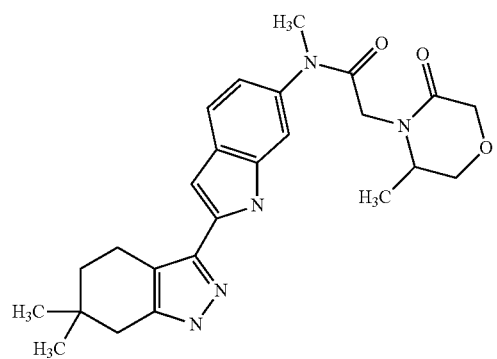 | $^1$H-NMR (DMSO-D$_6$) δ: 1.01 (6H, s), 1.08 (3H, d, J = 6.6 Hz), 1.55-1.61 (2H, m), 2.42 (2H, s), 2.64-2.71 (2H, m), 3.20 (3H, s), 3.47-3.55 (2H, m), 3.56-3.61 (1H, m), 3.76-3.81 (1H, m), 3.98 (1H, d, J = 16.5 Hz), 4.03 (1H, d, J = 16.8 Hz), 4.08-4.15 (1H, m), 6.59-6.64 (1H, m), 6.93-6.99 (1H, m), 7.31-7.36 (1H, m), 7.55-7.61 (1H, m), 11.46 (1H, br s), 12.54 (1H, br s). | 450 | 448 |
| 131 | 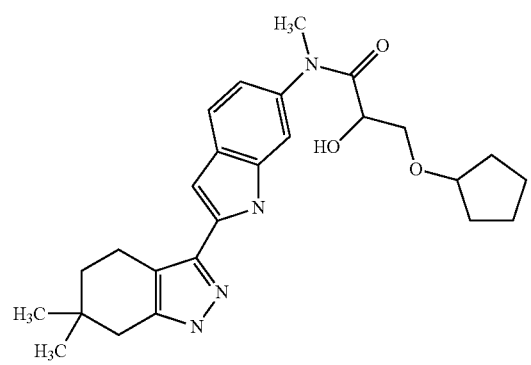 | $^1$H-NMR (DMSO-D$_6$) δ: 1.01 (6H, s), 1.32-1.63 (10H, m), 2.42 (2H, s), 2.62-2.73 (2H, m), 3.13-3.19 (1H, m), 3.20 (3H, s), 3.37-3.44 (1H, m), 3.64-3.70 (1H, m), 4.04-4.12 (1H, m), 4.92 (1H, d, J = 7.4 Hz), 6.56-6.64 (1H, m), 6.84-6.94 (1H, m), 7.23-7.31 (1H, m), 7.50-7.59 (1H, m), 11.46 (1H, br s), 12.54 (1H, br s). | 451 | 449 |

TABLE 1-27

| Ex. No. | structural formula | NMR | MS (M + H) | MS (M − H) |
|---|---|---|---|---|
| 132 | (structure) | ¹H-NMR (DMSO-D₆) δ: 0.94-0.98 (6H, m), 1.01 (6H, s), 1.54-1.61 (2H, m), 2.41 (2H, s), 2.63-2.71 (2H, m), 3.14-3.19 (1H, m), 3.20 (3H, s), 3.34-3.40 (1H, m), 3.41-3.47 (1H, m), 4.03-4.11 (1H, m), 4.90 (1H, d, J = 6.6 Hz), 6.56-6.63 (1H, m), 6.85-6.92 (1H, m), 7.24-7.31 (1H, m), 7.51-7.57 (1H, m), 11.45 (1H, br s), 12.53 (1H, br s). | 425 | 423 |
| 133 | (structure) | ¹H-NMR (DMSO-D₆) δ: 1.01 (6H, s), 1.06 (3H, d, J = 7.0 Hz), 1.39-1.73 (6H, m), 1.85-2.05 (2H, m), 2.41 (2H, s), 2.61-2.73 (2H, m), 2.88-2.96 (1H, m), 3.16 (3H, s), 3.19-3.27 (1H, m), 4.82-4.93 (1H, m), 6.53-6.62 (1H, m), 6.86-6.95 (1H, m), 7.23-7.34 (1H, m), 7.47-7.54 (1H, m), 11.37 (1H, br s), 12.53 (1H, br s). | 448 | 446 |
| 134 | (structure) | ¹H-NMR (DMSO-D₆) δ: 1.01 (6H, s), 1.09 (3H, d, J = 7.1 Hz), 1.55-1.61 (2H, m), 1.76-1.97 (2H, m), 2.04-2.11 (2H, m), 2.41 (2H, s), 2.64-2.71 (2H, m), 3.17 (3H, s), 3.21-3.28 (1H, m), 3.49-3.56 (1H, m), 4.58-4.66 (1H, m), 6.56-6.63 (1H, m), 6.88-6.94 (1H, m), 7.25-7.31 (1H, m), 7.51-7.57 (1H, m), 11.39 (1H, br s), 12.53 (1H, br s). | 434 | 432 |
| 135 | (structure) | ¹H-NMR (DMSO-D₆) δ: 0.99-1.04 (9H, m), 1.55-1.60 (2H, m), 2.21-2.29 (2H, m), 2.38-2.48 (2H, m), 2.41 (2H, s), 2.63-2.69 (2H, m), 3.16-3.23 (1H, m), 3.19 (3H, s), 3.45-3.50 (4H, m), 6.58-6.60 (1H, m), 6.86-6.90 (1H, m), 7.27-7.30 (1H, m), 7.52-7.56 (1H, m), 11.39 (1H, br s), 12.53 (1H, br s). | 436 | 434 |

TABLE 1-27-continued

| Ex. No. | structural formula | NMR | MS (M + H) | MS (M − H) |
|---|---|---|---|---|
| 136 | (structure) | ¹H-NMR (DMSO-D₆) δ: 0.99-1.07 (3H, m), 1.01 (6H, s), 1.39-1.50 (1H, m), 1.55-1.61 (2H, m), 2.08-2.24 (3H, m), 2.40-2.44 (2H, m), 2.65-2.71 (2H, m), 3.19 (3H, s), 3.40 (1H, d, J = 16.9 Hz), 3.68-3.76 (1H, m), 3.94 (1H, d, J = 16.9 Hz), 6.59-6.63 (1H, m), 6.92-6.98 (1H, m), 7.30-7.35 (1H, m), 7.56-7.61 (1H, m), 11.41 (1H, br s), 12.51 (1H, br s). | 434 | 432 |

TABLE 1-28

| Ex. No. | structural formula | NMR | MS (M + H) | MS (M − H) |
|---|---|---|---|---|
| 137 | (structure) | ¹H-NMR (DMSO-D₆) δ: 0.96-1.08 (3H, m), 1.01 (6H, s), 1.46-1.65 (4H, m), 1.71-1.90 (2H, m), 2.14-2.19 (2H, m), 2.41 (2H, s), 2.64-2.71 (2H, m), 3.19 (3H, s), 3.42-3.52 (2H, m), 4.04-4.11 (1H, m), 6.58-6.62 (1H, m), 6.91-6.97 (1H, m), 7.30-7.34 (1H, m), 7.54-7.59 (1H, m), 11.40 (1H, br s), 12.51 (1H, br s). | 448 | 446 |
| 138 | (structure) | ¹H-NMR (DMSO-D₆) δ: 1.01 (6H, s), 1.55-1.61 (2H, m), 2.18-2.25 (2H, m), 2.42 (2H, s), 2.65-2.71 (2H, m), 3.09-3.14 (2H, m), 3.20 (3H, s), 3.29-3.34 (2H, m), 3.51 (2H, s), 6.58-6.64 (1H, m), 6.88-6.94 (1H, m), 7.26-7.31 (1H, m), 7.55-7.60 (1H, m), 11.43 (1H, br s), 12.51 (1H, br s). | 456 | 454 |
| 139 | (structure) | ¹H-NMR (DMSO-D₆) δ: 1.01 (6H, s), 1.55-1.79 (4H, m), 1.84-1.95 (2H, m), 2.41 (2H, s), 2.64-2.70 (2H, m), 3.19 (3H, s), 3.59-3.66 (1H, m), 3.78-3.85 (1H, m), 4.16-4.23 (1H, m), 6.57-6.65 (1H, m), 6.85-6.92 (1H, m), 7.23-7.31 (1H, m), 7.52-7.58 (1H, m), 11.41 (1H, br s), 12.53 (1H, br s). | 393 | 391 |

TABLE 1-28-continued

| Ex. No. | structural formula | NMR | MS (M + H) | MS (M − H) |
|---|---|---|---|---|
| 140 | | $^1$H-NMR (DMSO-D$_6$) δ: 1.01 (6H, s), 1.54-1.78 (4H, m), 1.84-1.95 (2H, m), 2.41 (2H, s), 2.62-2.72 (2H, m), 3.18 (3H, s), 3.58-3.66 (1H, m), 3.78-3.85 (1H, m), 4.16-4.22 (1H, m), 6.56-6.64 (1H, m), 6.84-6.93 (1H, m), 7.21-7.29 (1H, m), 7.52-7.59 (1H, m), 11.41 (1H, br s), 12.53 (1H, br s). | 393 | 391 |
| 141 | | $^1$H-NMR (DMSO-D$_6$) δ: 1.01 (6H, s), 1.55-1.64 (6H, m), 2.05-2.11 (2H, m), 2.19-2.26 (2H, m), 2.42 (2H, s), 2.63-2.69 (2H, m), 3.10-3.15 (2H, m), 3.18 (3H, s), 3.34-3.40 (2H, m), 6.57-6.61 (1H, m), 6.83-6.88 (1H, m), 7.20-7.23 (1H, m), 7.52-7.56 (1H, m), 11.42 (1H, br s), 12.53 (1H, br s). | 448 | 446 |

TABLE 1-29

| Ex. No. | structural formula | NMR | MS (M + H) | MS (M − H) |
|---|---|---|---|---|
| 142 | | $^1$H-NMR (DMSO-D$_6$) δ: 1.01 (6H, s), 1.55-1.63 (3H, m), 2.04-2.14 (4H, m), 2.41 (2H, s), 2.44-2.53 (4H, m), 2.64-2.70 (2H, m), 3.21 (3H, s), 3.79-3.87 (1H, m), 6.57-6.62 (1H, m), 6.86-6.92 (1H, m), 7.23-7.28 (1H, m), 7.53-7.58 (1H, m), 11.37 (1H, br s), 12.51 (1H, br s). | 434 | 432 |

TABLE 1-29-continued
| Ex. No. | structural formula | NMR | MS (M + H) | MS (M − H) |
|---|---|---|---|---|
| 143 | 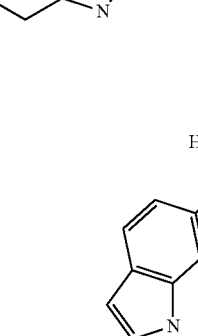 | $^1$H-NMR (DMSO-D$_6$) δ: 1.01 (6H, s), 1.46-1.54 (1H, m), 1.55-1.61 (2H, m), 1.91-2.19 (4H, m), 2.24-2.31 (1H, m), 2.41 (2H, s), 2.64-2.70 (2H, m), 3.19 (3H, s), 3.78-3.86 (1H, m), 6.58-6.63 (1H, m), 6.86-6.91 (1H, m), 7.22-7.28 (1H, m), 7.35 (1H, br s), 7.53-7.58 (1H, m), 11.41 (1H, br s), 12.53 (1H, br s). | 420 | 418 |
| 144 | 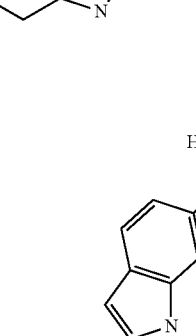 | $^1$H-NMR (DMSO-D$_6$) δ: 1.01 (6H, s), 1.55-1.61 (2H, m), 1.77-1.86 (2H, m), 2.07-2.13 (2H, m), 2.18-2.23 (2H, m), 2.41 (2H, s), 2.64-2.70 (2H, m), 3.15-3.21 (2H, m), 3.18 (3H, s), 3.29-3.35 (2H, m), 6.57-6.62 (1H, m), 6.84-6.89 (1H, m), 7.20-7.25 (1H, m), 7.52-7.57 (1H, m), 11.38 (1H, br s), 12.51 (1H, br s). | 434 | 432 |
| 145 | 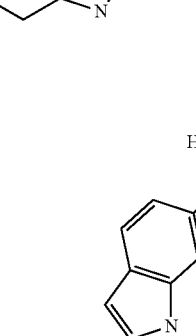 | $^1$H-NMR (DMSO-D$_6$) δ: 0.59 (3H, d, J = 6.0 Hz), 1.01 (6H, s), 1.51-1.62 (2H, m), 2.31-2.49 (2H, m), 2.41 (2H, s), 2.56-2.74 (3H, m), 2.82-2.95 (2H, m), 3.14-3.23 (1H, m), 3.18 (3H, s), 3.33-3.41 (1H, m), 3.43-3.50 (1H, m), 3.55-3.63 (1H, m), 6.55-6.64 (1H, m), 6.82-6.92 (1H, m), 7.22-7.30 (1H, m), 7.49-7.58 (1H, m), 11.39 (1H, br s), 12.53 (1H, br s). | 436 | 434 |
| 146 | 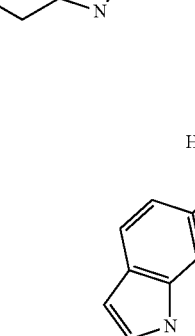 | $^1$H-NMR (DMSO-D$_6$) δ: −0.12-1.17 (6H, m), 1.01 (6H, s), 1.54-1.62 (2H, m), 2.19-2.48 (2H, m), 2.41 (2H, s), 2.60-2.92 (4H, m), 3.12-3.80 (4H, m), 3.17 (3H, s), 6.50-6.62 (1H, m), 6.84-6.99 (1H, m), 7.26-7.42 (1H, m), 7.48-7.58 (1H, m), 11.37-11.44 (1H, m), 12.53 (1H, br s). | 450 | 448 |

TABLE 1-30

| Ex No. | structural formula | NMR | MS (M + H) | MS (M − H) |
|---|---|---|---|---|
| 147 | | ¹H-NMR (DMSO-D₆) δ: 1.01 (6H, s), 1.10 (3H, d, J = 7.0 Hz), 1.53-1.62 (2H, m), 2.42 (2H, s), 2.62-2.76 (2H, m), 3.11-3.22 (1H, m), 3.18 (3H, s), 3.39-3.47 (1H, m), 3.64-3.73 (1H, m), 3.75-3.92 (3H, m), 4.91-5.00 (1H, m), 6.55-6.60 (1H, m), 6.91-6.97 (1H, m), 7.28-7.33 (1H, m), 7.50-7.56 (1H, m), 11.43 (1H, br s), 12.53 (1H, br s). | 450 | 448 |
| 148 | | ¹H-NMR (DMSO-D₆) δ: 1.01 (6H, s), 1.47-1.76 (6H, m), 1.96-2.04 (1H, m), 2.12 (3H, s), 2.41 (2H, s), 2.63-2.69 (2H, m), 2.83-2.91 (2H, m), 3.19 (3H, s), 6.58-6.62 (1H, m), 6.81-6.86 (1H, m), 7.19-7.23 (1H, m), 7.52-7.57 (1H, m), 11.37 (1H, br s), 12.53 (1H, br s). | 406 | 404 |
| 149 | | ¹H-NMR (DMSO-D₆) δ: 1.01 (6H, s), 1.47-1.76 (6H, m), 1.96-2.05 (1H, m), 2.12 (3H, s), 2.41 (2H, s), 2.63-2.70 (2H, m), 2.84-2.92 (2H, m), 3.19 (3H, s), 6.57-6.63 (1H, m), 6.80-6.87 (1H, m), 7.18-7.24 (1H, m), 7.52-7.58 (1H, m), 11.37 (1H, br s), 12.53 (1H, br s). | 406 | 404 |
| 150 | | ¹H-NMR (DMSO-D₆) δ: 1.01 (6H, s), 1.54-1.61 (2H, m), 1.79-1.94 (2H, m), 2.03-2.12 (1H, m), 2.19-2.29 (1H, m), 2.42 (2H, s), 2.57 (3H, s), 2.64-2.71 (2H, m), 3.24 (3H, s), 4.04-4.08 (1H, m), 6.60-6.63 (1H, m), 6.92-6.97 (1H, m), 7.29-7.32 (1H, m), 7.57-7.62 (1H, m), 11.44 (1H, br s), 12.54 (1H, br s). | 420 | 418 |

TABLE 1-30-continued
| Ex No. | structural formula | NMR | MS (M + H) | MS (M − H) |
|---|---|---|---|---|
| 151 | 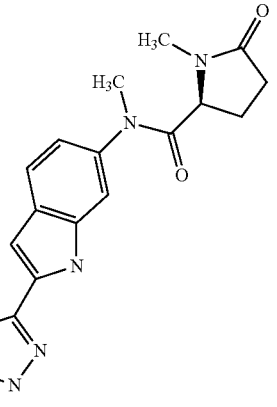 | $^1$H-NMR (DMSO-D$_6$) δ: 1.01 (6H, s), 1.55-1.61 (2H, m), 1.80-1.93 (2H, m), 2.03-2.12 (1H, m), 2.19-2.29 (1H, m), 2.42 (2H, s), 2.57 (3H, s), 2.64-2.71 (2H, m), 3.24 (3H, s), 4.03-4.08 (1H, m), 6.60-6.63 (1H, m), 6.91-6.97 (1H, m), 7.29-7.32 (1H, m), 7.57-7.61 (1H, m), 11.44 (1H, br s), 12.54 (1H, br s). | 420 | 418 |
TABLE 1-31
| Ex No. | structural formula | NMR | MS (M + H) | MS (M − H) |
|---|---|---|---|---|
| 152 | 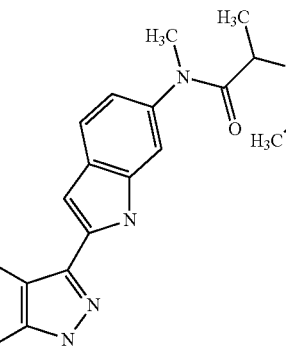<br>stereoisomer of Ex. No. 153 | $^1$H-NMR (DMSO-D$_6$) δ: 1.01 (6H, s), 1.15-1.25 (6H, m), 1.55-1.60 (2H, m), 2.41 (2H, s), 2.64-2.71 (2H, m), 2.88-2.99 (1H, m), 3.12-3.21 (1H, m), 3.16 (3H, s), 3.36-3.42 (1H, m), 3.82-3.88 (1H, m), 3.93-4.00 (1H, m), 4.47-4.55 (1H, m), 6.56-6.60 (1H, m), 6.90-6.95 (1H, m), 7.28-7.31 (1H, m), 7.50-7.55 (1H, m), 11.39 (1H, br s), 12.53 (1H, br s). | 464 | 462 |
| 153 | 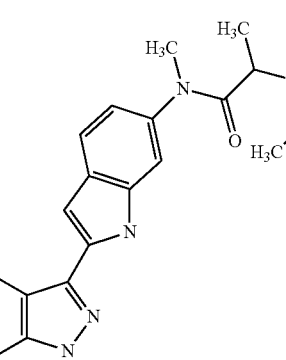<br>stereoisomer of Ex. No. 152 | $^1$H-NMR (DMSO-D$_6$) δ: 1.01 (6H, s), 1.15-1.26 (6H, m), 1.55-1.61 (2H, m), 2.41 (2H, s), 2.63-2.71 (2H, m), 3.19 (3H, s), 3.64-3.73 (2H, m), 379-3.89 (2H, m), 3.93-4.01 (1H, m), 4.90-4.98 (1H, m), 6.56-6.60 (1H, m), 6.91-6.97 (1H, m), 7.28-7.32 (1H, m), 7.50-7.55 (1H, m), 11.45 (1H, br s), 12.53 (1H, br s). | 464 | 462 |

TABLE 1-31-continued

| Ex No. | structural formula | NMR | MS (M + H) | MS (M − H) |
|---|---|---|---|---|
| 154 | | ¹H-NMR (DMSO-D₆) δ: 1.01 (6H, s), 1.55-1.61 (2H, m), 2.42 (2H, s), 2.65-2.70 (2H, m), 3.21 (3H, s), 3.54-3.60 (2H, m), 3.69 (2H, s), 4.21-4.28 (2H, m), 6.60-6.63 (1H, m), 6.91-6.95 (1H, m), 7.29-7.31 (1H, m), 7.57-7.61 (1H, m), 11.47 (1H, br s), 12.54 (1H, br s). | 422 | 420 |
| 155 | | ¹H-NMR (DMSO-D₆) δ: 1.01 (6H, s), 1.55-1.61 (2H, m), 2.39-2.46 (2H, m), 2.41 (2H, s), 2.64-2.71 (2H, m), 2.89-2.96 (2H, m), 3.00-3.04 (2H, m), 3.16 (3H, s), 3.21 (6H, s), 3.70-3.76 (2H, m), 6.57-6.62 (1H, m), 6.83-6.89 (1H, m), 7.20-7.26 (1H, m), 7.51-7.56 (1H, m), 11.40 (1H, brs), 12.53 (1H, br s). | 466 | 464 |
| 156 | | ¹H-NMR (DMSO-D₆) δ: 1.01 (6H, s), 1.53-1.62 (2H, m), 2.42 (2H, s), 2.63-2.72 (2H, m), 3.22 (3H, s), 4.43 (2H, s), 6.12-6.20 (1H, m), 6.28-6.35 (1H, m), 6.60-6.67 (1H, m), 6.99-7.05 (1H, m), 7.35-7.46 (2H, m), 7.51-7.57 (1H, m), 7.59-7.65 (1H, m), 11.50 (1H, br s), 12.55 (1H, br s). | 430 | 428 |

TABLE 1-32

| Ex No. | structural formula | NMR | MS (M + H) | MS (M − H) |
|---|---|---|---|---|
| 157 | | ¹H-NMR (DMSO-D₆) δ: 1.01 (6H, s), 1.55-1.61 (2H, m), 2.42 (2H, s), 2.65-2.71 (2H, m), 3.23 (3H, s), 4.71 (2H, s), 6.18-6.22 (1H, m), 6.62-6.66 (1H, m), 6.98-7.03 (1H, m), 7.34-7.41 (2H, m), 7.59-7.64 (2H, m), 11.48 (1H, br s), 12.55 (1H, br s). | 403 | 401 |

TABLE 1-32-continued

| Ex No. | structural formula | NMR | MS (M + H) | MS (M − H) |
|---|---|---|---|---|
| 158 | | ¹H-NMR (DMSO-D₆) δ: 1.01 (6H, s), 1.19-1.29 (1H, m), 1.32-1.69 (9H, m), 2.42 (2H, s), 2.62-2.74 (2H, m), 3.20 (3H, s), 3.29-3.38 (1H, m), 3.45-3.52 (1H, m), 3.74-3.84 (1H, m), 3.89-3.96 (1H, m), 4.63 (1H, br s), 6.60-6.64 (1H, m), 6.87-6.93 (1H, m), 7.27-7.31 (1H, m), 7.54-7.59 (1H, m), 11.42 (1H, br s), 12.54 (1H, br s). | 451 | 449 |
| 159 | | ¹H-NMR (DMSO-D₆) δ: 0.85 (3H, d, J = 6.0 Hz), 0.97 (3H, d, J = 6.2 Hz), 1.01 (6H, s), 1.54-1.61 (2H, m), 2.41 (2H, s), 2.63-2.71 (2H, m), 3.20 (3H, s), 3.30-3.38 (1H, m), 3.40-3.54 (2H, m), 3.95-4.00 (1H, m), 4.63 (1H, br s), 6.58-6.64 (1H, m), 6.87-6.92 (1H, m), 7.26-7.32 (1H, m), 7.54-7.59 (1H, m), 11.41 (1H, br s), 12.53 (1H, br s). | 425 | 423 |
| 160 | | ¹H-NMR (DMSO-D₆) δ: 1.01 (6H, s), 1.54-1.61 (2H, m), 1.68-1.78 (1H, m), 1.92-2.02 (1H, m), 2.08-2.27 (2H, m), 2.42 (2H, s), 2.64-2.72 (2H, m), 3.20 (3H, s), 3.24-3.30 (1H, m), 3.45-3.51 (1H, m), 3.57-3.67 (2H, m), 3.90-3.97 (1H, m), 4.72-4.77 (1H, m), 6.59-6.63 (1H, m), 6.91-6.96 (1H, m), 7.29-7.34 (1H, m), 7.56-7.61 (1H, m), 11.47 (1H, br s), 12.54 (1H, br s). | 450 | 448 |
| 161 | | ¹H-NMR (DMSO-D₆) δ: 0.92-1.38 (6H, m), 1.01 (6H, s), 1.56-1.61 (2H, m), 2.23-2.60 (4H, m), 2.41 (2H, s), 2.63-2.70 (2H, m), 3.23-3.83 (7H, m), 6.53-6.59 (1H, M), 6.69-6.89 (1H, m), 7.10-7.39 (1H, m), 7.43-7.48 (1H, m), 11.34 (1H, br s), 12.49 (1H, br s). | 450 | 448 |

TABLE 1-33

| Ex No. | structural formula | NMR | MS (M + H) | MS (M − H) |
|---|---|---|---|---|
| 162 | | ¹H-NMR (DMSO-D₆) δ: 0.98-1.05 (3H, m), 1.01 (6H, s), 1.44-1.54 (1H, m), 1.56-1.61 (2H, m), 2.10-2.19 (1H, m), 2.26-2.34 (1H, m), 2.42 (2H, s), 2.64-2.71 (2H, m), 3.19 (3H, s), 3.26-3.34 (2H, m), 3.65-3.76 (2H, m), 6.60-6.63 (1H, m), 6.90-6.95 (1H, m), 7.28-7.32 (1H, m), 7.56-7.60 (1H, m), 11.46 (1H, br s), 12.54 (1H, br s). | 434 | 432 |
| 163 | | ¹H-NMR (DMSO-D₆) δ: 1.01 (6H, s), 1.07 (6H, s), 1.55-1.61 (2H, m), 2.03 (2H, s), 2.42 (2H, s), 2.64-2.70 (2H, m), 3.09 (2H, s), 3.19 (3H, s), 3.70 (2H, s), 6.59-6.63 (1H, m), 6.89-6.95 (1H, m), 7.27-7.31 (1H, m), 7.55-7.60 (1H, m), 11.46 (1H, br s), 12.54 (1H, br s). | 448 | 446 |
| 164 | | ¹H-NMR (DMSO-D₆) δ: 1.01 (6H, s), 1.54-1.61 (2H, m), 1.99-2.07 (1H, m), 2.38-2.48 (1H, m), 2.42 (2H, s), 2.64-2.72 (2H, m), 3.12-3.22 (1H, m), 3.19 (3H, s), 3.56-3.65 (2H, m), 3.81-3.88 (1H, m), 4.23-4.30 (1H, m), 5.11 (1H, d, J = 4.4 Hz), 6.58-6.63 (1H, m), 6.90-6.96 (1H, m), 7.27-7.32 (1H, m), 7.55-7.61 (1H, m), 11.46 (1H, br s), 12.54 (1H, br s). | 436 | 434 |
| 165 | | ¹H-NMR (DMSO-D₆) δ: 1.01 (6H, s), 1.55-1.60 (2H, m), 1.68-2.00 (7H, m), 2.41 (2H, s), 2.63-2.70 (2H, m), 3.14-3.25 (3H, m), 3.32-3.52 (2H, m), 4.22-4.28 (1H, m), 6.57-6.63 (1H, m), 6.92-6.99 (1H, m), 7.30-7.37 (1H, m), 7.52-7.61 (1H, m), 11.39-11.44 (1H, m), 12.50-12.56 (1H, m). | 434 | 432 |

TABLE 1-33-continued
| Ex No. | structural formula | NMR | MS (M + H) | MS (M − H) |
|---|---|---|---|---|
| 166 | 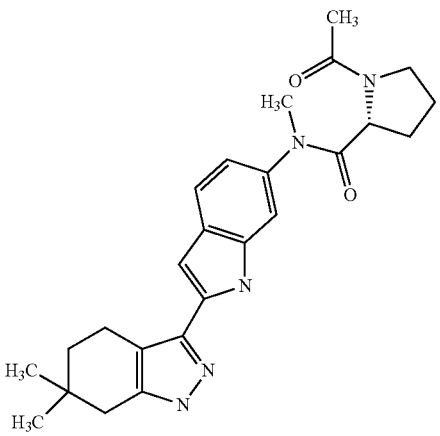 | ¹H-NMR (DMSO-D₆) δ: 1.01 (6H, s), 1.54-1.61 (2H, m), 1.62-2.01 (7H, m), 2.41 (2H, s), 2.61-2.73 (2H, m), 3.12-3.25 (3H, m), 3.36-3.55 (2H, m), 4.22-4.30 (1H, m), 6.57-6.66 (1H, m), 6.92-7.00 (1H, m), 7.31-7.43 (1H, m), 7.51-7.62 (1H, m), 11.39 (1H, br s), 12.53 (1H, br s). | 434 | 432 |
TABLE 1-34
| Ex No. | structural formula | NMR | MS (M + H) | MS (M − H) |
|---|---|---|---|---|
| 167 | 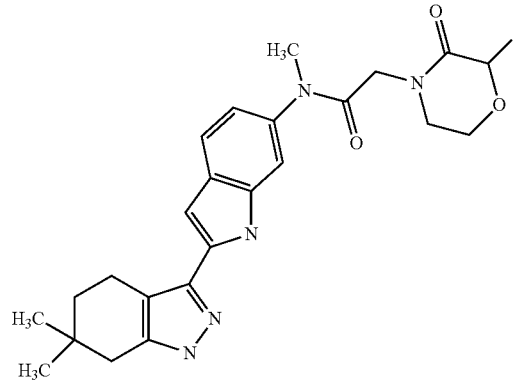 | ¹H-NMR (DMSO-D₆) δ: 1.01 (6H, s), 1.24 (3H, d, J = 6.8 Hz), 1.55-1.61 (2H, m), 2.42 (2H, s), 2.64-2.70 (2H, m), 3.17-3.24 (1H, m), 3.20 (3H, s), 3.46-3.54 (1H, m), 3.65-3.72 (1H, m), 3.73-3.80 (1H, m), 3.82-3.91 (2H, m), 4.09 (1H, q, J = 6.9 Hz), 6.59-6.63 (1H, m), 6.90-6.96 (1H, m), 7.29-7.32 (1H, m), 7.55-7.60 (1H, m), 11.47 (1H, br s), 12.54 (1H, br s). | 450 | 448 |
| 168 | 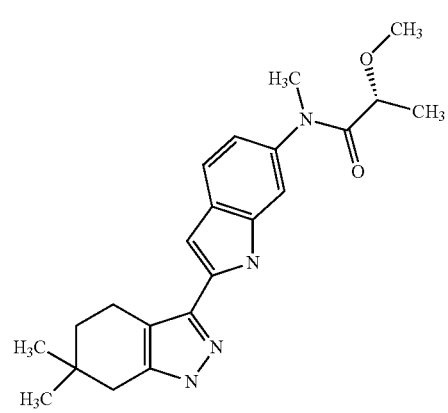 | ¹H-NMR (DMSO-D₆) δ: 1.01 (6H, s), 1.08 (3H, d, J = 6.6 Hz), 1.55-1.60 (2H, m), 2.41 (2H, s), 2.64-2.70 (2H, m), 3.04 (3H, s), 3.21 (3H, s), 3.79 (1H, q, J = 6.3 Hz), 6.58-6.64 (1H, m), 6.87-6.91 (1H, m), 7.21-7.29 (1H, m), 7.54-7.59 (1H, m), 11.39 (1H, br s), 12.53 (1H, br s). | 381 | 379 |

TABLE 1-34-continued
| Ex No. | structural formula | NMR | MS (M + H) | MS (M − H) |
|---|---|---|---|---|
| 169 | 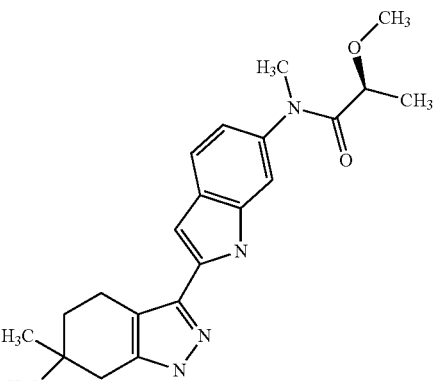 | ¹H-NMR (DMSO-D₆) δ: 1.01 (6H, s), 1.08 (3H, d, J = 6.4 Hz), 1.55-1.61 (2H, m), 2.41 (2H, s), 2.64-2.71 (2H, m), 3.04 (3H, s), 3.21 (3H, s), 3.79 (1H, q, J = 6.2 Hz), 6.59-6.63 (1H, m), 6.86-6.91 (1H, m), 7.23-7.29 (1H, m), 7.54-7.59 (1H, m), 11.35 (1H, br s), 12.51 (1H, br s). | 381 | 379 |
| 170 | 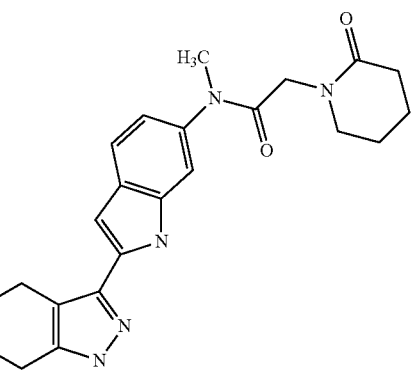 | ¹H-NMR (DMSO-D₆) δ: 1.01 (6H, s), 1.55-1.66 (3H, m), 1.82-1.91 (1H, m), 2.03-2.11 (1H, m), 2.36-2.44 (1H, m), 2.41 (2H, s), 2.65-2.71 (2H, m), 3.14-3.23 (1H, m), 3.19 (3H, s), 3.25-3.35 (1H, m), 3.60-3.68 (1H, m), 3.86-3.95 (2H, m), 4.87 (1H, d, J = 4.0 Hz), 6.59-6.64 (1H, m), 6.89-6.95 (1H, m), 7.28-7.34 (1H, m), 7.53-7.60 (1H, m), 11.40 (1H, br s), 12.51 (1H, br s). | 450 | 448 |
| 171 | 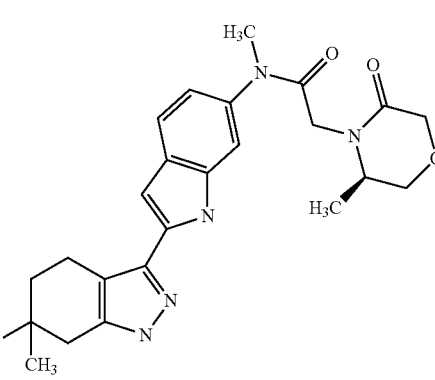 | ¹H-NMR (DMSO-D₆) δ: 1.01 (6H, s), 1.08 (3H, d, J = 6.3 Hz), 1.54-1.62 (2H, m), 2.42 (2H, s), 2.62-2.75 (2H, m), 3.20 (3H, s), 3.47-3.63 (3H m), 3.75-3.82 (1H, m), 3.98 (1H, d, J = 16.5 Hz), 4.03 (1H, d, J = 16.5 Hz), 4.08-4.16 (1H, m), 6.58-6.65 (1H, m), 6.93-7.01 (1H, m), 7.30-7.37 (1H, m), 7.55-7.62 (1H, m), 11.47 (1H, br s), 12.54 (1H, br s). | 450 | 448 |

TABLE 1-35
| Ex No. | structural formula | NMR | MS (M + H) | MS (M − H) |
|---|---|---|---|---|
| 172 | 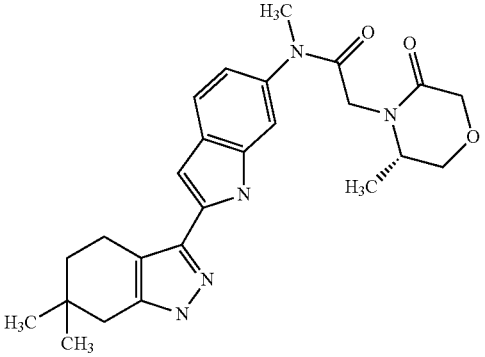 | $^1$H-NMR (DMSO-D$_6$) δ: 1.01 (6H, s), 1.08 (3H, d, J = 6.3 Hz), 1.54-1.62 (2H, m), 2.42 (2H, s), 2.63-2.71 (2H, m), 3.20 (3H, s), 3.47-3.62 (3H, m), 3.75-3.82 (1H, m), 3.98 (1H, d, J = 16.5 Hz), 4.03 (1H, d, J = 16.5 Hz), 4.08-4.16 (1H, m), 6.57-6.65 (1H, m), 6.92-7.01 (1H, m), 7.30-7.36 (1H, m), 7.55-7.62 (1H, m), 11.47 (1H, br s), 12.54 (1H, br s). | 450 | 448 |
| 173 | 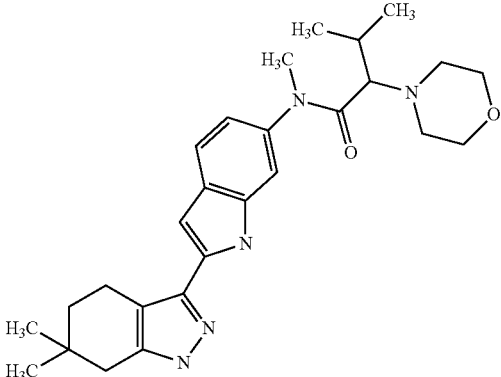 | $^1$H-NMR (DMSO-D$_6$) δ: 0.78 (3H, d, J = 6.4 Hz), 0.90 (3H, d, J = 6.4 Hz), 1.01 (6H, s), 1.55-1.61 (2H, m), 1.99-2.09 (1H, m), 2.30-2.38 (2H, m), 2.41 (2H, s), 2.51-2.56 (2H, m), 2.63-2.71 (2H, m), 2.82-2.88 (1H, m), 3.23 (3H, s), 3.41-3.50 (4H, m), 6.57-6.61 (1H, m), 6.82-6.88 (1H, m), 7.23-7.27 (1H, m), 7.51-7.56 (1H, m), 11.36 (1H, br s), 12.51 (1H, br s). | 464 | 462 |
| 174 | 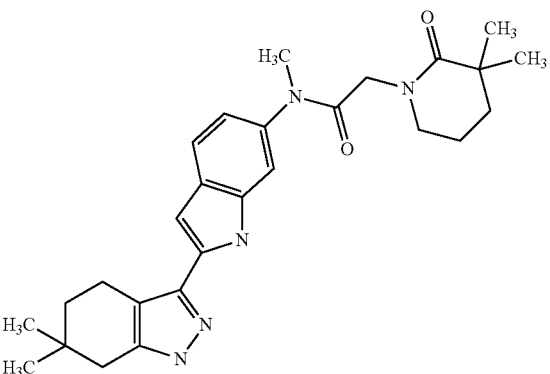 | $^1$H-NMR (DMSO-D$_6$) δ: 1.01 (6H, s), 1.05 (6H, s), 1.55-1.63 (4H, m), 1.69-1.76 (2H, m), 2.41 (2H, s), 2.64-2.70 (2H, m), 3.19 (3H, s), 3.22-3.27 (2H, m), 3.71 (2H, s), 6.58-6.63 (1H, m), 6.88-6.94 (1H, m), 7.28-7.32 (1H, m), 7.54-7.59 (1H, m), 11.41 (1H, br s), 12.51 (1H, br s). | 462 | 460 |
| 175 | 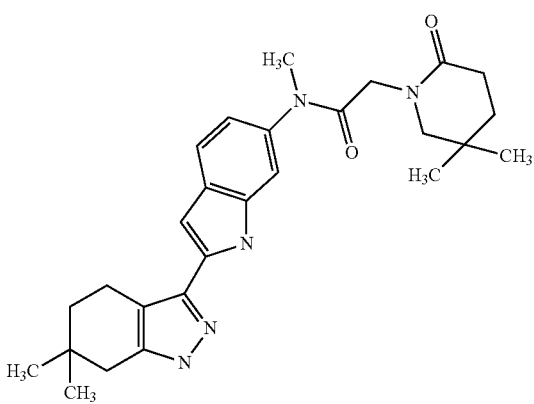 | $^1$H-NMR (DMSO-D$_6$) δ: 0.96 (6H, s), 1.01 (6H, s), 1.48-1.54 (2H, m), 1.55-1.61 (2H, m), 2.16-2.22 (2H, m), 2.41 (2H, s), 2.64-2.71 (2H, m), 2.98 (2H, s), 3.19 (3H, s), 3.75 (2H, s), 6.58-6.63 (1H, m), 6.88-6.95 (1H, m), 7.27-7.32 (1H, m), 7.53-7.59 (1H, m), 11.41 (1H, br s), 12.51 (1H, br s). | 462 | 460 |

TABLE 1-35-continued

| Ex No. | structural formula | NMR | MS (M + H) | MS (M − H) |
|---|---|---|---|---|
| 176 | | ¹H-NMR (DMSO-D₆) δ: 0.68-1.94 (11H, m), 1.01 (6H, s), 2.41 (2H, s), 2.64-2.71 (2H, m), 2.88-3.29 (9H, m), 6.56-6.63 (1H, m), 6.78-6.86 (1H, m), 7.16-7.23 (1H, m), 7.50-7.57 (1H, m), 11.35 (1H, br s), 12.50 (1H, br s). | 449 | 447 |

TABLE 1-36

| Ex No. | structural formula | NMR | MS (M + H) | MS (M − H) |
|---|---|---|---|---|
| 177 | | ¹H-NMR (DMSO-D₆) δ: 1.01 (6H, s), 1.55-1.62 (2H, m), 1.69-1.79 (1H, m), 1.92-2.03 (1H, m), 2.08-2.28 (2H, m), 2.42 (2H, s), 2.64-2.74 (2H, m), 3.20 (3H, s), 3.24-3.33 (1H, m), 3.45-3.52 (1H, m), 3.57-3.67 (2H, m), 3.89-3.98 (1H, m), 4.70-4.75 (1H, m), 6.59-6.63 (1H, m), 6.91-6.97 (1H, m), 7.30-7.34 (1H, m), 7.55-7.61 (1H, m), 11.43 (1H, br s), 12.51 (1H, br s). | 450 | 448 |
| 178 | | ¹H-NMR (DMSO-D₆) δ: 1.01 (6H, s), 1.56-1.61 (2H, m), 2.42 (2H, s), 2.64-2.71 (2H, m), 2.82-2.89 (3H, m), 3.17-3.22 (3H, m), 3.75 (2H, s), 5.00-5.06 (2H, m), 6.57-6.62 (1H, m), 6.70-6.94 (1H, m), 7.23-7.42 (6H, m), 7.48-7.59 (1H, m), 11.41 (1H, br s), 12.51 (1H, br s). | 500 | 498 |
| 179 | | ¹H-NMR (DMSO-D₆) δ: 1.01 (6H, s), 1.15 (9H, s), 1.55-1.60 (2H, m), 2.41 (2H, s), 2.65-2.70 (2H, m), 3.01 (3H, s), 3.19 (3H, s), 3.77 (2H, s), 6.58-6.64 (1H, m), 6.89-6.95 (1H, m), 7.29-7.34 (1H, m), 7.54-7.60 (1H, m), 11.41 (1H, br s), 12.50 (1H, br s). | 450 | 448 |

TABLE 1-36-continued

| Ex No. | structural formula | NMR | MS (M + H) | MS (M − H) |
|---|---|---|---|---|
| 180 | (structure) | ¹H-NMR (DMSO-D₆) δ: 1.01 (6H, s), 1.55-1.60 (2H, m), 2.41 (2H, s), 2.65-2.70 (2H, m), 2.73-2.90 (3H, m), 3.18-3.27 (6H, m), 3.77-4.07 (4H, m), 6.59-6.64 (1H, m), 6.91-6.97 (1H, m), 7.30-7.35 (1H, m), 7.55-7.60 (1H, m), 11.42 (1H, br s), 12.51 (1H, br s). | 438 | 436 |
| 181 | (structure) | ¹H-NMR (DMSO-D₆) δ: 1.01 (6H, s), 1.14 (3H, d, J = 6.4 Hz), 1.55-1.61 (2H, m), 2.42 (2H, s), 2.65-2.70 (2H, m), 3.14-3.26 (2H, m), 3.20 (3H, s), 3.71-3.94 (3H, m), 4.02 (2H, s), 6.60-6.61 (1H, m), 6.89-6.95 (1H, m), 7.29-7.32 (1H, m), 7.55-7.60 (1H, m), 11.43 (1H, br s), 12.51 (1H, br s). | 478 | 476 |

TABLE 1-37

| Ex No. | structural formula | NMR | MS (M + H) | MS (M − H) |
|---|---|---|---|---|
| 182 | (structure) | ¹H-NMR (DMSO-D₆) δ: 1.01 (6H, s), 1.14 (3H, d, J = 6.3 Hz), 1.55-1.61 (2H, m), 2.38-2.44 (2H, m), 2.64-2.71 (2H, m), 3.15-3.26 (2H, m), 3.20 (3H, s), 3.71-3.78 (1H, m), 3.80-3.95 (2H, m), 4.02 (2H, s), 6.60-6.63 (1H, m), 6.91-6.95 (1H, m), 7.29-7.32 (1H, m), 7.56-7.60 (1H, m), 11.48 (1H, br s), 12.55 (1H, br s). | 450 | 448 |
| 183 | (structure) | ¹H-NMR (DMSO-D₆) δ: 1.00 (6H, s), 1.01 (6H, s), 1.56-1.61 (2H, m), 1.73-1.79 (2H, m), 2.42 (2H, s), 2.65-2.71 (2H, m), 3.19 (3H, s), 3.26-3.30 (2H, m), 3.69 (2H, s), 6.59-6.65 (1H, m), 6.90-6.96 (1H, m), 7.27-7.34 (1H, m), 7.56-7.61 (1H, m), 11.47 (1H, br s), 12.55 (1H, br s). | 448 | 446 |

TABLE 1-37-continued

| Ex No. | structural formula | NMR | MS (M + H) | MS (M − H) |
|---|---|---|---|---|
| 184 | | ¹H-NMR (DMSO-D₆) δ: 1.01 (6H, s), 1.22 (6H, s), 1.53-1.62 (2H, m), 2.42 (2H, s), 2.65-2.70 (2H, m), 3.17-3.24 (2H, m), 3.20 (3H, s), 3.83 (2H, s), 3.97 (2H, s), 6.59-6.65 (1H, m), 6.91-6.96 (1H, m), 7.28-7.36 (1H, m), 7.55-7.61 (1H, m), 11.45 (1H, br s), 12.55 (1H, br s). | 464 | 462 |
| 185 | | ¹H-NMR (DMSO-D₆) δ: 1.01 (6H, s), 1.53-1.62 (2H, m), 2.42 (2H, s), 2.62-2.79 (4H, m), 3.15-3.43 (2H, m), 3.19 (3H, s), 3.57 (2H, s), 6.29 (1H, br s), 6.59-6.64 (1H, m), 6.89-6.94 (1H, m), 7.26-7.32 (1H, m), 7.55-7.61 (1H, m), 11.43 (1H, br s), 12.46 (1H, br s). | 421 | 419 |
| 186 | | ¹H-NMR (DMSO-D₆) δ: 1.01 (6H, s), 1.54-1.61 (2H, m), 2.41 (2H, s), 2.61 (3H, s), 2.65-2.71 (2H, m), 3.14-3.26 (2H, m), 3.18 (3H, s), 3.28-3.36 (2H, m), 3.59 (2H, s), 6.58-6.66 (1H, m), 6.87-6.96 (1H, m), 7.25-7.33 (1H, m), 7.54-7.61 (1H, m), 11.44 (1H, br s), 12.54 (1H, br s). | 435 | 433 |

TABLE 1-38

| Ex No. | structural formula | NMR | MS (M + H) | MS (M − H) |
|---|---|---|---|---|
| 187 | | ¹H-NMR (DMSO-D₆) δ: 1.01 (6H, s), 1.28-1.36 (2H, m), 1.39-1.50 (4H, m), 1.53-1.62 (4H, m), 2.35-2.44 (2H, m), 2.42 (2H, s), 2.64-2.70 (2H, m), 3.18 (3H, s), 3.41-3.47 (2H, m), 3.75 (2H, s), 6.58-6.63 (1H, m), 6.90-6.96 (1H, m), 7.28-7.33 (1H, m), 7.53-7.61 (1H, m), 11.44 (1H, br s), 12.53 (1H, br s). | 462 | 460 |

TABLE 1-38-continued

| Ex No. | structural formula | NMR | MS (M + H) | MS (M − H) |
|---|---|---|---|---|
| 188 | | ¹H-NMR (DMSO-D₆) δ: 0.96-1.05 (3H, m), 1.01 (6H, s), 1.54-1.61 (2H, m), 1.76-1.88 (1H, m), 2.27-2.40 (2H, m), 2.42 (2H, s), 2.64-2.71 (2H, m), 2.92-2.98 (1H, m), 3.19 (3H, s), 3.42-3.49 (1H, m), 3.63-3.76 (2H, m), 6.59-6.63 (1H, m), 6.90-6.96 (1H, m), 7.27-7.32 (1H, m), 7.55-7.61 (1H, m), 11.46 (1H, br s), 12.54 (1H, br s). | 434 | 432 |
| 189 | | ¹H-NMR (DMSO-D₆) δ: 0.98 (6H, s), 1.01 (6H, s), 1.49-1.55 (2H, m), 1.56-1.62 (2H, m), 1.98 (2H, s), 2.41 (2H, s), 2.63-2.72 (2H, m), 3.19 (3H, s), 3.23-3.31 (2H, m), 3.76 (2H, s), 6.58-6.64 (1H, m), 6.90-6.96 (1H, m), 7.28-7.34 (1H, m), 7.55-7.61 (1H, m), 11.46 (1H, br s), 12.54 (1H, br s). | 462 | 460 |
| 190 | | ¹H-NMR (DMSO-D₆) δ: 0.81-0.91 (3H, m), 1.00 (6H, s), 1.55-1.61 (2H, m), 1.69-1.85 (2H, m) 2.41 (2H, s), 2.63-2.70 (2H, m), 3.00-3.58 (5H, m), 3.32 (3H, s), 3.68-3.99 (4H, m), 6.62-6.67 (1H, m), 6.93-7.00 (1H, m), 7.31-7.36 (1H, m), 7.59-7.65 (1H, m), 10.09 (1H, br s), 11.47 (1H, br s), 12.57 (1H, br s). | 450 | 448 |
| 191 | | ¹H-NMR (DMSO-D₆) δ: 0.84 (3H, dd, J = 77.7, 38.8 Hz), 1.01 (6H, s), 1.54-1.62 (2H, m), 1.69-1.85 (2H, m), 2.42 (2H, s), 2.64-2.71 (2H, m), 2.99-3.55 (5H, m), 3.33 (3H, s), 3.70-4.01 (4H, m), 6.61-6.67 (1H, m), 6.92-7.01 (1H, m), 7.31-7.38 (1H, m), 7.59-7.66 (1H, m), 10.14 (1H, br s), 11.48 (1H, br s), 12.58 (1H, br s). | 450 | 448 |

TABLE 1-39

| Ex No. | structural formula | NMR | MS (M + H) | MS (M − H) |
|---|---|---|---|---|
| 192 | | ¹H-NMR (DMSO-D₆) δ: 1.01 (6H, s), 1.55-1.61 (2H, m), 1.82-1.97 (3H, m), 2.41 (2H, s), 2.65-2.70 (2H, m), 2.70-2.95 (3H, m), 3.17-3.25 (3H, m), 3.76-3.84 (2H, m), 6.59-6.63 (1H, m), 6.89-6.98 (1H, m), 7.28-7.34 (1H, m), 7.55-7.61 (1H, m), 11.45 (1H, br s), 12.53 (1H, br s). | 408 | 406 |
| 193 | | ¹H-NMR (DMSO-D₆) δ: 1.01 (6H, s), 1.10-1.19 (6H, m), 1.55-1.61 (2H, m), 2.23-2.45 (4H, m), 2.65-2.70 (2H, m), 2.73-2.99 (3H, m), 3.18-3.24 (3H, m), 3.81-3.94 (2H, m), 4.77-4.82 (1H, m), 6.59-6.64 (1H, m), 6.91-6.98 (1H, m), 7.30-7.35 (1H, m), 7.55-7.60 (1H, m), 11.41 (1H, br s), 12.51 (1H, br s). | 466 | 464 |
| 194 | | ¹H-NMR (DMSO-D₆) δ: 1.01 (6H, s), 1.15-1.62 (8H, m), 1.78-1.87 (2H, m), 2.14-2.64 (1H, m), 2.41 (2H, s), 2.65-2.70 (2H, m), 2.72-3.00 (3H, m), 3.16-3.25 (6H, m), 3.34-3.38 (1H, m), 3.73-3.87 (2H, m), 6.59-6.64 (1H, m), 6.90-6.98 (1H, m), 7.28-7.35 (1H, m), 7.54-7.62 (1H, m), 11.34-11.49 (1H, m), 12.50 (1H, br s). | 506 | 504 |
| 195 | | ¹H-NMR (DMSO-D₆) δ: 0.95-1.08 (9H, m), 1.01 (6H, s), 1.26 (3H, s), 1.54-1.60 (2H, m), 2.41 (2H, s), 2.55 (1H, s), 2.63-2.72 (2H, m), 2.66 (1H, s), 3.18 (3H, s), 4.60-4.76 (1H, m), 6.54-6.62 (1H, m), 6.82-6.92 (1H, m), 7.21-7.31 (1H, m), 7.50-7.55 (1H, m), 11.39 (1H, br s), 12.50 (1H, br s). | 480 | 478 |

TABLE 1-39-continued
| Ex No. | structural formula | NMR | MS (M + H) | MS (M − H) |
|---|---|---|---|---|
| 196 | 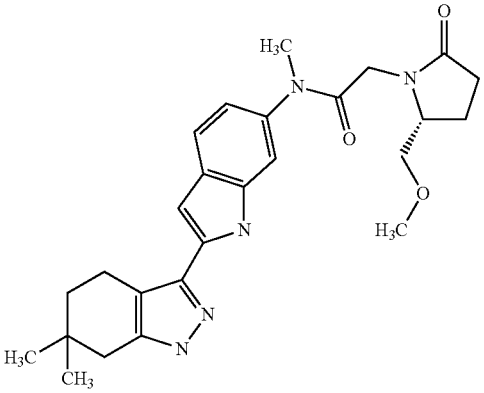 | ¹H-NMR (DMSO-D₆) δ: 1.01 (6H, s), 1.50-1.61 (3H, m), 1.94-2.07 (1H, m), 2.12-2.27 (2H, m), 2.42 (2H, s), 2.65-2.71 (2H, m), 3.19 (3H, s), 3.20 (3H, s), 3.25-3.35 (2H, m), 3.54-3.60 (1H, m), 3.74-3.82 (1H, m), 3.89-3.97 (1H, m), 6.60-6.64 (1H, m), 6.89-6.94 (1H, m), 7.29-7.33 (1H, m), 7.56-7.61 (1H, m), 11.43 (1H, br s), 12.52 (1H, br s). | 464 | 462 |
TABLE 1-40
| Ex No. | structural formula | NMR | MS (M + H) | MS (M − H) |
|---|---|---|---|---|
| 197 | 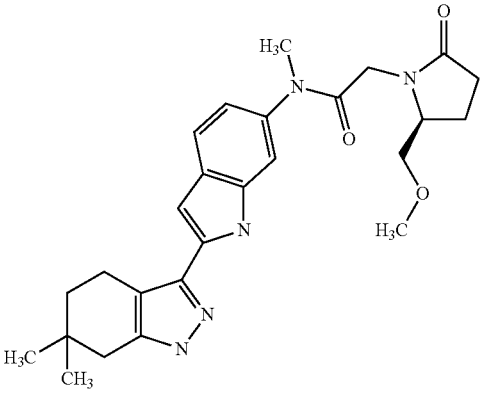 | ¹H-NMR (DMSO-D₆) δ: 1.01 (6H, s), 1.52-1.61 (3H, m), 1.96-2.06 (1H, m), 2.12-2.26 (2H, m), 2.42 (2H, s), 2.64-2.72 (2H, m), 3.20 (3H, s), 3.20 (3H, s), 3.25-3.37 (2H, m), 3.57 (1H, d, J = 16.5 Hz), 3.74-3.82 (1H, m), 3.93 (1H, d, J = 16.5 Hz), 6.59-6.64 (1H, m), 6.88-6.94 (1H, m), 7.27-7.33 (1H, m), 7.56-7.61 (1H, m), 11.43 (1H, br s), 12.51 (1H, br s). | 464 | 462 |
| 198 | 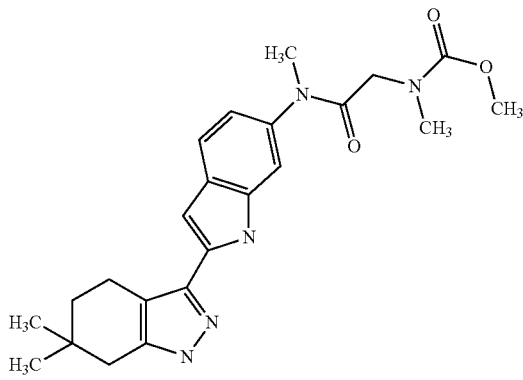 | ¹H-NMR (DMSO-D₆) δ: 1.01 (6H, s), 1.55-1.61 (2H, m), 2.41 (2H, s), 2.63-2.72 (2H, m), 2.76-2.85 (3H, m), 3.20 (3H, s), 3.50-3.59 (3H, m), 3.71 (2H, s), 6.58-6.65 (1H, m), 6.86-6.95 (1H, m), 7.24-7.33 (1H, m), 7.54-7.61 (1H, m), 11.44 (1H, br s), 12.53 (1H, br s). | 424 | 422 |

TABLE 1-40-continued
| Ex No. | structural formula | NMR | MS (M + H) | MS (M − H) |
|---|---|---|---|---|
| 199 | | ¹H-NMR (DMSO-D₆) δ: 0.88-0.98 (6H, m), 1.01 (6H, s), 1.55-1.61 (2H, m), 2.41 (2H, s), 2.65-2.70 (2H, m), 2.71-3.01 (4H, m), 3.16-3.25 (3H, m), 3.75-3.89 (2H, m), 6.59-6.65 (1H, m), 6.90-6.99 (1H, m), 7.29-7.35 (1H, m), 7.55-7.61 (1H, m), 11.45 (1H, br s), 12.53 (1H, br s). | 436 | 434 |
| 200 | | ¹H-NMR (DMSO-D₆) δ: 0.62-0.73 (4H, m), 1.01 (6H, s), 1.54-1.62 (2H, m), 1.87-1.95 (1H, m), 2.41 (2H, s), 2.65-2.71 (2H, m), 2.73-3.13 (3H, m), 3.16-3.26 (3H, m), 3.79-4.04 (2H, m), 6.57-6.64 (1H, m), 6.88-7.00 (1H, m), 7.26-7.36 (1H, m), 7.53-7.61 (1H, m), 11.44 (1H, br s), 12.5 (1H, br s). | 434 | 432 |
| 201 | | ¹H-NMR (DMSO-D₆) δ: 7.17 (3H, s), 7.42 (6H, s), 7.56 (3H, s), 7.95-8.02 (2H, m), 8.25-8.33 (1H, m), 8.55-8.64 (1H, m), 8.82 (2H, s), 9.05-9.12 (2H, m), 9.24-9.29 (1H, m), 9.61 (3H, s), 9.88-9.95 (1H, m), 10.16-10.23 (1H, m), 12.99-13.04 (1H, m), 13.25-13.32 (1H, m), 13.62-13.68 (1H, m), 13.95-13.99 (1H, m), 17.79 (1H, br s), 18.94 (1H, br s). | 421 | 419 |
TABLE 1-41
| Ex No. | structural formula | NMR | MS (M + H) | MS (M − H) |
|---|---|---|---|---|
| 202 | 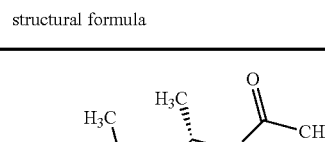 | ¹H-NMR (DMSO-D₆) δ: 0.82-1.04 (9H, m), 1.40-1.46 (2H, m), 1.62 (2H, s), 2.27 (2H, s), 2.49-2.67 (6H, m), 3.00-3.07 (3H, m), 4.31-4.83 (1H, m), 6.41-6.47 (1H, m), 6.70-6.77 (1H, m), 7.09-7.13 (1H, m), 7.34-7.43 (1H, m), 11.20-11.31 (1H, m), 12.35-12.41 (1H, m). | 422 | 420 |

TABLE 1-41-continued

| Ex No. | structural formula | NMR | MS (M + H) | MS (M − H) |
| --- | --- | --- | --- | --- |
| 203 | | ¹H-NMR (DMSO-D₆) δ: 0.72 (t, 2H, J = 7.4 Hz), 0.91 (t, 1H, J = 6.8 Hz), 1.01 (s, 6H), 1.04 (d, 2H, J = 7.1 Hz), 1.15 (d, 1H, J = 6.8 Hz), 1.58 (t, 3H, J = 6.3 Hz), 1.97-2.12 (m, 2H), 2.41 (s, 2H), 2.67 (s, 3H), 2.78 (s, 2H), 3.15-3.20 (m, 3H), 4.48-4.54 (m, 0.3H), 4.96-5.03 (m, 0.7H), 6.55-6.62 (m, 1H), 6.84-6.92 (m, 1H), 7.20-7.30 (m, 1H), 7.47-7.57 (m, 1H), 11.28-11.46 (m, 1H), 12.52 (br s, 1H). | 436 | 434 |
| 204 | | ¹H-NMR (DMSO-D₆) δ: 0.27-1.26 (1H, m), 1.01 (6H, s), 1.55-1.61 (2H, m), 2.41 (2H, s), 2.61-2.91 (5H, m), 3.14-3.21 (3H, m), 4.61-5.04 (1H, m), 6.55-6.61 (1H, m), 6.87-6.95 (1H, m), 7.22-7.32 (1H, m), 7.47-7.59 (1H, m), 11.32-11.47 (1H, m), 12.49-12.55 (1H, m). | 450 | 448 |
| 205 | | ¹H-NMR (DMSO-D₆) δ:- 0.21-1.75 (10H, m), 1.01 (6H, s), 2.41 (2H, s), 2.63-3.04 (5H, m), 3.13-3.23 (3H, m), 4.85-5.04 (1H, m), 6.54-6.60 (1H, m), 6.85-6.92 (1H, m), 7.21-7.31 (1H, m), 7.47-7.56 (1H, m), 11.31-11.41 (1H, m), 12.48-12.55 (1H, m). | 448 | 446 |
| 206 | | ¹H-NMR (DMSO-D₆) δ: 1.01 (s, 6H), 1.06 (t, 3H, J = 7.25 Hz), 1.58 (t, 2H, J = 6.45 Hz), 2.42 (s, 2H), 2.63-2.72 (m, 2H), 3.61-3.74 (m, 4H), 4.45 (t, 1H, J = 5.64 Hz), 6.61 (s, 1H), 6.83 (d, 1H, J = 7.86 Hz), 7.21 (s, 1H), 7.55 (d, 1H, J = 7.86 Hz), 11.41 (s, 1H), 12.55 (s, 1H). | 367 | 365 |

TABLE 1-42

| Ex. No. | structural formula | NMR | MS (M + H) | MS (M − H) |
|---|---|---|---|---|
| 207 | | ¹H-NMR(DMSO-D₆) δ: 1.01(s, 6H), 1.04(t, 3H, J = 7.05 Hz), 1.58(t, 2H, J = 6.45 Hz), 2.42(s, 2H), 2.67(s, 2H), 3.17(s, 3H), 3.62-3.72(m, 4H), 6.60(s, 1H), 6.84(d, 1H, J = 8.46 Hz), 7.21(s, 1H), 7.55(d, 1H, J = 8.46 Hz), 11.41(s, 1H), 12.54(s, 1H). | 381 | 379 |
| 208 | | ¹H-NMR(DMSO-D₆) δ: 1.01(s, 6H), 1.57(t, 2H, J = 6.45 Hz), 2.40(s, 2H), 2.65-2.67(br m, 2H), 4.09(t, 2H, J = 7.96 Hz), 4.43(t, 2H, J = 7.96 Hz), 6.53(s, 1H), 7.16(d, 1H, J = 8.87 Hz), 7.49(d, 1H, J = 8.87 Hz), 7.61(s, 1H), 11.24(s, 1H), 12.47 (s, 1H). | 351 | 349 |
| 209 | | ¹H-NMR(DMSO-D₆) δ: 0.89(t, 3H, J = 7.42 Hz), 1.01(s, 6H), 1.58(t, 2H, J = 6.25 Hz), 1.97(q, 2H, J = 7.42 Hz), 2.41(s, 2H), 2.63-2.71(m, 2H), 3.44-3.52(m, 2H), 3.69 (t, 2H, J = 6.36 Hz), 4.63 (t, 1H, J = 5.64 Hz), 6.59 (s, 1H), 6.86(d, 1H, J = 8.46 Hz), 7.24(s, 1H), 7.53(d, 1H, J = 8.46 Hz), 11.37(s, 1H), 12.52(s, 1H). | 381 | 379 |
| 210 | | ¹H-NMR(DMSO-D₆) δ: 1.00(s, 6H), 1.57(t, 2H, J = 6.25 Hz), 2.08(tt, 2H, J = 7.05, 7.05 Hz), 2.40(s, 2H), 2.46-2.51 (m, 2H), 2.59-2.72(m, 2H), 3.86(t, 2H, J = 7.05 Hz), 6.52(s, 1H), 7.20(d, 1H, J = 8.46 Hz), 7.46(d, 1H, J = 8.46 Hz), 7.69(s, 1H), 11.21(s, 1H), 12.47 (s, 1H). | 349 | 347 |

TABLE 1-42-continued
| Ex. No. | structural formula | NMR | MS (M + H) | MS (M − H) |
|---|---|---|---|---|
| 211 | 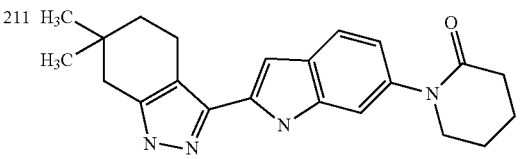 | ¹H-NMR(DMSO-D₆) δ: 1.01(s, 6H), 1.58(t, 2H, J = 6.25 Hz), 1.80-1.93 (m, 4H), 2.39(t, 2H, J = 6.25 Hz), 2.41(s, 2H), 2.62-2.71(m, 2H), 3.56-3.65(m, 2H), 6.55(s, 1H), 6.81(d, 1H, J = 8.46 Hz), 7.19(s, 1H), 7.46(d, 1H, J = 8.46 Hz), 11.30(s, 1H), 12.50(s, 1H). | 363 | 361 |
TABLE 1-43
| Ex. No. | structural formula | NMR | MS (M + H) | MS (M − H) |
|---|---|---|---|---|
| 212 | 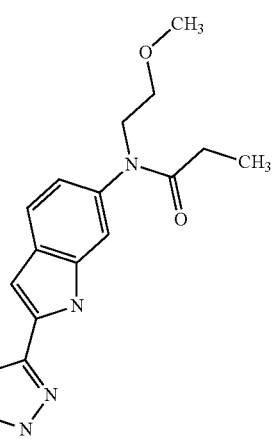 | ¹H-NMR(DMSO-D₆) δ: 0.89(t, 3H, J = 7.42 Hz), 1.01(s, 6H), 1.58 (t, 2H, J = 6.25 Hz), 1.97(q, 2H, J = 7.42 Hz), 2.41(s, 2H), 2.62-2.72(m, 2H), 3.21(s, 3H), 3.39(t, 2H, J = 6.04 Hz), 3.39(s, 2H), 3.79(t, 2H, J = 6.04 Hz), 6.60(s, 1H), 6.84 (d, 1H, J = 8.26 Hz), 7.24(s, 1H), 7.54(d, 1H, J = 8.26 Hz), 11.38 (s, 1H), 12.53(s, 1H). | 395 | 393 |
| 213 | 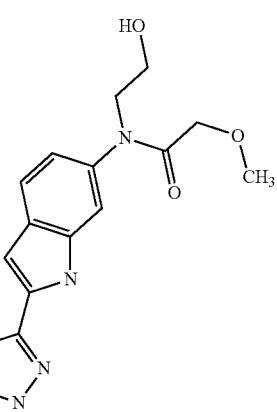 | ¹H-NMR(DMSO-D₆) δ: 1.01(s, 6H), 1.58(t, 2H, J = 6.18 Hz), 2.41(s, 2H), 2.63-2.70(m, 2H), 3.17(s, 3H), 3.48(q, 2H, J = 6.03 Hz), 3.64-3.74(m, 4H), 4.67(t, 1H, J = 5.62 Hz), 6.60 (s, 1H), 6.88(d, 1H, J = 8.16 Hz), 7.27(s, 1H), 7.53(d, 1H, J = 8.16 Hz), 11.41(s, 1H), 12.53 (s, 1H). | 397 | 395 |

TABLE 1-43-continued

| Ex. No. | structural formula | NMR | MS (M + H) | MS (M − H) |
|---|---|---|---|---|
| 214 | | ¹H-NMR(DMSO-D₆) δ: 1.01(s, 6H), 1.58(t, 2H, J = 6.03 Hz), 1.72(s, 3H), 2.41(s, 2H), 2.66 (t, 2H, J = 6.03 Hz), 3.47(td, 2H, J = 6.40, 6.00 Hz), 3.68(t, 2H, J = 6.61 Hz), 4.64(t, 1H, J = 5.68 Hz), 6.59(s, 1H), 6.88(d, 1H, J = 8.23 Hz), 7.25(s, 1H), 7.53(d, 1H, J = 8.23 Hz), 11.39(s, 1H), 12.53 (s, 1H). | 367 | 365 |
| 215 | | ¹H-NMR(DMSO-D₆) δ: 0.75-0.90(m, 2H), 0.98-1.14(m, 1H), 1.01(s, 6H), 1.29-1.42(m, 2H), 1.42-1.50(m, 1H), 1.51-1.65(m, 6H), 2.07-2.17 (m,1H), 2.11(s, 6H), 2.29(t, 2H, J = 7.05 Hz), 2.42(s, 2H), 2.64-2.72(m, 2H), 3.61-3.76 (m, 2H), 6.60(s, 1H), 6.84(d, 1H, J = 8.26 Hz), 7.24(s, 1H), 7.55(d, 1H, J = 8.26 Hz), 11.36(s, 1H), 12.54 (s, 1H). | 462 | 460 |
| 216 | | ¹H-NMR(DMSO-D₆) δ: 1.01(s, 6H), 1.38-1.48 (m, 2H), 1.54-1.73(m, 4H), 2.12(s, 6H), 2.29-2.31(m, 1H), 2.35-2.44 (m, 3H), 2.42(s, 2H), 2.63-2.74(m, 2H), 2.94 (t, 2H, J = 11.08 Hz), 3.64-3.78(m, 4H), 6.61 (s, 1H), 6.86(d, 1H, J = 8.06 Hz), 7.26(s, 1H), 7.56(d, 1H, J = 8.06 Hz), 11.37(s, 1H), 12.54 (s, 1H). | 464 | 462 |

TABLE 1-44

| Ex. No. | structural formula | NMR | MS (M + H) | MS (M − H) |
|---|---|---|---|---|
| 217 | | ¹H-NMR(DMSO-D₆) δ: 1.01(s, 6H), 1.58(t, 2H, J = 6.25 Hz), 1.66-1.78(m, 1H), 1.95-2.06(m, 1H), 2.15(s, 6H), 2.29-2.38(m, 2H), 2.41(s, 2H), 2.63-2.72(m, 2H), 2.79-2.86(m, 1H), 3.45-3.52(m, 1H), 3.53-3.64(m, 2H), 3.65-3.72(m, 1H), 3.71-3.82(br m, 1H), 6.61(s, 1H), 6.87(d, 1H, J = 8.26 Hz), 7.26(s, 1H), 7.56(d, 1H, J = 8.26 Hz), 11.40(s, 1H), 12.54(s, 1H). | 450 | 448 |
| 218 | | ¹H-NMR(DMSO-D₆) δ: 0.75-0.91(m, 1H), 0.86(t, 3H, J = 7.15 Hz), 1.01(s, 6H), 1.02-1.13(m, 1H), 1.20-1.50(m, 4H), 1.51-1.65(m, 8H), 2.07(s, 6H), 2.09-2.17(m, 1H), 2.20(t, 2H, J = 7.15 Hz), 2.42(s, 2H), 2.62-2.73(m, 2H), 3.53-3.66(m, 2H), 6.61(s, 1H), 6.83(d, 1H, J = 7.86 Hz), 7.22(s, 1H), 7.56(d, 1H, J = 7.86 Hz), 11.35(s, 1H), 12.54(s, 1H). | 476 | 44 |
| 219 | | ¹H-NMR(DMSO-D₆) δ: 0.62-0.76(m, 2H), 1.01(s, 7H), 1.08-1.22(m, 2H), 1.48-1.62(m, 7H), 1.62-1.74(m, 1H), 1.84(d, 2H, J = 6.85 Hz), 2.12(s, 6H), 2.30(t, 2H, J = 7.05 Hz), 2.42(s, 2H), 2.63-2.73(m, 2H), 3.67-3.78(m, 2H), 6.59(s, 1H), 6.81(d, 1H, J = 8.06 Hz), 7.21(s, 1H), 7.53(d, 1H, J = 8.06 Hz), 11.38(s, 1H), 12.53(s, 1H). | 476 | 474 |

TABLE 1-44-continued

| Ex. No. | structural formula | NMR | MS (M + H) | MS (M − H) |
|---|---|---|---|---|
| 220 | | ¹H-NMR(DMSO-D₆) δ: 1.01(s, 6H), 1.53-1.79 (m, 4H), 1.81-1.93(m, 2H), 2.13(s, 6H), 2.30 (t, 2H, J = 7.05 Hz), 2.42(s, 2H), 2.66(t, 2H, J = 6.04 Hz), 3.62 (td, 1H, J = 7.45, 4.30 Hz), 3.65-3.77(m, 2H), 3.81(q, 1H, J = 7.25 Hz), 4.11(dd, 1H, J = 7.25, 5.64 Hz), 6.60(s, 1H), 6.86(d, 1H, J = 8.26 Hz), 7.26 (s, 1H), 7.54(d, 1H, J = 8.26 Hz), 11.41(s, 1H), 12.54(s, 1H). | 450 | 448 |

TABLE 1-45

| Ex. No. | structural formula | NMR | MS (M + H) | MS (M − H) |
|---|---|---|---|---|
| 221 | | ¹H-NMR(DMSO-D₆) δ: 0.89-1.07(2H, m), 1.01(6H, s), 1.48(2H, d, J = 12.89 Hz), 1.57-1.59(2H, m), 1.89-1.92(3H, m), 2.15 (6H, s), 2.34(2H, s), 2.42(2H, s), 2.67(2H, s), 3.14-3.39(2H, m), 3.73(4H, d, J = 10.07 Hz), 3.92-4.07(0H, m), 6.61(1H, s), 6.83 (1H, d, J = 7.66 Hz), 7.23(1H, s), 7.55(1H, d, J = 7.66 Hz), 11.38 (1H, s), 12.53(1H, s). | 478 | 476 |
| 222 | | ¹H-NMR(DMSO-D₆) δ: 1.01(6H, s), 1.58(2H, t, J = 6.25 Hz), 2.14 (6H, s), 2.30(2H, t, J = 6.85 Hz), 2.42(2H, s), 2.67(2H, t, J = 5.84 Hz), 3.17(3H, s), 3.67 (2H, s), 3.72(2H, t, J = 6.65 Hz), 6.60(1H, s), 6.86(1H, d, J = 8.46 Hz), 7.26(1H, s), 7.54 (1H, d, J = 8.46 Hz), 11.42(1H, s), 12.54 (1H, s). | 424 | 422 |

TABLE 1-45-continued

| Ex. No. | structural formula | NMR | MS (M + H) | MS (M − H) |
|---|---|---|---|---|
| 223 | | ¹H-NMR(DMSO-D₆) δ: 1.00(6H, s), 1.41-1.44 (2H, m), 1.54-1.69 (6H, m), 2.07(6H, s), 2.20(2H, t, J = 7.07 Hz), 2.36-2.43(2H, m), 2.52-2.70(3H, m), 2.94(2H, t, J = 11.02 Hz), 3.62(2H, t, J = 7.30 Hz), 3.72(2H, dd, J = 11.36, 2.78 Hz), 6.61(1H, s), 6.85(1H, d, J = 8.12 Hz), 7.23 (1H, s), 7.56(1H, d, J = 8.12 Hz), 11.35(1H, s), 12.54(1H, s). | 478 | 476 |
| 224 | | ¹H-NMR(DMSO-D₆) δ: 1.00(6H, s), 1.56-1.75 (6H, m), 1.83-1.92 (2H, m), 2.10(6H, s), 2.24(2H, t, J = 6.96 Hz), 2.41(2H, s), 2.66 (2H, s), 3.56-3.70(3H, m), 3.81(1H, q, J = 7.19 Hz), 4.12(1H, dd, J = 7.54, 5.68 Hz), 6.60(1H, s), 6.85(1H, d, J = 8.35 Hz), 7.23 (1H, s), 7.55(1H, d, J = 8.35 Hz), 11.40(1H, s), 12.53(1H, s). | 464 | 462 |

TABLE 1-46

| Ex. No. | structural formula | NMR | MS (M + H) | MS (M − H) |
|---|---|---|---|---|
| 225 | | ¹H-NMR(DMSO-D₆) δ: 1.01(6H, s), 1.56-1.64 (4H, m), 1.71-1.75 (1H, m), 1.98-2.03 (1H, m), 2.08(6H, s), 2.22(2H, t, J = 7.05 Hz), 2.41(2H, s), 2.54-2.69(3H, m), 2.79-2.87(1H, m), 3.46-3.72(6H, m), 6.62 (1H, s), 6.85(1H, d, J = 8.06 Hz), 7.23(1H, s), 7.57(1H, d, J = 8.06 Hz), 11.37(1H, s), 12.53(1H, s). | 464 | 462 |
| 226 | | ¹H-NMR(DMSO-D₆) δ: 0.94-1.03(2H, m), 1.01(6H, s), 1.48(2H, d, J = 11.69 Hz), 1.56-1.64(4H, m), 1.91-1.92(1H, m), 1.91 (2H, s), 2.10(6H, s), 2.23(2H, t, J = 7.05 Hz), 2.42(2H, s), 2.65-2.69(2H, m), 3.20-3.26(2H, m), 3.63-3.74(4H, m), 6.61 (1H, s), 6.81(1H, d, J = 8.46 Hz), 7.20(1H, s), 7.56(1H, d, J = 8.46 Hz), 11.37(1H, s), 12.53(1H, s). | 492 | 40 |
| 227 | | ¹H-NMR(DMSO-D₆) δ: 1.00(6H, s), 1.57(2H, t, J = 6.29 Hz), 1.87 (1H, dd, J = 12.24, 9.15 Hz), 2.36-2.47 (1H, m), 2.40(2H, s), 2.65-2.67(2H, m), 3.74-3.78(2H, m), 4.25-4.34(1H, m), 5.68(1H, d, J = 5.73 Hz), 6.53(1H, s), 7.23 (1H, d, J = 8.38 Hz), 7.48(1H, d, J = 8.38 Hz), 7.74(1H, s), 11.22(1H, s), 12.46 (1H, s). | 365 | 363 |

TABLE 1-46-continued

| Ex. No. | structural formula | NMR | MS (M + H) | MS (M − H) |
|---|---|---|---|---|
| 228 | | ¹H-NMR(DMSO-D₆) δ: 1.00(6H, s), 1.57(2H, t, J = 6.29 Hz), 2.02-2.21(2H, m), 2.40 (2H, s), 2.62-2.73(3H, m), 3.63-3.75(2H, m), 3.76-3.88(2H, m), 4.77(1H, t, J = 5.18 Hz), 6.52(1H, s), 7.21 (1H, d, J = 8.38 Hz), 7.45(1H, d, J = 8.38 Hz), 7.70(1H, s), 11.21(1H, s), 12.46 (1H, s). | 379 | 377 |

TABLE 1-47

| Ex. No. | structural formula | NMR | MS (M + H) | MS (M − H) |
|---|---|---|---|---|
| 229 | | ¹H-NMR(DMSO-D₆) δ: 1.00(6H, s), 1.17(3H, d, J = 7.19 Hz), 1.57(2H, t, J = 6.38 Hz), 1.65-1.75 (1H, m), 2.29-2.35(1H, m), 2.40(2H, s), 2.57-2.70(3H, m), 3.77-3.82 (2H, m), 6.52(1H, s), 7.21(1H, d, J = 8.35 Hz), 7.46(1H, d, J = 8.35 Hz), 7.70(1H, s), 11.21(1H, s), 12.46(1H, s). | 363 | 61 |
| 230 | | ¹H-NMR(DMSO-D₆) δ: 1.00(6H, s), 1.06(3H, s), 1.57(2H, t, J = 6.29 Hz), 1.78-1.85(1H, m), 2.30-2.36(1H, m), 2.40 (2H, s), 2.66(2H, s), 3.27-3.30(1H, m), 3.58 (1H, dd, J = 10.26, 5.40 Hz), 3.78(2H, t, J = 7.17 Hz), 4.91(1H, t, J = 5.40 Hz), 6.52(1H, s), 7.23 (1H, d, J = 8.38 Hz), 7.46(1H, d, J = 8.38 Hz), 7.71(1H, s), 11.21 (1H, s), 12.46(1H, s). | 393 | 391 |

TABLE 1-47-continued
| Ex. No. | structural formula | NMR | MS (M + H) | MS (M − H) |
|---|---|---|---|---|
| 231 | 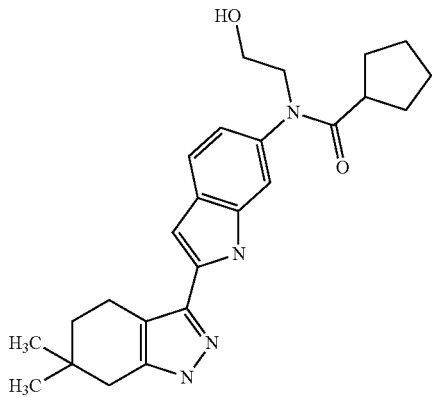 | $^1$H-NMR(DMSO-D$_6$) δ: 1.01(6H, s), 1.24-1.40 (2H, m), 1.48-1.67(8H, m), 2.41(2H, s), 2.49-2.55(1H, m), 2.66-2.69 (2H, m), 3.44-3.51(2H, m), 3.66-3.72(2H, m), 4.59(1H, t, J = 5.64 Hz), 6.60(1H, s), 6.86(1H, d, J = 8.06 Hz), 7.25(1H, s), 7.53(1H, d, J = 8.06 Hz), 11.31(1H, s), 12.50 (1H, s). | 421 | 419 |
| 232 | 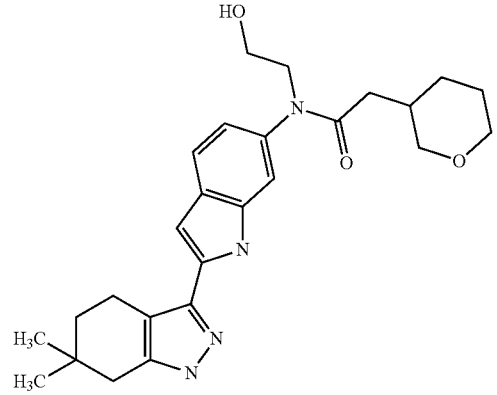 | $^1$H-NMR(DMSO-D$_6$) δ: 0.92-1.01(2H, m), 1.01 (6H, s), 1.47-1.50(2H, m), 1.55-1.60(2H, m), 1.88-1.95(1H, m), 1.92 (2H, s), 2.42(2H, s), 2.66-2.68(2H, m), 3.19-3.26(2H, m), 3.44-3.51 (2H, m), 3.68-3.74(4H, m), 4.62(1H, t, J = 5.44 Hz), 6.60(1H, s), 6.84 (1H, d, J = 8.46 Hz), 7.22(1H, s), 7.54(1H, d, J = 8.46 Hz), 11.38(1H, s), 12.53(1H, s). | 451 | 449 |
| 233 | 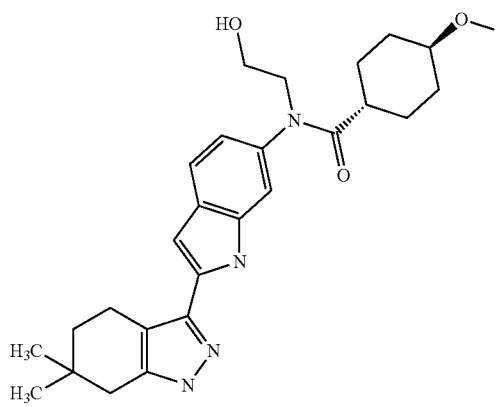 | $^1$H-NMR(DMSO-D$_6$) δ: 0.61-0.72(2H, m), 1.01 (6H, s), 1.37-1.49(2H, m), 1.55-1.70(4H, m), 1.84-1.93(2H, m), 2.02-2.14(1H, m), 2.41(2H, s), 2.64-2.73(2H, m), 2.95-3.04(1H, m), 3.13 (3H, s), 3.41-3.49(2H, m), 3.63-3.70(2H, m), 4.58(1H, t, J = 5.24 Hz), 6.60(1H, s), 6.86(1H, d, J = 8.06 Hz), 7.25(1H, s), 7.54(1H, d, J = 8.06 Hz), 11.32(1H, s), 12.51 (1H, s). | 465 | 463 |

TABLE 1-48

| Ex. No. | structural formula | NMR | MS (M + H) | MS (M − H) |
|---|---|---|---|---|
| 234 | | ¹H-NMR(DMSO-D₆) δ: 0.64-0.77(2H, m), 1.01 (6H, s), 1.35-1.47(2H, m), 1.54-1.65(4H, m), 1.67-1.77(2H, m), 1.98-2.10(1H, m), 2.42(2H, s), 2.63-2.75(2H, m), 2.68(2H, s), 3.17-3.29 (1H, m), 3.41-3.50(2H, m), 3.61-3.73(0H, m), 4.31(1H, d, J = 4.84 Hz), 4.57(1H, t, J = 5.44 Hz), 6.60(1H, s), 6.85 (1H, d, J = 8.06 Hz), 7.25(1H, s), 7.54(1H, d, J = 8.06 Hz), 11.32(1H, s), 12.50(1H, s). | 451 | 449 |
| 235 | | ¹H-NMR(DMSO-D₆) δ: 0.63-0.75(2H, m), 0.94-1.07(1H, m), 1.01(6H, s), 1.07-1.21(2H, m), 1.50-1.63(7H, m), 1.64-1.77(1H, m), 1.86(2H, d, J = 6.85 Hz), 2.42 (2H, s), 2.64-2.71(2H, m), 3.46-3.50(2H, m), 3.67-3.71(2H, m), 4.58 (1H, t, J = 5.44 Hz), 6.59 (1H, s), 6.82(1H, d, J = 8.06 Hz), 7.21(1H, s), 7.53(1H, d, J = 8.06 Hz), 11.33(1H, s), 12.50 (1H, s). | 449 | 447 |
| 236 | | ¹H-NMR(DMSO-D₆) δ: 1.01(6H, s), 1.42-1.45 (2H, m), 1.57-1.70 (4H, m), 2.37-2.46 (1H, m), 2.42(2H, s), 2.66-2.69(2H, m), 2.92-2.98(2H, m), 3.45-3.49(2H, m), 3.67-3.74(4H, m), 4.59(1H, t, J = 5.64 Hz), 6.60(1H, s), 6.88 (1H, d, J = 8.06 Hz), 7.27(1H, s), 7.54(1H, d, J = 8.06 Hz), 11.32 (1H, s), 12.50(1H, s). | 437 | 435 |

TABLE 1-48-continued
| Ex. No. | structural formula | NMR | MS (M + H) | MS (M − H) |
|---|---|---|---|---|
| 237 | 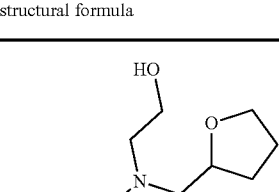 | ¹H-NMR(DMSO-D₆) δ: 1.01(6H, s), 1.56-1.75 (4H, m), 1.82-1.94 (2H, m), 2.41(2H, s), 2.62-2.72(2H, m), 3.42-3.55(2H, m), 3.57-3.74(3H, m), 3.81(1H, q, J = 7.12 Hz), 4.14(1H, dd, J = 7.25, 5.64 Hz), 4.63 (1H, t, J = 5.64 Hz), 6.59(1H, s), 6.88(1H, d, J = 8.06 Hz), 7.27 (1H, s), 7.53(1H, d, J = 8.06 Hz), 11.36(1H, s), 12.50(1H, s). | 423 | 421 |
TABLE 1-49
| Ex. No. | structural formula | NMR | MS (M + H) | MS (M − H) |
|---|---|---|---|---|
| 238 | 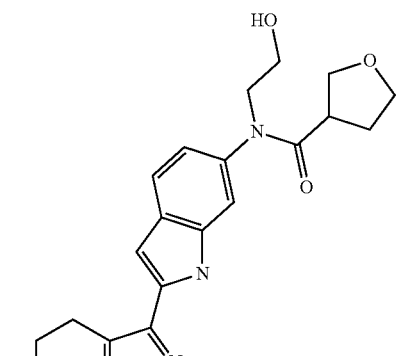 | ¹H-NMR(DMSO-D₆) δ: 1.01(6H, s), 1.54-1.62 (2H, m), 1.68-1.77 (1H, m), 1.97-2.06 (1H, m), 2.42(2H, s), 2.61-2.71(2H, m), 2.80-2.88(1H, m), 3.45-3.76(8H, m), 4.61(1H, t, J = 5.44 Hz), 6.60(1H, s), 6.88 (1H, d, J = 8.06 Hz), 7.26(1H, s), 7.55(1H, d, J = 8.06 Hz), 11.35 (1H, s), 12.50(1H, s). | 423 | 421 |
| 239 | 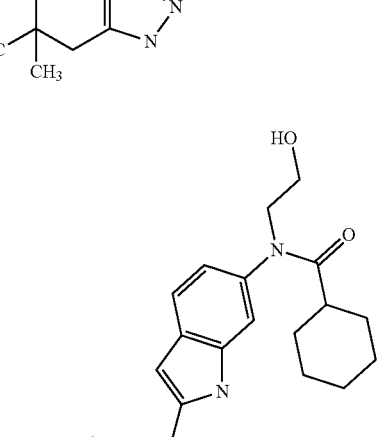 | ¹H-NMR(DMSO-D₆) δ: 0.75-0.90(2H, m), 0.98-1.12(1H, m), 1.01(6H, s), 1.31-1.47 (3H, m), 1.52-1.63 (6H, m), 2.08-2.19 (1H, m), 2.41(2H, s), 2.63-2.71(2H, m), 3.41-3.50(3H, m), 3.62-3.73(2H, m), 4.60(1H, t, J = 5.62 Hz), 6.60(1H, s), 6.85 (1H, d, J = 8.16 Hz), 7.24(1H, s), 7.54(1H, d, J = 8.16 Hz), 11.34 (1H, s), 12.52(1H, s). | 435 | 433 |

TABLE 1-49-continued
| Ex. No. | structural formula | NMR | MS (M + H) | MS (M − H) |
|---|---|---|---|---|
| 240 | 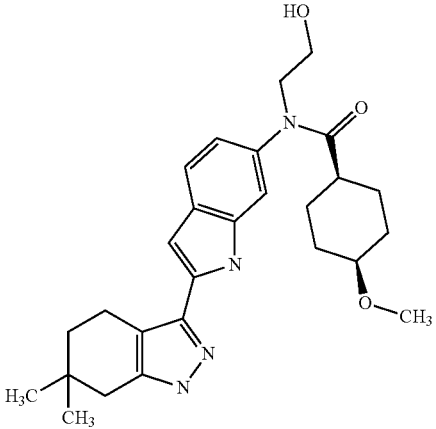 | ¹H-NMR(DMSO-D₆) δ: 0.92-1.02(2H, m), 1.01(6H, s), 1.27-1.38 (2H, m), 1.54-1.79 (6H, m), 2.11-2.23 (1H, m), 2.41(2H, s), 2.65-2.71(2H, m), 3.18-3.23(1H, m), 3.43-3.48(2H, m), 3.64-3.67(2H, m), 4.60(1H, t, J = 5.62 Hz), 6.60(1H, s), 6.86 (1H, d, J = 8.16 Hz), 7.25(1H, s), 7.54(1H, d, J = 8.16 Hz), 8.31 (0H, s), 11.34(1H, s), 12.52(1H, s). | 465 | 463 |
| 241 | 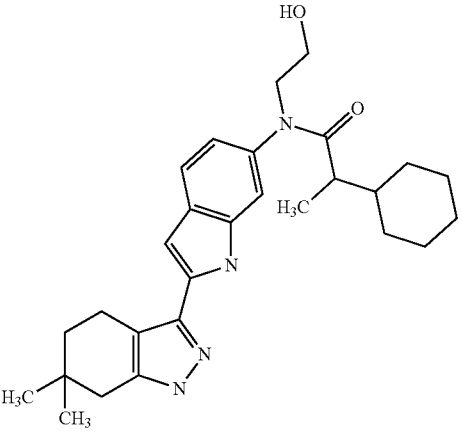 | ¹H-NMR(DMSO-D₆) δ: 0.43-0.62(1H, m), 0.67-0.90(1H, m), 0.90(3H, d, J = 6.62 Hz), 1.01(6H, s), 1.05-1.19(2H, m), 1.35-1.44(1H, m), 1.50-1.68(6H, m), 1.94-2.07(1H, m), 2.41 (2H, s), 2.63-2.71(2H, m), 3.43-3.53(2H, m), 3.56-3.81(2H, m), 4.61(1H, t, J = 5.51 Hz), 6.59(1H, s), 6.82 (1H, d, J = 7.94 Hz), 7.23(1H, s), 7.54(1H, d, J = 7.94 Hz), 11.34 (1H, s), 12.52(1H, s). | 463 | 461 |
TABLE 1-50
| Ex. No. | structural formula | NMR | MS (M + H) | MS (M − H) |
|---|---|---|---|---|
| 242 | 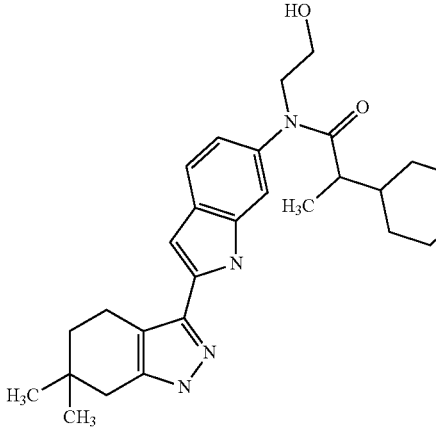 | ¹H-NMR(DMSO-D₆) δ: 0.74-1.20(2H, m), 0.91(3H, d, J = 6.62 Hz), 1.01(6H, s), 1.42-1.71(5H, m), 1.99-2.10(1H, m), 2.41 (2H, s), 2.64-2.71(2H, m), 3.16-3.23(2H, m), 3.43-3.84(6H, m), 4.62(1H, t, J = 5.40 Hz), 6.60(1H, s), 6.84 (1H, d, J = 7.94 Hz), 7.24(1H, s), 7.55(1H, d, J = 7.94 Hz), 11.35 (1H, s), 12.52(1H, s). | 465 | 463 |

TABLE 1-50-continued

| Ex. No. | structural formula | NMR | MS (M + H) | MS (M − H) |
|---|---|---|---|---|
| 243 | | ¹H-NMR(DMSO-D₆) δ: 1.01(6H, s), 1.35(3H, s), 1.54-1.60(2H, m), 2.01-2.07(1H, m), 2.28-2.35(1H, m), 2.41(2H, s), 2.62-2.70 (2H, m), 3.25(3H, s), 3.72-3.86(2H, m), 6.54(1H, s), 7.22(1H, d, J = 8.38 Hz), 7.49 (1H, d, J = 8.38 Hz), 7.74(1H, s), 11.25 (1H, s), 12.47(1H, s). | 393 | 391 |
| 244 | | ¹H-NMR(DMSO-D₆) δ: 1.01(6H, s), 1.30(3H, s), 1.57(2H, t, J = 6.40 Hz), 2.09(2H, t, J = 6.84 Hz), 2.41(2H, s), 2.62-2.70(2H, m), 3.67-3.85(2H, m), 5.45(1H, s), 6.53(1H, s), 7.23(1H, d, J = 8.38 Hz), 7.48(1H, d, J = 8.38 Hz), 7.74(1H, s), 11.24(1H, s), 12.46 (1H, s). | 379 | 377 |
| 245 | stereoisomer of Ex. No. 246 | ¹H-NMR(DMSO-D₆) δ: 1.01(6H, s), 1.04-1.20 (1H, m), 1.30-1.51 (1H, m), 1.58(2H, t, J = 6.45 Hz), 1.64-1.74 (2H, m), 2.42(2H, s), 2.50-2.57(1H, m), 2.64-2.70(2H, m), 2.90-2.96(1H, m), 3.03-3.14(1H, m), 3.36-3.59(3H, m), 3.62-3.79(4H, m), 4.66-4.71(2H, m), 6.60(1H, s), 6.87(1H, d, J = 8.06 Hz), 7.27 (1H, s), 7.54(1H, d, J = 8.06 Hz), 11.42(1H, s), 12.53(1H, s). | 467 | 465 |

TABLE 1-51
| Ex. No. | structural formula | NMR | MS (M + H) | MS (M − H) |
|---|---|---|---|---|
| 246 | 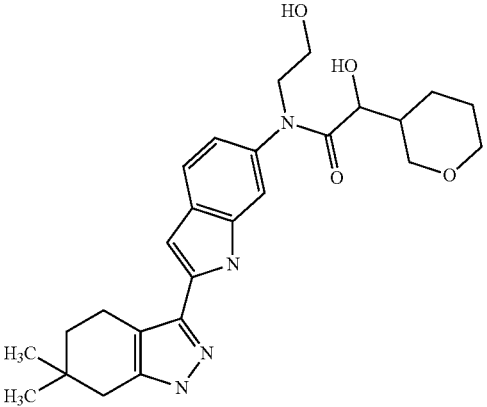 stereoisomer of Ex. No. 245 | ¹H-NMR(DMSO-D₆) δ: 0.98-1.16(2H, m), 1.00 (6H, s), 1.28-1.53(2H, m), 1.57(2H, t, J = 6.25 Hz), 1.73-1.83(1H, m), 2.41(2H, s), 2.63-2.70 (2H, m), 2.95-3.00(1H, m), 3.07-3.14(1H, m), 3.44-3.78(7H, m), 4.66 (1H, t, J = 5.44 Hz), 4.91(1H, d, J = 8.06 Hz), 6.60(1H, s), 6.87 (1H, d, J = 8.06 Hz), 7.27(1H, s), 7.53(1H, d, J = 8.06 Hz), 11.40 (1H, s), 12.52(1H, s). | 467 | 65 |
| 247 | 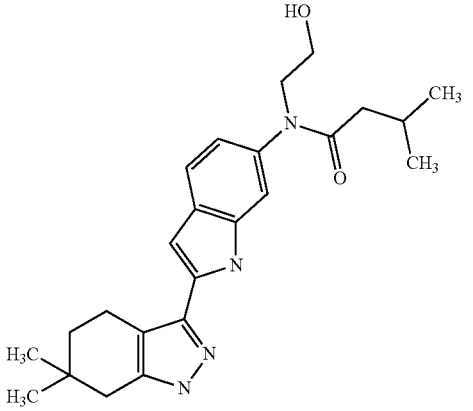 | ¹H-NMR(DMSO-D₆) δ: 0.76(6H, d, J = 6.85 Hz), 1.01(6H, s), 1.58 (2H, t, J = 6.25 Hz), 1.87(2H, d, J = 6.85 Hz), 1.95-1.99(1H, m), 2.41(2H, s), 2.63-2.70 (2H, m), 3.45-3.51(2H, m), 3.67-3.72(2H, m), 4.54-4.68(1H, m), 6.60 (1H, s), 6.83(1H, d, J = 8.46 Hz), 7.22(1H, s), 7.53(1H, d, J = 8.46 Hz), 11.36(1H, s), 12.52 (1H, s). | 409 | 407 |
| 248 | 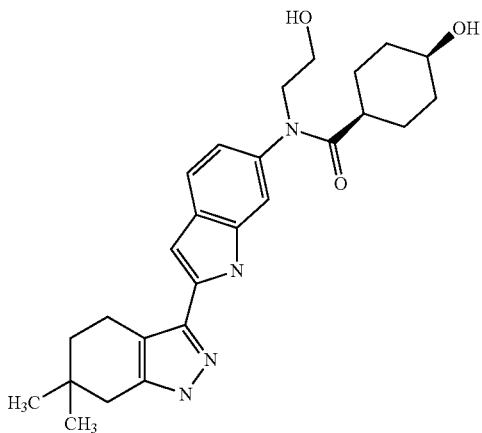 | ¹H-NMR(DMSO-D₆) δ: 0.94-1.08(1H, m), 1.01(6H, s), 1.21-1.33 (3H, m), 1.49-1.61 (4H, m), 1.73-1.85 (2H, m), 2.09-2.18 (1H, m), 2.41(2H, s), 2.64-2.71(2H, m), 3.46(2H, t, J = 6.65 Hz), 3.56-3.73(3H, m), 6.61(1H, s), 6.86(1H, dd, J = 8.46, 1.81 Hz), 7.25(1H, s), 7.54(1H, d, J = 8.46 Hz), 11.32 (1H, s), 12.52(1H, s). | 451 | 449 |

TABLE 1-51-continued
| Ex. No. | structural formula | NMR | MS (M + H) | MS (M − H) |
|---|---|---|---|---|
| 249 | 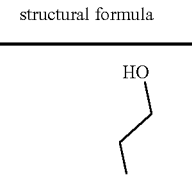 | ¹H-NMR(DMSO-D₆) δ: 0.92-1.01(2H, m), 1.01(6H, s), 1.47-1.50 (2H, m), 1.55-1.60 (2H, m), 1.88-1.95 (1H, m), 1.92(2H, s), 2.42(2H, s), 2.66-2.68 (2H, m), 3.19-3.26 (2H, m), 3.44-3.51 (2H, m), 3.68-3.74 (4H, m), 4.62(1H, t, J = 5.44 Hz), 6.60(1H, s), 6.84(1H, d, J = 8.46 Hz), 7.22(1H, s), 7.54(1H, d, J = 8.46 Hz), 11.38(1H, s), 12.53(1H, s). | 451 | 449 |
TABLE 1-52
| Ex. No. | structural formula | NMR | MS (M + H) | MS (M − H) |
|---|---|---|---|---|
| 250 |  | ¹H-NMR(DMSO-D₆) δ: 1.00(6H, s), 1.07-1.32 (5H, m), 1.49-1.95 (9H, m), 2.05-2.14 (1H, m), 2.40(2H, s), 2.50-2.58(1H, m), 2.65(2H, s), 3.66-3.86 (2H, m), 6.52(1H, s), 7.18(1H, d, J = 8.12 Hz), 7.45(1H, d, J = 8.12 Hz), 7.68(1H, s), 11.19(1H, s), 12.46 (1H, s). | 431 | 429 |
| 251 |  | ¹H-NMR(DMSO-D₆) δ: 0.80-1.78(14H, m), 1.00(6H, s), 1.99-2.17 (1H, m), 2.40(2H, s), 2.59-2.70(2H, m), 3.46-3.82(4H, m), 4.79(1H, s), 6.52(1H, s), 7.20(1H, d, J = 8.35 Hz), 7.45(1H, d, J = 8.35 Hz), 7.70(1H, s), 11.19(1H, s), 12.46 (1H, s). | 461 | 459 |

TABLE 1-52-continued

| Ex. No. | structural formula | NMR | MS (M + H) | MS (M − H) |
|---|---|---|---|---|
| 252 | | ¹H-NMR(DMSO-D₆) δ: 1.01(6H, s), 1.01(3H, d, J = 6.72 Hz), 1.58 (2H, t, J = 6.25 Hz), 2.18-2.30(2H, m), 2.39-2.48(2H, m), 2.41(2H, s), 2.62-2.71 (2H, m), 3.13(1H, q, J = 6.72 Hz), 3.46-3.52 (6H, m), 3.59-3.78 (2H, m), 4.61(1H, t, J = 5.44 Hz), 6.59(1H, s), 6.89(1H, s), 7.29 (1H, s), 7.52(1H, d, J = 8.06 Hz), 11.33(1H, s), 12.50(1H, s). | 466 | 464 |
| 253 | | ¹H-NMR(DMSO-D₆) δ: 1.01(6H, s), 1.58(2H, t, J = 6.06 Hz), 1.67 (4H, s), 2.12-2.21(2H, m), 2.42(2H, s), 2.63-2.73(2H, m), 3.17-3.25(2H, m), 3.44-3.52(2H, m), 3.69 (2H, t, J = 6.51 Hz), 3.73(2H, s), 4.65(1H, t, J = 5.73 Hz), 6.60 (1H, s), 6.92(1H, d, J = 7.94 Hz), 7.31(1H, s), 7.55(1H, d, J = 7.94 Hz), 11.43(1H, s), 12.53(1H, s). | 464 | 462 |
| 254 | | ¹H-NMR(DMSO-D₆) δ: 1.01(6H, s), 1.58(2H, t, J = 6.25 Hz), 2.27-2.35(3H, m), 2.41 (2H, s), 2.67(3H, t, J = 6.25 Hz), 2.83(2H, s), 3.28(2H, s), 3.44-3.52 (4H, m), 3.68(2H, t, J = 6.45 Hz), 4.61(1H, t, J = 5.64 Hz), 6.60(1H, s), 6.88(1H, d, J = 8.06 Hz), 7.29(1H, s), 7.53(1H, d, J = 8.06 Hz), 11.33(1H, s), 12.43(1H, s). | 452 | 450 |

TABLE 1-53

| Ex. No. | structural formula | NMR | MS (M + H) | MS (M − H) |
|---|---|---|---|---|
| 255 | | $^1$H-NMR(DMSO-D$_6$) δ: 1.01(6H, s), 1.02(3H, d, J = 6.45 Hz), 1.58 (2H, t, J = 6.25 Hz), 2.22-2.31(2H, m), 2.39-2.48(4H, m), 2.64-2.71(2H, m), 3.13(1H, q, J = 6.45 Hz), 3.42-3.56(6H, m), 3.60-3.79(2H, m), 4.62(1H, t, J = 5.44 Hz), 6.60(1H, s), 6.88 (1H, d, J = 8.46 Hz), 7.31(1H, s), 7.53(1H, d, J = 8.46 Hz), 11.32 (1H, s), 12.50(1H, s). | 466 | 464 |
| 256 | | $^1$H-NMR(DMSO-D$_6$) δ: 1.01(6H, s), 1.43-1.68 (8H, m), 2.31-2.45 (4H, m), 2.64-2.72 (2H, m), 3.31(2H, s), 3.43-3.51(2H, m), 3.68(2H, t, J = 6.51 Hz), 3.78(2H, s), 4.64 (1H, t, J = 5.40 Hz), 6.61(1H, s), 6.92(1H, d, J = 7.72 Hz), 7.32 (1H, s), 7.56(1H, d, J = 7.72 Hz), 11.42(1H, s), 12.52(1H, s). | 478 | 476 |
| 257 | | $^1$H-NMR(DMSO-D$_6$) δ: 1.01(6H, s), 1.01(3H, d, J = 7.06 Hz), 1.43-1.54(2H, m), 1.58 (1H, t, J = 6.29 Hz), 2.10-2.19(1H, m), 2.24-2.35(1H, m), 2.42(2H, s), 2.64-2.70 (2H, m), 3.23-3.30 (2H, m), 3.44-3.51 (2H, m), 3.64-3.73 (4H, m), 4.66(1H, t, J = 5.62 Hz), 6.61(1H, s), 6.92(1H, d, J = 8.38 Hz), 7.32(1H, s), 7.57(1H, d, J = 8.38 Hz), 11.45(1H, s), 12.53(1H, s). | 464 | 462 |

TABLE 1-53-continued
| Ex. No. | structural formula | NMR | MS (M + H) | MS (M − H) |
|---|---|---|---|---|
| 258 | | ¹H-NMR(DMSO-D₆) δ: 0.96-1.07(13H, m), 1.22-1.32(2H, m), 1.49-1.61(4H, m), 1.74-1.87(2H, m), 2.06-2.19(1H, m), 2.41(2H, s), 2.64-2.71 (2H, m), 3.58-3.68 (3H, m), 4.21(1H, s), 6.60(1H, s), 6.82(1H, d, J = 8.60 Hz), 7.20 (1H, s), 7.55(1H, d, J = 8.60 Hz), 11.33(1H, s), 12.52(1H, s). | 435 | 433 |
TABLE 1-54
| Ex. No. | structural formula | NMR | MS (M + H) | MS (M − H) |
|---|---|---|---|---|
| 259 | | ¹H-NMR (DMSO-D₆) δ: 0.95-1.07 (8H, m), 1.23-1.32 (2H, m), 1.48-1.62 (4H, m), 1.72-1.87 (2H, m), 2.09-2.20 (1H, m), 2.41 (2H, s), 2.62-2.72 (2H, m), 3.21 (3H, s), 3.38 (2H, t, J = 6.18 Hz), 3.59-3.65 (1H, m), 3.71-3.82 (2H, m), 4.21 (1H, d, J = 2.87 Hz), 6.61 (1H, s), 6.84 (1H, d, J = 8.38 Hz), 7.25 (1H, s), 7.54 (1H, d, J = 8.38 Hz), 11.34 (1H, s), 12.53 (1H, s). | 465 | 463 |
| 260 | | ¹H-NMR (DMSO-D₆) δ: 1.01 (6H, s), 1.05 (3H, t, J = 7.25 Hz), 1.24 (3H, d, J = 6.85 Hz), 1.58 (2H, t, J = 6.45 Hz), 2.42 (2H, s), 2.64-2.71 (2H, m), 3.16-3.23 (1H, m), 3.44-3.53 (1H, m), 3.63-3.84 (5H, m), 3.84-3.92 (1H, m), 4.08 (1H, q, J = 6.85 Hz), 6.61 (1H, s), 6.88 (1H, d, J = 7.66 Hz), 7.28 (1H, s), 7.58 (1H, d, J = 8.06 Hz), 11.41 (1H, s), 12.51 (1H, s). | 464 | 462 |
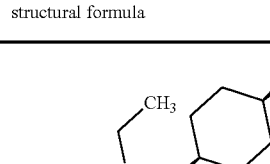

TABLE 1-54-continued

| Ex. No. | structural formula | NMR | MS (M + H) | MS (M − H) |
|---|---|---|---|---|
| 261 | | ¹H-NMR (DMSO-D₆) δ: 1.01 (6H, s), 1.02-1.09 (6H, m), 1.58 (2H, t, J = 6.25 Hz), 2.41 (2H, s), 2.64-2.72 (2H, m), 3.42-3.73 (5H, m), 3.78 (1H, dd, J = 11.48, 3.43 Hz), 4.00 (2H, dd, J = 18.54, 16.52 Hz), 4.08 (1H, d, J = 16.52 Hz), 6.62 (1H, s), 6.92 (1H, d, J = 8.46 Hz), 7.31 (1H, s), 7.59 (1H, d, J = 8.46 Hz), 11.40 (1H, s), 12.51 (1H, s). | 464 | 462 |
| 262 | | ¹H-NMR (DMSO-D₆) δ: 1.01 (6H, s), 1.07 (3H, d, J = 6.45 Hz), 1.58 (2H, t, J = 6.45 Hz), 2.41 (2H, s), 2.65-2.71 (2H, m), 3.22 (3H, s), 3.41 (2H, t, J = 6.04 Hz), 3.44-3.53 (2H, m), 3.57 (1H, dd, J = 11.48, 3.83 Hz), 3.75-3.84 (3H, m), 4.00 (2H, dd, J = 18.33, 16.52 Hz), 4.10 (1H, d, J = 16.52 Hz), 6.62 (1H, s), 6.93 (1H, d, J = 8.06 Hz), 7.34 (1H, s), 7.58 (1H, d, J = 8.06 Hz), 11.41 (1H, s), 12.51 (1H, s). | 494 | 492 |

TABLE 1-55

| Ex. No. | structural formula | NMR | MS (M + H) | MS (M − H) |
|---|---|---|---|---|
| 263 | | ¹H-NMR (DMSO-D₆) δ: 0.75-0.88 (1H, m), 0.91 (3H, d, J = 6.85 Hz), 0.96-1.18 (11H, m), 1.45-1.54 (2H, m), 1.58 (2H, t, J = 6.45 Hz), 1.60-1.71 (1H, m), 1.98-2.09 (1H, m), 2.41 (2H, s), 2.68 (2H, t, J = 6.45 Hz), 3.20 (2H, t, J = 11.69 Hz), 3.58-3.83 (3H, m), 6.61 (1H, s), 6.80 (1H, d, J = 8.46 Hz), 7.20 (1H, s), 7.57 (1H, d, J = 8.46 Hz), 11.30 (1H, s), 12.49 (1H, s). | 449 | 447 |

TABLE 1-55-continued
| Ex. No. | structural formula | NMR | MS (M + H) | MS (M − H) |
|---|---|---|---|---|
| 264 | 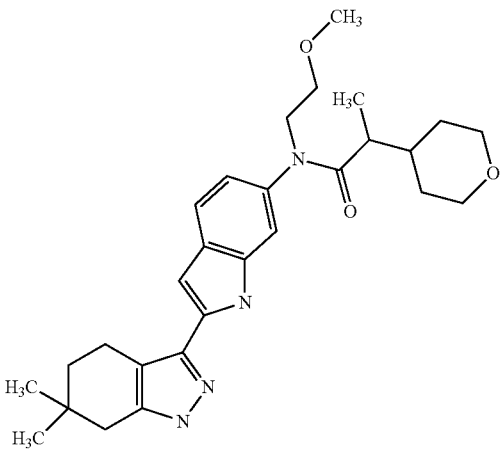 | ¹H-NMR (DMSO-D₆) δ: 0.75-0.89 (1H, m), 0.89 (3H, t, J = 8.66 Hz), 0.97-1.19 (2H, m), 1.01 (6H, s), 1.45-1.55 (2H, m), 1.57-1.70 (1H, m), 1.58 (2H, t, J = 6.25 Hz), 2.00-2.12 (1H, m), 2.41 (2H, s), 2.62-2.72 (2H, m), 3.15-3.24 (5H, m), 3.36-3.47 (2H, m), 3.61-4.01 (3H, m), 6.61 (1H, s), 6.82 (1H, d, J = 8.06 Hz), 7.25 (1H, s), 7.55 (1H, d, J = 8.06 Hz), 11.32 (1H, s), 12.50 (1H, s). | 479 | 477 |
| 265 | 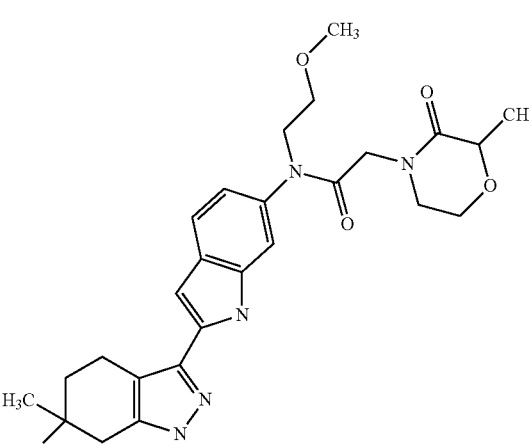 | ¹H-NMR (DMSO-D₆) δ: 1.01 (6H, s), 1.24 (3H, d, J = 6.84 Hz), 1.58 (2H, t, J = 6.29 Hz), 2.42 (2H, s), 2.63-2.74 (2H, m), 3.15-3.25 (4H, m), 3.39 (2H, t, J = 5.95 Hz), 3.43-3.53 (1H, m), 3.62-3.94 (6H, m), 4.08 (1H, q, J = 6.76 Hz), 6.61 (1H, s), 6.90 (1H, d, J = 8.38 Hz), 7.31 (1H, s), 7.57 (1H, d, J = 8.38 Hz), 11.47 (1H, s), 12.54 (1H, s). | 494 | 42 |
| 266 | 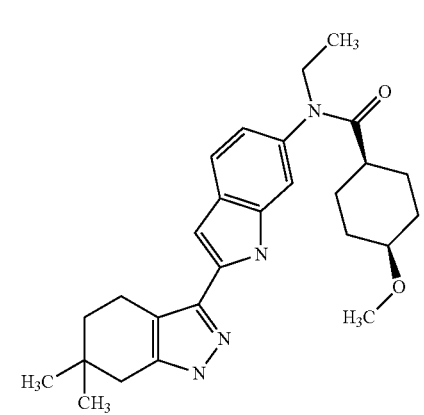 | ¹H-NMR (DMSO-D₆) δ: 0.93-1.04 (5H, m), 1.01 (6H, s), 1.27-1.36 (2H, m), 1.55-1.79 (4H, m), 1.58 (2H, t, J = 6.38 Hz), 2.11-2.21 (1H, m), 2.41 (2H, s), 2.63-2.72 (2H, m), 3.15 (3H, s), 3.18-3.23 (1H, m), 3.63 (2H, q, J = 6.96 Hz), 6.60 (1H, s), 6.82 (1H, d, J = 8.12 Hz), 7.20 (1H, s), 7.55 (1H, d, J = 8.12 Hz), 11.35 (1H, s), 12.53 (1H, s). | 449 | 447 |

TABLE 1-56

| Ex. No. | structural formula | NMR | MS (M + H) | MS (M − H) |
|---|---|---|---|---|
| 267 | | ¹H-NMR (DMSO-D₆) δ: 0.92-1.05 (2H, m), 1.01 (6H, s), 1.27-1.36 (2H, m), 1.51-1.81 (4H, m), 1.58 (2H, t, J = 6.26 Hz), 2.13-2.23 (1H, m), 2.41 (2H, s), 2.63-2.72 (2H, m), 3.15 (3H, s), 3.18-3.23 (1H, m), 3.20 (3H, s), 3.38 (2H, t, J = 6.15 Hz), 3.69-3.82 (2H, m), 6.60 (1H, s), 6.84 (1H, d, J = 8.35 Hz), 7.24 (1H, s), 7.54 (1H, d, J = 8.35 Hz), 11.36 (1H, s), 12.53 (1H, s). | 479 | 477 |
| 268 | | ¹H-NMR (DMSO-D₆) δ: 0.92-1.09 (2H, m), 1.01 (6H, s), 1.04 (3H, t, J = 7.05 Hz), 1.48 (2H, d, J = 12.89 Hz), 1.58 (2H, t, J = 6.45 Hz), 1.92 (3H, s), 2.42 (2H, s), 2.67 (2H, t, J = 6.45 Hz), 3.18-3.27 (2H, m), 3.67 (2H, q, J = 7.05 Hz), 3.68-3.76 (2H, m), 6.60 (1H, s), 6.79 (1H, d, J = 8.06 Hz), 7.18 (1H, s), 7.55 (1H, d, J = 8.06 Hz), 11.34 (1H, s), 12.51 (1H, s). | 435 | 433 |
| 269 | | ¹H-NMR (DMSO-D₆) δ: 0.92-1.05 (2H, m), 1.01 (6H, s), 1.44-1.52 (2H, m), 1.58 (2H, t, J = 6.25 Hz), 1.92 (3H, s), 2.42 (2H, s), 2.63-2.71 (2H, m), 3.18-3.27 (2H, m), 3.21 (3H, s), 3.40 (2H, t, J = 6.04 Hz), 3.68-3.76 (2H, m), 3.76-3.84 (2H, m), 6.60 (1H, s), 6.81 (1H, d, J = 8.46 Hz), 7.22 (1H, s), 7.54 (1H, d, J = 8.46 Hz), 11.35 (1H, s), 12.50 (1H, s). | 465 | 463 |

TABLE 1-56-continued

| Ex. No. | structural formula | NMR | MS (M + H) | MS (M − H) |
|---|---|---|---|---|
| 270 | 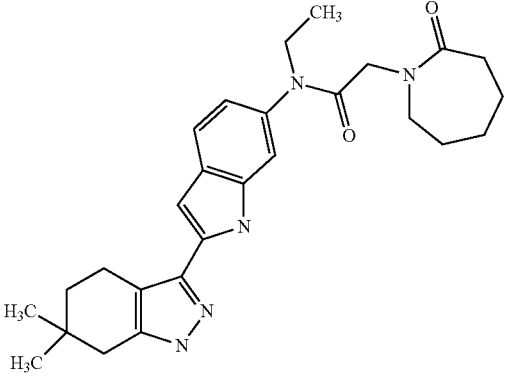 | ¹H-NMR (DMSO-D₆) δ: 1.01 (6H, s), 1.04 (3H, t, J = 6.98 Hz), 1.45-1.54 (2H, m), 1.54-1.65 (6H, m), 2.34-2.41 (2H, m), 2.42 (2H, s), 2.63-2.71 (2H, m), 3.28-3.34 (2H, m), 3.66 (2H, q, J = 6.98 Hz), 3.77 (2H, s), 6.61 (1H, s), 6.87 (1H, d, J = 8.46 Hz), 7.27 (1H, s), 7.56 (1H, d, J = 8.46 Hz), 11.39 (1H, s), 12.51 (1H, s). | 462 | 460 |

TABLE 1-57

| Ex. No. | structural formula | NMR | MS (M + H) | MS (M − H) |
|---|---|---|---|---|
| 271 | 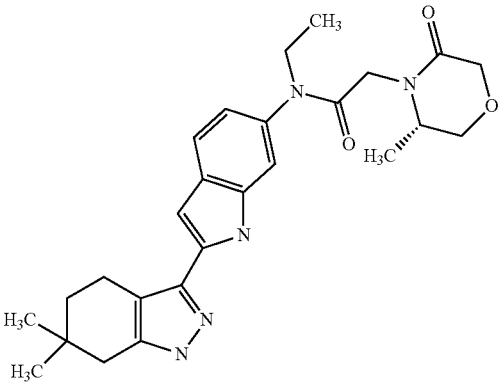 | ¹H-NMR (DMSO-D₆) δ: 1.01 (6H, s), 1.05 (3H, t, J = 7.05 Hz), 1.07 (3H, d, J = 6.04 Hz), 1.58 (2H, t, J = 6.04 Hz), 2.42 (2H, s), 2.67 (2H, t, J = 6.04 Hz), 3.46 (1H, d, J = 16.52 Hz), 3.47-3.54 (1H, m), 3.54-3.61 (1H, m), 3.61-3.73 (2H, m), 3.75-3.82 (1H, m), 3.95-4.05 (2H, m), 4.08 (1H, d, J = 16.52 Hz), 6.61 (1H, s), 6.91 (1H, d, J = 8.06 Hz), 7.30 (1H, s), 7.58 (1H, d, J = 8.06 Hz), 11.40 (1H, s), 12.51 (1H, s). | 464 | 462 |
| 272 | 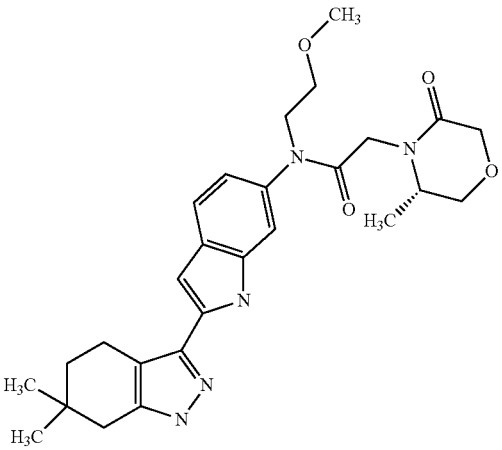 | ¹H-NMR (DMSO-D₆) δ: 1.01 (6H, s), 1.07 (3H, d, J = 6.04 Hz), 1.58 (2H, t, J = 6.25 Hz), 2.42 (2H, s), 2.63-2.71 (2H, m), 3.22 (3H, s), 3.41 (2H, t, J = 6.04 Hz), 3.43-3.53 (2H, m), 3.54-3.60 (1H, m), 3.73-3.85 (3H, m), 3.94-4.05 (2H, m), 4.10 (1H, d, J = 16.52 Hz), 6.61 (1H, s), 6.93 (1H, d, J = 8.46 Hz), 7.34 (1H, s), 7.58 (1H, d, J = 8.46 Hz), 11.42 (1H, s), 12.51 (1H, s). | 494 | 4 |

TABLE 1-57-continued

| Ex. No. | structural formula | NMR | MS (M + H) | MS (M − H) |
|---|---|---|---|---|
| 273 | | ¹H-NMR (DMSO-D₆) δ: 0.66-0.81 (1H, m), 0.94-1.09 (2H, m), 1.01 (6H, s), 1.04 (3H, t, J = 7.12 Hz), 1.21-1.38 (2H, m), 1.53-1.95 (8H, m), 2.42 (2H, s), 2.61-2.73 (2H, m), 2.86-2.97 (1H, m), 3.09 (1H, s), 3.17 (2H, s), 3.66 (2H, q, J = 7.12 Hz), 6.61 (1H, s), 6.78 (1H, d, J = 8.06 Hz), 7.17 (1H, s), 7.54 (1H, d, J = 8.46 Hz), 11.32 (1H, s), 12.51 (1H, s). | 463 | 461 |
| 274 | | ¹H-NMR (DMSO-D₆) δ: 0.67-0.81 (1H, m), 0.92-1.09 (2H, m), 1.01 (6H, s), 1.21-1.38 (2H, m), 1.52-1.94 (8H, m), 2.41 (2H, s), 2.64-2.72 (2H, m), 2.86-2.96 (1H, m), 3.09 (1H, s), 3.17 (2H, s), 3.21 (3H, s), 3.40 (2H, t, J = 6.04 Hz), 3.75-3.83 (2H, m), 6.59 (1H, s), 6.80 (1H, d, J = 7.66 Hz), 7.21 (1H, s), 7.53 (1H, d, J = 7.66 Hz), 11.35 (1H, s), 12.50 (1H, s). | 493 | 491 |

TABLE 1-58

| Ex. No. | structural formula | NMR | MS (M + H) | MS (M − H) |
|---|---|---|---|---|
| 275 | | ¹H-NMR (DMSO-D₆) δ: 1.01 (6H, s), 1.01 (3H, d, J = 6.72 Hz), 1.06 (3H, t, J = 7.05 Hz), 1.58 (2H, t, J = 6.25 Hz), 2.21-2.31 (2H, m), 2.39-2.49 (2H, m), 2.41 (2H, s), 2.63-2.70 (2H, m), 3.12 (1H, q, J = 6.72 Hz), 3.48 (4H, t, J = 4.43 Hz), 3.60-3.72 (2H, m), 6.59 (1H, s), 6.84 (1H, d, J = 8.87 Hz), 7.25 (1H, s), 7.54 (1H, d, J = 8.87 Hz), 11.33 (1H, s), 12.50 (1H, s). | 450 | 448 |

TABLE 1-58-continued

| Ex. No. | structural formula | NMR | MS (M + H) | MS (M − H) |
|---|---|---|---|---|
| 276 | | $^1$H-NMR (DMSO-D$_6$) δ: 1.01 (6H, s), 1.01 (3H, d, J = 6.85 Hz), 1.58 (2H, t, J = 6.45 Hz), 2.21-2.31 (2H, m), 2.39-2.48 (2H, m), 2.41 (2H, s), 2.63-2.71 (2H, m), 3.14 (1H, q, J = 6.85 Hz), 3.23 (3H, s), 3.38-3.46 (2H, m), 3.48 (4H, t, J = 4.43 Hz), 3.65-3.94 (2H, m), 6.59 (1H, s), 6.86 (1H, br s), 7.30 (1H, s), 7.53 (1H, d, J = 8.06 Hz), 11.34 (1H, s), 12.50 (1H, s). | 480 | 478 |
| 277 | | $^1$H-NMR (DMSO-D$_6$) δ: 1.01 (6H, s), 1.05 (3H, t, J = 7.25 Hz), 1.22 (6H, s), 1.58 (2H, t, J = 6.25 Hz), 2.42 (2H, s), 2.65-2.71 (2H, m), 3.21 (2H, s), 3.68 (2H, q, J = 7.25 Hz), 3.78 (2H, s), 3.97 (2H, s), 6.62 (1H, s), 6.89 (1H, d, J = 8.46 Hz), 7.29 (1H, s), 7.59 (1H, d, J = 8.46 Hz), 11.41 (1H, s), 12.51 (1H, s). | 478 | 476 |
| 278 | | $^1$H-NMR (DMSO-D$_6$) δ: 1.01 (6H, s), 1.22 (6H, s), 1.58 (2H, t, J = 6.45 Hz), 2.42 (2H, s), 2.68 (2H, t, J = 6.45 Hz), 3.20 (2H, s), 3.22 (3H, s), 3.40 (2H, t, J = 5.84 Hz), 3.79 (2H, s), 3.81 (2H, t, J = 5.84 Hz), 3.97 (2H, s), 6.62 (1H, s), 6.90 (1H, d, J = 8.46 Hz), 7.33 (1H, s), 7.58 (1H, d, J = 8.46 Hz), 11.42 (1H, s), 12.51 (1H, s). | 508 | 506 |

TABLE 1-58-continued
| Ex. No. | structural formula | NMR | MS (M + H) | MS (M − H) |
|---|---|---|---|---|
| 279 | 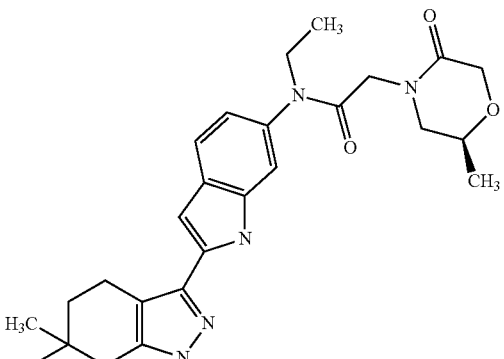 | $^1$H-NMR (IDMSO-D$_6$) δ: 1.01 (6H, s), 1.05 (3H, t, J = 7.17 Hz), 1.13 (3H, d, J = 5.95 Hz), 1.58 (2H, t, J = 6.06 Hz), 2.41 (2H, s), 2.65-2.71 (2H, m), 3.15-3.25 (2H, m), 3.63-3.73 (3H, m), 3.80-3.90 (2H, m), 4.02 (2H, s), 6.62 (1H, s), 6.89 (1H, d, J = 8.38 Hz), 7.28 (1H, s), 7.59 (1H, d, J = 8.38 Hz), 11.45 (1H, s), 12.54 (1H, s). | 464 | 462 |
TABLE 1-59
| Ex. No. | structural formula | NMR | MS (M + H) | MS (M − H) |
|---|---|---|---|---|
| 280 | 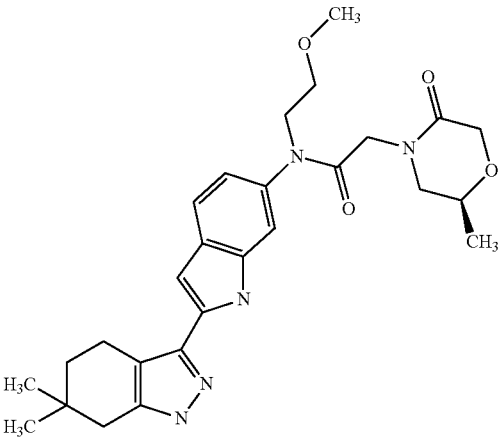 | $^1$H-NMR (DMSO-D$_6$) δ: 1.01 (6H, s), 1.13 (3H, d, J = 6.03 Hz), 1.58 (2H, t, J = 6.38 Hz), 2.42 (2H, s), 2.64-2.72 (2H, m), 3.14-3.25 (5H, m), 3.39 (2H, t, J = 6.03 Hz), 3.70 (1H, d, J = 16.70 Hz), 3.78-3.91 (4H, m), 4.02 (2H, s), 6.62 (1H, s), 6.90 (1H, d, J = 8.12 Hz), 7.32 (1H, s), 7.58 (1H, d, J = 8.12 Hz), 11.47 (1H, s), 12.54 (1H, s). | 494 | 492 |
| 281 | 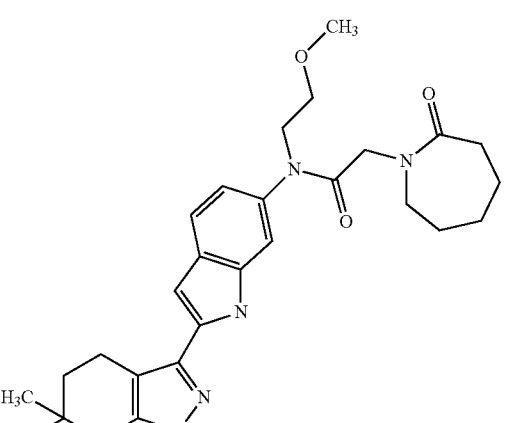 | $^1$H-NMR (DMSO-D$_6$) δ: 1.01 (6H, s), 1.44-1.66 (8H, m), 2.34-2.46 (4H, m), 2.64-2.72 (2H, m), 3.21 (3H, s), 3.28-3.35 (2H, m), 3.39 (2H, t, J = 6.03 Hz), 3.75-3.82 (4H, m), 6.61 (1H, s), 6.90 (1H, d, J = 8.12 Hz), 7.31 (1H, s), 7.56 (1H,. d, J = 8.12 Hz), 11.44 (1H, s), 12.54 (1H, s). | 492 | 490 |

TABLE 1-59-continued

| Ex. No. | structural formula | NMR | MS (M + H) | MS (M − H) |
|---|---|---|---|---|
| 282 | | ¹H-NMR (DMSO-D₆) δ: 1.01 (6H, s), 1.05 (3H, t, J = 7.19 Hz), 1.13 (3H, d, J = 6.26 Hz), 1.58 (2H, t, J = 6.38 Hz), 2.42 (2H, s), 2.64-2.72 (2H, m), 3.14-3.26 (2H, m), 3.62-3.74 (3H, m), 3.79-3.90 (2H, m), 4.02 (2H, s), 6.62 (1H, s), 6.89 (1H, d, J = 8.35 Hz), 7.28 (1H, s), 7.59 (1H, d, J = 8.35 Hz), 11.46 (1H, s), 12.54 (1H, s). | 464 | 462 |
| 283 | | ¹H-NMR (DMSO-D₆) δ: 1.01 (6H, s), 1.13 (3H, d, J = 6.26 Hz), 1.58 (2H, t, J = 6.26 Hz), 2.42 (2H, s), 2.64-2.71 (2H, m), 3.14-3.26 (5H, m), 3.39 (2H, t, J = 5.91 Hz), 3.70 (1H, d, J = 16.46 Hz), 3.77-3.91 (4H, m), 4.02 (2H, s), 6.62 (1H, s), 6.90 (1H, d, J = 8.35 Hz), 7.32 (1H, s), 7.58 (1H, d, J = 8.35 Hz), 11.47 (1H, s), 12.55 (1H, s). | 494 | 492 |

TABLE 1-60

| Ex. No. | structural formula | NMR | MS (M + H) | MS (M − H) |
|---|---|---|---|---|
| 284 | | ¹H-NMR (DMSO-D₆) δ: 1.00 (6H, s), 1.01 (6H, s), 1.04 (3H, t, J = 7.28 Hz), 1.58 (2H, t, J = 6.18 Hz), 1.75 (2H, t, J = 6.73 Hz), 2.42 (2H, s), 2.64-2.71 (2H, m), 3.24-3.32 (2H, m), 3.64 (2H, s), 3.67 (2H, q, J = 7.28 Hz), 6.62 (1H, s), 6.89 (1H, d, J = 8.16 Hz), 7.27 (1H, s), 7.59 (1H, d, J = 8.16 Hz), 11.45 (1H, s), 12.54 (1H, s). | 462 | 460 |

TABLE 1-60-continued
| Ex. No. | structural formula | NMR | MS (M + H) | MS (M − H) |
|---|---|---|---|---|
| 285 | 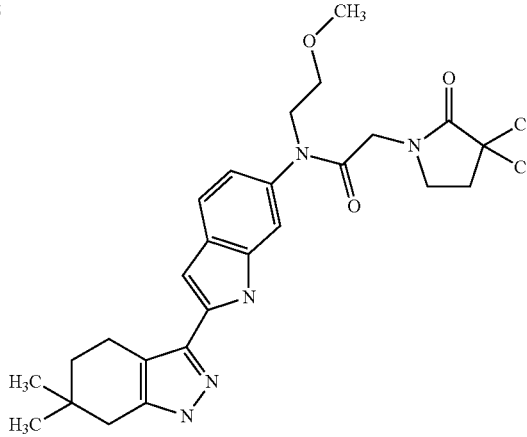 | ¹H-NMR (DMSO-D₆) δ: 1.00 (6H, s), 1.01 (6H, s), 1.58 (2H, t, J = 6.45 Hz), 1.76 (2H, t, J = 6.85 Hz), 2.42 (2H, s), 2.64-2.71 (2H, m), 3.22 (3H, s), 3.24-3.31 (2H, m), 3.39 (2H, t, J = 5.84 Hz), 3.65 (2H, s), 3.80 (2H, t, J = 6.04 Hz), 6.62 (1H, s), 6.90 (1H, d, J = 7.66 Hz), 7.31 (1H, s), 7.58 (1H, d, J = 8.46 Hz), 11.42 (1H, s), 12.51 (1H, s). | 492 | 490 |
| 286 | 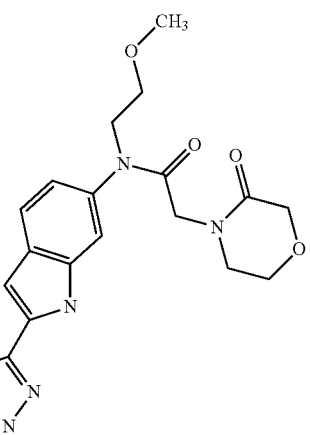 | ¹H-NMR (DMSO-D₆) δ: 1.01 (6H, s), 1.58 (2H, t, J = 6.26 Hz), 2.42 (2H, s), 2.62-2.72 (2H, m), 3.22 (3H, s), 3.29-3.36 (2H, m), 3.40 (2H, t, J = 5.91 Hz), 3.75-3.85 (6H, m), 4.00 (2H, s), 6.62 (1H, s), 6.91 (1H, d, J = 8.35 Hz), 7.32 (1H, s), 7.58 (1H, d, J = 8.35 Hz), 11.47 (1H, s), 12.55 (1H, s). | 480 | 478 |
| 287 | 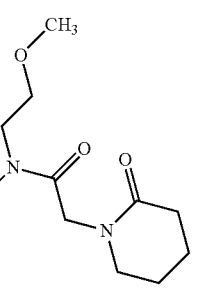 | ¹H-NMR (DMSO-D₆) δ: 1.01 (6H, s), 1.58 (2H, t, J = 6.26 Hz), 1.63-1.72 (4H, (4H, m), 2.13-2.20 (2H, m), 2.41 (2H, s), 2.64-2.72 (2H, m), 3.21 (5H, s), 3.39 (2H, t, J = 5.91 Hz), 3.73 (2H, s), 3.80 (2H, t, J = 5.91 Hz), 6.61 (1H, s), 6.90 (1H, d, J = 8.35 Hz), 7.31 (1H, s), 7.57 (1H, d, J = 8.35 Hz), 11.45 (1H, s), 12.54 (1H, s). | 478 | 476 |

TABLE 1-61

| Ex. No. | structural formula | NMR | MS (M + H) | MS (M − H) |
|---|---|---|---|---|
| 288 | | ¹H-NMR (DMSO-D₆) δ: 1.01 (6H, s), 1.05 (3H, t, J = 7.19 Hz), 1.58 (2H, t, J = 6.26 Hz), 2.42 (2H, s), 2.63-2.72 (2H, m), 3.28-3.36 (2H, m), 3.68 (2H, q, J = 7.11 Hz), 3.75-3.82 (4H, m), 4.00 (2H, s), 6.62 (1H, s), 6.90 (1H, d, J = 8.12 Hz), 7.28 (1H, s), 7.59 (1H, d, J = 8.12 Hz), 11.45 (1H, s), 12.54 (1H, s). | 450 | 44 |
| 289 | | ¹H-NMR (DMSO-D₆) δ: 1.01 (6H,s), 1.04 (3H, t, J = 7.19 Hz), 1.58 (2H, t, J = 6.26 Hz), 1.64-1.71 (4H, m), 2.12-2.20 (2H, m), 2.41 (2H, s), 2.64-2.71 (2H, m), 3.18-3.25 (2H, m), 3.66 (2H, q, J = 7.19 Hz), 3.72 (2H, s), 6.61 (1H, s), 6.88 (1H, d, J = 8.35 Hz), 7.27 (1H, s), 7.57 (1H, d, J = 8.35 Hz), 11.44 (1H, s), 12.54 (1H, s). | 448 | 446 |
| 290 | | ¹H-NMR (DMSO-D₆) δ: 1.01 (6H, s), 1.04 (3H, t, J = 6.25 Hz), 1.08 (6H, s), 1.58 (2H, t, J = 6.45 Hz), 2.13 (2H, s), 2.41 (2H, s), 2.62-2.71 (2H, m), 3.69 (2H, q, J = 6.25 Hz), 4.97 (1H, s), 6.60 (1H, s), 6.81 (1H, d, J = 8.06 Hz), 7.19 (1H, s), 7.56 (1H, d, J = 8.06 Hz), 11.39 (1H, s), 12.54 (1H, s). | 409 | 407 |
| 291 | | ¹H-NMR (DMSO-D₆) δ: 0.97-1.10 (3H, m), 1.01 (6H, s), 1.58 (2H, t, J = 6.29 Hz), 1.95 (2H, s), 2.41 (2H, s), 2.64-2.70 (2H, m), 2.71 (2H, s), 2.92 (2H, s), 3.62-3.80 (4H, m), 6.59-6.64 (1H, m), 6.85-6.93 (1H, m), 7.24-7.31 (1H, m), 7.55-7.62 (1H, m), 11.42 (1H, s), 12.54 (1H, s). | 422 | 420 |

TABLE 1-61-continued
| Ex. No. | structural formula | NMR | MS (M + H) | MS (M − H) |
|---|---|---|---|---|
| 292 | 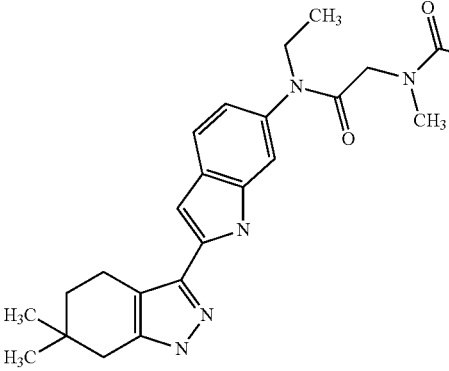 | $^1$H-NMR (DMSO-D$_6$) δ: 0.87-1.09 (6H, m), 1.01 (6H, s), 1.58 (2H, t, J = 6.40 Hz), 2.04-2.31 (2H, m), 2.42 (2H, s), 2.64-2.71 (2H, m), 2.73 (1H, s), 2.92 (2H, s), 3.61-3.80 (4H, m), 6.59-6.63 (1H, m), 6.85-6.93 (1H, m), 7.24-7.30 (1H, m), 7.54-7.62 (1H, m), 11.43 (1H, s), 12.53 (1H, s). | 436 | 434 |
TABLE 1-62
| Ex. No. | structural formula | NMR | MS (M + H) | MS (M − H) |
|---|---|---|---|---|
| 293 | 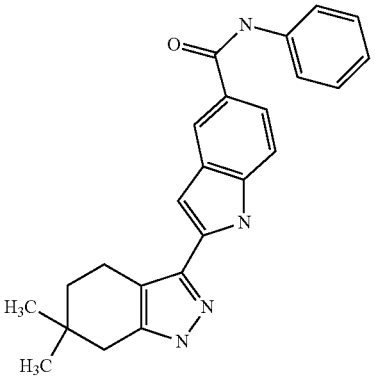 | $^1$H-NMR (DMSO-D$_6$) δ: 1.02 (s, 6H), 1.59 (t, 2H, J = 6.28 Hz), 2.42 (s, 2H), 2.69 (s, 2H), 6.70 (s, 1H), 7.07 (dd, 1H, J = 11.59, 4.11 Hz), 7.32-7.36 (m, 2H), 7.46 (d, 1H, J = 8.69 Hz), 7.71 (d, 1H, J = 8.21 Hz), 7.81 (dd, 2H, J = 8.57, 1.09 Hz), 8.21 (s, 1H), 10.09 (s, 1H), 11.57 (s, 1H), 12.56 (s, 1H). | 385 | 383 |
| 294 | 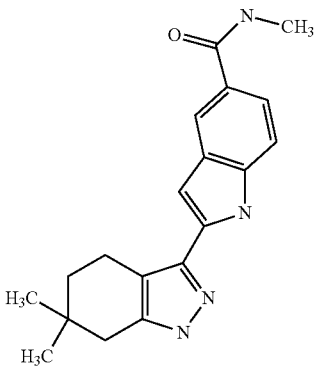 | $^1$H-NMR (DMSO-D$_6$) δ: 1.01 (s, 6H), 1.58 (t, 2H, J = 6.16 Hz), 2.42 (s, 2H), 2.68 (t, 2H, J = 6.04 Hz), 2.79 (d, 3H, J = 4.35 Hz), 6.63 (d, 1H, J = 1.21 Hz), 7.38 (d, 1H, J = 8.45 Hz), 7.57 (dd, 1H, J = 8.45, 1.69 Hz), 8.04 (s, 1H), 8.22 (d, 1H, J = 4.59 Hz), 11.46 (s, 1H), 12.53 (s, 1H). | 323 | 321 |

TABLE 1-62-continued

| Ex. No. | structural formula | NMR | MS (M + H) | MS (M − H) |
|---|---|---|---|---|
| 295 | | ¹H-NMR (DMSO-D₆) δ: 0.99 (s, 6H), 1.55 (t, 2H, J = 6.40 Hz), 2.39 (s, 2H), 2.62 (s, 2H), 3.39 (s, 3H), 6.47 (s, 1H), 6.97 (d, 1H, J = 8.45 Hz), 7.08-7.25 (m, 6H), 7.49 (s, 1H), 11.34 (s, 1H), 12.49 (s, 1H). | 399 | 7 |
| 296 | | ¹H-NMR (DMSO-D₆) δ: 1.01 (s, 6H), 1.58 (t, 2H, J = 6.40 Hz), 2.41 (s, 2H), 2.67 (s, 2H), 2.99 (s, 6H), 6.62 (s, 1H), 7.11 (d, 1H, J = 8.21 Hz), 7.40 (d, 1H, J = 8.21 Hz), 7.58 (s, 1H), 11.42 (s, 1H), 12.53 (s, 1H). | 337 | 335 |
| 297 | | ¹H-NMR (DMSO-D₆) δ: 1.01 (s, 6H), 1.58 (t, 2H, J = 6.28 Hz), 2.42 (s, 2H), 2.68 (t, 2H, J = 5.92 Hz), 6.62 (s, 1H), 7.04 (s, 1H), 7.37 (d, 1H, J = 8.45 Hz), 7.62 (d, 1H, J = 8.45 Hz), 7.78 (s, 1H), 8.10 (s, 1H), 11.47 (s, 1H), 12.53 (s, 1H). | 309 | 307 |

TABLE 1-63
| Ex. No. | structural formula | NMR | MS (M + H) | MS (M − H) |
|---|---|---|---|---|
| 298 | 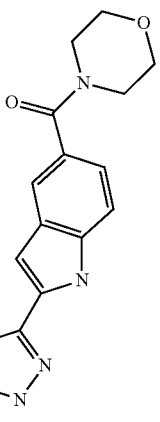 | ¹H-NMR (DMSO-D₆) δ: 1.02 (d, 6H, J = 8.58 Hz), 1.58 (t, 2H, J = 6.26 Hz), 2.41 (s, 2H), 2.66 (d, 2H, J = 5.10 Hz), 3.57 (t, 8H, J = 15.07 Hz), 6.63 (s, 1H), 7.12 (d, 1H, J = 8.58 Hz), 7.41 (d, 1H, J = 8.58 Hz), 7.59 (s, 1H), 11.47 (s, 1H), 12.54 (s, 1H). | 379 | 377 |
| 299 | 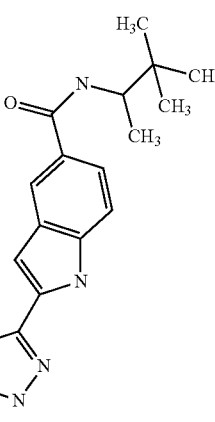 | ¹H-NMR (DMSO-D₆) δ: 0.92 (s, 9H), 1.01 (s, 6H), 1.09 (d, 3H, J = 6.84 Hz), 1.58 (t, 2H, J = 5.95 Hz), 2.42 (s, 2H), 2.67 (s, 2H), 4.01 (dd, 1H, J = 9.37, 6.95 Hz), 6.64 (s, 1H), 7.38 (d, 1H, J = 8.60 Hz), 7.57 (dd, 1H, J = 8.60, 1.54 Hz), 7.73 (d, 1H, J = 9.26 Hz), 8.05 (s, 1H), 11.44 (s, 1H), 12.53 (s, 1H). | 393 | 391 |
| 300 | 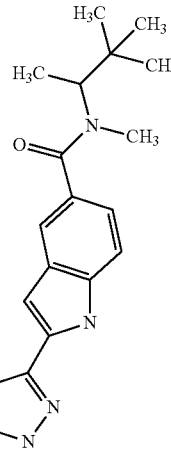 | ¹H-NMR (DMSO-D₆) δ: 0.76 (s, 4H), 1.01 (s, 11H), 1.19 (d, 3H, J = 18.84 Hz), 1.58 (t, 2H, J = 6.03 Hz), 2.41 (s, 2H), 2.68 (s, 2H), 2.82 (s, 3H), 6.62 (s, 1H), 7.04 (s, 1H), 7.42-7.49 (m, 2H), 11.40 (s, 1H), 12.52 (s, 1H). | 407 | 405 |

TABLE 1-63-continued
| Ex. No. | structural formula | NMR | MS (M + H) | MS (M − H) |
|---|---|---|---|---|
| 301 | 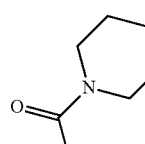 | ¹H-NMR (DMSO-D₆) δ: 0.99 (d, 6H, J = 13.67 Hz), 1.40 (s, 2H), 1.58 (t, 2H, J = 6.18 Hz), 1.69 (s, 1H), 1.88 (s, 1H), 2.41-2.51 (m, 3H), 2.66-3.07 (m, 4H), 3.48 (d, 1H, J = 9.92 Hz), 3.84 (s, 1H), 4.88 (s, 1H), 6.61 (s, 1H), 7.08 (d, 1H, J = 8.38 Hz), 7.39 (d, 1H, J = 8.38 Hz), 7.55 (s, 1H), 11.44 (s, 1H), 12.54 (s, 1H). | 393 | 391 |
TABLE 1-64
| Ex. No. | structural formula | NMR | MS (M + H) | MS (M − H) |
|---|---|---|---|---|
| 302 | 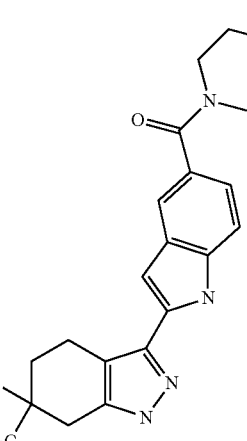 | ¹H-NMR (DMSO-D₆) δ: 1.02 (d, 6H, J = 11.69 Hz), 1.35 (d, 2H, J = 9.04 Hz), 1.58 (t, 2H, J = 6.06 Hz), 1.74 (s, 2H), 2.41 (s, 2H), 2.67 (t, 2H, J = 5.84 Hz), 3.17 (dd, 2H, J = 16.32, 6.40 Hz), 3.70-3.84 (m, 3H), 4.77 (d, 1H, J = 3.97 Hz), 6.62 (s, 1H), 7.08 (dd, 1H, J = 8.38, 1.32 Hz), 7.39 (d, 1H, J = 8.38 Hz), 7.54 (s, 1H), 11.45 (s, 1H), 12.54 (s, 1H). | 393 | 391 |
| 303 | 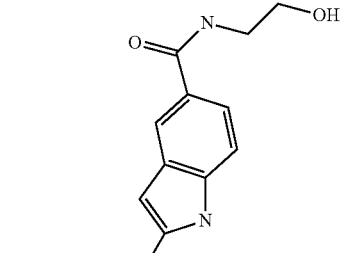 | ¹H-NMR (DMSO-D₆) δ: 1.01 (s, 6H), 1.58 (s, 2H), 2.42 (s, 2H), 2.68 (s, 2H), 3.30-3.35 (m, 2H), 3.52 (q, 2H, J = 6.03 Hz), 4.71 (t, 1H, J = 5.51 Hz), 6.63 (s, 1H), 7.38 (d, 1H, J = 838 Hz), 7.59 (d, 1H, J = 8.38 Hz), 8.07 (s, 1H), 8.22 (s, 1H), 11.48 (s, 1H), 12.54 (s, 1H). | 353 | 351 |

TABLE 1-64-continued

| Ex. No. | structural formula | NMR | MS (M + H) | MS (M − H) |
|---|---|---|---|---|
| 304 | 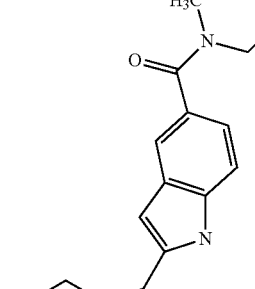 | ¹H-NMR (DMSO-D₆) δ: 1.01 (s, 6H), 1.58 (t, 2H, J = 6.18 Hz), 2.41 (s, 2H), 2.67 (s, 2H), 3.00 (s, 3H), 3.17 (dd, 1H, J = 5.29, 1.76 Hz), 3.40-3.50 (m, 3H), 4.76 (t, 1H, J = 5.40 Hz), 6.60 (s, 1H), 7.10 (d, 1H, J = 8.38 Hz), 7.38 (d, 1H, J = 8.38 Hz), 7.57 (s, 1H), 11.42 (s, 1H), 12.53 (s, 1H). | 367 | 365 |
| 305 | 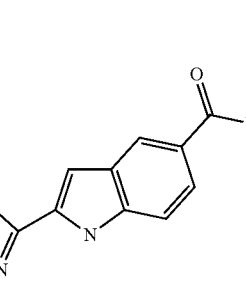 | ¹H-NMR (DMSO-D₆) δ: 1.01 (s, 6H), 1.58 (t, 2H, J = 6.25 Hz), 2.42 (s, 2H), 2.69 (s, 2H), 3.66 (s, 3H), 4.01 (d, 2H, J = 5.64 Hz), 6.66 (s, 1H), 7.41 (d, 1H, J = 8.46 Hz), 7.61 (d, 1H, J = 8.46 Hz), 8.10 (s, 1H), 8.75 (t, 1H, J = 5.64 Hz), 11.54 (s, 1H), 12.56 (s, 1H). | 381 | 379 |
| 306 | 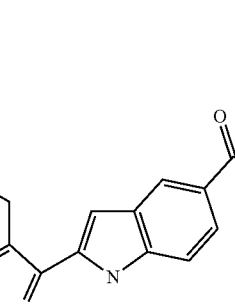 | ¹H-NMR (DMSO-D₆) δ: 1.01 (s, 6H), 1.58 (t, 2H, J = 6.45 Hz), 2.42 (s, 2H), 2.69 (t, 2H, J = 6.04 Hz), 3.92 (d, 2H, J = 5.64 Hz), 6.67 (d, 1H, J = 1.21 Hz), 7.41 (d, 1H, J = 8.46 Hz), 7.62 (dd, 1H, J = 8.46, 1.61 Hz), 8.10 (s, 1H), 8.63 (t, 1H, J = 5.84 Hz), 11.50 (s, 1H), 12.54 (s, 2H). | 367 | 365 |

TABLE 1-65

| Ex. No. | structural formula | NMR | MS (M + H) | MS (M − H) |
|---|---|---|---|---|
| 307 | 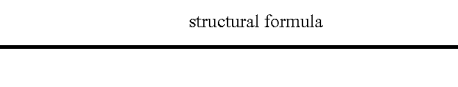 | ¹H-NMR (DMSO-D₆) δ: 1.01 (s, 6H), 1.10 (d, 6H, J = 6.18 Hz), 1.58 (t, 2H, J = 6.29 Hz), 2.42 (s, 2H), 2.68 (s, 2H), 3.39 (q, 2H, J = 6.03 Hz), 3.49 (t, 2H, J = 6.29 Hz), 3.55-3.61 (m, 1H), 6.63 (s, 1H), 7.38 (d, 1H, J = 8.38 Hz), 7.59 (d, 1H, J = 8.38 Hz), 8.06 (s, 1H), 8.27 (s, 1H), 11.48 (s, 1H), 12.55 (s, 1H). | 395 | 393 |

TABLE 1-65-continued

| Ex. No. | structural formula | NMR | MS (M + H) | MS (M − H) |
|---|---|---|---|---|
| 308 | | ¹H-NMR (DMSO-D₆) δ: 0.87 (t, 3H, J = 7.39 Hz), 1.02 (s, 6H), 1.51-1.58 (m, 4H), 2.43 (s, 2H), 2.69 (s, 2H), 3.33-3.53 (m, 6H), 6.64 (s, 1H), 7.39 (d, 1H, J = 8.38 Hz), 7.60 (d, 1H, J = 8.38 Hz), 8.07 (s, 1H), 8.30 (s, 1H), 11.50 (s, 1H), 12.55 (s, 1H). | 395 | 393 |
| 309 | | ¹H-NMR (DMSO-D₆) δ: 1.01 (s, 6H), 1.58 (t, 2H, J = 6.29 Hz), 2.42 (s, 2H), 2.68 (s, 2H), 3.64 (q, 2H, J = 5.88 Hz), 4.12 (t, 2H, J = 6.06 Hz), 6.64 (s, 1H), 6.91-6.99 (m, 3H), 7.27-7.32 (m, 2H), 7.39 (d, 1H, J = 8.60 Hz), 7.62 (d, 1H, J = 8.82 Hz), 8.10 (s, 1H), 8.50 (t, 1H, J = 5.07 Hz), 11.50 (s, 1H), 12.55 (s, 1H). | 429 | 427 |
| 310 | | ¹H-NMR (DMSO-D₆) δ: 1.01 (s, 6H), 1.58 (t, 2H, J = 6.29 Hz), 2.42 (s, 2H), 2.68 (t, 2H, J = 6.06 Hz), 3.28 (s, 3H), 3.43-3.48 (m, 4H), 6.63 (d, 1H, J = 1.32 Hz), 7.38 (d, 1H, J = 8.60 Hz), 7.59 (dd, 1H, J = 8.60, 1.54 Hz), 8.07 (s, 1H), 8.30 (t, 1H, J = 4.96 Hz), 11.49 (s, 1H), 12.54 (s, 1H). | 367 | 365 |
| 311 | | ¹H-NMR (DMSO-D₆) δ: 1.01 (s, 6H), 1.58 (t, 2H, J = 6.18 Hz), 2.41 (s, 2H), 2.68 (s, 2H), 3.03 (s, 3H), 3.69 (s, 3H), 4.22 (s, 2H), 6.64 (s, 1H), 7.13 (s, 1H), 7.45-7.54 (m, 2H), 11.48 (s, 1H), 12.55 (s, 1H). | 395 | 393 |
| 312 | | ¹H-NMR (DMSO-D₆) δ: 1.01 (s, 6H), 1.58 (t, (s, 2H), 2.68 (t, 2H, J = 2H, J = 6.38 Hz), 2.41 (s, 2H), 2.68 (t, 2H, J = 6.15 Hz), 3.02 (s, 3H), 4.03-4.14 (m, 2H), 6.64 (s, 1H), 7.03-7.13 (m, 1H), 7.43-7.58 (m, 2H), 11.46 (s, 1H), 12.65 (s, 2H). | 381 | 379 |

TABLE 1-65-continued

| Ex. No. | structural formula | NMR | MS (M + H) | MS (M − H) |
|---|---|---|---|---|
| 313 | | ¹H-NMR (DMSO-D₆) δ: 1.01 (s, 6H), 1.58 (t, 2H, J = 6.29 Hz), 2.41 (s, 2H), 2.67 (s, 2H), 2.99 (s, 3H), 3.26 (br s, 3H), 3.48 (br s, 4H), 6.61 (s, 1H), 7.09 (d, 1H, J = 7.94 Hz), 7.39 (d, 1H, J = 8.16 Hz), 7.55 (s, 1H), 11.43 (s, 1H), 12.53 (s, 1H). | 381 | 379 |

TABLE 1-66

| Ex. No. | structural formula | NMR | MS (M + H) | MS (M − H) |
|---|---|---|---|---|
| 314 | | ¹H-NMR (DMSO-D₆) δ: 1.00 (s, 6H), 1.57 (t, 2H, J = 6.29 Hz), 2.41 (s, 2H), 2.66 (br s, 2H), 2.90 (s, 3H), 4.65 (s, 2H), 6.62 (s, 1H), 7.15-7.42 (m, 7H), 7.63 (s, 1H), 11.45 (s, 1H), 12.53 (s, 1H). | 413 | 411 |
| 315 | | ¹H-NMR (DMSO-D₆) δ: 1.01 (s, 6H), 1.58 (t, 2H, J = 6.29 Hz), 2.42 (s, 2H), 2.68 (br s, 2H), 4.49 (d, 2H, J = 5.95 Hz), 6.64 (s, 1H), 7.21-7.45 (m, 6H), 7.64 (d, 1H, J = 8.38 Hz), 8.13 (s, 1H), 8.86 (t, 1H, J = 5.73 Hz), 11.50 (s, 1H), 12.55 (s, 1H). | 399 | 397 |
| 316 | | ¹H-NMR (DMSO-D₆) δ: 1.01 (s, 6H), 1.58 (t, 2H, J = 6.25 Hz), 2.42 (s, 2H), 2.68 (br s, 2H), 4.76 (d, 2H, J = 6.04 Hz), 6.66 (s, 1H), 7.42 (d, 1H, J = 8.87 Hz), 7.63-7.72 (m, 3H), 8.14 (s, 1H), 9.21 (t, 1H, J = 5.64 Hz), 11.55 (s, 1H), 12.56 (s, 1H). | 406 | 404 |
| 317 | | ¹H-NMR (DMSO-D₆) δ: 1.01 (s, 6H), 1.58 (t, 2H, J = 6.25 Hz), 2.42 (s, 2H), 2.69 (t, 2H, J = 6.25 Hz), 4.74 (d, 2H, J = 5.64 Hz), 6.66 (s, 1H), 7.36-7.44 (m, 1H), 7.65 (d, 1H, J = 7.25 Hz), 8.14 (s, 1H), 8.58 (t, 1H, J = 3.02 Hz), 8.95 (s, 1H), 11.52 (s, 1H), 12.55 (s, 1H). | 391 | 389 |

TABLE 1-66-continued

| Ex. No. | structural formula | NMR | MS (M + H) | MS (M − H) |
|---|---|---|---|---|
| 318 | | $^1$H-NMR (DMSO-D$_6$) δ: 1.02 (s, 6H), 1.59 (t, 2H, J = 6.25 Hz), 2.42 (s, 2H), 2.68 (br s, 2H), 4.32 (d, 2H, J = 5.64 Hz), 6.50 (t, 1H, J = 1.41 Hz), 6.64 (s, 1H), 7.39 (d, 1H, J = 8.46 Hz), 7.59-7.63 (m, 3H), 8.09 (s, 1H), 8.66 (t, 1H, J = 5.84 Hz), 11.50 (s, 1H), 12.56 (s, 1H). | 389 | 387 |
| 319 | | $^1$H-NMR (DMSO-D$_6$) δ: 1.01 (s, 6H), 1.58 (t, 2H, J = 6.25 Hz), 2.41 (s, 2H), 2.68 (t, 2H, J = 6.25 Hz), 3.60 (s, 3H), 4.45 (d, 2H, J = 5.24 Hz), 5.89 (dd, 1H, J = 3.43, 2.62 Hz), 5.97 (dd, 1H, J = 3.43, 1.81 Hz), 6.64 (dd, 2H, J = 5.04, 3.02 Hz), 7.38 (d, 1H, J = 8.46 Hz), 7.62 (dd, 1H, J = 8.46, 1.61 Hz), 8.10 (d, 1H, J = 1.21 Hz), 8.55 (t, 1H, J = 5.44 Hz), 11.51 (s, 1H). | 402 | 400 |

TABLE 1-67

| Ex. No. | structural formula | NMR | MS (M + H) | MS (M − H) |
|---|---|---|---|---|
| 320 | | $^1$H-NMR (DMSO-D$_6$) δ: 1.01 (s, 6H), 1.33 (s, 6H), 1.58 (t, 2H, J = 6.25 Hz), 2.41 (s, 2H), 2.67 (s, 2H), 3.51 (s, 2H), 4.97-5.10 (m, 1H), 6.63 (s, 1H), 7.36-7.37 (m, 2H), 7.53 (d, 1H, J = 8.46 Hz), 8.01 (s, 1H), 11.47 (s, 1H), 12.54 (s, 1H). | 381 | 379 |
| 321 | | $^1$H-NMR (DMSO-D$_6$) δ: 1.01 (s, 6H), 1.58 (t, 2H, J = 6.25 Hz), 2.42 (s, 2H), 2.68 (t, 2H, J = 5.64 Hz), 3.26 (s, 3H), 3.56 (s, 3H), 6.66 (s, 1H), 7.34-7.43 (m, 2H), 7.85 (s, 1H), 11.50 (s, 1H), 12.55 (s, 1H). | 353 | 351 |
| 322 | | $^1$H-NMR (DMSO-D$_6$) δ: 1.01 (s, 6H), 1.58 (t, 2H, J = 6.25 Hz), 2.44-2.48 (m, 8H), 2.68 (s, 2H), 3.40 (q, 2H, J = 6.58 Hz), 3.58 (t, 4H, J = 4.43 Hz), 6.63 (s, 1H), 7.38 (d, 1H, J = 8.46 Hz), 7.57 (d, 1H, J = 9.27 Hz), 8.05 (s, 1H), 8.20 (t, 1H, J = 5.44 Hz), 11.49 (s, 1H), 12.55 (s, 1H). | 422 | 420 |

TABLE 1-67-continued

| Ex. No. | structural formula | NMR | MS (M + H) | MS (M − H) |
|---|---|---|---|---|
| 323 | (structure) | ¹H-NMR (DMSO-D₆) δ: 1.01 (s, 6H), 1.58 (t, 2H, J = 6.25 Hz), 2.25 (s, 6H), 2.42 (s, 2H), 2.68 (s, 2H), 3.38 (q, 4H, J = 6.45 Hz), 6.64 (s, 1H), 7.38 (d, 1H, J = 8.06 Hz), 7.58 (d, 1H, J = 8.06 Hz), 8.05 (s, 1H), 8.20 (s, 1H), 11.49 (s, 1H), 12.55 (s, 1H). | 380 | 378 |
| 324 | (structure) | ¹H-NMR (DMSO-D₆) δ: 1.01 (s, 6H), 1.59 (t, 2H, J = 6.25 Hz), 2.42 (s, 2H), 2.69 (t, 2H, J = 5.84 Hz), 6.69 (s, 1H), 7.45 (d, 1H, J = 8.66 Hz), 7.75 (dd, 1H, J = 8.66, 1.41 Hz), 8.29 (s, 1H), 11.69 (s, 1H), 12.02 (br s, 1H), 12.24 (br s, 1H), 12.60 (s, 1H). | 409 | 407 |
| 325 | (structure) | ¹H-NMR (DMSO-D₆) δ: 1.02 (s, 6H), 1.59 (t, 2H, J = 6.04 Hz), 2.42 (s, 2H), 2.70 (s, 2H), 4.10 (s, 3H), 6.70 (s, 1H), 7.47 (d, 1H, J = 8.87 Hz), 7.83 (d, 1H, J = 8.87 Hz), 8.38 (s, 1H), 11.70 (s, 1H), 12.55-12.60 (m, 2H). | 423 | 421 |
| 326 | (structure) | ¹H-NMR (DMSO-D₆) δ: 1.01 (s, 6H), 1.47 (s, 6H), 1.59 (t, 2H, J = 6.25 Hz), 2.42 (s, 2H), 2.68 (t, 2H, J = 5.84 Hz), 6.65 (s, 1H), 7.39 (d, 1H, J = 8.66 Hz), 7.59 (dd, 1H, J = 8.66, 1.81 Hz), 8.09 (s, 1H), 8.24 (s, 1H), 11.47 (s, 1H). | 395 | 393 |

TABLE 1-68

| Ex. No. | structural formula | NMR | MS (M + H) | MS (M − H) |
|---|---|---|---|---|
| 327 | (structure) | ¹H-NMR (DMSO-D₆) δ: 1.01 (s, 6H), 1.36 (s, 9H), 1.44 (s, 6H), 1.59 (t, 2H, J = 6.25 Hz), 2.42 (s, 2H), 2.68 (d, 2H, J = 6.04 Hz), 6.64 (s, 1H), 7.38 (d, 1H, J = 8.46 Hz), 7.56 (d, 1H, J = 8.46 Hz), 8.05 (s, 1H), 8.24 (s, 1H), 11.49 (s, 1H), 12.55 (s, 1H). | 451 | 449 |

TABLE 1-68-continued

| Ex. No. | structural formula | NMR | MS (M + H) | MS (M − H) |
|---|---|---|---|---|
| 328 | 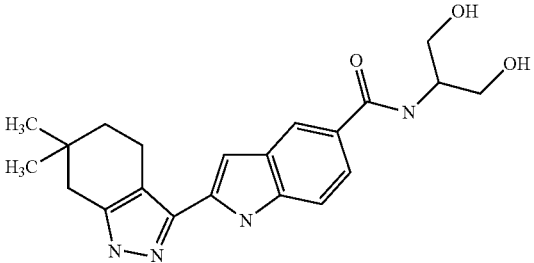 | ¹H-NMR (DMSO-D₆) δ: 1.01 (s, 6H), 1.58 (t, 2H, J = 6.25 Hz), 2.42 (s, 2H), 2.67 (s, 2H), 3.54 (t, 4H, J = 5.84 Hz), 3.98 (dd, 1H, J = 13.70, 6.04 Hz), 4.65 (t, 2H, J = 5.84 Hz), 6.64 (s, 1H), 7.38 (d, 1H, J = 8.06 Hz), 7.60 (d, 1H, J = 9.27 Hz), 7.72 (d, 1H, J = 8.06 Hz), 8.09 (s, 1H), 11.49 (s, 1H), 12.55 (s, 1H). | 383 | 381 |
| 329 | 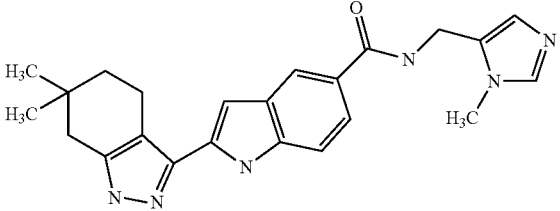 | ¹H-NMR (DMSO-D₆) δ: 2H, J = 6.45 Hz), 2.41 (s, 2H), 2.67 (s, 2H), 3.64 (s, 3H), 4.47 (d, 2H, J = 5.64 Hz), 6.63 (s, 1H), 6.83 (s, 1H), 7.38 (d, 1H, J = 8.46 Hz), 7.54 (s, 1H), 7.61 (d, 1H, J = 8.46 Hz), 8.09 (s, 1H), 8.63 (s, 1H), 11.50 (s, 1H), 12.55 (s, 1H). | 403 | 401 |
| 330 | 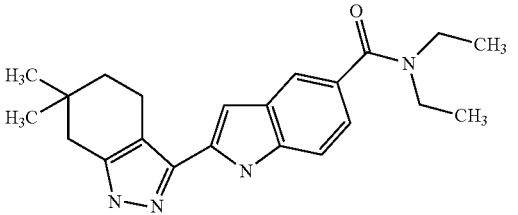 | ¹H-NMR (DMSO-D₆) δ: 1.01 (s, 6H), 1.11 (t, 6H, J = 6.65 Hz), 1.58 (t, 2H, J = 6.45 Hz), 2.41 (s, 2H), 2.63-2.72 (m, 2H), 3.25-3.46 (br m, 4H), 6.61 (s, 1H), 7.04 (d, 1H, J = 8.06 Hz), 7.39 (d, 1H, J = 8.06 Hz), 7.50 (s, 1H), 11.42 (s, 1H), 12.54 (s, 1H). | 365 | 363 |
| 331 | 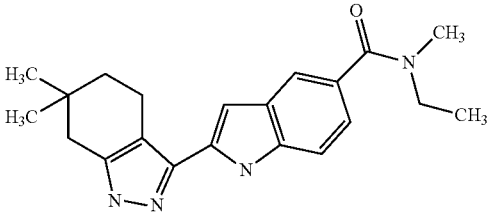 | ¹H-NMR (DMSO-D₆) δ: 1.01 (s, 6H), 1.11 (t, 3H, J = 6.65 Hz), 1.58 (t, 2H, J = 6.25 Hz), 2.41 (s, 2H), 2.68 (t, 2H, J = 6.25 Hz), 2.95 (s, 3H), 3.34-3.36 (m, 2H), 6.63 (d, 1H, J = 1.21 Hz), 7.08 (dd, 1H, J = 8.46, 1.21 Hz), 7.40 (d, 1H, J = 8.46 Hz), 7.54 (s, 1H), 11.40 (s, 1H). | 351 | 349 |
| 332 | 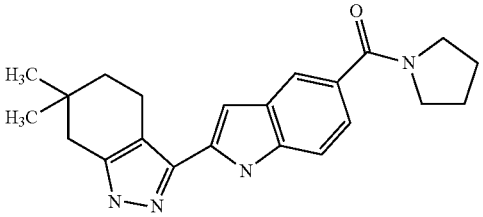 | ¹H-NMR (DMSO-D₆) δ: 1.01 (s, 6H), 1.58 (t, 2H, J = 6.45 Hz), 1.84 (d, 4H, J = 16.92 Hz), 2.41 (s, 2H), 2.66-2.68 (m, 2H), 3.48 (t, 4H, J = 6.65 Hz), 6.62 (s, 1H), 7.24 (d, 1H, J = 8.46 Hz), 7.38 (d, 1H, J = 8.46 Hz), 7.71 (s, 1H), 11.44 (s, 1H), 12.54 (s, 1H). | 363 | 361 |

TABLE 1-69

| Ex. No. | structural formula | NMR | MS (M + H) | MS (M − H) |
|---|---|---|---|---|
| 333 | 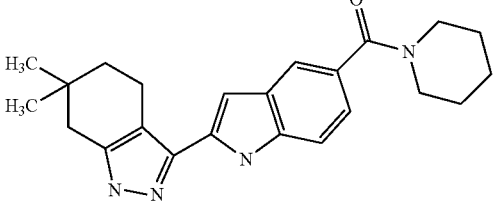 | $^1$H-NMR (DMSO-D$_6$) δ: 1.01 (s, 6H), 1.52-1.62 (m, 8H), 2.41 (s, 2H), 2.63-2.71 (m, 2H), 3.48 (s, 4H), 6.61 (s, 1H), 7.07 (d, 1H, J = 7.66 Hz), 7.39 (d, 1H, J = 7.66 Hz), 7.53 (s, 1H), 11.44 (s, 1H), 12.54 (s, 1H). | 377 | 375 |
| 334 | 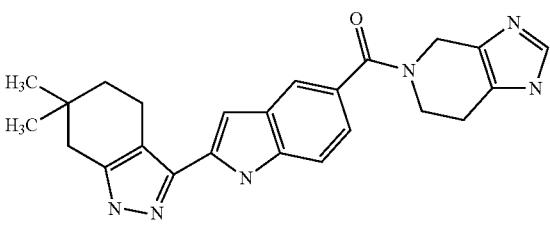 | $^1$H-NMR (DMSO-D$_6$) δ: 1.01 (s, 6H), 1.58 (t, 2H, J = 6.25 Hz), 2.42 (s, 2H), 2.62-2.72 (m, 4H), 3.75 (br s, 2H), 4.52 (br s, 2H), 6.65 (s, 1H), 7.15 (d, 1H, J = 8.46 Hz), 7.43 (d, 1H, J = 8.46 Hz), 7.49 (s, 1H), 7.62 (s, 1H), 11.48 (s, 1H), 12.55 (s, 1H). | 415 | 413 |
| 335 | 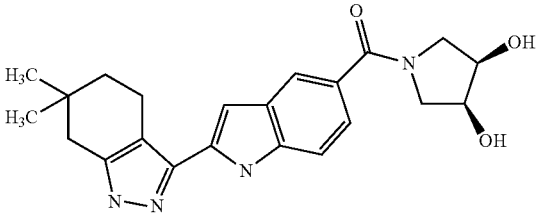 | $^1$H-NMR (DMSO-D$_6$) δ: 1.01 (s, 6H), 1.58 (t, 2H, J = 6.25 Hz), 2.41 (s, 2H), 2.63-2.72 (m, 2H), 3.34-3.40 (m, 2H), 3.58 (d, 1H, J = 5.44 Hz), 3.61 (d, 1H, J = 5.44 Hz), 3.98 (br s, 1H), 4.09 (br s, 1H), 4.92 (br s, 2H), 6.63 (s, 1H), 7.22 (d, 1H, J = 8.06 Hz), 7.39 (d, 1H, J = 8.06 Hz), 7.69 (s, 1H), 11.46 (s, 1H), 12.54 (s, 1H). | 395 | 393 |
| 336 | 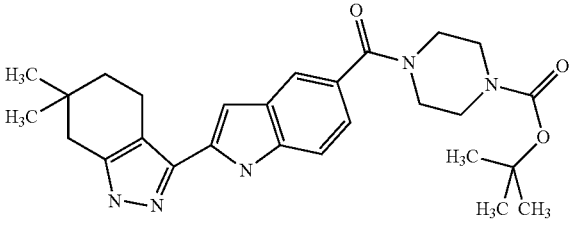 | $^1$H-NMR (DMSO-D$_6$) δ: 1.01 (s, 6H), 1.40 (d, 9H, J = 6.45 Hz), 1.58 (t, 2H, J = 6.25 Hz), 2.42 (s, 2H), 2.63-2.71 (m, 2H), 3.38 (br s, 4H), 3.50 (br s, 4H), 6.62 (s, 1H), 7.12 (d, 1H, J = 8.26 Hz), 7.41 (d, 1H, J = 8.26 Hz), 7.59 (s, 1H), 11.47 (s, 1H), 12.55 (s, 1H). | 478 | 476 |
| 337 | 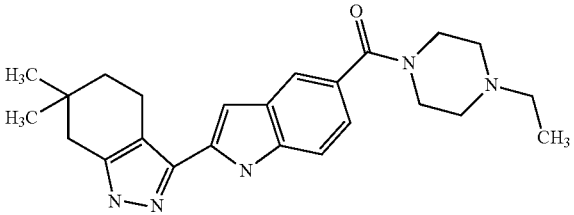 | $^1$H-NMR (DMSO-D$_6$) δ: 0.96-1.09 (m, 9H), 1.58 (t, 2H, J = 6.25 Hz), 2.26-2.50 (m, 6H), 2.41 (s, 2H), 2.61-2.75 (m, 2H), 3.40-3.66 (m, 4H), 6.63 (s, 1H), 7.10 (d, 1H, J = 8.46 Hz), 7.40 (d, 1H, J = 8.46 Hz), 7.56 (s, 1H), 11.46 (s, 1H), 12.55 (s, 1H). | 406 | 404 |

TABLE 1-69-continued

| Ex. No. | structural formula | NMR | MS (M + H) | MS (M − H) |
|---|---|---|---|---|
| 338 | | ¹H-NMR (DMSO-D₆) δ: 1.01 (s, 6H), 1.58 (t, 2H, J = 6.45 Hz), 2.41 (s, 2H), 2.63-2.71 (m, 2H), 3.24 (s, 3H), 3.37 (s, 3H), 3.43-3.52 (m, 2H), 3.57-3.71 (m, 2H), 3.84-3.94 (m, 1H), 3.95-4.05 (m, 1H), 6.64 (s, 1H), 7.24 (d, 1H, J = 8.26 Hz), 7.40 (d, 1H, J = 8.26 Hz), 7.71 (s, 1H), 11.46 (s, 1H), 12.54 (s, 1H). | 423 | 421 |

TABLE 1-70

| Ex. No. | structural formula | NMR | MS (M + H) | MS (M − H) |
|---|---|---|---|---|
| 339 | | ¹H-NMR (DMSO-D₆) δ: 0.99 (s, 6H), 1.54 (d, 2H, J = 5.51 Hz), 2.39 (s, 2H), 2.61 (s, 2H), 3.38 (s, 3H), 6.45 (s, 1H), 6.86 (d, 1H, J = 7.94 Hz), 7.18-7.23 (m, 7H), 11.28 (s, 1H), 12.50 (s, 1H). | 399 | 397 |
| 340 | | ¹H-NMR (DMSO-D₆) δ: 0.89 (t, 3H, J = 7.54 Hz), 1.01 (s, 6H), 1.59 (d, 2H, J = 6.40 Hz), 1.99 (q, 2H, J = 7.66 Hz), 2.41 (s, 2H), 2.67 (s, 1H), 3.17 (s, 4H), 6.58 (s, 1H), 6.94 (d, 1H, J = 9.04 Hz), 7.41 (s, 2H), 11.39 (s, 1H), 12.54 (s, 1H). | 351 | 349 |

TABLE 1-70-continued

| Ex. No. | structural formula | NMR | MS (M + H) | MS (M − H) |
|---|---|---|---|---|
| 341 | | ¹H-NMR (DMSO-D₆) δ: 1.01 (s, 6H), 1.41-1.66 (m, 6H), 2.41 (s, 3H), 2.67 (s, 2H), 2.94 (t, 2H, J = 11.68 Hz), 3.16 (s, 3H), 3.72 (d, 2H, J = 9.42 Hz), 6.60 (s, 1H), 6.96 (d, 1H, J = 9.42 Hz), 7.41-7.45 (m, 2H), 11.45 (s, 1H), 12.55 (s, 1H). | 407 | 405 |
| 342 | | ¹H-NMR (DMSO-D₆) δ: 0.75 (d, 6H, J = 6.40 Hz), 1.01 (s, 6H), 1.58 (t, 2H, J = 6.29 Hz), 1.91-1.97 (m, 3H), 2.42 (s, 2H), 2.66 (d, 2H, J = 5.95 Hz), 3.18 (s, 3H), 6.58 (s, 1H), 6.90 (d, 1H, J = 8.38 Hz), 7.38-7.41 (m, 2H), 11.41 (s, 1H), 12.54 (s, 1H). | 379 | 377 |

TABLE 1-71

| Ex. No. | structural formula | NMR | MS (M + H) | MS (M − H) |
|---|---|---|---|---|
| 343 | | ¹H-NMR (DMSO-D₆) δ: 1.01 (s, 6H), 1.58 (t, 2H, J = 6.29 Hz), 2.41 (s, 2H), 2.67 (s, 2H), 3.20 (t, 4H, J = 14.00 Hz), 3.69 (s, 2H), 6.58 (s, 1H), 6.95 (d, 1H, J = 7.94 Hz), 7.41-7.43 (m, 2H), 11.43 (s, 1H), 12.54 (s, 1H). | 353 | 351 |

TABLE 1-71-continued

| Ex. No. | structural formula | NMR | MS (M + H) | MS (M − H) |
|---|---|---|---|---|
| 344 | | ¹H-NMR (DMSO-D₆) δ: 1.01 (s, 6H), 1.58 (t, 2H, J = 6.29 Hz), 2.41 (s, 2H), 2.67 (d, 2H, J = 4.85 Hz), 6.55 (s, 1H), 7.35 (d, 2H, J = 5.51 Hz), 7.50-7.58 (m, 3H), 7.95-7.98 (m, 3H), 10.07 (s, 1H), 11.20 (s, 1H), 12.49 (s, 1H). | 385 | 383 |
| 345 | | ¹H-NMR (DMSO-D₆) δ: 1.00 (s, 6H), 1.10 (t, 3H, J = 7.50 Hz), 1.57 (t, 2H, J = 6.29 Hz), 2.30 (q, 2H, J = 7.57 Hz), 2.40 (s, 2H), 2.67 (d, 2H, J = 5.29 Hz), 6.49 (s, 1H), 7.16-7.26 (m, 2H), 7.81 (s, 1H), 9.61 (s, 1H), 11.11 (s, 1H), 12.47 (s, 1H). | 337 | 335 |
| 346 | | ¹H-NMR (DMSO-D₆) δ: 0.92 (3H, s), 0.96-1.06 (2H, m), 1.21-1.39 (2H, m), 1.50-1.80 (6H, m), 2.21-2.33 (1H, m), 2.29 (1H, d, J = 16.52 Hz), 2.55 (1H, d, J = 16.52 Hz), 2.57-2.73 (2H, m), 3.16 (6H, s), 3.18-3.24 (1H, m), 3.26 (2H, d, J = 5.24 Hz), 4.62 (1H, t, J = 5.24 Hz), 6.59 (1H, s), 6.86 (1H, d, J = 7.66 Hz), 7.23 (1H, s), 7.54 (1H, d, J = 7.66 Hz), 11.32 (1H, s), 12.50 (1H, s). | 451 | 449 |
| 347 | | ¹H-NMR (DMSO-D₆) δ: 0.98 (3H, s), 1.53-1.75 (6H, m), 2.11-2.21 (2H, m), 2.35 (1H, d, J = 16.12 Hz), 2.56 (1H, d, J = 15.72 Hz), 2.61-2.70 (2H, m), 3.15-3.26 (7H, m), 3.28 (3H, s), 3.77 (2H, s), 6.60 (1H, s), 6.92 (1H, d, J = 7.66 Hz), 7.29 (1H, s), 7.56 (1H, d, J = 7.66 Hz), 11.45 (1H, s), 12.55 (1H, s). | 464 | 462 |

TABLE 1-72
| Ex. No. | structural formula | NMR | MS (M + H) | MS (M − H) |
|---|---|---|---|---|
| 348 | 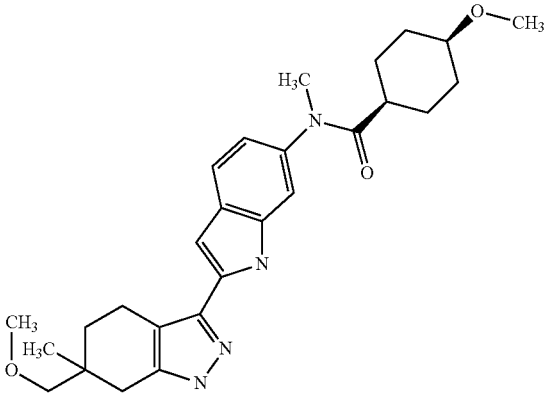 | ¹H-NMR (DMSO-D₆) δ: 0.95-1.06 (2H, m), 0.98 (3H, s), 1.28-1.36 (2H, m), 1.54-1.79 (6H, m), 2.20-2.29 (1H, m), 2.35 (1H, d, J = 16.12 Hz), 2.56 (1H, d, J = 16.12 Hz), 2.62-2.70 (2H, m), 3.15 (6H, s), 3.19 (2H, s), 3.19-3.24 (1H, m), 3.28 (3H, s), 6.60 (1H, s), 6.86 (1H, d, J = 8.06 Hz), 7.23 (1H, s), 7.55 (1H, d, J = 8.06 Hz), 11.36 (1H, s), 12.54 (1H, s). | 465 | 463 |
| 349 | 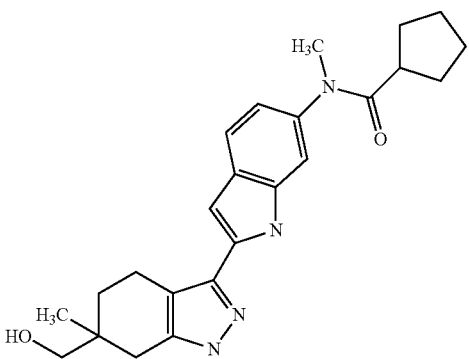 | ¹H-NMR (DMSO-D₆) δ: 0.92 (3H, s), 1.21-1.39 (2H, m), 1.46-1.72 (8H, m), 2.29 (1H, d, J = 15.88 Hz), 2.43-2.75 (4H, m), 3.18 (3H, s), 3.23-3.29 (2H, m), 4.65 (1H, t, J = 4.96 Hz), 6.58 (1H, s), 6.86 (1H, d, J = 8.38 Hz), 7.23 (1H, s), 7.54 (1H, d, J = 8.38 Hz), 11.36 (1H, s), 12.52 (1H, s). | 407 | 405 |
| 350 | 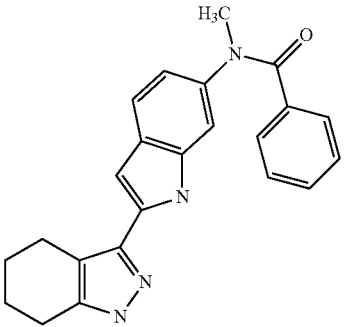 | ¹H-NMR (DMSO-D₆) δ: 1.68-1.81 (m, 4H), 2.56-2.68 (m, 4H), 3.39 (s, 3H), 6.46 (s, 1H), 6.81 (d, 1H, J = 8.35 Hz), 7.07 (s, 1H), 7.12-7.23 (m, 3H), 7.28 (d, 2H, J = 6.72 Hz), 7.37 (d, 1H, J = 8.35 Hz), 11.23 (s, 1H), 12.52 (s, 1H). | 371 | 369 |
| 351 | 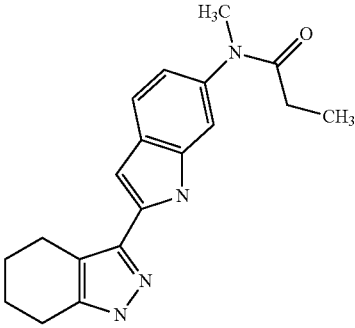 | ¹H-NMR (DMSO-D₆) δ: 0.91 (t, 3H, J = 7.42 Hz), 1.73-1.83 (m, 4H), 2.01 (q, 2H, J = 7.42 Hz), 2.58-2.71 (m, 4H), 3.18 (s, 3H), 6.56 (s, 1H), 6.86 (d, 1H, J = 8.12 Hz), 7.22 (s, 1H), 7.54 (d, 1H, J = 8.12 Hz), 11.40 (s, 1H), 12.57 (s, 1H). | 323 | 321 |

TABLE 1-72-continued

| Ex. No. | structural formula | NMR | MS (M + H) | MS (M − H) |
|---|---|---|---|---|
| 352 | 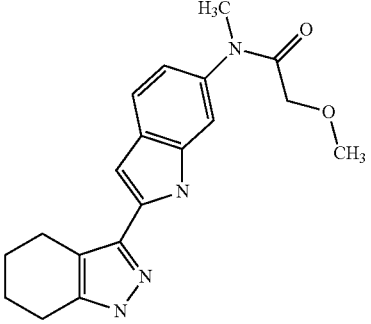 | ¹H-NMR (DMSO-D₆) δ: 1.71-1.84 (m, 4H), 2.56-2.74 (m, 4H), 3.18 (s, 3H), 3.19 (s, 3H), 3.73 (s, 2H), 6.57 (s, 1H), 6.88 (d, 1H, J = 8.00 Hz), 7.24 (s, 1H), 7.54 (d, 1H, J = 8.00 Hz), 11.43 (s, 1H), 12.58 (s, 1H). | 339 | 337 |

TABLE 1-73

| Ex. No. | structural formula | NMR | MS (M + H) | MS (M − H) |
|---|---|---|---|---|
| 353 | 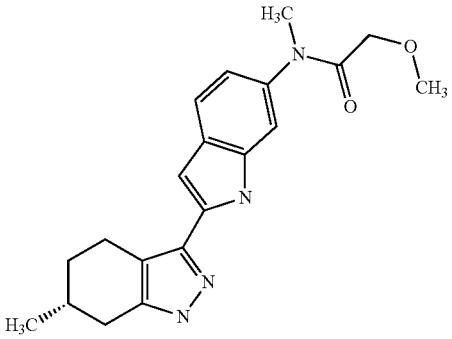 | ¹H-NMR (DMSO-D₆) δ: 1.08 (d, 3H, J = 6.45 Hz), 1.34-1.49 (m, 1H), 1.82-1.97 (m, 2H), 2.15-2.27 (m, 1H), 2.58-2.69 (m, 1H), 2.70-2.82 (m, 2H), 3.18 (s, 3H), 3.19 (s, 3H), 3.73 (s, 2H), 6.57 (s, 1H), 6.88 (d, 1H, J = 8.26 Hz), 7.24 (s, 1H), 7.54 (d, 1H, J = 8.26 Hz), 11.42 (s, 1H), 12.55 (s, 1H). | 353 | 351 |
| 354 | 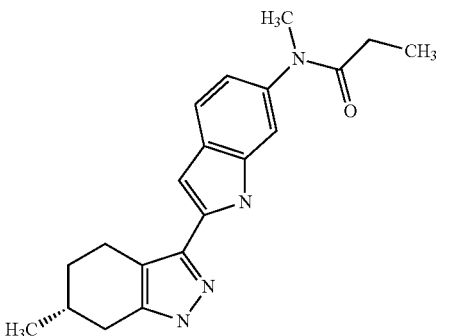 | ¹H-NMR (DMSO-D₆) δ: 0.91 (t, 3H, J = 7.42 Hz), 1.08 (d, 3H, J = 6.85 Hz), 1.33-1.49 (m, 1H), 1.83-1.95 (m, 2H), 2.01 (q, 2H, J = 7.42 Hz), 2.15-2.27 (m, 1H), 2.57-2.69 (m, 1H), 2.69-2.82 (m, 2H), 3.17 (s, 3H), 6.56 (s, 1H), 6.86 (d, 1H, J = 8.26 Hz), 7.22 (s, 1H), 7.54 (d, 1H, J = 8.26 Hz), 11.38 (s, 1H), 12.54 (s, 1H). | 337 | 335 |
| 355 | 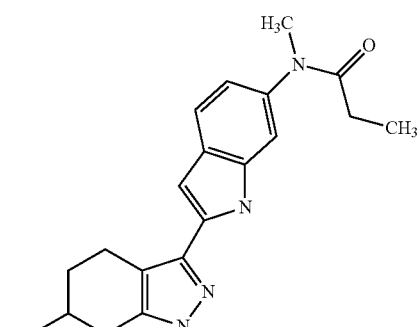 | ¹H-NMR (DMSO-D₆) δ: 0.91 (t, 3H, J = 7.38 Hz), 1.08 (d, 3H, J = 6.49 Hz), 1.34-1.49 (m, 1H), 1.83-1.95 (m, 2H), 2.01 (q, 2H, J = 7.38 Hz), 2.15-2.27 (m, 1H), 2.56-2.69 (m, 1H), 2.70-2.83 (m, 2H), 3.18 (s, 3H), 6.57 (s, 1H), 6.86 (d, 1H, J = 8.12 Hz), 7.22 (s, 1H), 7.54 (d, 1H, J = 8.12 Hz), 11.40 (s, 1H), 12.55 (s, 1H). | 337 | 335 |

TABLE 1-73-continued

| Ex. No. | structural formula | NMR | MS (M + H) | MS (M − H) |
|---|---|---|---|---|
| 356 | | ¹H-NMR (DMSO-D₆) δ: 1.08 (d, 3H, J = 6.62 Hz), 1.34-1.50 (m, 1H), 1.83-1.98 (m, 2H), 2.15-2.27 (m, 1H), 2.58-2.69 (m, 1H), 2.70-2.84 (m, 2H), 3.18 (s, 3H), 3.19 (s, 3H), 3.73 (s, 2H), 6.57 (s, 1H), 6.88 (d, 1H, J = 7.83 Hz), 7.24 (s, 1H), 7.54 (d, 1H, J = 7.83 Hz), 11.42 (s, 1H), 12.54 (s, 1H). | 353 | 351 |
| 357 | | ¹H-NMR (DMSO-D₆) δ: 1.06 (d, 3H, J = 6.49 Hz), 1.31-1.47 (m, 1H), 1.80-1.94 (m, 2H), 2.13-2.25 (m, 1H), 2.53-2.64 (m, 1H), 2.65-2.78 (m, 2H), 3.39 (s, 3H), 6.46 (s, 1H), 6.81 (d, 1H, J = 8.23 Hz), 7.07 (s, 1H), 7.15-7.19 (m, 3H), 7.28 (d, 2H, J = 6.72 Hz), 7.37 (d, 1H, J = 8.23 Hz), 11.23 (s, 1H), 12.50 (s, 1H). | 385 | 383 |

TABLE 1-74

| Ex. No. | structural formula | NMR | MS (M + H) | MS (M − H) |
|---|---|---|---|---|
| 358 | | ¹H-NMR (DMSO-D₆) δ: 1.06 (d, 3H, J = 6.49 Hz), 1.31-1.47 (m, 1H), 1.79-1.94 (m, 2H), 2.11-2.25 (m, 1H), 2.55-2.64 (m, 1H), 2.65-2.78 (m, 2H), 3.39 (s, 3H), 6.46 (s, 1H), 6.81 (d, 1H, J = 8.23 Hz), 7.07 (s, 1H), 7.12-7.23 (m, 3H), 7.28 (d, 2H, J = 6.49 Hz), 7.37 (d, 1H, J = 8.23 Hz), 11.23 (s, 1H), 12.50 (s, 1H). | 385 | 383 |
| 359 | | ¹H-NMR (DMSO-D₆) δ: 0.95 (d, 6H, J = 5.95 Hz), 1.72-1.84 (m, 4H), 2.59-2.73 (m, 4H), 3.18 (s, 3H), 3.39-3.48 (m, 1H), 3.75 (s, 2H), 6.57 (s, 1H), 6.88 (d, 1H, J = 8.16 Hz), 7.25 (s, 1H), 7.54 (d, 1H, J = 8.16 Hz), 11.41 (s, 1H), 12.56 (s, 1H). | 367 | 365 |

TABLE 1-74-continued

| Ex. No. | structural formula | NMR | MS (M + H) | MS (M − H) |
|---|---|---|---|---|
| 360 | | ¹H-NMR (DMSO-D₆) δ: 1.75 (s, 3H), 1.76-1.82 (m, 4H), 2.57-2.72 (m, 4H), 3.17 (s, 3H), 6.56 (s, 1H), 6.88 (d, 1H, J = 8.12 Hz), 7.23 (s, 1H), 7.54 (d, 1H, J = 8.12 Hz), 11.40 (s, 1H), 12.57 (s, 1H). | 309 | 307 |
| 361 | | ¹H-NMR (DMSO-D₆) δ: 0.76 (d, 6H, J = 6.49 Hz), 1.72-1.84 (m, 4H), 1.91 (d, 2H, J = 6.72 Hz), 1.92-2.04 (m, 1H), 2.57-2.73 (m, 4H), 3.18 (s, 3H), 6.56 (s, 1H), 6.83 (d, 1H, J = 8.23 Hz), 7.19 (s, 1H), 7.54 (d, 1H, J = 8.23 Hz), 11.39 (s, 1H), 12.57 (s, 1H). | 351 | 349 |
| 362 | | ¹H-NMR (DMSO-D₆) δ: 1.74-1.82 (m, 4H), 2.58-2.72 (m, 4H), 3.23 (s, 3H), 4.42 (s, 2H), 6.59 (s, 1H), 6.75 (d, 2H, J = 7.88 Hz), 6.90 (t, 1H, J = 7.30 Hz), 7.02 (d, 1H, J = 7.65 Hz), 7.23 (t, 2H, J = 7.88 Hz), 7.38 (s, 1H), 7.59 (d, 1H, J = 8.35 Hz), 11.47 (s, 1H), 12.58 (s, 1H). | 401 | 399 |

TABLE 1-75

| Ex. No. | structural formula | NMR | MS (M + H) | MS (M − H) |
|---|---|---|---|---|
| 363 | | ¹H-NMR (DMSO-D₆) δ: 1.01 (s, 3H), 1.04 (s, 3H), 2.48 (dd, 2H, J = 53.80, 15.92 Hz), 2.72-3.04 (m, 2H), 3.51 (t, 1H, J = 5.04 Hz), 4.61 (dd, 2H, J = 85.63, 11.89 Hz), 5.09 (s, 2H), 6.59 (s, 1H), 6.89 (d, 1H, J = 8.26 Hz), 7.22-7.39 (m, 11H), 7.48 (d, 1H, J = 8.26 Hz), 11.29 (s, 1H), 12.52 (s, 1H). | 535 | 533 |

TABLE 1-75-continued

| Ex. No. | structural formula | NMR | MS (M + H) | MS (M − H) |
|---|---|---|---|---|
| 364 | | ¹H-NMR (DMSO-D₆) δ: 0.91 (t, 3H, J = 7.29 Hz), 1.03 (d, 6H, J = 15.72 Hz), 2.01 (q, 2H, J = 7.29 Hz), 2.49 (dd, 23H, J = 54.60, 15.92 Hz), 2.74-3.03 (m, 2H), 3.18 (s, 3H), 3.51 (t, 1H, J = 5.04 Hz), 4.61 (dd, 2H, J = 86.84, 11.89 Hz), 6.65 (s, 1H), 6.88 (d, 1H, J = 8.26 Hz), 7.20-7.39 (m, 6H), 7.56 (d, 1H, J = 8.26 Hz), 11.38 (s, 1H), 12.58 (br s, 1H). | 457 | 455 |
| 365 | | ¹H-NMR (DMSO-D₆) δ: 0.91 (3H, t, J = 7.42 Hz), 1.76-1.90 (2H, m), 2.01 (2H, q, J = 7.42 Hz), 2.51-2.77 (4H, m), 2.93 (2H, dd, J = 15.19, 4.29 Hz), 3.18 (3H, s), 4.01-4.03 (1H, m), 4.84 (1H, d, J = 3.94 Hz), 6.55 (1H, s), 6.87 (1H, d, J = 8.12 Hz), 7.23 (1H, s), 7.56 (1H, d, J = 8.12 Hz), 11.39 (1H, s), 12.57 (1H, s). | 339 | 37 |
| 366 | | ¹H-NMR (DMSO-D₆) δ: 1.74-1.90 (2H, m), 2.53-2.76 (5H, m), 2.90-2.94 (1H, m), 3.17 (3H, s), 3.18 (3H, s), 3.73 (2H, s), 3.96-4.05 (1H, m), 4.83 (1H, d, J = 3.71 Hz), 6.55 (1H, s), 6.89 (1H, d, J = 7.88 Hz), 7.24 (1H, s), 7.55 (1H, d, J = 8.12 Hz), 11.42 (1H, s), 12.58 (1H, s). | 355 | 33 |
| 367 | | ¹H-NMR (DMSO-D₆) δ: 1.69-1.89 (2H, m), 2.45-2.74 (5H, m), 2.86-2.90 (1H, m), 3.39 (3H, s), 3.93-4.02 (1H, m), 4.81 (1H, s), 6.44 (1H, s), 6.81 (1H, d, J = 8.12 Hz), 7.07 (1H, s), 7.15-7.18 (3H, m), 7.28 (2H, d, J = 6.49 Hz), 7.38 (1H, d, J = 8.12 Hz), 11.22 (1H, s), 12.52 (1H, s). | 387 | 385 |

TABLE 1-76

| Ex. No. | structural formula | NMR | MS (M + H) | MS (M − H) |
|---|---|---|---|---|
| 368 | | ¹H-NMR (DMSO-D₆) δ: 0.90 (3H, t, J = 7.42 Hz), 1.82-2.05 (2H, m), 2.00 (4H, q, J = 7.42 Hz), 2.56-2.75 (3H, m), 2.98-2.99 (1H, m), 3.17 (3H, s), 3.33 (3H, s), 3.72 (1H, d, J = 5.57 Hz), 6.59 (1H, s), 6.87 (1H, d, J = 8.58 Hz), 7.22 (1H, s), 7.55 (1H, d, J = 8.58 Hz), 11.39 (1H, s), 12.60 (1H, s). | 353 | 351 |
| 369 | | ¹H-NMR (DMSO-D₆) δ: 1.85-1.98 (2H, m), 2.61-2.72 (3H, m), 2.96-3.00 (1H, m), 3.17 (3H, s), 3.18 (3H, s), 3.33 (2H, s), 3.69-3.75 (1H, m), 3.73 (3H, s), 6.60 (1H, s), 6.89 (1H, d, J = 8.12 Hz), 7.25 (1H, s), 7.55 (1H, d, J = 8.12 Hz), 11.43 (1H, s), 12.61 (1H, s). | 369 | 367 |
| 370 | | ¹H-NMR (DMSO-D₆) δ: 1.85-1.93 (2H, m), 2.61-2.65 (3H, m), 2.91-2.95 (1H, m), 3.31 (3H, s), 3.39 (3H, s), 3.69 (1H, d, J = 5.80 Hz), 6.49 (1H, s), 6.81 (1H, d, J = 8.58 Hz), 7.07 (1H, s), 7.15-7.18 (3H, m), 7.27-7.28 (2H, m), 7.38 (1H, d, J = 8.58 Hz), 11.22 (1H, s), 12.55 (1H, s). | 401 | 399 |
| 371 | | ¹H-NMR (DMSO-D₆) δ: 0.90 (4H, t, J = 7.30 Hz), 1.10 (3H, d, J = 6.03 Hz), 1.12 (3H, d, J = 6.03 Hz), 1.73-1.96 (2H, m), 2.01 (2H, q, J = 7.30 Hz), 2.53-2.71 (4H, m), 2.94-2.98 (1H, m), 3.17 (3H, s), 3.80 (1H, sept,) = 6.03 Hz), 3.84-3.94 (1H, m), 6.57 (1H, s), 6.86 (1H, d, J = 7.88 Hz), 7.22 (1H, s), 7.54 (1H, d, J = 7.88 Hz), 11.37 (1H, s), 12.58 (1H, s). | 381 | 379 |

TABLE 1-76-continued

| Ex. No. | structural formula | NMR | MS (M + H) | MS (M – H) |
|---|---|---|---|---|
| 372 | | ¹H-NMR (DMSO-D₆) δ: 0.91 (3H, t, J = 7.39 Hz), 0.98 (3H, s), 1.01 (3H, s), 2.01 (2H, q, J = 7.39 Hz), 2.39 (1H, d, J = 16.10 Hz), 2.51 (9H, d, J = 16.10 Hz), 2.70 (1H, dd, J = 16.54, 5.07 Hz), 2.92 (1H, dd, J = 16.54, 4.41 Hz), 3.18 (3H, s), 3.25 (1H, dd, J = 5.07, 4.41 Hz), 3.34 (4H, s), 6.65 (1H, s), 6.88 (1H, d, J = 8.16 Hz), 7.24 (1H, s), 7.56 (1H, d, J = 8.16 Hz), 11.38 (1H, s), 12.55 (1H, s). | 381 | 379 |

TABLE 1-77

| Ex. No. | structural formula | NMR | MS (M + H) | MS (M – H) |
|---|---|---|---|---|
| 373 | | ¹H-NMR (DMSO-D₆) δ: 0.91 (3H, t, J = 7.45 Hz), 0.96 (6H, s), 2.01 (2H, q, J = 7.45 Hz), 2.37 (1H, d, J = 16.12 Hz), 2.53-2.61 (1H, m), 2.57 (1H, d, J = 16.12 Hz), 2.83-2.92 (1H, m), 3.18 (3H, s), 3.58-3.61 (1H, m), 4.70 (1H, d, J = 4.84 Hz), 6.55 (1H, s), 6.86 (1H, d, J = 8.46 Hz), 7.23 (1H, s), 7.55 (1H, d, J = 8.46 Hz), 11.35 (1H, s), 12.50 (1H, s). | 367 | 365 |
| 374 | | ¹H-NMR (DMSO-D₆) δ: 1.00 (6H, s), 1.57 (2H, t, J = 6.25 Hz), 2.04 (3H, s), 2.40 (2H, s), 2.60-2.68 (2H, m), 6.48 (1H, s), 7.04 (1H, dd, J = 8.46, 1.61 Hz), 7.37 (1H, d, J = 8.46 Hz), 7.87 (1H, s), 9.78 (1H, s), 11.12 (1H, s), 12.42 (1H, s). | 323 | 321 |
| 375 | | ¹H-NMR (DMSO-D₆) δ: 1.01 (6H, s), 1.21 (3H, d, J = 6.85 Hz), 1.57 (2H, t, J = 6.25 Hz), 2.40 (2H, s), 2.49-2.69 (6H, m), 3.22 (1H, q, J = 6.85 Hz), 3.58-3.67 (4H, m), 6.49 (1H, s), 7.08 (1H, d, J = 8.46 Hz), 7.39 (1H, d, J = 8.46 Hz), 7.89 (1H, s), 9.65 (1H, s), 11.17 (1H, s), 12.44 (1H, s). | 422 | 420 |

TABLE 1-78

| Ex. No. | structural formula | NMR | MS (M + H) | MS (M − H) |
|---|---|---|---|---|
| 376 | | ¹H-NMR (DMSO-D₆) δ: 0.98 (d, 3H, J = 6.45 Hz), 1.01 (s, 6H), 1.58 (t, 2H, J = 6.25 Hz), 2.23-2.29 (m, 1H), 2.41 (s, 2H), 2.49-2.56 (m, 1H), 2.66-2.69 (m, 2H), 3.17 (q, 1H, J = 6.72 Hz), 3.22 (s, 3H), 4.39-4.41 (m, 1H), 6.62 (s, 1H), 6.87 (d, 1H, J = 8.26 Hz), 7.26 (s, 1H), 7.57 (d, 1H, J = 8.26 Hz), 11.38 (s, 1H), 12.54 (s, 1H). | 410 | 408 |
| 377 | | ¹H-NMR (DMSO-D₆) δ: 0.97 (d, 3H, J = 6.69 Hz), 1.01 (s, 6H), 1.58 (t, 2H, J = 6.29 Hz), 2.41 (s, 2H), 2.63-2.72 (m, 2H), 3.19 (s, 3H), 3.37 (q, 1H, J = 6.69 Hz), 6.61 (s, 1H), 6.91 (d, 1H, J = 8.16 Hz), 7.28 (s, 1H), 7.56 (d, 1H, J = 8.16 Hz), 11.42 (s, 1H), 12.55 (s, 1H). | 366 | 364 |
| 378 | | ¹H-NMR (DMSO-D₆) δ: 1.01 (6H, s), 1.01 (3H, d, J = 5.64 Hz), 1.58 (2H, t, J = 6.25 Hz), 2.41 (2H, s), 2.56-2.72 (3H, m), 3.18 (3H, s), 3.20-3.48 (5H, m), 3.62-3.73 (1H, m), 4.44-4.54 (1H, m), 6.28-6.35 (1H, m), 6.59 (1H, s), 6.88 (1H, d, J = 8.46 Hz), 7.27 (1H, s), 7.54 (1H, d, J = 8.46 Hz), 11.39 (1H, s), 12.53 (1H, s). | 452 | 450 |
| 379 | | ¹H-NMR (DMSO-D6) δ: 1.01 (6H, s), 1.04 (3H, d, J = 6.85 Hz), 1.58 (2H, t, J = 6.25 Hz), 2.41 (2H, s), 2.58 (1H, q, J = 6.18 Hz), 2.68 (2H, t, J = 5.84 Hz), 3.05-3.52 (10H, m), 6.61 (1H, s), 6.90 (1H, d, J = 8.46 Hz), 7.30 (1H, s), 7.55 (1H, d, J = 8.46 Hz), 11.37 (1H, s), 12.52 (1H, s). | 468 | 466 |
| 380 | | ¹H-NMR (DMSO-D₆) δ: 1.01 (6H, s), 1.26 (3H, d, J = 6.72 Hz), 1.58 (2H, t, J = 6.15 Hz), 2.43 (2H, s), 2.68 (2H, t, J = 6.26 Hz), 3.05 (2H, s), 3.28 (3H, s), 3.73 (2H, t, J = 5.10 Hz), 3.87 (1H, d, J = 5.80 Hz), 4.06 (2H, s), 6.67 (1H, d, J = 1.39 Hz), 7.01 (1H, dd, J = 8.35, 1.86 Hz), 7.39 (1H, s), 7.62 (1H, d, J = 8.12 Hz), 8.93 (1H, s), 9.20 (1H, s), 11.58 (1H, s). | 468 | 466 |

TABLE 1-78-continued

| Ex. No. | structural formula | NMR | MS (M + H) | MS (M − H) |
|---|---|---|---|---|
| 381 | (structure with morpholine, indole, tetrahydroindazole, HCl) | ¹H-NMR (DMSO-D₆) δ: 1.00 (6H, s), 1.36 (3H, d, J = 5.8 Hz), 1.56-1.60 (2H, m), 2.42 (2H, s), 2.66-2.69 (2H, m), 2.96-3.20 (2H, m), 3.23-3.46 (6H, m), 3.69-3.87 (4H, m), 6.60-6.66 (1H, m), 6.87-7.01 (1H, m), 7.27-7.37 (1H, m), 7.51-7.64 (1H, m), 10.44 (1H, br s), 11.54 (1H, br s), 12.60 (1H, br s). | 436 | 434 |

Experimental Example

ITK Inhibitory Activity (1) Preparation of hITK Enzyme hITK enzyme was prepared by strongly expressing FLAG-tagged full-length hITK in Sf9 cells, and purifying same by anti-FLAG antibody column.

(2) Preparation of biotinylated GST-SLP76

Biotinylated GST-SLP76 was prepared by strongly expressing GST-tagged SLP76 (aa95-175) in *Escherichia coli*, purifying same by glutathion sepharose column and biotinylating same.

(3) Preparation of Solution (i) buffer for dilution: 20 mmol/L 3-(N-morpholino)propanesulfonic acid (pH 7.0) (DOJINDO LABORATORIES), 10 mmol/L magnesium chloride (Sigma-Aldrich Corporation), 1 mmol/L dithiothreitol (Nacalai Tesque, Inc.), 0.1% gelatin (Sigma-Aldrich Corporation)

(ii) substrate solution: 0.2 μg/mL biotinylated GST-SLP76, 100 μmol/L ATP (Sigma-Aldrich Corporation), prepared with buffer for dilution (iii) test compound solution: test compound, 50% dimethyl sulfoxide (DMSO), prepared with buffer for dilution (iv) enzyme solution: 50 ng/mL hITK enzyme, prepared with buffer for dilution (v) control solution: solution after removal of test compound from the mixture of the above-mentioned (i), (ii) and (iii)

(vi) blank solution: solution after removal of ATP from the mixture of the above-mentioned (i), (ii) and (iii)

(vii) detection buffer: 0.1 μg/mL Anti-Phosphotyrosine (PT66)-Cryptate (Cisbio), 2.5 μg/mL streptavidin-binding XL665 (Cisbio), 50 mmol/L 4-(2-hydroxyethyl)-1-piperazineethanesulfonic acid (pH 7.4) (Nacalai Tesque, Inc.), 30 mmol/L EDTA (NipponGene), 0.1% TritonX (Sigma-Aldrich Corporation), 200 mmol/L potassium fluoride (Wako Pure Chemical Industries, Ltd.), 0.05% bovine serum albumin (Sigma-Aldrich Corporation)

(4) Measurement of ITK Inhibitory Activity

A substrate solution (25 μL/well), a test compound solution (5 μL/well) and an enzyme solution (20 μL/well) were added into 96 well half-area white plate (plate, Corning Incorporated 3642) to start a kinase reaction. The plate was stood still at room temperature for 10 min. Then, a detection buffer (50 μL/well) was added to the plate. After 2 hr from the addition of the detection buffer, fluorescence intensity at 620 nm (excited at 337 nm), and fluorescence intensity at 665 nm (excited at 620 nm) were measured by a fluorescence microplate reader.

The Ratio (fluorescence intensity at 665 nm/fluorescence intensity at 620 nm×10000) of each test compound was calculated from the measured fluorescence intensity. Simultaneously, the measurement was performed using a blank solution and a control solution, and % of control value of each test compound was calculated from the following formula.

% of control=(Ratio of test compound−Ratio of blank)/(Ratio of control−Ratio of blank)×100
ITK inhibitory rate (%)=100−(% of control)

The $IC_{50}$ value was calculated from the test compound concentrations at 2 points sandwiching 50% ITK inhibitory rate. The results are shown in Table 2 in nM values. The numerical value in % in the Table shows the ITK inhibitory rate (%) at the concentration indicated in the parenthesis.

TABLE 2

| Ex. No. | ITK $IC_{50}$ (nM) |
|---|---|
| 1 | 7 |
| 2 | 5 |
| 3 | 39 |
| 4 | 2 |
| 5 | 3 |
| 6 | 2 |
| 7 | 39 |
| 8 | 3 |
| 9 | 334 |
| 10 | 45 |
| 11 | 36 |
| 12 | 33 |
| 13 | 99 |
| 14 | 40 |
| 15 | 9 |
| 16 | 25 |
| 17 | 5 |
| 18 | 45 |
| 19 | 23 |
| 20 | 47 |
| 21 | 30 |
| 22 | 40 |
| 23 | 18 |
| 24 | 25 |
| 25 | 26 |
| 26 | 85 |
| 27 | 327 |
| 28 | 201 |
| 29 | 85 |
| 30 | 10 |
| 31 | 34 |
| 32 | 4 |
| 33 | 11 |
| 34 | 5 |
| 35 | 5 |
| 36 | <3 |

TABLE 2-continued

| Ex. No. | ITK IC$_{50}$ (nM) |
|---|---|
| 37 | 8 |
| 38 | 5 |
| 39 | 4 |
| 40 | 6 |
| 41 | 4 |
| 42 | 22 |
| 43 | 6 |
| 44 | <3 |
| 45 | <3 |
| 46 | 5 |
| 47 | 8 |
| 48 | 6 |
| 49 | 3 |
| 50 | 4 |
| 51 | 26 |
| 52 | <3 |
| 53 | 8 |
| 54 | 18 |
| 55 | <3 |
| 56 | <3 |
| 57 | 17 |
| 58 | 6 |
| 59 | 7 |
| 60 | 5 |
| 61 | 6 |
| 62 | 4 |
| 63 | 6 |
| 64 | 6 |
| 65 | 55 |
| 66 | 3 |
| 67 | 4 |
| 68 | 7 |
| 69 | 4 |
| 70 | 3 |
| 71 | <3 |
| 72 | 9 |
| 73 | <3 |
| 74 | 4 |
| 75 | 34 |
| 76 | 4 |
| 77 | 6 |
| 78 | 7 |
| 79 | 13 |
| 80 | 3 |
| 81 | 8 |
| 82 | 7 |
| 83 | <3 |
| 84 | <3 |
| 85 | 4 |
| 86 | <3 |
| 87 | <3 |
| 88 | 3 |
| 89 | <3 |
| 90 | 4 |
| 91 | 13 |
| 92 | 10 |
| 93 | 48 |
| 94 | 4 |
| 95 | 3 |
| 96 | 3 |
| 97 | 20 |
| 98 | 3 |
| 99 | 26 |
| 100 | 5 |
| 101 | 13 |
| 102 | 117 |
| 103 | 3 |
| 104 | 4 |
| 105 | 2 |
| 106 | 7 |
| 107 | 10 |
| 108 | 15 |
| 109 | 6 |
| 110 | 7 |
| 111 | 9 |
| 112 | 7 |
| 113 | 9 |
| 114 | 5 |

TABLE 2-continued

| Ex. No. | ITK IC$_{50}$ (nM) |
|---|---|
| 115 | 4 |
| 116 | 9 |
| 117 | 6 |
| 118 | 3 |
| 119 | 3 |
| 120 | 5 |
| 121 | 5 |
| 122 | 20 |
| 123 | 2 |
| 124 | 12 |
| 125 | 1 |
| 126 | 8 |
| 127 | 1 |
| 128 | 2 |
| 129 | 5 |
| 130 | 2 |
| 131 | 25 |
| 132 | 13 |
| 133 | 10 |
| 134 | 8 |
| 135 | 6 |
| 136 | 2 |
| 137 | 2 |
| 138 | 3 |
| 139 | 2 |
| 140 | 2 |
| 141 | 10 |
| 142 | 5 |
| 143 | 3 |
| 144 | 9 |
| 145 | 3 |
| 146 | 11 |
| 147 | 8 |
| 148 | 19 |
| 149 | 10 |
| 150 | 2 |
| 151 | 3 |
| 152 | 14 |
| 153 | 5 |
| 154 | 2 |
| 155 | 9 |
| 156 | <1 |
| 157 | 1 |
| 158 | 5 |
| 159 | 7 |
| 160 | 1 |
| 161 | 22 |
| 162 | 1 |
| 163 | 1 |
| 164 | 3 |
| 165 | 5 |
| 166 | 1 |
| 167 | 1 |
| 168 | 3 |
| 169 | 3 |
| 170 | <1 |
| 171 | 1 |
| 172 | 2 |
| 173 | 13 |
| 174 | 2 |
| 175 | 2 |
| 176 | 7 |
| 177 | 2 |
| 178 | 4 |
| 179 | 1 |
| 180 | <1 |
| 181 | 1 |
| 182 | 2 |
| 183 | 1 |
| 184 | 1 |
| 185 | 2 |
| 186 | 1 |
| 187 | 2 |
| 188 | 1 |
| 189 | 1 |
| 190 | 4 |
| 191 | 7 |
| 192 | 2 |

TABLE 2-continued

| Ex. No. | ITK IC$_{50}$ (nM) |
|---|---|
| 193 | 2 |
| 194 | 2 |
| 195 | 20 |
| 196 | 4 |
| 197 | 2 |
| 198 | 1 |
| 199 | 2 |
| 200 | 1 |
| 201 | 10 |
| 202 | 14 |
| 203 | 12 |
| 204 | 49.2% (30 nM) |
| 205 | 27 |
| 206 | 5 |
| 207 | 4 |
| 208 | 29 |
| 209 | 4 |
| 210 | 36 |
| 211 | 33 |
| 212 | 5 |
| 213 | <3 |
| 214 | <3 |
| 215 | <3 |
| 216 | 8 |
| 217 | <3 |
| 218 | <3 |
| 219 | 4 |
| 220 | <3 |
| 221 | 3 |
| 222 | <3 |
| 223 | 5 |
| 224 | 1 |
| 225 | 2 |
| 226 | 2 |
| 227 | 34 |
| 228 | 40 |
| 229 | 38 |
| 230 | 25 |
| 231 | 2 |
| 232 | 3 |
| 233 | 10 |
| 234 | 16 |
| 235 | 8 |
| 236 | 6 |
| 237 | 2 |
| 238 | 2 |
| 239 | 5 |
| 240 | 3 |
| 241 | 23 |
| 242 | 3 |
| 243 | 24 |
| 244 | 23 |
| 245 | 10 |
| 246 | 7 |
| 247 | 4 |
| 248 | 2 |
| 249 | 7 |
| 250 | 139 |
| 251 | 34 |
| 252 | 11 |
| 253 | 2 |
| 254 | 5 |
| 255 | 3 |
| 256 | 1 |
| 257 | 1 |
| 258 | 4 |
| 259 | 3 |
| 260 | <1 |
| 261 | 1 |
| 262 | 3 |
| 263 | 7 |
| 264 | 10 |
| 265 | 2 |
| 266 | 7 |
| 267 | 5 |
| 268 | 5 |
| 269 | 6 |
| 270 | 2 |

TABLE 2-continued

| Ex. No. | ITK IC$_{50}$ (nM) |
|---|---|
| 271 | 3 |
| 272 | 3 |
| 273 | 11 |
| 274 | 9 |
| 275 | 2 |
| 276 | 4 |
| 277 | 1 |
| 278 | 1 |
| 279 | <1 |
| 280 | 2 |
| 281 | 1 |
| 282 | 2 |
| 283 | 2 |
| 284 | 1 |
| 285 | 2 |
| 286 | 2 |
| 287 | 1 |
| 288 | 1 |
| 289 | <1 |
| 290 | 8 |
| 291 | 1 |
| 292 | 2 |
| 293 | 263 |
| 294 | 51 |
| 295 | 138 |
| 296 | 58 |
| 297 | 48 |
| 298 | 44 |
| 299 | 74 |
| 300 | 221 |
| 301 | 37 |
| 302 | 39 |
| 303 | 33 |
| 304 | 27 |
| 305 | 13 |
| 306 | 27 |
| 307 | 61 |
| 308 | 49 |
| 309 | 102 |
| 310 | 47 |
| 311 | 32 |
| 312 | 27 |
| 313 | 47 |
| 314 | 143 |
| 315 | 60 |
| 316 | 47 |
| 317 | 21 |
| 318 | 45 |
| 319 | 46 |
| 320 | 49 |
| 321 | 48 |
| 322 | 41 |
| 323 | 34 |
| 324 | 140 |
| 325 | 246 |
| 326 | 42 |
| 327 | 132 |
| 328 | 26 |
| 329 | 13 |
| 330 | 80 |
| 331 | 60 |
| 332 | 46 |
| 333 | 106 |
| 334 | 31 |
| 335 | 26 |
| 336 | 78 |
| 337 | 49 |
| 338 | 33 |
| 339 | 842 |
| 340 | 129 |
| 341 | 333 |
| 342 | 245 |
| 343 | 135 |
| 344 | 278 |
| 345 | 88 |
| 346 | 5 |
| 347 | 4 |
| 348 | 8 |

TABLE 2-continued

| Ex. No. | ITK IC$_{50}$ (nM) |
|---|---|
| 349 | 2 |
| 350 | 62 |
| 351 | 24 |
| 352 | 37 |
| 353 | 16 |
| 354 | 16 |
| 355 | 9 |
| 356 | 9 |
| 357 | 29 |
| 358 | 38 |
| 359 | 21 |
| 360 | 67 |
| 361 | 20 |
| 362 | 12 |
| 363 | 485 |
| 364 | 45 |
| 365 | 45 |
| 366 | 82 |
| 367 | 75 |
| 368 | 131 |
| 369 | 207 |
| 370 | 204 |
| 371 | 112 |
| 372 | 11 |
| 373 | 8 |
| 374 | 130 |
| 375 | 110 |
| 376 | 2 |
| 377 | 6 |
| 378 | 2 |
| 379 | 4 |
| 380 | 2 |
| 381 | 2 |

In the test for the compounds of Examples 380 and 381, the ATP concentration of the substrate solutions was 6 µmol/L.

From the above results, it is clear that the compound of the present invention has an ITK inhibitory action.

Formulation Example 1

Production of Capsule

| 1) compound of Example 1 | 30 mg |
|---|---|
| 2) microcrystalline cellulose | 10 mg |
| 3) lactose | 19 mg |
| 4) magnesium stearate | 1 mg |

1), 2), 3) and 4) are mixed and filled in a gelatin capsule.

Formulation Example 2

Production of Tablet

| 1) compound of Example 1 | 10 g |
|---|---|
| 2) lactose | 50 g |
| 3) cornstarch | 15 g |
| 4) carmellose calcium | 44 g |
| 5) magnesium stearate | 1 g |

The entire amounts of 1), 2) and 3) and 30 g of 4) are kneaded with water, vacuum dried and sieved. The sieved powder is mixed with 14 g of 4) and 1 g of 5), and the mixture is tableted by a tableting machine. In this way, 1000 tablets each containing 10 mg of the compound of Example 1 per tablet are obtained.

INDUSTRIAL APPLICABILITY

Hence, the indole compound of the present invention can be a medicament effective for the treatment or prophylaxis of inflammatory diseases, allergic diseases, autoimmune diseases, transplant rejection and the like.

The invention claimed is:

1. A compound represented by the following formula [I] or a pharmaceutically acceptable salt thereof:

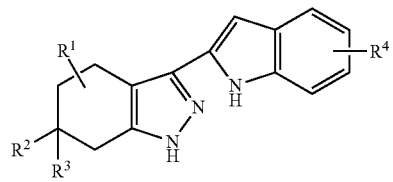

[I]

wherein, $R^1$ is (1) a hydrogen atom, (2) a hydroxy group, or (3) a $C_{1-6}$ alkoxy group optionally substituted by $C_{6-10}$ aryl group(s);

$R^2$ and $R^3$ are the same or different and each is (1) a hydrogen atom, or (2) a $C_{1-6}$ alkyl group optionally substituted by 1 to 3 substituents selected from (a) a hydroxy group, and (b) a $C_{1-6}$ alkoxy group; and $R^4$ is a group represented by

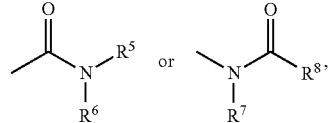

which is bonded to the 5-position or the 6-position of the indole ring, wherein $R^5$ is (1) a hydrogen atom, or (2) a $C_{1-6}$ alkyl group, and $R^6$ is (1) a hydrogen atom, (2) a $C_{1-6}$ alkyl group optionally substituted by 1 to 3 substituents selected from (a) a hydroxy group, (b) a $C_{1-6}$ alkoxy group, (c) a carboxy group, (d) a $C_{1-6}$ alkoxy-carbonyl group, (e) a $C_{6-10}$ aryl group, (f) a $C_{6-10}$ aryloxy group, (g) an amino group optionally mono- or di-substituted by $C_{1-6}$ alkyl group(s), (h) a 5- or 6-membered unsaturated heterocyclic group optionally substituted by $C_{1-6}$ alkyl group(s), and (i) a 5- or 6-membered saturated heterocyclic group, (3) a $C_{1-6}$ alkoxy group,
(4) a $C_{6-10}$ aryl group, or
(5) a 5- or 6-membered unsaturated heterocyclic group optionally substituted by 1 to 3 substituents selected from
  (a) a hydroxy group, and
  (b) a $C_{1-6}$ alkoxy group, or
$R^5$ and $R^6$ form, together with the nitrogen atom they are bonded to, a 5- or 6-membered cyclic amine (said cyclic amine is optionally condensed with 5- or 6-membered unsaturated heterocycle) optionally substituted by 1 to 3 substituents selected from
  (a) a hydroxy group,
  (b) a $C_{1-6}$ alkyl group,
  (c) a $C_{1-6}$ alkoxy group, and
  (d) a $C_{1-6}$ alkoxy-carbonyl group;
$R^7$ is
(1) a hydrogen atom, or
(2) a $C_{1-6}$ alkyl group optionally substituted by 1 to 3 substituents selected from
  (a) a hydroxy group,
  (b) a $C_{1-6}$ alkoxy group, and
  (c) an amino group optionally mono- or di-substituted by $C_{1-6}$ alkyl group(s), and
$R^8$ is
(1) a $C_{1-6}$ alkyl group optionally substituted by 1 to 3 substituents selected from
  (a) a hydroxy group,
  (b) a $C_{1-6}$ alkoxy group optionally substituted by $C_{6-10}$ aryl group(s),
  (c) a $C_{3-6}$ cycloalkyl group optionally substituted by $C_{1-6}$ alkoxy group(s),
  (d) a $C_{6-10}$ aryl group,
  (e) a 5- or 6-membered unsaturated heterocyclic group optionally substituted by oxo group(s),
  (f) a 5- to 8-membered saturated heterocyclic group optionally substituted by 1 to 3 substituents selected from
    (i) a hydroxy group,
    (ii) a $C_{1-6}$ alkyl group optionally substituted by 1 to 3 substituents selected from a hydroxy group and a $C_{1-6}$ alkoxy group,
    (iii) a $C_{1-6}$ alkoxy group, and
    (iv) an oxo group,
  (g) a $C_{3-6}$ cycloalkyloxy group,
  (h) a $C_{6-10}$ aryloxy group,
  (i) a 5- or 6-membered unsaturated heterocyclyloxy group,
  (j) a 5- or 6-membered saturated heterocyclyloxy group, and
  (k) an amino group optionally mono- or di-substituted by substituents selected from
    (i) a $C_{1-6}$ alkyl group optionally substituted by 1 to 3 substituents selected from a hydroxy group, a carboxy group and a carboxy-$C_{1-6}$ alkoxy group,
    (ii) a $C_{1-6}$ alkyl-carbonyl group optionally substituted by 1 to 3 substituents selected from a hydroxy group and a $C_{1-6}$ alkoxy group,
    (iii) a $C_{1-6}$ alkoxy-carbonyl group optionally substituted by $C_{6-10}$ aryl group(s), and
    (iv) a $C_{3-6}$ cycloalkyl-carbonyl group optionally substituted by $C_{1-6}$ alkoxy group(s),
(2) a $C_{1-6}$ alkoxy group optionally substituted by $C_{6-10}$ aryl group(s),
(3) a $C_{3-6}$ cycloalkyl group optionally substituted by 1 to 3 substituents selected from
  (a) a hydroxy group, and
  (b) a $C_{1-6}$ alkoxy group,
(4) a $C_{6-10}$ aryl group optionally substituted by $C_{1-6}$ alkyl group(s) optionally substituted by 1 to 3 halogen atoms,
(5) an amino group optionally mono- or di-substituted by $C_{1-6}$ alkyl group(s) optionally substituted by $C_{6-10}$ aryl group(s),
(6) a 5- or 6-membered unsaturated heterocyclic group optionally substituted by $C_{1-6}$ alkyl group(s),
(7) a 5- or 6-membered saturated heterocyclic group optionally substituted by 1 to 3 substituents selected from
  (a) a $C_{1-6}$ alkyl group,
  (b) a $C_{1-6}$ alkyl-carbonyl group, and
  (c) an oxo group,
(8) a $C_{3-6}$ cycloalkyloxy group, or
(9) a $C_{6-10}$ aryl-carbonyl group, or
$R^7$ and $R^8$ form, together with the nitrogen atom and carbon atom they are bonded to, a 5- or 6-membered cyclic amine substituted by an oxo group and optionally further substituted by 1 to 3 substituents selected from
  (a) a hydroxy group,
  (b) a $C_{1-6}$ alkyl group optionally substituted by hydroxy group(s),
  (c) a $C_{1-6}$ alkoxy group, and
  (d) a $C_{3-6}$ cycloalkyl group.

2. A compound represented by the following formula [I-a] or a pharmaceutically acceptable salt thereof:

[I-a]

wherein,
$R^1$ is
(1) a hydrogen atom,
(2) a hydroxy group, or
(3) a $C_{1-6}$ alkoxy group optionally substituted by $C_{6-10}$ aryl group(s);
$R^2$ and $R^3$ are the same or different and each is
(1) a hydrogen atom, or
(2) a $C_{1-6}$ alkyl group optionally substituted by 1 to 3 substituents selected from
  (a) a hydroxy group, and
  (b) a $C_{1-6}$ alkoxy group;
$R^{7\prime}$ is a $C_{1-6}$ alkyl group optionally substituted by 1 to 3 substituents selected from
  (a) a hydroxy group,
  (b) a $C_{1-6}$ alkoxy group, and
  (c) an amino group optionally mono- or di-substituted by $C_{1-6}$ alkyl group(s), and
$R^8$ is
(1) a $C_{1-6}$ alkyl group optionally substituted by 1 to 3 substituents selected from
  (a) a hydroxy group,
  (b) a $C_{1-6}$ alkoxy group optionally substituted by $C_{6-10}$ aryl group(s),
  (c) a $C_{3-6}$ cycloalkyl group optionally substituted by $C_{1-6}$ alkoxy group(s),
  (d) a $C_{6-10}$ aryl group,
  (e) a 5- or 6-membered unsaturated heterocyclic group optionally substituted by oxo group(s), (f) a 5- to 8-membered saturated heterocyclic group optionally substituted by 1 to 3 substituents selected from
  (i) a hydroxy group,
  (ii) a $C_{1-6}$ alkyl group optionally substituted by 1 to 3 substituents selected from a hydroxy group and a $C_{1-6}$ alkoxy group,
  (iii) a $C_{1-6}$ alkoxy group, and
  (iv) an oxo group,
(g) a $C_{3-6}$ cycloalkyloxy group,
(h) a $C_{6-10}$ aryloxy group,
(i) a 5- or 6-membered unsaturated heterocyclyloxy group,
(j) a 5- or 6-membered saturated heterocyclyloxy group, and
(k) an amino group optionally mono- or di-substituted by substituents selected from
  (i) a $C_{1-6}$ alkyl group optionally substituted by 1 to 3 substituents selected from a hydroxy group, a carboxy group and a carboxy-$C_{1-6}$ alkoxy group,
  (ii) a $C_{1-6}$ alkyl-carbonyl group optionally substituted by 1 to 3 substituents selected from a hydroxy group and a $C_{1-6}$ alkoxy group,
  (iii) a $C_{1-6}$ alkoxy-carbonyl group optionally substituted by $C_{6-10}$ aryl group(s), and
  (iv) a $C_{3-6}$ cycloalkyl-carbonyl group optionally substituted by $C_{1-6}$ alkoxy group(s),
(2) a $C_{1-6}$ alkoxy group optionally substituted by $C_{6-10}$ aryl group(s),
(3) a $C_{3-6}$ cycloalkyl group optionally substituted by 1 to 3 substituents selected from
  (a) a hydroxy group, and
  (b) a $C_{1-6}$ alkoxy group,
(4) a $C_{6-10}$ aryl group optionally substituted by $C_{1-6}$ alkyl group(s) optionally substituted by 1 to 3 halogen atoms,
(5) an amino group optionally mono- or di-substituted by $C_{1-6}$ alkyl group(s) optionally substituted by $C_{6-10}$ aryl group(s),
(6) a 5- or 6-membered unsaturated heterocyclic group optionally substituted by $C_{1-6}$ alkyl group(s),
(7) a 5- or 6-membered saturated heterocyclic group optionally substituted by 1 to 3 substituents selected from
  (a) a $C_{1-6}$ alkyl group,
  (b) a $C_{1-6}$ alkyl-carbonyl group, and
  (c) an oxo group,
(8) a $C_{3-6}$ cycloalkyloxy group, or
(9) a $C_{6-10}$ aryl-carbonyl group, or
$R^{7'}$ and $R^8$ form, together with the nitrogen atom and carbon atom they are bonded to, a 5- or 6-membered cyclic amine substituted by an oxo group and optionally further substituted by 1 to 3 substituents selected from
  (a) a hydroxy group,
  (b) a $C_{1-6}$ alkyl group optionally substituted by hydroxy group(s),
  (c) a $C_{1-6}$ alkoxy group, and
  (d) a $C_{3-6}$ cycloalkyl group.

3. The compound according to claim 2, wherein
$R^1$ is a hydrogen atom; and
$R^2$ and $R^3$ are the same or different and each is a $C_{1-6}$ alkyl group,
or a pharmaceutically acceptable salt thereof.

4. The compound according to claim 3, wherein
$R^{7'}$ is a $C_{1-6}$ alkyl group; and
$R^8$ is a $C_{1-6}$ alkyl group substituted by 1 to 3 substituents selected from
  (a) a hydroxy group,
  (b) a $C_{1-6}$ alkoxy group optionally substituted by $C_{6-10}$ aryl group(s),
  (c) a $C_{3-6}$ cycloalkyl group optionally substituted by $C_{1-6}$ alkoxy group(s),
  (d) a $C_{6-10}$ aryl group,
  (e) a 5- or 6-membered unsaturated heterocyclic group optionally substituted by oxo group(s),
  (f) a 5- to 8-membered saturated heterocyclic group optionally substituted by 1 to 3 substituents selected from
    (i) a hydroxy group,
    (ii) a $C_{1-6}$ alkyl group optionally substituted by 1 to 3 substituents selected from a hydroxy group and a $C_{1-6}$ alkoxy group,
    (iii) a $C_{1-6}$ alkoxy group, and
    (iv) an oxo group,
  (g) a $C_{3-6}$ cycloalkyloxy group,
  (h) a $C_{6-10}$ aryloxy group,
  (i) a 5- or 6-membered unsaturated heterocyclyloxy group,
  (j) a 5- or 6-membered saturated heterocyclyloxy group, and
  (k) an amino group optionally mono- or di-substituted by substituents selected from
    (i) a $C_{1-6}$ alkyl group optionally substituted by 1 to 3 substituents selected from a hydroxy group, a carboxy group and a carboxy-$C_{1-6}$ alkoxy group,
    (ii) a $C_{1-6}$ alkyl-carbonyl group optionally substituted by 1 to 3 substituents selected from a hydroxy group and a $C_{1-6}$ alkoxy group,
    (iii) a $C_{1-6}$ alkoxy-carbonyl group optionally substituted by $C_{6-10}$ aryl group(s), and
    (iv) a $C_{3-6}$ cycloalkyl-carbonyl group optionally substituted by $C_{1-6}$ alkoxy group(s),
or a pharmaceutically acceptable salt thereof.

5. A compound selected from the following formulas:

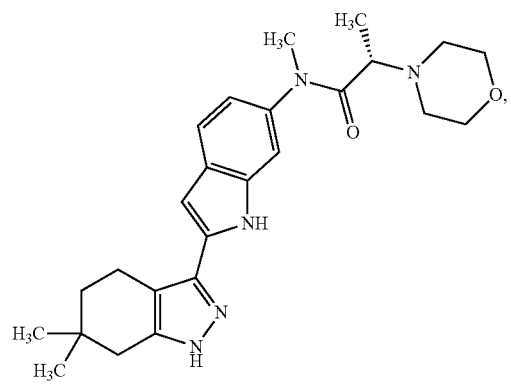

321
-continued
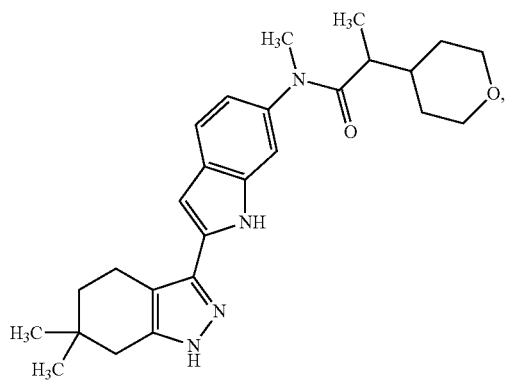
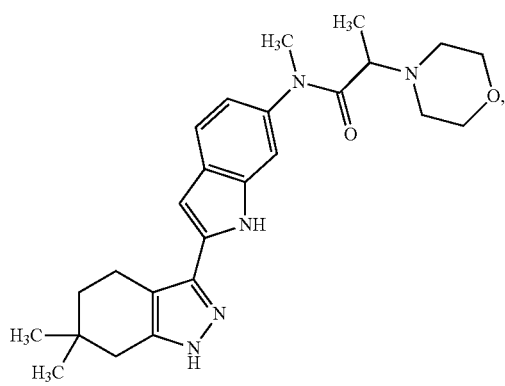
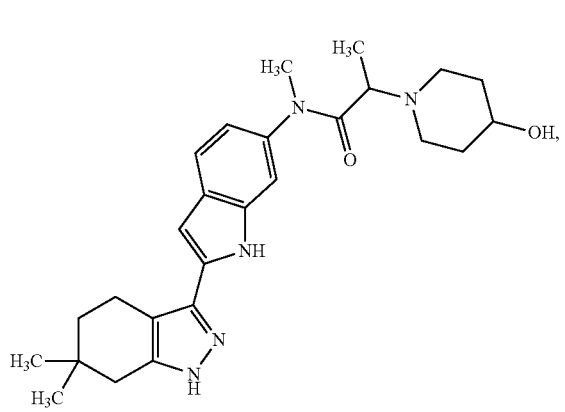
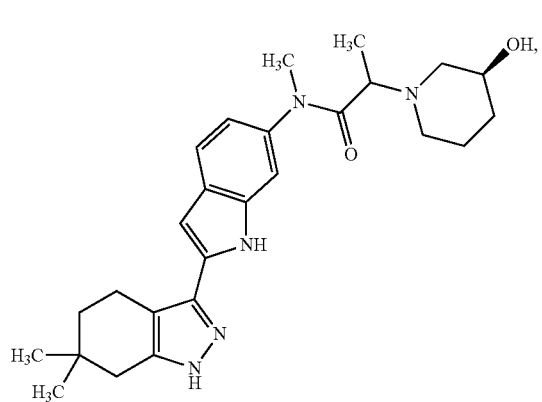
322
-continued
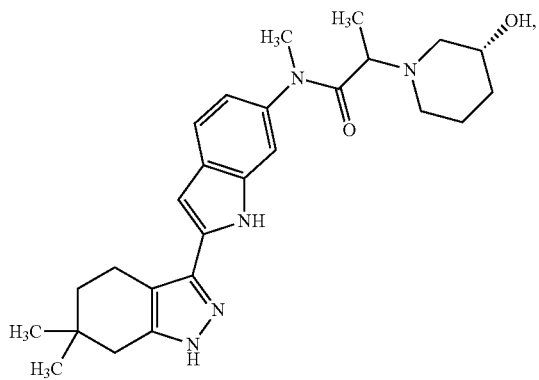
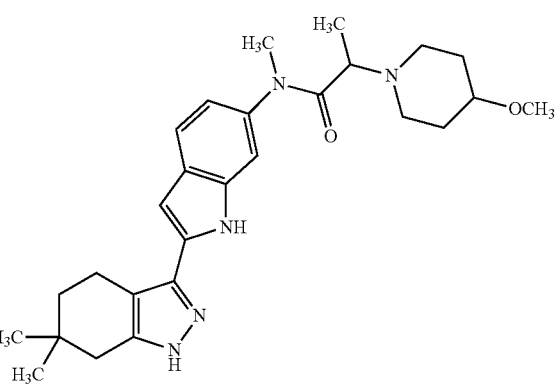
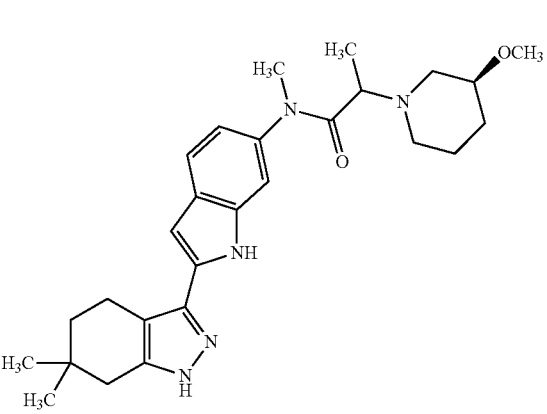
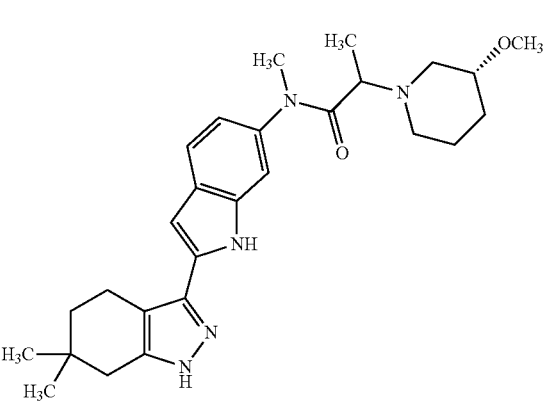

323
-continued
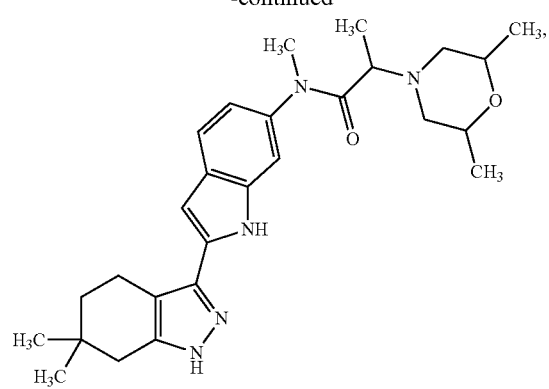
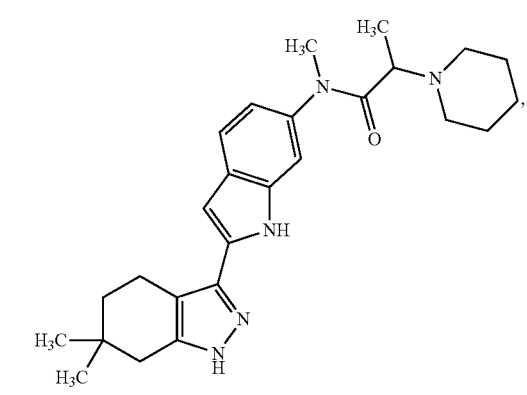
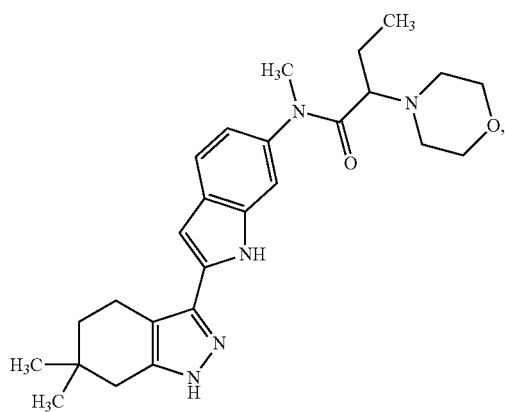
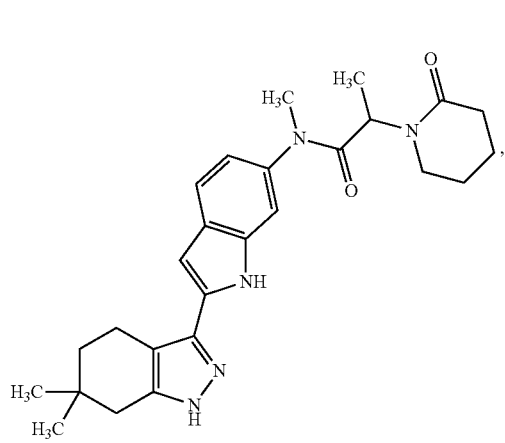
324
-continued
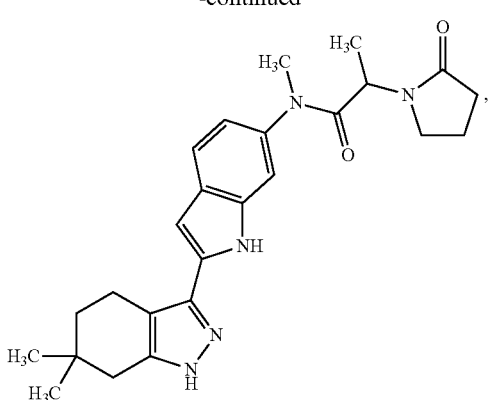
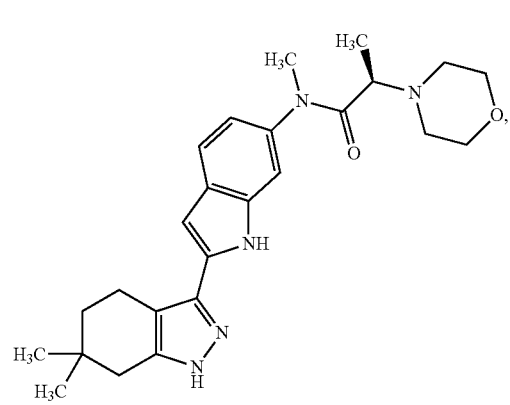
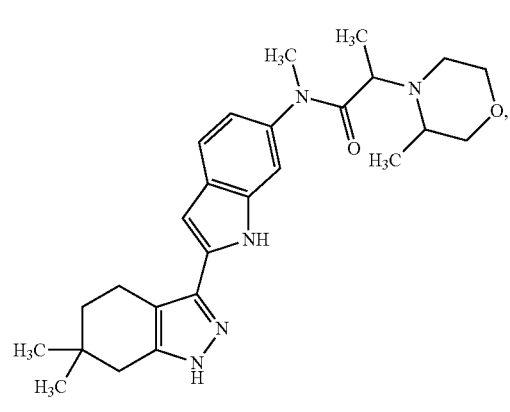
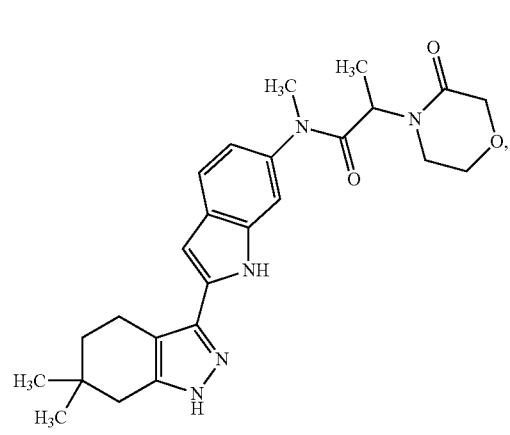

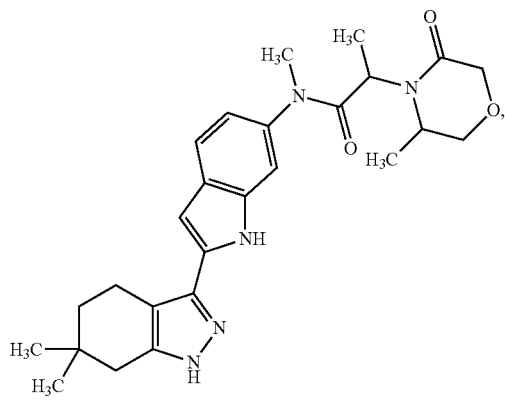
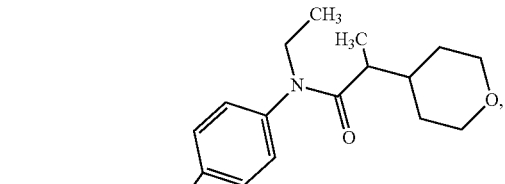
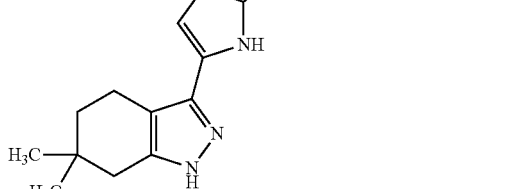
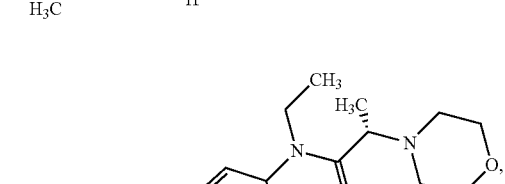
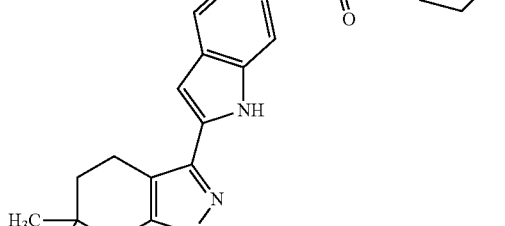
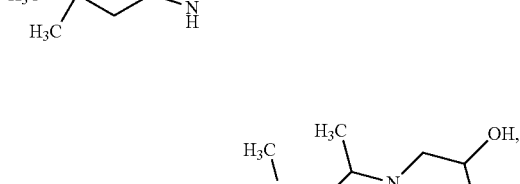
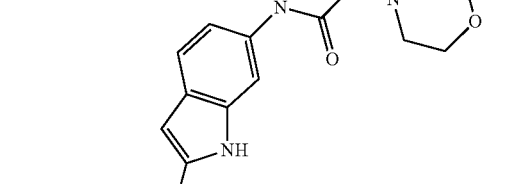
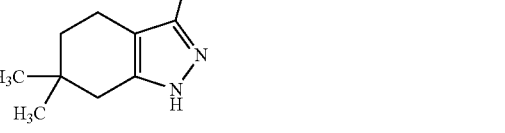
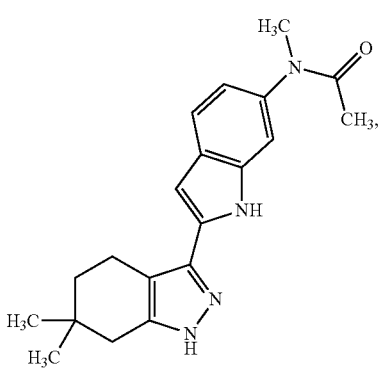

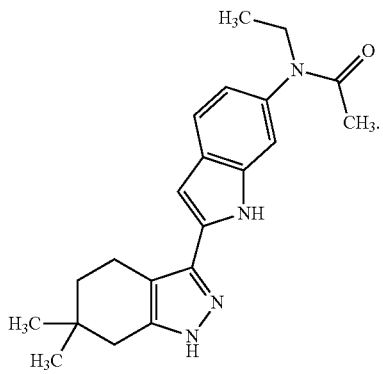

and a pharmaceutically acceptable salt thereof.

6. A pharmaceutical composition comprising the compound according to claim 1, or a pharmaceutically acceptable salt thereof, and a pharmaceutically acceptable carrier.

7. A method of inhibiting ITK in a mammal, comprising administering a pharmaceutically effective amount of the compound according to claim 1, or a pharmaceutically acceptable salt thereof, to the mammal, thereby inhibiting ITK in the mammal.

8. A method for treating inflammatory bowel disease in a mammal, comprising administering a pharmaceutically effective amount of the compound according to claim 1, or a pharmaceutically acceptable salt thereof, to the mammal, thereby treating inflammatory bowel disease in the mammal.

9. A method for treating rheumatoid arthritis in a mammal, comprising administering a pharmaceutically effective amount of the compound according to claim 1, or a pharmaceutically acceptable salt thereof, to the mammal, thereby treating rheumatoid arthritis in the mammal.

10. A method for treating an allergic disease in a mammal, comprising administering a pharmaceutically effective amount of the compound according to claim 1, or a pharmaceutically acceptable salt thereof, to a mammal having an allergic disease selected from the group consisting of atopic dermatitis, asthma, and allergic rhinitis, thereby treating the allergic disease in the mammal.

11. A method for treating systemic lupus erythematosus in a mammal, comprising administering a pharmaceutically effective amount of the compound according to claim 1, or a pharmaceutically acceptable salt thereof, to the mammal, thereby treating systemic lupus erythematosus in the mammal.

12. A method for treating psoriasis in a mammal, comprising administering a pharmaceutically effective amount of the compound according to claim 1, or a pharmaceutically acceptable salt thereof, to the mammal, thereby treating psoriasis in the mammal.

13. A method of suppressing rejection in transplantation in a mammal, comprising administering a pharmaceutically effective amount of the compound according to claim 1, or a pharmaceutically acceptable salt thereof, to the mammal, thereby suppressing rejection in transplantation in the mammal.

14. A pharmaceutical composition comprising the compound according to claim 5, or a pharmaceutically acceptable salt thereof, and a pharmaceutically acceptable carrier.

15. A method of inhibiting ITK in a mammal, comprising administering a pharmaceutically effective amount of the compound according to claim 5, or a pharmaceutically acceptable salt thereof, to the mammal, thereby inhibiting ITK in the mammal.

16. A method for treating inflammatory bowel disease in a mammal, comprising administering a pharmaceutically effective amount of the compound according to claim 5, or a pharmaceutically acceptable salt thereof, to the mammal, thereby treating inflammatory bowel disease in the mammal.

17. A method for treating rheumatoid arthritis in a mammal, comprising administering a pharmaceutically effective amount of the compound according to claim 5, or a pharmaceutically acceptable salt thereof, to the mammal, thereby treating rheumatoid arthritis in the mammal.

18. A method for treating an allergic disease in a mammal, comprising administering a pharmaceutically effective amount of the compound according to claim 5, or a pharmaceutically acceptable salt thereof, to a mammal having an allergic disease selected from the group consisting of atopic dermatitis, asthma, and allergic rhinitis, thereby treating the allergic disease in the mammal.

19. A method for treating systemic lupus erythematosus in a mammal, comprising administering a pharmaceutically effective amount of the compound according to claim 5, or a pharmaceutically acceptable salt thereof, to the mammal, thereby treating systemic lupus erythematosus in the mammal.

20. A method for treating psoriasis in a mammal, comprising administering a pharmaceutically effective amount of the compound according to claim 5 or a pharmaceutically acceptable salt thereof, to the mammal, thereby treating psoriasis in the mammal.

21. A method of suppressing rejection in transplantation in a mammal, comprising administering a pharmaceutically effective amount of the compound according to claim 5, or a pharmaceutically acceptable salt thereof, to the mammal, thereby suppressing rejection in transplantation in the mammal.

22. The compound of claim 1 that is

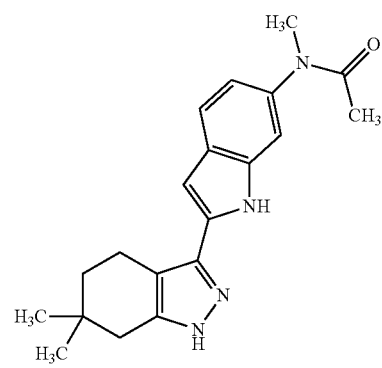

or a pharmaceutically acceptable salt thereof.

23. The compound of claim 1 that is or a pharmaceutically acceptable salt thereof.

24. The compound of claim 1 that is or a pharmaceutically acceptable salt thereof.

25. The compound of claim 1 that is t,572 or a pharmaceutically acceptable salt thereof.

26. The compound of claim 1 that is t,573 or a pharmaceutically acceptable salt thereof.

27. The compound of claim 1 that is t,574 or a pharmaceutically acceptable salt thereof.

28. A pharmaceutical composition comprising the compound according to any one of claims 22-27, or a pharmaceutically acceptable salt thereof, and a pharmaceutically acceptable carrier.

29. A method of inhibiting ITK in a mammal, comprising administering a pharmaceutically effective amount of the compound according to any one of claims 22-27, or a pharmaceutically acceptable salt thereof, to the mammal, thereby inhibiting ITK in the mammal.

30. A method for treating inflammatory bowel disease in a mammal, comprising administering a pharmaceutically effective amount of the compound according to any one of claims 22-27, or a pharmaceutically acceptable salt thereof, to the mammal, thereby treating inflammatory bowel disease in the mammal.

31. A method for treating rheumatoid arthritis in a mammal, comprising administering a pharmaceutically effective amount of the compound according to any one of claims 22-27, or a pharmaceutically acceptable salt thereof, to the mammal, thereby treating rheumatoid arthritis in the mammal.

32. A method for treating an allergic disease in a mammal, comprising administering a pharmaceutically effective amount of the compound according to any one of claims 22-27, or a pharmaceutically acceptable salt thereof, to a mammal having an allergic disease selected from the group consisting of atopic dermatitis, asthma, and allergic rhinitis, thereby treating the allergic disease in the mammal.

33. A method for treating systemic lupus erythematosus in a mammal, comprising administering a pharmaceutically effective amount of the compound according to any one of claims 22-27, or a pharmaceutically acceptable salt thereof, to the mammal, thereby treating systemic lupus erythematosus in the mammal.

34. A method for treating psoriasis in a mammal, comprising administering a pharmaceutically effective amount of the compound according to any one of claims 22-27, or a pharmaceutically acceptable salt thereof, to the mammal, thereby treating psoriasis in the mammal.

35. A method of suppressing rejection in transplantation in a mammal, comprising administering a pharmaceutically effective amount of the compound according to any one of claims 22-27, or a pharmaceutically acceptable salt thereof, to the mammal, thereby suppressing rejection in transplantation in the mammal.

36. The compound of claim 22, wherein the pharmaceutically acceptable salt is a pharmaceutically acceptable acid addition salt.

37. The compound of claim 23, wherein the pharmaceutically acceptable salt is a pharmaceutically acceptable acid addition salt.

38. The compound of claim 24, wherein the pharmaceutically acceptable salt is a pharmaceutically acceptable acid addition salt.

39. The compound of claim 25, wherein the pharmaceutically acceptable salt is a pharmaceutically acceptable acid addition salt.

40. The compound of claim 26, wherein the pharmaceutically acceptable salt is a pharmaceutically acceptable acid addition salt.

41. The compound of claim 27, wherein the pharmaceutically acceptable salt is a pharmaceutically acceptable acid addition salt.

42. The pharmaceutical composition of claim 28, wherein the pharmaceutically acceptable salt is a pharmaceutically acceptable acid addition salt.

43. The method according to claim 29, wherein the pharmaceutically acceptable salt is a pharmaceutically acceptable acid addition salt.

44. The method according to claim 30, wherein the pharmaceutically acceptable salt is a pharmaceutically acceptable acid addition salt.

45. The method according to claim 31, wherein the pharmaceutically acceptable salt is a pharmaceutically acceptable acid addition salt.

46. The method according to claim 32, wherein the pharmaceutically acceptable salt is a pharmaceutically acceptable acid addition salt.

47. The method according to claim 33, wherein the pharmaceutically acceptable salt is a pharmaceutically acceptable acid addition salt.

48. The method according to claim 34, wherein the pharmaceutically acceptable salt is a pharmaceutically acceptable acid addition salt.

49. The method according to claim 35, wherein the pharmaceutically acceptable salt is a pharmaceutically acceptable acid addition salt.

* * * * *

UNITED STATES PATENT AND TRADEMARK OFFICE
CERTIFICATE OF CORRECTION

PATENT NO.      : 8,299,070 B2
APPLICATION NO. : 12/954438
DATED           : October 30, 2012
INVENTOR(S)     : Inoue et al.

It is certified that error appears in the above-identified patent and that said Letters Patent is hereby corrected as shown below:

In the Claims

Claim 5, column 327, line 22:

"and a pharmaceutically acceptable salt thereof." should read "or a pharmaceutically acceptable salt thereof."

Claim 25 should read "The compound of claim 1 that is

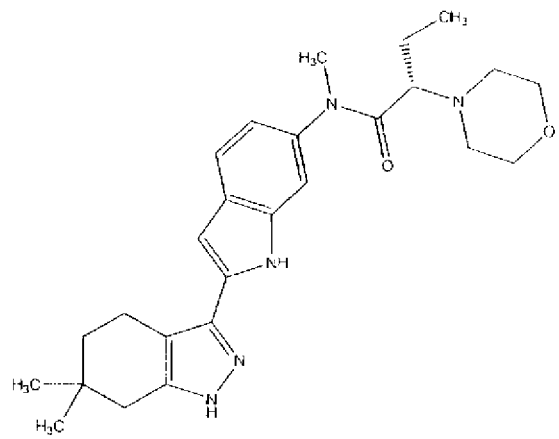

or a pharmaceutically acceptable salt thereof."

Signed and Sealed this
Twenty-first Day of May, 2013

Teresa Stanek Rea
*Acting Director of the United States Patent and Trademark Office*

Claim 26 should read "The compound of claim 1 that is
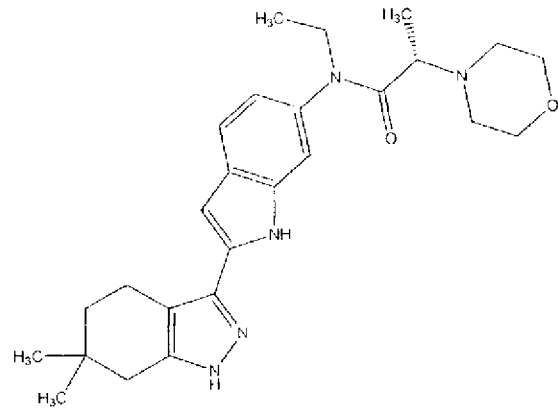
or a pharmaceutically acceptable salt thereof."
Claim 27 should read "The compound of claim 1 that is
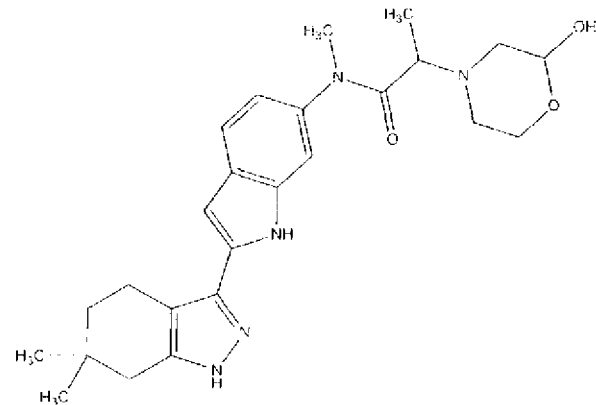
or a pharmaceutically acceptable salt thereof."